US008153658B2

(12) United States Patent
Hachiya et al.

(10) Patent No.: US 8,153,658 B2
(45) Date of Patent: Apr. 10, 2012

(54) PIPERIDINE DERIVATIVE OR SALT THEREOF

(75) Inventors: Shunichiro Hachiya, Tokyo (JP); Kazuhiro Ikegai, Tokyo (JP); Ryotaro Ibuka, Tokyo (JP); Taisuke Takahashi, Tokyo (JP); Makoto Oku, Tokyo (JP); Ryushi Seo, Tokyo (JP); Yoh Terada, Tokyo (JP); Masanao Sanagi, Tokyo (JP)

(73) Assignee: Astellas Pharma, Inc., Tokyo (JP)

( * ) Notice: Subject to any disclaimer, the term of this patent is extended or adjusted under 35 U.S.C. 154(b) by 243 days.

(21) Appl. No.: 12/514,869

(22) PCT Filed: Nov. 14, 2007

(86) PCT No.: PCT/JP2007/072063
§ 371 (c)(1),
(2), (4) Date: May 14, 2009

(87) PCT Pub. No.: WO2008/059854
PCT Pub. Date: May 22, 2008

(65) Prior Publication Data
US 2010/0029687 A1 Feb. 4, 2010

(30) Foreign Application Priority Data

Nov. 16, 2006 (JP) .................................. 2006-310026

(51) Int. Cl.
A61K 31/4525 (2006.01)
A61K 31/4535 (2006.01)
A61K 31/454 (2006.01)
A61K 31/4545 (2006.01)
C07D 409/12 (2006.01)
C07D 405/04 (2006.01)
C07D 413/04 (2006.01)
C07D 411/04 (2006.01)
C07D 401/04 (2006.01)
C07D 401/12 (2006.01)

(52) U.S. Cl. ........ 514/319; 514/318; 514/324; 514/326; 514/330; 514/331; 514/323; 514/322; 546/194; 546/199; 546/196; 546/202; 546/205; 548/198; 548/210; 548/209

(58) Field of Classification Search .................. 514/319, 514/318, 324, 326, 330, 331, 323, 322; 546/205, 546/194, 199, 196, 202, 198, 210, 209
See application file for complete search history.

(56) References Cited

U.S. PATENT DOCUMENTS 5,328,917 A * 7/1994 Jakobsen et al. ............. 514/331
5,854,268 A * 12/1998 Baker et al. .................. 514/383
7,585,886 B2 * 9/2009 Hachiya et al. ............... 514/423
2007/0225296 A1 * 9/2007 Miyazaki et al. ........ 514/255.05

FOREIGN PATENT DOCUMENTS

| EP | 1553084 A1 | 7/2005 |
|---|---|---|
| EP | 1757582 A1 | 2/2007 |
| EP | 1882684 A1 | 1/2008 |
| JP | 6-500076 A | 1/1994 |
| JP | 7-506380 A | 7/1995 |
| WO | 92/01672 A1 | 2/1992 |
| WO | 94/18959 A1 | 9/1994 |
| WO | WO 9937635 A1 * | 7/1999 |
| WO | 03/101964 A1 | 12/2003 |
| WO | 2005/115975 A1 | 12/2005 |
| WO | 2006/004195 A1 | 1/2006 |
| WO | 2006/123725 A1 | 11/2006 |

OTHER PUBLICATIONS

Edward M. Brown, et al.; "Cloning and characterization of an extracellular $Ca^{2+}$ -sensing receptor from bovine parathyroid"; Nature Publishing Group; vol. 366 pp. 575-580; Dec. 1993.
Adi Cohen, et al.; "Calcimimetics: therapeutic potential in hyperparathyroidism"; Current Opinion in Pharmacology; Elsevier Science Ltd., 2002; vol. 2 pp. 734-739.
Melanie S. Joy, et al.; "Calcimimetics and the Treatment of Primary and Secondary Hyperparathyroidism"; The Annuls of Pharmacotherapy Nov. 2004; vol. 38 pp. 1871-1880.
Sensipar (cinacalcet HCl) tablets; Amgen Inc; 2004; vol. 9 pp. 1-17.
Jeannie M. Ray, et al.; "Expression of the Calcium-sensing Receptor on Human Antral Gastrin Cells in Culture"; The American Society for Clinical Investigation, Inc.; May 1997; vol. 99 No. 10 pp. 2328-2333. Sam X. Chang, et al.; "Expression of calcium-sensing receptor in rat colonic epithelium: evidence for modulation of fluid secretion", The American Physiological Society 2002; American Journal of physiology—Gastrointestinal and Liver Physiology; vol. 283, pp. 240-250.
Jason I. E. Bruce, et al.; "Molecular and Functional Identification of a $Ca^{2+}$ (Polyvalent Cation)-sensing Receptor in Rat Pancreas"; The Journal of Biological Chemistry, by the American Society for Biochemistry and Molecular Biology, Inc., 1999; vol. 274, No. 29, pp. 20561-20568.
Susanne G. Straub, et al.; "The Calcimimetic R-467 Potentiates Insulin Secretion in Pancreatic β cells by Activation of a Nonspecific Cation Channel"; The American Society for Biochemistry and Molecular Biology, Inc.; 2000 The Journal of Biological Chemistry; vol. 275 No. 25, pp. 18777-18784.
International Search Report for PCT/JP2007/072063, dated Jan. 22, 2008.
International Preliminary Examination Report, for PCT/JP2007/072063, dated Jan. 22, 2008.
Extended European Search Report dated Aug. 23, 2010 issued in Application No. 07831793.0.

* cited by examiner

Primary Examiner — Joseph Kosack
Assistant Examiner — Matthew Coughlin
(74) Attorney, Agent, or Firm — Sughrue Mion, PLLC

(57) ABSTRACT

To provide a compound which can be used for treating diseases in which a calcium sensing receptor (CaSR) participates, particularly hyperparathyroidism. It was found that a novel piperidine derivative which is characterized in that one of a 3-position and a 4-position is substituted with an aminomethyl group substituted with an arylalkyl group or the like and the other position is substituted with aryl, heteroaryl or the like, or a salt thereof, has an excellent CaSR agonistic regulatory action, and also has excellent selectivity with a CYP2D6 inhibitory action having a possibility of causing drug interaction. Based on the above, this novel piperidine derivative is useful as a therapeutic agent for diseases in which CaSR participates (hyperparathyroidism, renal osteodystrophy, hypercalcemia, and the like).

11 Claims, No Drawings

PIPERIDINE DERIVATIVE OR SALT THEREOF

TECHNICAL FIELD

The present invention relates to a medicine, particularly to a novel piperidine derivative that is useful as a therapeutic agent for diseases in which a calcium sensing receptor (CaSR) participates, such as hyperparathyroidism.

BACKGROUND ART

Extracellular $Ca^{2+}$ concentration plays a very important role in various living body functions including maintenance of life. Thus, serum $Ca^{2+}$ concentration is strictly controlled in a very narrow range by a number of regulatory mechanisms.

A parathyroid hormone (PTH) is a polypeptide hormone produced in and secreted from parathyroid glands, and mainly regulates serum $Ca^{2+}$ concentration. This PTH increases serum $Ca^{2+}$ concentration by accelerating bone resorption, and accelerating reabsorption of calcium in the kidney. Increase in the serum $Ca^{2+}$ concentration inhibits the secretion of PTH, but on the contrary, decrease in the $Ca^{2+}$ concentration accelerates the secretion of PTH, so it is believed that the serum $Ca^{2+}$ concentration is controlled, in a sense, by a negative feedback mechanism.

Included in the hyperparathyroidism in which excessive secretion of PTH continuously occurs are primary hyperparathyroidism considered to be due to adenoma, hyperplasia, cancer or the like of the parathyroid itself and secondary hyperparathyroidism caused by renal function reduction and the like.

It has been reported that many renal insufficiency patients also suffer from secondary hyperparathyroidism. The secondary hyperparathyroidism is one of the causative diseases of renal osteodystrophy including ectopic calcification, and is considered to be the cause of lowering QOL of renal insufficiency patients due to bone fracture, bone pain and the like, and of the death of renal insufficiency patients caused by a cardiovascular disease considered to be resulted from calcification in the cardiovascular system. Thus, the secondary hyperparathyroidism is a big problem in the clinical field.

In the secondary hyperparathyroidism caused by renal insufficiency, excessive secretion of PTH is generated triggered by the reduction of serum $Ca^{2+}$ concentration caused by lowering of the phosphorus excretion ability in the kidney and the reduction of active vitamin D. It is considered that this excessive secretion of PTH is continued and exacerbated by further reduction of renal function, parathyroid hyperplasia, resistance of the PTH target organ, and the like.

At present, a vitamin D replenishment therapy is mainly carried out as an internal therapy for the secondary hyperparathyroidism. However, since the vitamin D preparations increase the serum $Ca^{2+}$ concentration, they have an administration limit, so that it is not the state of being able to carry out sufficient treatment. Based on the above, concern has been directed toward the development of a therapeutic agent for secondary hyperparathyroidism, which has high efficacy and does not increase serum $Ca^{2+}$ concentration.

Calcium sensing receptor (CaSR) has been cloned initially as a G-protein coupled receptor (GPCR) which can sense extracellular $Ca^{2+}$ in bovine parathyroid (Non-Patent Document 1). The CaSR has a function to change the intracellular $Ca^{2+}$ concentration by sensing extracellular $Ca^{2+}$ concentration, and thereby to regulate the production of molecules related to the $Ca^{2+}$ metabolism regulation, typified by PTH.

As a fact to support this, many reports have been published that active mutations of human CaSR cause familial hypercalcemia and inactive mutations of human CaSR cause familial hypocalcemia. In addition, reduction of sensitivity of the parathyroid gland for $Ca^{2+}$ has been observed in both primary and secondary hyperparathyroidism.

It is considered that an agonistic regulatory agent of CaSR reduces PTH secretion without increasing serum $Ca^{2+}$ concentration, by increasing the $Ca^{2+}$ sensitivity through its direct action upon CaSR of the parathyroid gland. Recently, it has been reported that an agonistic regulatory agent of CaSR, cinacalcet, has an activity to inhibit PTH secretion by increasing the $Ca^{2+}$ sensitivity of CaSR through its direct action upon CaSR of the parathyroid gland (Non-Patent Documents 2 and 3). Cinacalcet is expected to be a novel therapeutic agent for hyperparathyroidism which may be used concomitantly with a vitamin D preparation used already as the known remedy, a $Ca^{2+}$-containing phosphate absorbent that has been used for the purpose of treating hyperphosphatemia, and the like.

However, it has been reported that cinacalcet has a strong activity to inhibit CYP2D6 which is one of the subtypes of cytochrome p450 (CYP). This CYP2D6 also plays an important role in the metabolism of various drugs used in the clinical field. Since cinacalcet inhibits CYP2D6, there is a danger of causing drug-drug interaction (DDI) by changing the pharmacokinetics of a drug through the delay of metabolism of a drug metabolized by CYP2D6 (Non-Patent Document 4). Based on the above, concern has been directed toward development of a strong CaSR regulatory agent free from CYP2D6 inhibitory activity.

It is considered that mRNA of CaSR is expressed in various tissues including the kidney and the parathyroid gland which is a main PTH secreting tissue and CaSR takes part in various physiological roles.

It is expected that an agent which regulates CaSR antagonistically or agonistically (CaSR regulator) could become a therapeutic agent of various diseases including bone disease and diseases of upper and lower digestive organs (Non-Patent Documents 5 and 6), diabetes mellitus (Non-Patent Documents 7 and 8), hypo-/hyper-function of pituitary (Non-Patent Document 9), and the like, in addition to the aforementioned hyperparathyroidism.

Regarding the CaSR regulator, there are reports of the following Patent Documents 1 to 3.

In the Patent Document 1, the compounds represented by the following formula (A) and formula (B) including a broad range of the compounds are disclosed. However, there is no specific disclosure on the compound of the present invention.

[Chem. 1]

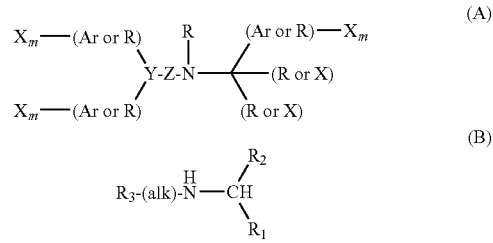

(wherein Ar, R, and $R_3$ represent the following meanings.

Ar: a hydrophobic substance.

R: hydrogen, methyl, ethyl, propyl, isopropyl, butyl, isobutyl, cyclopentyl, cyclohexyl, cycloheptyl, cyclooctyl, indenyl, indanyl, or 2-, 3- or 4-piperidyl.

$R_3$: a monocyclic or bicyclic aryl or cycloalkyl having 5 or 6 ring constituting atoms, which may be substituted.

See the documents as described above for other signs.)

A compound represented by the following formula (C) is disclosed in the Patent Document 2. However, in the compound represented by formula (C), an amino group is directly linked to a nitrogen-containing ring. Further, there is no portion corresponding to $R^2$ of the compound of the present invention.

[Chem. 2]

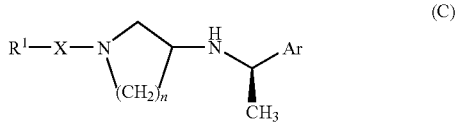

(C)

(See the Documents as Described Above for Other Signs in the Formula.)

In addition, Patent Document 3 which has been filed by the present applicant and published after the priority date of the present application discloses a pyrrolidine derivative represented by the following formula (D). However, the nitrogen-containing hetero ring containing A and B is restricted to a pyrrolidine ring.

[Chem. 3]

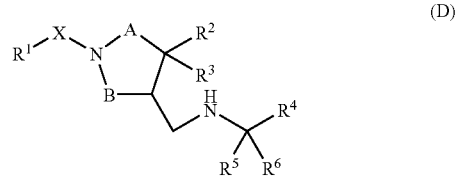

(D)

(wherein A and B represent —C($R^7$)($R^{7a}$)— or —C(O)—. See the documents as described above for other signs.)

Furthermore, regarding the piperidine derivative, there are the reports of the following Patent Documents 4 and 5.

Patent Document 4 describes that a piperidine derivative represented by the following formula (E) has an activity for preventing the calcium overload in the brain cells, and is effective for neurodegenerative diseases such as oxygen deficiency.

However, the compound (E) has no portion corresponding to $R^4$ of the compound of the present invention. Further, it has no description on the effectiveness on a CaSR regulatory action and hyperparathyroidism.

[Chem. 4]

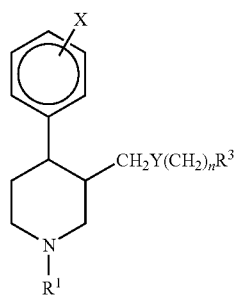

(E)

(wherein Y means O, S, or NR, n means 0 to 4, and $R^3$ means 3,4-methylenedioxyphenyl, phenyl, naphthyl, or a 5- or 6-membered hetero ring group. See the documents as described above for other signs.)

Patent Document 5 describes that a piperidine derivative represented by the following formula (F) has a tachykin receptor-agonistic activity, and is effective for pains, inflammation, allergy, and the like. However, for the compound (F), the substituent on a 4-position of the piperidine is an amide or an ester. Further, it has no description on the effectiveness of a CaSR regulatory action and hyperparathyroidism.

[Chem. 5]

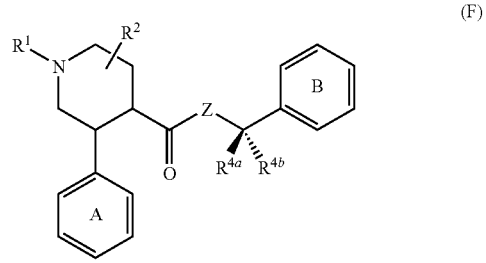

(F)

(wherein Z means O or N($R^3$). See the documents as described above for other signs.)

[Non-Patent Document 1] Brown et al., Nature, (England), 1993, vol. 366, p. 575-580

[Non-Patent Document 2] Cohen et al., Current Opinion in Pharmacology, (Holland), 2002, vol. 2, p/734-739

[Non-Patent Document 3] Joy et al., The Annals of Pharmacotherapy, (USA), 2004, vol. 38, p. 1871-1880

[Non-Patent Document 4] "Sensipar™ (registered trademark) (cinacalcet HCl) Tablets)", [online], 2004, FDA [retrieved date: Mar. 28, 2005], Internet, (URL: http://www.fda.gov./cder/foi/label/2004/21688-Sensipar-lbl.pdf).

[Non-Patent Document 5] Jeannine et al., "The Journal of Clinical Investigation", (USA), 1997, vol. 99, p. 2328-2333

[Non-Patent Document 6] Cheng et al., "The American Journal of Physiology-Gastrointestinal and Liver Physiology", (USA), 2002, vol. 283, p. G240-G250

[Non-Patent Document 7] Bruce et al., "The Journal of Biological Chemistry", (USA), 1999, vol. 274, p. 20561-20568

[Non-Patent Document 8] Straub et al., "The Journal of Biological Chemistry", (USA), 2000, vol. 275, p. 18777-18784

[Non-Patent Document 9] Emanuel et al., Molecular Endocrinology, (USA), 1996, vol. 10, p. 555-565

[Patent Document 1] Pamphlet of International Publication No. 94/18959

[Patent Document 2] Pamphlet of International Publication No. 2005/115975

[Patent Document 3] Pamphlet of International Publication No. 2006/123725

[Patent Document 4] Pamphlet of International Publication No. 03/101964

[Patent Document 5] Pamphlet of International Publication No. 2006/004195

DISCLOSURE OF THE INVENTION

Problem that the Invention is to Solve

It is an object of the present invention to provide a medicine having a novel CaSR regulatory action, particularly a novel compound that is useful as a therapeutic agent for hyperparathyroidism.

Means For Solving The Problem

Since the already existing CaSR regulators are not satisfactory in terms of either efficacy or safety, great concern has been directed toward the provision of a CaSR regulator having superior efficacy and safety. Under such a situation, we have carried out intensive studies with the aim of developing a CaSR regulator having superior efficacy and safety. As a result, it was found that a novel piperidine derivative having a substituted aminomethyl group on one position and an aryl or heteroaryl group on the other position, and the like, can show a strong CaSR agonistic regulatory action. In addition, it was also found that such the novel piperidine derivative had high selectivity against CYP2D6 inhibitory activity having a possibility of causing drug interaction, thus completing the present invention.

That is, the present invention relates to a piperidine derivative represented by the general formula (I) or a pharmaceutically acceptable salt thereof

[Chem. 6]

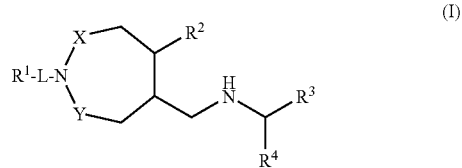

(I)

[wherein the signs have the following meanings:

X and Y: any one being —CH$_2$—, and the other being a single bond.

L: a single bond, *—C(O)—, *—OC(O)—, or *—N(R$^0$)C(O)—, wherein * represents the bonding to R$^1$.

R$^0$: —H or lower alkyl.

R$^1$: —H, or C$_{1-12}$ alkyl, lower alkenyl, cycloalkyl, cycloalkenyl, aryl or a hetero ring group, each of which may be substituted.

R$^2$: C$_{1-12}$ alkyl, lower alkenyl, cycloalkyl, cycloalkenyl, or aryl or heteroaryl, each of which may be substituted.

R$^3$: aryl or heteroaryl which may be respectively substituted.

R$^4$: lower alkyl

The same shall apply hereinafter.]

In addition, the present invention also relates to a pharmaceutical composition which comprises the aforementioned piperidine derivative or a pharmaceutically acceptable salt thereof (which may be hereinafter referred to "a compound described in the formula (I) or a pharmaceutically acceptable salt thereof", "a compound (1)", or the like"), and a pharmaceutically acceptable carrier, particularly a pharmaceutical composition which is a calcium sensing receptor regulating agent, a therapeutic agent for hyperparathyroidism, a therapeutic agent for renal osteodystrophy, or a therapeutic agent for hypercalcemia.

That is, the present invention relates to:

(1) a pharmaceutical composition which comprises the compound as described in the formula (I) or a pharmaceutically acceptable salt thereof and a pharmaceutically acceptable carrier;

(2) the pharmaceutical composition as described in (1), which is a calcium sensing receptor regulating agent;

(3) the pharmaceutical composition as described in (1), which is a therapeutic agent for hyperparathyroidism;

(4) the pharmaceutical composition as described in (1), which is a therapeutic agent for renal osteodystrophy, (5) the pharmaceutical composition described in (1), which is a therapeutic agent for hypercalcemia;

(6) a use of the compound as described in the formula (I) or a pharmaceutically acceptable salt thereof, for producing a calcium sensing receptor regulating agent, a therapeutic agent for hyperparathyroidism, a therapeutic agent for renal osteodystrophy, or a therapeutic agent for hypercalcemia; and (7) a method for treating hyperparathyroidism, renal osteodystrophy, or hypercalcemia, the method comprises administering a therapeutically effective amount of the compound described in the formula (I) or a salt thereof to a patient.

Effects of the Invention

The compound of the present invention is useful as a therapeutic agent for hyperparathyroidism, and the like, since it has a CaSR receptor regulating agent action.

Hereinafter, the present invention will be described in detail.

In the definition of the present specification, "alkyl", "alkenyl", "alkylene", and "alkenylene" mean straight or branched hydrocarbon chains unless otherwise specifically noted.

The "lower alkyl" is preferably alkyl having 1 to 6 carbon atoms (which is hereinafter abbreviated as C$_{1-6}$), specifically a methyl group, an ethyl group, an n-propyl group, an isopropyl group, an n-butyl group, an isobutyl group, a sec-butyl group, a tert-butyl group, an n-pentyl group, an n-hexyl group, or the like. More preferably, it is C$_{1-4}$ alkyl, particularly preferably methyl, ethyl, n-propyl, or isopropyl.

The "lower alkenyl" is preferably C$_{2-6}$ alkenyl, specifically a vinyl group, a propenyl group, a butenyl group, a pentenyl group, a 1-methylvinyl group, a 1-methyl-2-propenyl group, a 1,3-butadienyl group, a 1,3-pentadienyl group, or the like. More preferably, it is C$_{2-4}$ alkenyl, particularly preferably vinyl or propenyl.

The "lower alkylene" is preferably C$_{1-6}$ alkylene, specifically a methylene group, an ethylene group, a trimethylene group, a tetramethylene group, a pentamethylene group, a hexamethylene group, a propylene group, a methylmethylene group, an ethylethylene group, a 1,2-dimethylethylene group, a 1,1,2,2-tetramethylethylene group, or the like. More preferably, it is C$_{2-4}$ alkylene, particularly preferably methylene, ethylene, or trimethylene.

The "lower alkenylene" is preferably a C$_{2-6}$ alkenylene group, specifically, a vinylene group, an ethylidine group, a propenylene group, a butenylene group, a pentenylene group, a hexenylene group, a 1,3-butadienylene group, a 1,3-pentadienylene group, or the like. More preferably, it is C$_{2-4}$ alkenylene, particularly preferably, vinylene, ethylidine, or propenylene.

The "halogen" means F, Cl, Br, or I.

The "halogeno-lower alkyl" means C$_{1-6}$ alkyl substituted with one or more halogen, specifically, a fluoromethyl group, a difluoromethyl group, a trifluoromethyl group, a 2,2,2-trifluoroethyl group, a pentafluoroethyl group, a hexafluoropropyl group, or the like. Preferably, it is lower alkyl substituted with 1 to 5 halogen(s), more preferably, trifluoromethyl.

The "cycloalkyl" is a $C_{3-10}$ saturated hydrocarbon ring group, which may have a bridge. Specifically, it is a cyclopropyl group, a cyclobutyl group, a cyclopentyl group, a cyclohexyl group, a cycloheptyl group, a cyclooctyl group, an adamantyl group, or the like. Preferably, it is $C_{3-8}$ cycloalkyl, more preferably $C_{3-6}$ cycloalkyl, particularly preferably, cyclopropyl, cyclobutyl, cyclopentyl, or cyclohexyl.

The "cycloalkenyl" is $C_{3-15}$ cycloalkenyl, which may have a bridge, and comprises a ring group condensed with a benzene ring at a double bond site.

Specifically, it is a cyclopentenyl group, a cyclopentadienyl group, a cyclohexenyl group, a cyclohexadienyl group, a 1-tetrahydronaphthyl group, a 1-indenyl group, a 9-fluorenyl group, a norbronenyl group, or the like. More preferably, it is $C_{5-10}$ cycloalkenyl, particularly preferably, cyclopentenyl and cyclohexenyl.

The "aryl" is a $C_{6-14}$ monocyclic to tricyclic aromatic hydrocarbon ring group, and includes a ring group condensed with $C_{5-8}$ cycloalkene at a double bond site. Specifically, it is a phenyl group, a naphthyl group, a 5-tetrahydronaphthyl group, a 4-indenyl group, a 1-fluorenyl group, or the like. More preferably, it is phenyl or naphthyl, and even more preferably, phenyl.

The "hetero ring" group means a ring group selected from i) a 3- to 8-membered (preferably 5- to 7-membered) monocyclic hereto ring, which contains 1 to 4 hetero atoms selected from O, S and N, and ii) a bicyclic 8- to 14-membered (preferably 9- to 11-membered) hereto ring containing 1 to 5 hetero atoms selected from O, S and N, and a tricyclic 11- to 20-membered (preferably 12- to 15-membered) hetero ring, which is formed by a condensation of the monocyclic hetero ring and one or two rings selected from a monocyclic hetero ring, benzene ring, $C_{5-8}$ cycloalkane, and $C_{5-8}$ cycloalkene. It may form an oxide or dioxide in which the ring atom S or N is oxidized.

The "hetero ring" group is preferably aziridinyl, azetidinyl, pyrrolidinyl, piperidinyl, piperazinyl, homopiperazinyl, oxiranyl, oxetanyl, tetrahydrofuranyl, tetrahydropyranyl, morpholinyl, homomorpholinyl, pyrrolyl, imidazolyl, triazolyl, tetrazolyl, pyridyl, pyrimidinyl, pyrazinyl, furyl, thienyl, oxazolyl, oxadiazolyl, thiazolyl, thiadiazolyl, indolyl, indolizinyl, benzimidazolyl, imidazo[1,2-a]pyridinyl, quinoxalinyl, quinolyl, isoquinolyl, quinazolyl, cinnolinyl, phthalazyl, benzofuranyl, benzothienyl, benzoxazolyl, benzothiazolyl, carbazolyl, or quinuclidinyl, more preferably, pyrrolidinyl, piperidinyl, piperazinyl, morpholinyl, pyrrolyl, tetrazolyl, pyridyl, pyrimidinyl, pyrazinyl, furyl, thienyl, oxazolyl, thiazolyl, indolyl, quinolyl, benzofuranyl, benzothienyl, benzooxazolyl, or benzothiazolyl, particularly preferably, pyrrolidinyl, piperidinyl, pyrrolyl, tetrazolyl, pyridyl, furyl, thienyl, triazolyl, or benzothienyl.

The "heteroaryl" is a hetero ring group which is aromatic, among the above-mentioned hetero ring groups, and examples thereof include pyrrolyl, imidazolyl, triazolyl, tetrazolyl, pyridyl, pyrimidinyl, pyrazinyl, furyl, thienyl, oxazolyl, oxadiazolyl, thiazolyl, thiadiazolyl, indolyl, indolizinyl, benzoimidazolyl, imidazo[1,2-a]pyridinyl, quinoxalinyl, quinolyl, isoquinolyl, quinazolyl, cinnolinyl, phthalazyl, benzofuranyl, benzothienyl, benzooxazolyl, benzothiazolyl, carbazolyl, and the like, preferably, pyrrolyl, tetrazolyl, pyridyl, pyrimidinyl, pyrazinyl, furyl, thienyl, oxazolyl, thiazolyl, indolyl, quinolyl, benzofuranyl, benzothienyl, benzooxazolyl, and benzothiazolyl, particularly preferably, pyrrolyl, tetrazolyl, pyridyl, furyl, thienyl, thiazoly, and benzothienyl.

The "may be substituted" means "not substituted" or "substituted with the same or different 1 to 5 substituent(s)". Further, if a plurality of substituents are contained, such the substituents may be the same as or different from each other.

The substituent in the "aryl" and the "hetero ring group" which may be respectively substituted regarding $R^1$ is preferably a group selected from the following group $G^1$, more preferably, a group selected from the group consisting of lower alkyl, halogen, halogeno-lower alkyl, —$OR^0$, —$CO_2R^0$, and a hetero ring group, even more preferably, a group selected from the group consisting of lower alkyl, halogen, halogeno-lower alkyl, —O-lower alkyl, —$CO_2H$ and tetrazole.

Group $G^1$: halogen, nitro, lower alkyl, halogeno-lower alkyl, —$OR^0$, —$CO_2R^0$, —$C(O)N(R^0)_2$, —$C(O)N(R^0)S(O)_2$- lower alkyl, —$C(O)N(R^0)S(O)_2$-lower alkylene-$OR^0$, —$N(R^0)_2$, —$NR^0$—$C(O)R^0$, aryl, a hetero ring group, oxo, lower alkylene-$CO_2R^0$, lower alkenylene-$CO_2R^0$, lower alkylene-aryl, lower alkylene-hetero ring group, —O-lower alkylene-$CO_2R^0$, —$N(R^0)$-lower alkylene-$CO_2R^0$, and —$S(O)_n$-lower alkylene-$CO_2R^0$. (n means 0, 1, or 2. The same shall apply hereinafter.)

Here, the aryl and the hetero ring group in the group $G^1$ may be respectively substituted with a group selected from the following group P.

Group P: halogen, lower alkyl, halogeno-lower alkyl, —$OR^0$, —O-halogeno-lower alkyl, oxo, and —$CO_2R^0$.

The substituent in the "cycloalkyl" and the "cycloalkenyl", which may be substituted, regarding $R^1$ is preferably a group selected from the following group $G^2$.

Group $G^2$: halogen, lower alkyl, hetero ring group, —$OR^0$, and —$CO_2R^0$.

The substituent in the "$C_{1-2}$ alkyl" and "lower alkenyl", which may be substituted, regarding $R^1$ is preferably a group selected from the following group $G^3$, more preferably, —$CO_2R^0$, or the aryl or hetero ring group, each of which may be substituted with a group selected from the group consisting of halogen, —$OR^0$, —$CO_2R^0$, and a hetero ring group.

Group $G^3$: halogen, —$OR^0$, —O-aryl, —O-hetero ring group, —$N(R^0)_2$, —$N(R^0)$-aryl, —$N(R^0)$-hetero ring group, —$N(R^0)C(O)R^0$, —O-lower alkylene-$CO_2R^0$, —$N(R^0)$-lower alkylene-$CO_2R^0$, —$S(O)_n$-lower alkylene-$CO_2R^0$, —$CO_2R^0$, —$C(O)N(R^0)_2$, —$C(O)N(R^0)$— aryl, —$C(O)N(R^0)$-hetero ring group, —$C(O)$-aryl, —$C(O)$-hetero ring group, cycloalkyl, aryl, and a hetero ring group.

Here, the cycloalkyl in the group $G^3$ may be substituted with a group selected from the group $G^2$, and the aryl and hetero ring group may be substituted with a group selected from the group $G^1$.

The substituent in the "aryl" and the "heteroaryl" which may be respectively substituted regarding $R^2$ is preferably a group selected from the following group $G^4$, more preferably halogen, lower alkyl, or halogeno-lower alkyl, even more preferably halogen.

Group $G^4$: halogen, lower alkyl, halogeno-lower alkyl, —$OR^0$, and —O-halogeno-lower alkyl.

The substituent in the "aryl" and the "heteroaryl" which may be respectively substituted regarding $R^3$ is preferably a group selected from the group $G^4$, more preferably —O-lower alkyl.

A preferred embodiment of the present invention is described in the following.

(a) $R^1$ is preferably $C_{1-12}$ alkyl, cycloalkyl, aryl, or a hetero ring group which is respectively substituted with a group selected from the group consisting of —$CO_2H$ and tetrazole (wherein the $C_{1-12}$ alkyl, cycloalkyl, aryl, and hetero ring group may be further substituted); more preferably, lower alkyl, aryl, or heteroaryl which is respectively substituted with a group selected from the group consisting of —CO$_2$H and tetrazole (wherein the lower alkyl, aryl and heteroaryl may be further substituted); even more preferably, aryl or heteroaryl which is respectively substituted with a group selected from the group consisting of —CO$_2$H and tetrazole (wherein the aryl group and heteroaryl may be further substituted with a group selected from the group consisting of lower alkyl, halogen, halogeno-lower alkyl and —O-lower alkyl); and particularly preferably, phenyl or pyridyl, which is respectively substituted with a group selected from the group consisting of —CO$_2$H and tetrazole (wherein the phenyl and pyridyl may be further substituted with a group selected from the group consisting of lower alkyl, halogen, halogeno-lower alkyl, and —O-lower alkyl).

(b) L is preferably a single bond, —C(O)—, —OC(O)—, or —NHC(O)—, more preferably a single bond.

(c) R$^2$ is preferably phenyl which may be substituted, more preferably phenyl which may be substituted with halogen, lower alkyl, or halogeno-lower alkyl, even more preferably, phenyl which may be substituted with halogen.

(d) R$^3$ is preferably aryl or benzothienyl which may be respectively substituted, more preferably, aryl which may be substituted with —O-lower alkyl or benzothienyl, even more preferably, naphthyl which may be substituted with —O-lower alkyl or benzothiazole.

(e) R$^4$ is preferably methyl.

(f) for X and Y, preferably, X is a single bond, and Y is —CH$_2$—.

Furthermore, a compound consisting of a combination of the aforementioned preferred groups of (a) through (f) is more preferred.

In addition, other preferred embodiments of the compound of the present invention represented by the general formula (I) are shown below.

(1) The compound described in the formula (I) or a salt thereof, wherein R$^4$ is methyl.

(2) The compound as described in (1) or a salt thereof, wherein X is a single bond, and Y is —CH$_2$—.

(3) The compound as described in (2) or a salt thereof, wherein R$^3$ is aryl which may be substituted with —O-lower alkyl, or benzothienyl.

(4) The compound as described in (3) or a salt thereof, wherein R$^2$ is phenyl which may be substituted with a group selected from the group consisting of halogen, lower alkyl, and halogeno-lower alkyl.

(5) The compound as described in (4) or a salt thereof, wherein L is a single bond.

(6) The compound as described in (5) or a salt thereof, wherein R$^1$ is aryl or heteroaryl which is respectively substituted with a group selected from the group consisting of —CO$_2$H and tetrazole (wherein the aryl and heteroaryl may be respectively further substituted with a group selected from lower alkyl, halogen, halogeno-lower alkyl, and —O-lower alkyl).

(7) A compound described in the formula (I), which is selected from the group consisting of:

3-[3-(2-fluorophenyl)-4-({[(1R)-1-(1-naphthyl)ethyl]amino}methyl)piperidin-1-yl]benzoic acid, 5-chloro-6-[4-({[(1R)-1-(3-methoxyphenyl)ethyl]amino}methyl)-3-phenylpiperidin-1-yl]nicotinic acid, 6-[4-({[(1R)-1-(1-naphthyl)ethyl]amino}methyl)-3-phenylpiperidin-1-yl]pyridine-2-carboxylic acid, 6-[4-({[(1R)-1-(1-naphthyl)ethyl]amino}methyl)-3-phenylpiperidin-1-yl]-4-(trifluoromethyl)nicotinic acid, 6-[3-(3-fluorophenyl)-4-({[(1R)-1-(1-naphthyl)ethyl]amino}methyl)piperidin-1-yl]-4-(trifluoromethyl)nicotinic acid, 6-[3-(2-fluorophenyl)-4-({[(1R)-1-(1-naphthyl)ethyl]amino}methyl)piperidin-1-yl]nicotinic acid, 3-[3-(3-fluorophenyl)-4-({[(1R)-1-(1-naphthyl)ethyl]amino}methyl)piperidin-1-yl]benzoic acid, 2-[4-({[(1R)-1-(1-naphthyl)ethyl]amino}methyl)-3-phenylpiperidin-1-yl]-1,3-thiazole-4-carboxylic acid, 4-chloro-6-[4-({[(1R)-1-(1-naphthyl)ethyl]amino}methyl)-3-phenylpiperidin-1-yl]nicotinic acid, 6-[3-(3-fluorophenyl)-4-({[(1R)-1-(1-naphthyl)ethyl]amino}methyl)piperidin-1-yl]pyridine-2-carboxylic acid, 6-[3-(2-fluorophenyl)-4-({[(1R)-1-(1-naphthyl)ethyl]amino}methyl)piperidin-1-yl]pyridine-2-carboxylic acid, and 5-chloro-6-[3-(2-fluorophenyl)-4-({[(1R)-1-(1-naphthyl)ethyl]amino}methyl)piperidin-1-yl]nicotinic acid, or a pharmaceutically acceptable salt thereof.

The compounds of the present invention may exist in other geometrical isomer or tautomer forms depending on the kind of substituents. In the present specification, there may be description on only one form of the isomers, but the isomers, as well as the separated counterparts of these isomers or mixtures thereof are included in the present invention.

Also, since the compound (1) may have an asymmetric carbon and axial asymmetry, the (R) and (S) optical isomers based on this may be present. The present invention includes both of the mixtures and the separated counterparts of all of these optical isomers.

In addition, a pharmaceutically acceptable prodrug of the compound (1) is also included in the present invention. The pharmaceutically acceptable prodrug is a compound having a group which may be converted into an amino group, OH, CO$_2$H, or the like by solvolysis or under a physiological condition. Examples of the group capable of forming a prodrug include those which are described in "Prog. Med., vol. 5, p. 2157-2161 (1985), and "Tyakuhin no Kaihatsu (Development of Medicines) (Hirokawa Shoten, 1990), vol. 7, Bunshi Sekkei (Molecular Design), p. 163-198.

Furthermore, the compounds of the present invention may form acid addition salts or salts with bases sometimes depending on the kind of substituents, and such the salts that are pharmaceutically acceptable are included the present invention. Specific examples thereof include acid addition salts with inorganic acids such as hydrochloric acid, hydrobromic acid, hydroiodic acid, sulfuric acid, nitric acid, phosphoric acid, and the like, and with organic acids, such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, and the like, salts with inorganic bases, such as sodium, potassium, magnesium, calcium, aluminum, and the like, and the organic bases, such as methylamine, ethylamine, ethanolamine, lysine, ornithine and the like, ammonium salts, and the like.

In addition, the present invention also includes various hydrates and solvates of the compound of the present invention and a pharmaceutically acceptable salt thereof and their polymorphic substances. Also, the present invention includes the compounds labeled with various radioactive or non-radioactive isotopes.

(Production Process)

The compound of the present invention and a pharmaceutically acceptable salt thereof may be produced by applying various known synthetic methods making use of their basic skeletons or their characteristics based on the kind of substituents. In that case, depending on the kind of functional group, it is sometimes effective in view of production techniques to replace the functional group with an appropriate protecting group (a group which may be easily converted into the aforementioned functional group), during the steps of from starting materials to intermediates. Examples of such a functional group include an amino group, a hydroxyl group, a carboxyl group, and the like, and as their protecting groups, the protecting groups described for example in "Protective Groups in Organic Synthesis", edited by Greene and Wuts (3rd edition, 1999) may be exemplified, which may be optionally selected and used in response to the reaction conditions. By such a method, the desired compound may be obtained by introducing the aforementioned protecting group to carry out the reaction, and then removing the protecting group as occasion demands.

In addition, a prodrug of the compound (1) may be produced by introducing a specified group during the steps of from starting materials to intermediates, similar to the aforementioned protecting groups, or by carrying out the reaction using the obtained compounds (1) of the present invention. The reaction may be carried out by employing methods conventionally known by those skilled in the art, such as common esterification, amidation, dehydration, and the like.

Hereinbelow, typical production processes of the compounds of the present invention will be explained. Each of the production processes may be carried out with reference to references distributed in the description herein. In addition, the production processes of the present invention are not limited to these examples.

First Production Process: Reductive Amination 1

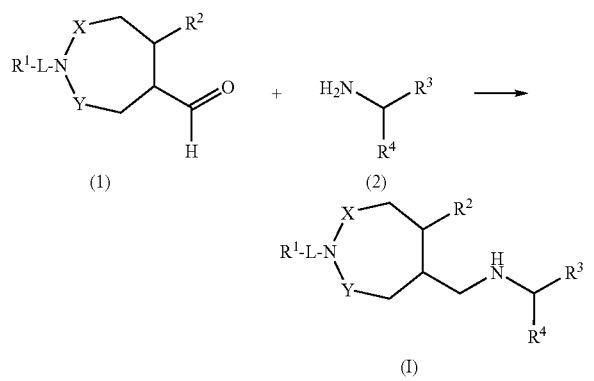

This production process is a process for obtaining the compound (I) of the present invention by reacting a compound (1) and a compound (2).

The reaction is carried out in a solvent inert to the reaction using the compound (1) and the compound (2) in an equal amount of the two, or in such a ratio that any one of the two is excessive, with stirring in the presence of a reducing agent, at −45° C. to under heating under reflux, preferably at 0° C. to room temperature, usually for 0.1 hours to 5 days. Here, the solvent is not particularly limited, but examples thereof include alcohols such as methanol, ethanol, and the like, ethers such as diethylether, tetrahydrofuran (THF), dioxane, dimethoxyethane, and the like, or a mixture thereof. Examples of the reducing agent include sodium cyanoborohydride, sodium triacetoxyborohydride, sodium borohydride, or a reducing agent-carrying polystryrene resin, for example, MP-triacetoxyborohydride (Argonaut Technologies, USA), and the like. It is desirable in some cases to carry out the reaction in the presence of a dehydrating agent such as molecular sieves, and the like, or an acid such as acetic acid, hydrochloric acid, titanium (IV) isopropoxide complex, and the like. Depending on the reaction, in a case where an imine compound formed as an intermediate in the reaction system may be stably isolated, a reducing reaction may be separately carried out after obtaining the aforementioned imine compound. Further, instead of the treatment with the reducing agent, the reaction may be carried out in a solvent such as methanol, ethanol, and ethyl acetate, in the presence or absence of an acid such as acetic acid, hydrochloric acid, and the like, a reducing catalyst (for example, palladium on carbon, Raney nickel, and the like). In this case, it is preferable that the reaction is carried out under a hydrogen atmosphere from normal pressure to 50 atm, from 0° C. to under heating. Also, an isocyanate-carrying polystyrene resin, such as PS-Isocyanate (Argonaut Technologies, Inc., USA), and the like may be used, in order to remove an excessive amount of amine after completion of the reaction.

Second Production Process: Hydrolysis

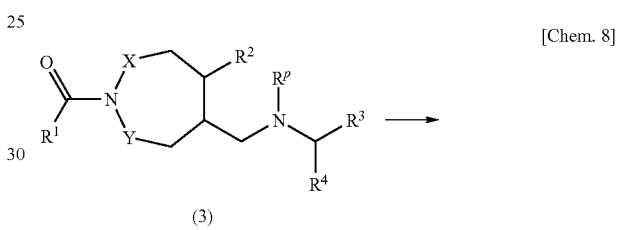

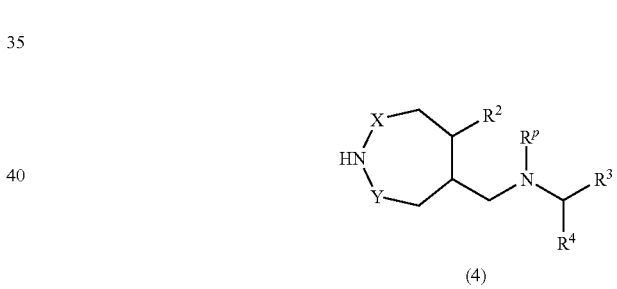

($R^p$ Means —H or a Protecting Group (Preferably a Tert-Butoxycarbonyl (Boc) group). The same shall apply hereinafter.)

This production process is a process for obtaining a compound (4) by hydrolyzing a compound (3).

The hydrolysis reaction can be carried out in accordance with the process as described, for example, in the aforementioned "Protective Groups in Organic Synthesis".

Third Production Process: Reductive Amination 2

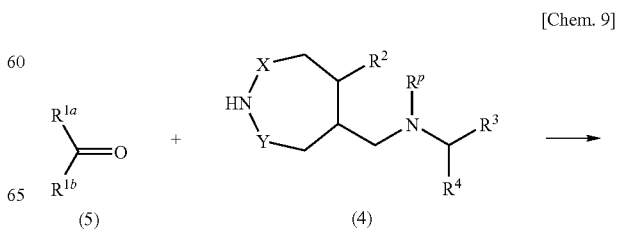

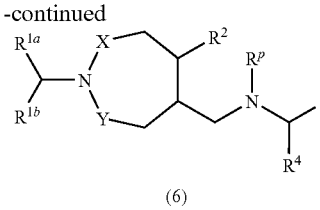

(6)

(wherein $R^{1a}$ and $R^{1b}$ represent a residue of $R^1$. The same shall apply hereinafter.)

This production process is a process for obtaining a compound (6) by reacting a compound (5) and a compound (4).

The reaction can be carried out in the same manner as in the first production process.

Fourth production process: Nucleophilic substitution reaction

[Chem. 10]

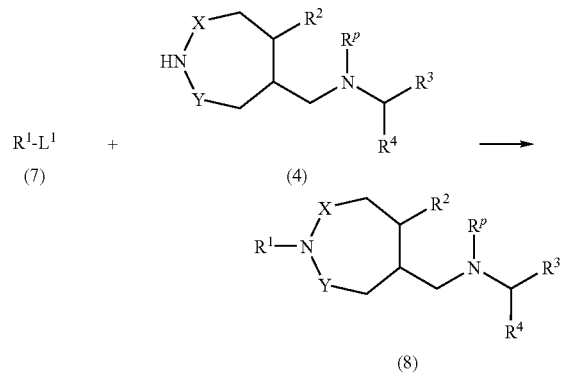

(wherein $L^1$ represents a leaving group. The same shall apply hereinafter.)

This production process is a process for obtaining a compound (8) by reacting a compound (7) with the compound (4). Here, examples of the leaving group for $L^1$ include halogen, methanesulfonyloxy, p-toluenesulfonyloxy, and the like.

The reaction is carried out in a solvent inert to the reaction or without a solvent using the compound (7) and the compound (4) in an equal amount of the two, or in such a ratio that any one of the two is excessive, with stirring under cooling to heating under reflux, preferably, at 0° C. to 80° C., usually for 0.1 hours to 5 days. Here, the solvent is not particularly limited, but examples thereof include aromatic hydrocarbons such as benzene, toluene, xylene, and the like, ethers such as diethylether, tetrahydrofuran, dioxane, dimethoxyethane, and the like, halogenated hydrocarbons such as dichloromethane, 1,2-dichloroethane, chloroform, and the like, N,N-dimethylformamide (DMF), dimethylsulfoxide (DMSO), ethyl acetate, acetonitrile, or a mixture thereof. It is advantageous in some cases in advancing the reaction smoothly to carry out the reaction in the presence of organic bases such as triethylamine, N,N-diisopropylethylamine, N-methylmorpholine, and the like, an inorganic bases such as potassium carbonate, sodium carbonate or potassium hydroxide, and the like.

Fifth Production Process: Amidation

[Chem.11]

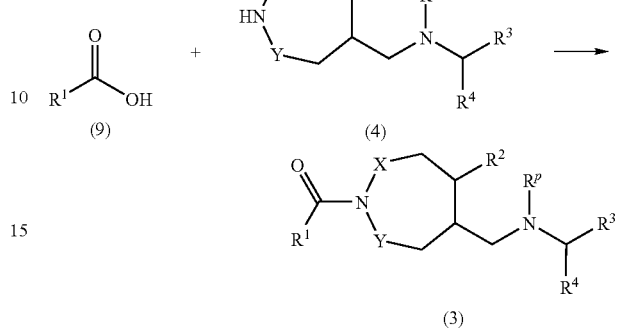

This production process is a process for obtaining the compound (3) by reacting a compound (9) with the compound (4).

The reaction is carried out in a solvent inert to the reaction using the compound (9) and the compound (4) in an equal amount of the two, or in such a ratio that any one of the two is excessive in the presence of a condensing agent, with stirring under cooling to heating, preferably at −20° C. to 60° C., usually for 0.1 hours to 5 days. Here, the solvent is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethylether, tetrahydrofuran, dioxane, dimethoxyethane, and the like, N,N-dimethylformamide, dimethylsulfoxide, ethyl acetate, acetonitrile or water, or a mixture thereof. Examples of the condensing agent include 1-(3-dimethylaminopropyl)-3-ethylcarbodiimide (WSC), dicyclohexylcarbodiimide, 1,1'-carbonyldiimidazole (CDI), diphenylphosphoryl azide (DPPA), phosphorus oxychloride, and the like, but not limited thereto. Alternatively, a condensing agent-carrying polystryrene resin, for example, PS-carbodiimide (Argonaut Technologies, USA), a PL-DCC resin (Polymer Laboratories, UK) may be used. It is desirable in some cases to use an additive (for example, 1-hydroxybenzotriazole (HOBt), N-hydroxysuccinimide (HONSu), and the like for the reaction. It is advantageous in some cases in advancing the reaction smoothly to carry out the reaction in the presence of organic bases such as triethylamine, N,N-diisopropylethylamine, or N-methylmorpholine, and the like, or an inorganic bases such as potassium carbonate, sodium carbonate or potassium hydroxide, and the like. Also, an isocyanate-carrying polystyrene resin, such as PS-Isocyanate (Argonaut Technologies, Inc., USA), and the like may be used, in order to remove an excessive amount of amine after completion of the reaction.

In addition, a process in which the carboxylic acid (9) is brought to a reactive derivative and then allowed to undergo reaction with the amine compound (4) can also be used. Here, examples of the reactive derivative of the carboxylic acid include acid halides obtained by the reaction with a halogenation agent such as phosphorus oxychloride, thionyl chloride, and the like, a mixed acid anhydride obtained by the reaction with isobutyl chloroformate, an active ester obtained by condensation with HOBt, and the like. The reaction of these reactive derivatives with the compound (4) can be carried out in a solvent inert to the reaction such as halogenated hydrocarbons, aromatic hydrocarbons, ethers, and the like, under cooling to heating, preferably, at −20° C. to 60° C.

Sixth Production Process: Carbamation

[Chem.12]

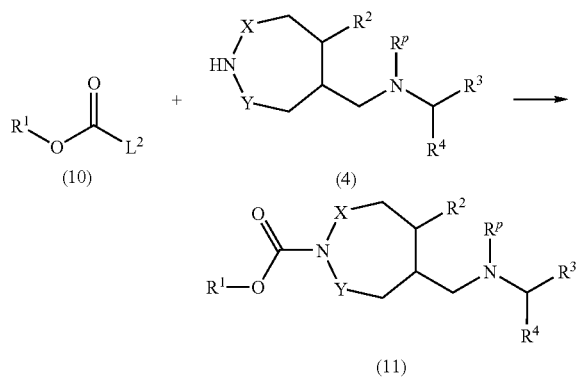

(wherein L² means a residue of a carbamation agent. The same shall apply hereinafter.)

This production process is a process for obtaining a compound (11) by reacting a compound (10) with the compound (4).

For the reaction, the carbamation condition, for example, as described in "Jikken Kagaku Koza (Experimental Chemistry Course) (4th edition)", vol. 20, (1992), p. 355-365 (Maruzen), edited by The Chemical Society of Japan, or the aforementioned "Protective Groups in Organic Synthesis" may be employed. The reaction can be carried out in a solvent inert to the reaction using the amine compound (4) and the carbamation agent (10) in an equal amount of the two, or in such a ratio that any one of the two is excessive such as aromatic hydrocarbons such as benzene, toluene, xylene, and the like, esters such as ethyl acetate, ethers such as diethylether, tetrahydrofuran, dioxane, dimethoxyethane, and the like, halogenated hydrocarbons such as dichloromethane, 1,2-dichloroethane, chloroform, and the like, alcohols, ketones such as acetone, methylethyl ketone, and the like, DMF, N,N-dimethylacetamide (DMA), N-methylpyrrolidone (NMP), DMSO, acetonitrile, pyridine, water, and the like, under cooling to heating under reflux. Examples of the carbamation agent (10) include acid halide (chloroformate, and the like), acid anhydrides (a mixed acid anhydride obtained by the reaction with ethyl chlorocarbonate, chlorobenzyl carbonate, chlorophenyl carbonate, p-toluenesulfonic acid, isovaleric acid, and the like, or a symmetric acid anhydride), an active ester (an ester which may be prepared using phenol which may be substituted with electron withdrawing group (for example, a nitro group, a fluorine atom, and the like), CDI, HONSu or the like), and the like. The reactive derivatives can be produced in the standard method. Depending on the compound, it is advantageous in some cases in advancing the reaction smoothly to carry out the reaction in the presence of an organic base (triethylamine, diisopropylethylamine, N-methylmorpholine, pyridine, 4-(N,N-dimethylamino)pyridine, or the like is suitably used) or a metal salt base (potassium carbonate, cesium carbonate, sodium hydroxide, potassium hydroxide, sodium hydride, potassium tert-butoxide, or the like is suitably used). The preparation of the carbamation agent using p-nitrophenol or CDI, and the carbamation may be carried out, for example, in accordance with the method of Vatele et al. ("Tetrahedron", 2004, vol. 60, p. 4251-4260) or the like. Also, preparation of the carbamation agent using HONSu for example and the carbamation may be carried out in accordance with the method of Ghosh et al. ("Tetrahedron Letters", 1992, vol. 33, p. 2781-2784) or the like.

Seventh Production Process: Ureation

[Chem.13]

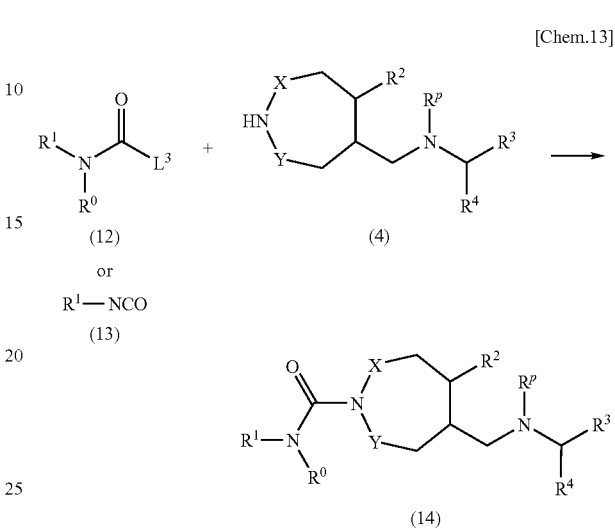

(wherein L³ means a residue of an ureation agent. The same shall apply hereinafter.)

This production process is a process for obtaining a compound (14) by reacting the compound (4) with a compound (12) or a compound (13).

For the reaction, for example, the method described in "Jikken Kagaku Koza (Experimental Chemistry Course) (4th edition)", vol. 20, (1992) (Maruzen), p. 355-365, edited by The Chemical Society of Japan, or the like may be employed. The reaction can be carried out using the amine compound (4) and the ureation agent (12) or (13) in an equal amount of the two, or in such a ratio that any one of the two is excessive, in a solvent inert to the reaction, such as aromatic hydrocarbons such as benzene, toluene, xylene, and the like, esters such as ethyl acetate, and the like, ethers such as diethylether, tetrahydrofuran, dioxane, dimethoxyethane, and the like, halogenated hydrocarbons such as dichloromethane, 1,2-dichloroethane, chloroform, and the like, alcohols such as methanol, ethanol, and the like, ketones such as acetone, methylethyl ketone, and the like, DMF, DMA, NMP, DMSO, acetonitrile, pyridine, water, or the like, under cooling to heating under reflux. Depending on the compound, it is advantageous in some cases in advancing the reaction smoothly to carry out the reaction in the presence of an organic base (triethylamine, diisopropylethylamine, N-methylmorpholine, pyridine, 4-(N,N-dimethylamino)pyridine, or the like is suitably used) or a metal salt base (potassium carbonate, cesium carbonate, sodium hydroxide, potassium hydroxide, sodium hydride, potassium tert-butoxide, or the like is suitably used).

Examples of the ureation agent (12) include an acid halide (for example, chloroformate or the like), an acid anhydride (for example, a mixed acid anhydride obtained by the reaction with ethyl chlorocarbonate, benzyl chlorocarbonate, phenyl chlorocarbonate, p-toluenesulfonic acid, isovaleric acid or the like, or a symmetric acid anhydride), an active ester (an ester which may be prepared using phenol which may be substituted with electron withdrawing group (for example, nitro group, fluorine atom or the like), CDI, HONSu or the like), an acid azide and the like. These ureation agents may be produced in the standard method. For example, the preparation of the ureation agent using p-nitrophenol and the ureation may be carried out in accordance with the method of Tor et al. ("Tetrahedron Letters", 2001, vol. 42, p. 1445-1447) or the like.

For example, the preparation of the ureation agent using CDI may be carried out in accordance with the method of Batey et al. ("Tetrahedron Letters", 1998, vol. 39, p. 6267-6270), the method of Koga et al. ("Bioorganic & Medicinal Chemistry Letters", 1998, vol. 8, p. 1471-1476) and the like. For example, the preparation of the ureation agent using HONSu and the ureation may be carried out in accordance with the method of Ogura et al. ("Tetrahedron Letters", 1983, vol. 24, p. 4569-4572) or the like. For example, the preparation of the ureation agent using acid azide and the ureation may be carried out in accordance with the method of Carceller et al. ("Journal of Medicinal Chemistry", 1996, vol. 39, p. 487-493), the method of Ryng et al. ("Pharmazie", 1999, vol. 54, p. 359-361) and the like.

Eighth Production Process: Palladium Coupling

[Chem. 14]

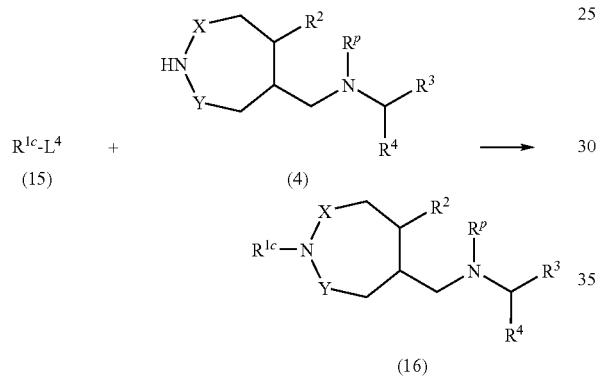

(wherein $R^{1c}$ means aryl or heteroaryl which may be respectively substituted, and $L^4$ means a leaving group. The same shall apply hereinafter.)

This production process is a process for obtaining a compound (16) by reacting a compound (15) with the compound (4). Here, examples of the leaving group in $L^4$ include halogen, a trifluoromethanesulfonyloxy group, and the like.

The reaction can be carried out using the amine compound (4) and the compound (15) in an equal amount of the two, or in such a ratio that any one of the two is excessive, in a solvent inert to the reaction, such as aromatic hydrocarbons such as benzene, toluene, xylene, and the like, ethers such as diethylether, tetrahydrofuran, dioxane, dimethoxyethane, and the like, alcohols such as methanol, ethanol, tert-butyl alcohol, and the like, DMF, DMA, NMP, or the like, from at room temperature to heating under reflux, in the presence of a palladium catalyst and a base. As the palladium catalyst, palladium complexes such as bis(tri-tert-butyl phosphine) palladium(0), tris(dibenzylideneacetone)palladium(0), acetic acidpalladium, and the like, or palladium catalyst prepared using phosphine ligands such as tri-O-toluoylphosphine, 2,2'-bis(diphenylphosphino)-1,1'-binaphthyl, 2-dicyclohexylphosphino-2'-(N,N-dimethylamino)biphenyl, and the like, are suitably used. Examples of the base include sodium carbonate, potassium carbonate, cesium carbonate, potassium tert-butoxide, and sodium tert-butoxide. Potassium phosphate is suitably used.

Furthermore, in a case where $R^P$ is a protecting group in the aforementioned second to eighth production processes, the deprotection of the protecting group can be carried out by using a method known to a person skilled in the art, for example, according to the method described in "Protective Groups in Organic Synthesis".

Ninth Production Process, and Other Production Processes

The compound of the present invention having various functional groups, such as a carboxylic group, an amide group, a hydroxyl group, an alkylamino group, and the like can be prepared by using the compound of the present invention having the corresponding ester group, carboxylic group, amino group, and the like as a starting material, for example, by using methods apparent to a person skilled in the art, well-known methods, or modified methods thereof.

(Starting Material Synthesis)

The starting compound that is used for the preparation of the compound (1) of the present invention can be produced, for example, by the following method, well-known methods, or modified methods thereof (Starting Material Synthesis 1)

[Chem. 15]

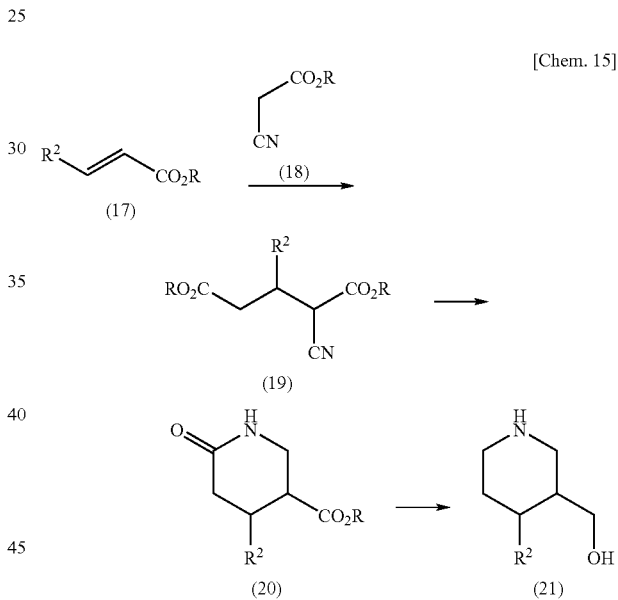

(wherein R means lower alkyl. The same shall apply hereinafter.)

A compound (17) and a compound (18) can be subjected to Michael addition to obtain a compound (19). The Michael addition reaction can be carried out, for example, in the presence of a base such as sodium hydride, and the like.

A cyano group of the compound (19) can be reduced, and intramolecularly cyclized to obtain a compound (20). The reduction of the cyano group can be carried out, for example, by using sodium borohydride as a reducing agent in the presence of cobalt chloride.

An ester group and an amide group of the compound (20) can be reduced to obtain a compound (21). The reduction of the ester group and the amide group can be carried out, for example, by using lithium aluminum hydride as a reducing agent.

19
(Starting Material Synthesis 2)

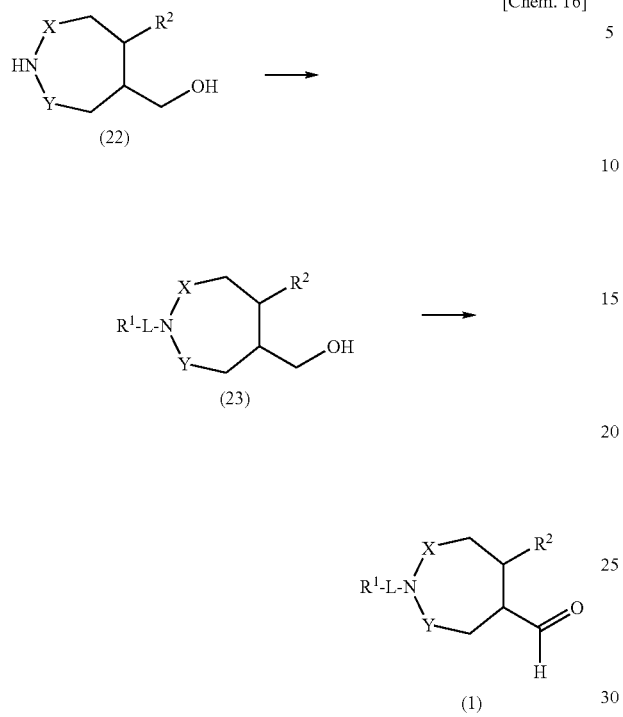

The compound (22) can be subjected to reductive amination, a nucleophilic substitution reaction, amidation, carbamation, or ureation to obtain a compound (23). The nucleophilic substitution reaction, amidation, carbamation, and ureation can be respectively carried out in the same manner as in the third to seventh production processes.

The compound (23) can be oxidized to obtain an aldehyde compound (1). For the oxidation reaction, for example, Swern oxdiation or Dess-Martin oxidation can be employed.

(Starting Material Synthesis 3)

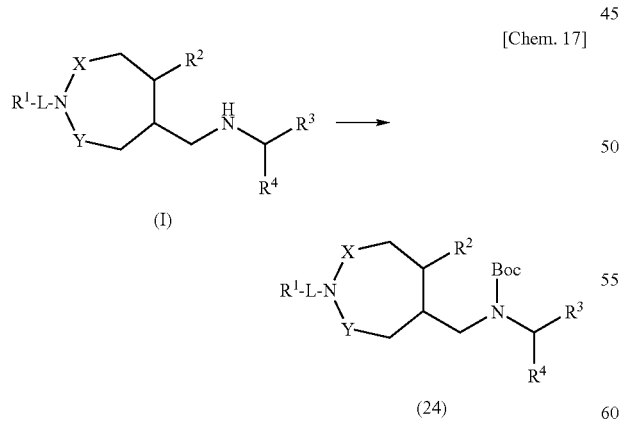

The compound (1) can be subjected to Boc-addition to obtain a compound (24).

The Boc-addition can be carried out, for example, by the method as described in the aforementioned "Protective Groups in Organic Synthesis".

20
(Starting Material Synthesis 4)

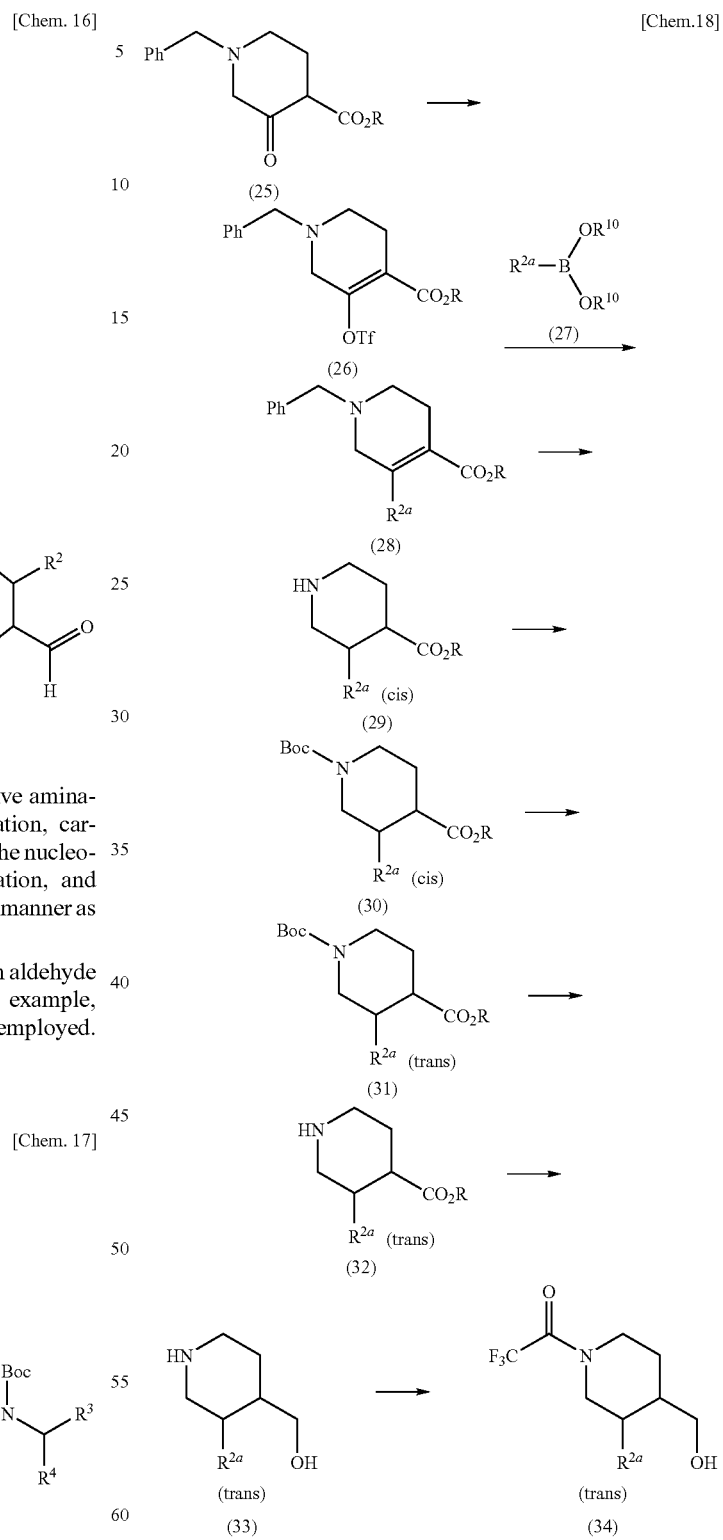

(wherein $R^{2a}$ means aryl or heteroaryl, Tf means a trifluoromethanesulfonyl group, and $R^{10}$ means —H or lower alkyl, may be the same as or different from each other, or two of $R^{10}$ may be combined to form lower alkylene. The same shall apply hereinafter.)

The compound (25) can be trifluoromethylsulfonylated to obtain a compound (26). The reaction can be carried out, for example, by using trifluoromethylsulfonic anhydride as a trifluoromethylsulfonylating agent in the presence of a base such as sodium hydride, and the like.

The compound (26) and the compound (27) can be coupled to obtain a compound (28). The coupling reaction can be carried out in the presence of a base and a palladium catalyst. As the base, preferred is an inorganic base such as sodium carbonate, potassium carbonate, sodium hydroxide, and the like. Also, as the palladium catalyst, preferred tetrakis(triphenylphosphine)palladium, dichlorobis(triphenylphosphine)palladium, 1,1'-bis(biphenylphosphino)ferrocene palladium chloride, and the like.

The compound (28) can be hydrogenated to obtain a compound (29). The reaction can be carried out, for example, under a hydrogen atmosphere in the presence of a catalyst such as palladium on carbon, platinum oxide, Raney nickel, and the like.

The compound (29) can be subjected to Boc-addition to obtain a compound (30). The Boc-addition can be carried out, for example, by the method as described in the aforementioned "Protective Groups in Organic Synthesis".

The compound (30) can be isomerized to obtain a compound (31). The reaction can be carried out, for example, by using sodium ethoxide as a base.

The compound (31) can be subjected to Boc-elimination to obtain a compound (32). The Boc-elimination can be carried out, for example, by the method as described in the aforementioned "Protective Groups in Organic Synthesis".

The compound (32) can be reduced to obtain a compound (33). The reaction can be carried out, for example, by using lithium aluminum hydride as a reducing agent.

The compound (33) can be trifluoroacetylated to obtain a compound (34). The reaction can be carried out, for example, in the same manner as in the amidation of the fifth production process.

The compound of the present invention is isolated and purified as its free compound, a pharmaceutically acceptable salt, a hydrate, and a solvate thereof, or a polymorphic crystal substance. The pharmaceutically acceptable salt of the compound (I) of the present invention can be produced after carrying out a conventional salt formation treatment.

The isolation and purification can be carried out by employing common chemical operations such as extraction, fractional crystallization, and various types of fractional chromatography.

Various isomers can be isolated by selecting a suitable starting compound, or by making use of the difference in a physicochemical property between isomer. For example, the optical isomers can be derived into a stereochemically pure isomer by means of general optical resolution methods (for example, fractional crystallization for inducing diastereomeric salts with optically active bases or acids, and a technique such as a chiral filler-aided column chromatography). In addition, the isomers can also be produced using an appropriate optically active starting compound.

The excellent CaSR agonistic regulatory action of the compound (1) of the present invention was confirmed by the following tests.

Test 1. Human calcium sensing receptor (CaSR) agonism test

1) Preparation of Human CaSR Expression Vector

A DNA fragment coding for human CaSR was cloned in the standard method.

Illustratively, using 203 to 2387 of NM_000388 as a DNA fragment D4, and 2210 to 3633 as a DNA fragment B2, they were amplified using a human kidney cDNA (manufactured by Invitrogen) as the template and using a DNA polymerase (a registered trade name: Pyrobest, manufactured by Takara Bio), and respectively cloned into a pCR2.1 vector using a pCR2.1-Topo vector (manufactured by Invitrogen). Next, the DNA fragments prepared by digesting the pCR2.1-D4 with SpeI and XbaI were inserted into the same sites of pcDNA3.1/Zeo(+) vector. Successively, the fragments prepared by digesting pCR2.1-B2 with SacI and XbaI were inserted into the SacI and XbaI sites of previously prepared pcDNA3.1/Zeo(+)-D4(SpeI-XbaI), thereby obtaining a human CaSR expression vector pcDNA3.1/Zeo(+)-hCaSR in which a human CaSR open reading frame (ORF) was contained in the pcDNA3.1/Zeo(+) vector.

2) Preparation of Human CaSR Expression Cell

The human CaSR expression vector was transferred into a HEK 293 cell using a transfection reagent (registered trademark: FuGene 6, manufactured by Roche Diagnostics). After the gene transfer, this was cultured in a DMEM (manufactured by Invitrogen) medium containing 40 µg/ml Zeocin (registered trademark, manufactured by Invitrogen) and a 10% fetal bovine serum at 37° C. for 2 weeks in the presence of 5% $CO_2$, thereby obtaining Zeocin-resistant clones. A human CaSR stably expressing HEK 293 clone was obtained from these clones by selection using the responsiveness to extracellular $Ca^{2+}$ as an index.

3) Human CaSR Agonism Test

The HEK 293 cell stably expressing human CaSR was inoculated into a poly-D-lysine-coated black clear bottom 96 well plate (manufactured by BD Biosciences). Hanks' balanced salt solution (HBSS) ($Ca^{2+}$ (−), $Mg^{2+}$ (−), manufactured by Invitrogen) containing a 20 mM HEPES (2-[4-(2-hydroxyethyl)-1-piperazinyl]ethanesulfonic acid) buffer (pH 7.4), 2.5 mM of probenecid (manufactured by Sigma), and 0.1% of bovine serum albumin was prepared as a washing buffer. After the inoculation and the subsequent overnight culturing, the medium was discarded, the washing buffer supplemented with 1 mM $CaCl_2$ and 10 µM Fluo-3 AM (trade name, manufactured by DOJINDO) was added thereto in 100 µl per well portions, and then the incubation was carried out at 37° C. for 1 hour in the presence of 5% $CO_2$. This was washed twice with 200 µl of the washing buffer, replaced by 100 µl of the washing buffer supplemented with 0.5 mM $CaCl_2$ and allowed to stand still for 10 minutes, and then the responsiveness to each compound to be evaluated was detected using a plate reader for fluorometry image analysis use (registered trademark: FLIPR, manufactured by Molecular Devices). In this connection, the compound to be evaluated was used by optionally diluting with the washing buffer supplemented with 0.5 mM $Ca^{2+}$.

The human CaSR agonistic activity strength of each compound to be evaluated was calculated by defining the solvent group as 0% and the 2 mM of $Ca^{2+}$ in the final concentration group as 100%, and the compound concentration showing 50% activity ($EC_{50}$) was calculated from a concentration-activity curve by the method of least squares.

As a result, it was revealed that the compounds of the present invention have a strong human CaSR agonistic activity. Activity strengths of the typical compounds of the present invention are shown in Table 1. Here, Ex represents Example No. as denoted below (the same shall apply hereinafter).

TABLE 1

| Ex | $EC_{50}$ (nM) |
|---|---|
| 3 | 1.8 |
| 13 | 2.9 |
| 25 | 13 |
| 30 | 5.5 |
| 31 | 5.0 |
| 32 | 7.5 |
| 33 | 20 |
| 34 | 8.1 |
| 35 | 7.6 |
| 39 | 2.6 |
| 52 | 13 |
| 53 | 3.8 |
| 87 | 11 |
| 98 | 17 |
| 104 | 14 |

Test 2. Measurement of Rat Plasma Calcium Concentration and Plasma PTH Concentration The compounds of the present invention were administered to rats, and their influences upon the plasma calcium concentration and the plasma PTH concentration were examined. The test was carried out by single oral administration of the compounds of the present invention and the control compounds to 5 to 6 normal male rats, or male rats with renal failure, respectively As a vehicle group, 0.5% of a methyl cellulose (MC) solution was administered at a dose of 5 ml/kg. As a reference compound, cinacalcet was dissolved in the MC solution and administered at a dose of 3 mg/kg. Each of the compounds of the present invention was dissolved or suspended in the MC solution, and administered at a dose of 1, 3 or 10 mg/kg.

Blood samples were collected from the orbital venous plexus under ether anesthesia before the administration and 2 hours, 4 hours, or 8 hours in some cases, after the administration, and the plasma calcium concentration was measured using Calcium E-Test Wako (manufactured by Wako Pure Chemical Industries), and the plasma PTH concentration was measured using a Rat Intact PTH ELISA Kit (manufactured by Immutopics).

As a result, it was able to be confirmed that the compounds of the present invention have an action to reduce the plasma calcium and plasma PTH levels by the in vivo test. The results of the typical compounds of the present invention in normal male rats are shown in Table 2.

TABLE 2

| Ex | Rat plasma calcium concentration reducing ratio (%) 2 hours after administration (3 mg/kg) |
|---|---|
| 25 | 17 |
| 31 | 24 |
| 32 | 34 |
| 33 | 29 |
| 35 | 33 |
| 39 | 23 |
| 52 | 26 |
| 53 | 20 |

Test 3. Human CYP2D6 Inhibition Test

Inhibitory activity evaluation for CYP2D6 was carried out by measuring it in accordance, roughly, with a reference ("Drug Metabolism and Disposition", 2001, vol. 29, p. 1196-1200).

Final concentrations of the reagents in the enzyme reaction solution were respectively set to CYP2D6=7.5 pmol/mL (manufactured by BD Gentest, Catalog No. 456217), reduced type nicotinamide adenine dinucleotide phosphate (NADPH) regeneration system (0.0081 mM nicotinamide adenine dinucleotide phosphate (NADP+), 0.41 mM glucose-6-phosphate, 0.41 mM $MgCl_2$, 0.4 units glucose-6-phosphate dehydrogenase), and a fluorescence substrate AMMC=1.5 μM, 100 mM potassium phosphate buffer (pH 7.4). Each compound was made into a 50% acetonitrile solution and added to the enzyme reaction solution (acetonitrile final concentration 2.5%). The enzyme reaction was carried out at 37° C. for 30 minutes, the reaction was stopped using a stopping liquid (0.1 M tris(hydroxymethyl)aminomethane (Tris-base):acetonitrile=20:80), and the fluorescence intensity was then measured. The concentration showing 50% inhibition ($IC_{50}$) was calculated from the thus obtained fluorescence intensity, by defining the enzyme activity at a time of no compound addition as 100%.

As a result, it was revealed that the compounds of the present invention have a weak human CYP2D6 inhibitory activity. The CYP2D6 inhibitory strengths of the typical compounds of the present invention are shown in Table 3.

TABLE 3

| Ex | $IC_{50}$ (μM) |
|---|---|
| 3 | ≧20 |
| 13 | ≧20 |
| 25 | ≧20 |
| 30 | ≧20 |
| 34 | ≧20 |
| 35 | ≧20 |
| 52 | ≧20 |
| 87 | ≧20 |
| 98 | ≧20 |

The results of each test as described above confirmed that the compound of the present invention has a CaSR antagonistic activity, and also has excellent selectivity against a CYP2D6 inhibitory action having a possibility of causing drug interaction. In this regard, it is apparent that the compound of the present invention is useful as a therapeutic agent for diseases in which CaSR is concerned, such as hyperparathyroidism, renal osteodystrophy, hypercalcemia, and the like.

The preparation containing one or two or more kinds of the compound (1) of the present invention or a salt thereof as an active ingredient can be prepared in accordance with a method that is generally employed, using a pharmaceutical carrier, excipient, and the like, generally used in the art.

The administration of the composition can be accompanied by any mode of oral administration via tablets, pills, capsules, granules, powders or liquid preparations; and parenteral administration via injections such as intraarticular, intravenous, or intramuscular injections, suppositories, eye drops, eye ointments, transdermal liquid preparations, ointments, transdermal patches, transmucosal liquid preparations, transmucosal patches, inhalations, and the like.

Regarding the solid composition of the present invention for oral administration, tablets, powders, granules, or the like are used. In such a solid composition, one or two or more kinds of the active ingredients are mixed with at least one inactive excipient such as lactose, mannitol, glucose, hydroxypropylcellulose, microcrystalline cellulose, starch, polyvinyl pyrrolidone, and/or aluminum magnesium aluminometasilicate, and the like. In a conventional method, the composition may contain inactive additives such as a lubricant such as magnesium stearate, a disintegrator such as carboxymethylstarch sodium, and the like, a stabilizing agent, and a solubilizing agent. As occasion demands, the tablets or pills may be coated with a film of a sugar coating, or a gastric or enteric coating material.

The liquid composition for oral administration includes a pharmaceutically acceptable emulsion, a solution, a suspension, a syrup, an elixir, and the like, and contains a generally used inert diluent such as purified water or ethanol. In addition to the inert diluent, this liquid composition may contain an auxiliary agent such as a solubilizing agent, a moistening agent, a suspending agent, a sweetener, a flavoring agent, a fragrance, and an antiseptic.

Injections for parenteral administration include sterile aqueous or non-aqueous liquid preparations, suspensions and emulsions. As the aqueous solvent, for example, distilled water for injection and physiological saline are included. Examples of the non-aqueous solvent include propylene glycol, polyethylene glycol, plant oils such as olive oil, alcohols such as ethanol, or Polysorbate 80 (Pharmacopoeia). Such a composition may further contain a tonicity agent, an antiseptic, a moistening agent, an emulsifying agent, a dispersing agent, a stabilizing agent, or a solubilizing agent. These are sterilized, for example, by filtration through a bacteria retaining filter, blending of a bactericide, or irradiation. In addition, these can also be used by producing a sterile solid composition, and dissolving or suspending it in sterile water or a sterile solvent for injection prior to its use.

The drug for external use includes ointments, plasters, creams, jellies, patches, sprays, lotions, eye drops, eye ointments, and the like. The drug contains generally used ointment bases, lotion bases, aqueous or non-aqueous solutions, suspensions, emulsions, and the like. Examples of the ointment bases or lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate, and the like.

Regarding a transmucosal agent such as an inhalation and a transnasal agent, those in a solid, liquid, or semi-solid state are used, and may be produced in accordance with a conventionally known method. For example, a known excipient, and also a pH adjusting agent, an antiseptic, a surfactant, a lubricant, a stabilizing agent, a thickening agent, and the like may be optionally added thereto. For their administration, an appropriate device for inhalation or blowing may be used. For example, a compound may be administered alone or as a powder of formulated mixture, or as a solution or suspension by combining it with a pharmaceutically acceptable carrier, using a conventionally known device or sprayer, such as a measured administration inhalation device. The dry powder inhaler, or the like may be for single or multiple administration use, and a dry powder or a powder-containing capsule may be used. Alternatively, this may be in a form such as a high pressure aerosol spray, and the like which uses an appropriate propellant, for example, a suitable gas such as chlorofluoroalkane, hydrofluoroalkane, carbon dioxide, and the like.

In oral administration, the daily dose may be generally from about 0.001 to 100 mg/kg, preferably from 0.1 to 30 mg/kg, and further more preferably 0.1 to 10 mg/kg per body weight, and this is administered in one portion or dividing it into 2 to 4 portions. Also, in the case of intravenous administration, the daily dose is from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided in response to an individual case by taking the symptoms, the age, and the gender, and the like of the subject into consideration.

The compound of the present invention can be used in combination of various therapeutic or prophylactic agents for the diseases, in which the compound of the present invention is considered effective. The combined preparation may be administered simultaneously or separately and continuously, or at a desired time interval. The preparations to be co-administered may be a blend, or prepared individually.

EXAMPLES

Hereinbelow, the processes for producing the compound (1) of the present invention will be described in more detail with reference to the following Examples, but the compounds of the present invention are not limited to the compounds described in the following Examples. Furthermore, the processes for producing the starting compounds will be described in Production Examples.

In addition, the following abbreviations are used in Examples, Preparative Examples, and Tables as below.

PEx: Production Example, Ex: Example, No: Compound No., MS: m/z values in mass spectrometry (EI: EI-MS, (unless otherwise stated, it represents $(M)^+$); FAB: FAB-MS, ESI: ESI-MS, API: API-MS (following the ionization, + represents positive ions, and − represents negative ions. unless otherwise specifically stated, a positive ion represents $(M+H)^+$, and a negative ion represents $(M-H)^-$.)), NMR1: δ (ppm) of the peaks in $^1$H-NMR using DMSO-$d_6$, NMR: δ (ppm) of the peaks in $^1$H-NMR in CDCl$_3$, DBU:1,8-diazabicyclo[5.4.0]-7-undecene, Me: methyl, Syn: production process (the numeral shows that it was produced using a corresponding starting material, in the same manner as the case of an Example compound having its number as the Example No. A plurality of numbers indicates that it was produced by carrying out the reaction sequentially in the same manner). PSyn: production process (the numeral shows that it was produced using a corresponding starting material, in the same manner as the case of a Production Example compound having its number as the Production Example No. A plurality of numbers indicates that it was produced by carrying out the reaction sequentially in the same manner). Further, HCl in the structural formula indicates that the compound is hydrochloride. Note: Racemi means that the compound is a racemic product. A diastereo mixture means that the compound is a diastereo mixture. 3,4-Trans means that a 3-position and a 4-position of the piperidine are trans-arranged. Further, a dash is shown in the number as in 1',2'-cis and represents the configuration of cycloalkyl on a 1-position of a piperidine. For example, 1',2'-cis means that the configuration of cycloalkyl on a 1-position of a piperidine is a cis arrangement. A low-polarity compound and a high-polarity compound each mean that the compound is in a low-polarity fraction or in a high-polarity fraction in terms of TLC (MERCK Ltd.) or silica gel (60F$_{254}$) for the corresponding diastereomers.)

Production Example 1

To a mixed solution of 5 g of methyl cyanoacetate, 20 mL of methanol, and 20 mL of toluene was added 1.61 g of sodium hydride (55% oil-dispersion) under ice-cooling. After stirring at room temperature for 30 minutes, to the reaction mixture was added 3.24 mL of methyl cinnamate, followed by stirring at 66° C. for 15 hours. The reaction mixture was cooled to room temperature, and 1 M hydrochloric acid was then added thereto to adjust the pH of the solution to about 7.

After extraction with ethyl acetate, the organic layer was dried over anhydrous sodium sulfate. After filtration, the filtrate was concentrated under reduced pressure, and the obtained residue was purified by silica gel column chromatography (hexane-ethyl acetate) to obtain 5.19 g of dimethyl 2-cyano-3-phenylpentanedioate.

Production Example 2

To a solution of 22.38 g of methyl acetate in 24.2 mL of toluene was added 11.66 g of sodium methoxide (28 wt % of methanol solution) at room temperature. To the obtained white suspension was added 5.00 g of 2-fluorobenzaldehyde at room temperature. After stirring at room temperature for 2 hours, methyl cyanoacetate and 7.77 g of sodium methoxide (28 wt % of a methanol solution) were further added thereto, followed by stirring at 65° C. overnight. The reaction mixture was cooled to room temperature, and 1 M hydrochloric acid (70 mL) and saturated brine were added thereto in this order, followed by extraction with ethyl acetate. The organic layer was dried over anhydrous sodium sulfate, and after filtration, the filtrate was concentrated under reduced pressure, and the residue was purified by silica gel column chromatography (hexane-ethyl acetate) to obtain 4.66 g of dimethyl 2-cyano-3-(2-fluorophenyl)pentanedioate as a pale yellow oily substance.

Production Example 3

To 1.0 L of a solution of 20.0 g of dimethyl 2-cyano-3-phenylpentanedioate and 36.4 g of cobalt chloride (TI) hexahydrate in methanol was added carefully 17.4 g of sodium borohydride under ice-cooling. After stirring at room temperature for 30 minutes, 1 M hydrochloric acid (1.0 L) was added thereto, followed by further stirring at room temperature for 30 minutes. The reaction mixture was concentrated under reduced pressure to a half amount thereof, and then extracted with ethyl acetate. The organic layer was washed with saturated brine, and dried over anhydrous sodium sulfate. After filtration, the filtrate was concentrated under reduced pressure, and the residue was purified by silica gel column chromatography (chloroform-methanol) to obtain 3.84 g of methyl rel-(3R,4S)-6-oxo-4-phenylpiperidine-3-carboxylate as a white solid.

Production Example 4

(1) To a suspension of 1.8 g of lithium aluminum hydride in 40 mL of toluene—40 mL of THF was added 6.3 g of methyl rel-(3R,4S)-6-oxo-4-phenylpiperidine-3-carboxylate at room temperature. The reaction mixture was stirred at 75° C. for 35 hours. After completion of the reaction, it was cooled to room temperature, and 1.0 mL of water, 1.0 mL of a 1 M aqueous sodium hydroxide solution, and 1.0 mL of water added thereto in this order, followed by stirring for 10 minutes. This mixture was dried over anhydrous sodium sulfate, the insolubles were removed by filtration, and the filtrate was then concentrated under reduced pressure to obtain a white solid of 4.37 g of rel-[(3R,4S)-4-phenylpiperidin-3-yl]methanol as a crude product. ESI+: 192

(2) To a mixture of 4.34 g of the obtained crude rel-[(3R, 4S)-4-phenylpiperidin-3-yl]methanol, 9.40 mL of triethylamine, and 150 mL of toluene was added dropwise 4.80 mL of trifluoroacetic anhydrdate under ice-cooling. The reaction mixture was stirred at room temperature for 30 minutes, and 100 mL of THF and 100 mL of a saturated aqueous sodium hydrogen carbonate solution were then added thereto, followed by further vigorously stirring for 30 minutes. After extraction with ethyl acetate, the organic layer was washed with saturated brine, and dried over anhydrous sodium sulfate. After filtration, the filtrate was concentrated under reduced pressure, and the residue was purified by silica gel column chromatography (hexane-ethyl acetate) to obtain 3.69 g of rel-[(3R,4S)-4-phenyl-1-(trifluoroacetyl)piperidin-3-yl]methanol.

Production Example 5

To a solution of 1.42 g of (1R)-1-(1-naphthyl)-N-{[4-phenyl-1-(trifluoroacetyl)piperidin-3-yl]methyl}ethaneamine in 15 mL of THF were added a solution of 1.82 g of di-tert-butyl-dicarbonate in 15 mL of THF and 1.75 mL of triethylamine at room temperature, followed by stirring at 60° C. overnight. The reaction mixture was cooled at room temperature, and 22 mL of methanol and 50 mL of a 1 M aqueous sodium hydroxide solution were then added thereto, followed by stirring at room temperature for 30 minutes. After extraction with ethyl acetate, the organic layer was washed with saturated brine, and dried over anhydrous sodium sulfate. After filtration, the filtrate was concentrated under reduced pressure, and the residue was purified by silica gel column chromatography (chloroform-methanol) to obtain 864 mg of tert-butyl[(1R)-1-(1-naphthyl)ethyl][(4-phenylpiperidin-3-yl)methyl]carbamate.

Production Example 6

To a solution of 1.24 g of (1R)—N-{[4-(2-fluorophenyl)-1-(trifluoroacetyl)piperidin-3-yl]methyl}-1-(1-naphthyl)ethaneamine in 20 mL of THF were added a solution of 2.36 g of di-tert-butyl-dicarbonate in 10 mL of THF and 2.26 mL of triethylamine at room temperature, followed by heating at 60° C. and stirring overnight. The reaction mixture was cooled at room temperature, and then concentrated under reduced pressure, and the residue was purified by silica gel column chromatography (hexane-ethyl acetate) to obtain 703 mg of tert-butyl {[4-(2-fluorophenyl)-1-(trifluoroacetyl)piperidin-3-yl]methyl}[(1R)-1-(1-naphthyl)ethyl]carbamate (Production Example 6-1, low-polarity fraction, Rf value 0.29 (eluting solvent: hexane/ethyl acetate=7/1)) and tert-butyl {[4-(2-fluorophenyl)-1-(trifluoroacetyl)piperidin-3-yl]methyl}[(1R)-1-(1-naphthyl)ethyl]carbamate 700 mg (Production Example 6-2, high-polarity fraction, Rf value 0.21 (eluting solvent: hexane/ethyl acetate=7/1)) as a colorless foamy substance, respectively.

Production Example 7

1.00 g of ethyl 2,6-dichloronicotinate was dissolved in 10 mL of methylene chloride, and 1.05 g of sodium methoxide (28 wt % of methanol solution) was added thereto at room temperature. After stirring at room temperature for 2 days, the reaction mixture was concentrated, and the residue was purified by silica gel column chromatography (hexane-ethyl acetate) to obtain 511 mg of methyl 6-chloro-2-methoxynicotinate as a white solid.

Production Example 8

695 mg of tert-butyl {[4-(2-fluorophenyl)-1-(trifluoroacetyl)piperidin-3-yl]methyl}[(1R)-1-(1-naphthyl)ethyl]carbamate was dissolved in 5 mL of THF-2 mL of methanol, and 1 mL of a 1 M aqueous sodium hydroxide solution was added thereto, followed by stirring at room temperature for 30 minutes. The reaction mixture was concentrated under reduced pressure, and chloroform was added to the obtained residue, followed by drying over anhydrous sodium sulfate. After filtration, the filtrate was concentrated under reduced pressure to obtain 636 mg of a colorless foamy substance of tert-butyl {[4-(2-fluorophenyl)piperidin-3-yl]methyl}[(1R)-1-(1-naphthyl)ethyl]carbamate as a crude product.

Production Example 9

382 mg of rel-[(3R,4S)-4-(4-fluorophenyl)piperidin-3-yl]methanol (Astatech, Inc., USA) was dissolved in 5 mL of dichloromethane, 5 mL of water and 755 mg of sodium carbonate were added thereto, and cooled at 0° C., and then 785 mg of methyl 4-[(chlorocarbonyl)oxy]benzoate (Fluka) was added in portions, followed by stirring for 1 hour. The reaction mixture was extracted with chloroform, washed with a saturated aqueous sodium carbonate solution, the organic layer was then dried over anhydrous sodium sulfate, and after filtration, the filtrate was concentrated under reduced pressure.

The obtained residue was washed with diisopropylether under stirring to obtain 490 mg of 4-(methoxycarbonyl)phenyl rel-(3R,4S)-4-(4-fluorophenyl)-3-(hydroxymethyl)piperidine-1-carboxylate as a white powder.

Production Example 10

To a solution of 888 mg of 4-(methoxycarbonyl)phenyl 4-(4-fluorophenyl)-3-({[(1R)-1-(1-naphthyl)ethyl]amino}methyl)piperidine-1-carboxylate in 9 mL of dichloromethane were added 0.7 mL of triethylamine and 868 mg of di-tert-butyl carbonate, followed by stirring at room temperature for 37 hours. The reaction mixture was concentrated under reduced pressure, and the residue was purified by silica gel chromatography (hexane-ethyl acetate) to obtain 503 mg of 4-(methoxycarbonyl)phenyl 3-({(tert-butoxycarbonyl)[(1R)-1-(1-naphthyl)ethyl]amino}methyl)-4-(4-fluorophenyl)piperidine-1-carboxylate as a pale yellow foamy substance.

Production Example 11

To a solution of 5.43 g of 4-nitrophenyl chloroformate in 100 mL of dichloromethane was added 2.4 mL of pyridine under ice-cooling, and 5 g of methyl 4-amino-3-chlorobenzoate was added to the obtained mixture, followed by stirring at room temperature overnight. The reaction mixture was concentrated under reduced pressure, and ethyl acetate was added to the residue, followed by washing with 1 M hydrochloric acid, water, a saturated aqueous sodium hydrogen carbonate solution, water, and a saturated aqueous sodium chloride solution in this order. The organic layer was dried over anhydrous sodium sulfate, and after filtration, the filtrate was concentrated under reduced pressure. The obtained solid was dissolved in 200 mL of toluene under heating, and left to be cooled to room temperature, and further cooled in an ice bath. The precipitated solid was collected by filtration, and dried under reduced pressure to obtain 5.59 g of methyl 3-chloro-4-{[(4-nitrophenoxy)carbonyl]amino}benzoate as a white solid.

Production Example 12

(1) Preparation of a catalyst: An asymmetric rhodium catalyst was prepared in accordance with a method in the pamphlet of International Patent Publication WO 1998/42643. A mixture of 75.3 mg of (1R,2S)-(+)-cis-1-amino-2-indanole and 156 mg of a dimer of dichloro(pentamethylcyclopentadienyl) rhodium(III) dichloride (Strem Chemicals, Inc.) was dissolved in 63 mL of isopropanol. The solution was degassed, and substituted at an argon atmosphere. The obtained suspension was stirred at 40° C. for 2 hours, and then cooled to room temperature to prepare an orange asymmetric rhodium catalyst solution.

(2) To a solution of 4.45 g of 1-(1-benzothiene-3-yl)ethanone in 95 mL of isopropanol was added the asymmetric rhodium catalyst solution prepared as described above. Under reduced pressure (about 6600 Pa), an isopropanol solution of sodium isopropoxide (0.1 M, 10.0 mL) was added thereto. Further, the pressure was reduced to about 3700 Pa, followed by stirring at room temperature for 2 hours. To the reaction mixture was added acetic acid (2 mL) to stop the reaction, followed by concentrating under reduced pressure, and the residue was purified by silica gel column chromatography (hexane-ethyl acetate) to obtain (1S)-1-(1-benzothiene-3-yl)ethanol (4.48 g, 94% ee) as a pale yellow oily substance. (HPLC analysis condition: CHIRALCEL OD-H column manufactured by (DAICEL CHEMICAL INDUSTRIES. Ltd., eluting solvent hexane/isopropanol=90/10, flow rate 1.0 mLmin$^{-1}$, retention time: 8.1 min (S-isomer), 12.6 min (R-isomer)) EI: 178

(3) The process was carried out with reference to a method of Thompson, et al. (J. Org. Chem. 1993, 58, 5886). Under an argon atmosphere, a mixture of 5.50 g of (1S)-1-(1-benzothiene-3-yl)ethanol and 7.98 g of DPPA was dissolved in toluene, and 5.54 mL of DBU was then added thereto in an ice bath. After stirring for 30 min under ice-cooling, it was further stirred at room temperature for 15 hours. The reaction mixture was washed with water and 1 M hydrochloric acid in this order, and then dried over anhydrous sodium sulfate. After filtration, the filtrate was concentrated under reduced pressure, and the residue was purified by silica gel column chromatography (hexane-ethyl acetate) to obtain 5.86 g of (1R)-1-(1-benzothiene-3-yl)ethylazide as a colorless oily substance. EI: 203

(4) 5.57 g of (1R)-1-(1-benzothiene-3-yl)ethylazide, 557 mg of 10% palladium/carbon, and 250 mL of ethyl acetate were mixed, followed by vigorously stirring for 2 hours at a normal pressure under a hydrogen atmosphere. After substituting with argon, the insolubles were filtered on a celite layer, and the filtrate was concentrated under reduced pressure. The obtained residue was dissolved in 20 mL of ethanol, and 7.0 mL of a 4 M hydrogen chloride/1,4-dioxane solution was added thereto at room temperature, followed by stirring for 5 minutes and concentrating under reduced pressure again. Crystallization was repeatedly carried out twice with an ethanol solvent to obtain (1R)-1-(1-benzothiene-3-yl)ethaneamine hydrochloride (2.35 g, 96% ee) as a white solid. (HPLC analysis condition: CHIRALCEL OD-H column manufactured by DAICEL CHEMICAL INDUSTRIES. Ltd., eluting solvent: hexane/isopropanol=90/10, flow rate 1.0 mL min$^{-1}$, retention time: 10.4 min (R-isomer), 12.2 min (S-isomer))

Production Example 13

(1) A suspension of 11.8 g of sodium hydride (60% oil dispersion) in 600 mL of diethylether was cooled to 0° C., and 40.0 g of ethyl 1-benzyl-3-oxopiperidine-4-carboxylate hydrochloride was then added thereto, followed by stirring at 0° C. for 30 minutes. To the reaction mixture was added 26.4 mL of trifluoromethane sulfonic anhydride, followed by further stirring at 0° C. for 1 hour. After adding saturated ammonium chloride solution thereto to stop the reaction, the organic layer was then separated, and the aqueous layer was extracted with ethyl acetate. The mixed organic layer was washed with saturated brine, and dried over anhydrous sodium sulfate. After filtration, the filtrate was concentrated under reduced pressure, and dried to obtain ethyl 1-benzyl-5-{[(trifluoromethyl)sulfonyl]oxy}-1,2,3,6-tetrahydropyridine-4-carboxylate
(dark brown oily substance, 64.3 g) as a crude product. FAB+: 394

(2) A mixture of 64.3 g of the obtained crude product of ethyl 1-benzyl-5-{[(trifluoromethyl)sulfonyl]oxy}-1,2,3,6-tetrahydropyridine-4-carboxylate, 19.7 g of phenyl boronic acid, 22.3 g of potassium carbonate, 600 mL of dimethoxyethane, and 4.66 g of tetrakis(triphenylphosphine)palladium was stirred at 90° C. overnight. After cooling to room temperature, the insolubles were filtered on a celite layer. The filtrate was concentrated under reduced pressure, to the obtained residue was added chloroform, followed by washing with water, and the organic layer was dried over anhydrous sodium sulfate. After filtration, the filtrate was concentrated under reduced pressure, and the residue was purified by silica gel column chromatography (hexane-ethyl acetate) to obtain 35.9 g of ethyl 1-benzyl-5-phenyl-1,2,3,6-tetrahydropyridine-4-carboxylate as a yellow oily substance.

Production Example 14

(1) To a mixture of 9.98 g of ethyl 1-benzyl-5-phenyl-1,2,3,6-tetrahydropyridine-4-carboxylate, 10.31 g of ammonium formate, and 90 mL of methanol was added 1.49 g of 10% palladium/carbon while suspending it in 10 mL of water and 10 mL of methanol. The reaction mixture was vigorously stirred at 60° C. for 2 hours. After cooling to room temperature, the insolubles were filtered on a celite layer, and the filtrate was concentrated under reduced pressure. To the obtained residue was added chloroform, followed by washing with saturated aqueous sodium bicarbonate. The organic layer was dried over anhydrous sodium sulfate. After filtration, the filtrate was concentrated under reduced pressure, and dried to obtain 7.09 g of a pale yellow oily substance of ethyl rel-(3R,4S)-3-phenylpiperidine-4-carboxylate as a crude product. ESI+: 234

(2) 5.58 g of the obtained crude product of ethyl rel-(3R,4S)-3-phenylpiperidine-4-carboxylate was dissolved in 55 mL of THF, and 5.0 mL of triethylamine and 6.26 g of di-tert-butyl-dicarbonate were added thereto, followed by stirring at room temperature for 2 days. The reaction mixture was concentrated under reduced pressure, and the residue was purified by silica gel column chromatography (hexane-ethyl acetate) to obtain 7.06 g of 1-tert-butyl 4-ethyl rel-(3R,4S)-3-phenylpiperidine-1,4-dicarbonate as a pale yellow oily substance.

Production Example 15

To a solution of 26.5 g of 1-tert-butyl 4-ethyl rel-(3R,4S)-3-phenylpiperidine-1,4-dicarbonate in 200 mL of toluene was added 2.94 g of potassium t-butoxide at room temperature, followed by stirring overnight while heating under reflux. The reaction mixture was cooled to room temperature, and neutralized by addition of 27 mL of 1 M hydrochloric acid, ethyl acetate was added thereto, and the organic layer was collected by separation. The organic layer was washed with water and saturated brine in this order, and dried over anhydrous sodium sulfate. After filtration, the filtrate was concentrated under reduced pressure, and dried to obtain 25.8 g of 1-tert-butyl 4-ethyl rel-(3R,4R)-3-phenylpiperidine-1,4-dicarbonate as a white waxy solid.

Production Example 16

To 1.40 g of 1-tert-butyl 4-ethyl rel-(3R,4R)-3-phenylpiperidine-1,4-dicarbonate was added 10 mL of a 4 M hydrogen chloride/1,4-dioxane solution, followed by stirring at room temperature overnight. To the reaction mixture was added ethyl acetate, the precipitated solid was suspended, then isolated by filtration, and dried under reduced pressure to obtain 1.05 g of ethyl rel-(3S,4S)-3-phenylpiperidine-4-carboxylate hydrochloride as a white solid.

Production Example 17

(1) To a suspension of 6.00 g of lithium aluminum hydride in 115 mL of toluene—115 mL of THF was carefully added 17.7 g of ethyl rel-(3S,4S)-3-phenylpiperidine-4-carboxylate hydrochloride at room temperature, followed by stirring at room temperature for 5 hours. Under ice-cooling, to reaction mixture was added 20 mL of methanol to stop the reaction, and 6 mL of water, 18 mL of a 15 w % aqueous sodium hydroxide solution, and 18 mL of water were then added in this order, followed by stirring for 10 minutes. The insolubles were removed by filtration, and the fitrate was then concentrated under reduced pressure to obtain 12.9 g of a white solid of rel-[(3R,4R)-3-phenylpiperidin-4-yl]methanol as a crude product. ESI+: 192

(2) To a solution of 3.59 g of the crude rel-[(3R,4R)-3-phenylpiperidin-4-yl]methanol and 10.46 mL of triethylamine in 70 mL of toluene was added 5.30 mL of trifluoroacetic anhydride under ice-cooling. After stirring at room temperature for 30 minutes, and to the reaction mixture were added 50 mL of a saturated aqueous sodium hydrogen carbonate solution and 50 mL of THF, followed by vigorously stirring for 30 minutes. The organic layer was collected by separation, washed with a saturated aqueous sodium chloride solution, and dried over anhydrous sodium sulfate. After filtration, the filtrate was concentrated under reduced pressure, and the residue was purified by silica gel column chromatography (hexane-ethyl acetate) to obtain 5.143 g of rel-[(3R,4R)-3-phenyl-1-(trifluoroacetyl)piperidin-4-yl]methanol as a pale yellow oily substance.

Production Example 18

To a solution of 2.15 g of (1R)-1-(1-naphthyl)-N-{[3-phenyl-1-(trifluoroacetyl)piperidin-4-yl]methyl}ethanamine in 43.0 mL of THF were added 2.72 mL of triethylamine and 2.13 g of di-tert-butyl-dicarbonate at room temperature, followed by stirring at 60° C. overnight. After cooling to room temperature, the reaction mixture was concentrated under reduced pressure, and the residue was purified by silica gel column chromatography (hexane-ethyl acetate) to obtain two diastereomers of 1.21 g of a low-polarity fraction of tert-butyl [(1R)-1-(1-naphthyl)ethyl] {[3-phenyl-1-(trifluoroacetyl)piperidin-4-yl]methyl}carbamate (Production Example 18-1, Rf value 0.57 (hexane/ethyl acetate=7/1)) and 1.20 g of a high-polarity fraction of tert-butyl
[(1R)-1-(1-naphthyl)ethyl] {[3-phenyl-1-(trifluoroacetyl) piperidin-4-yl]methyl}carbamate (Production Example 18-2, Rf value 0.42 (hexane/ethyl acetate=7/1)) as a colorless foamy substance, respectively.

Production Example 19

(1) To 500 mg of rel-[(3R,4R)-3-phenyl-1-(trifluoroacetyl) piperidin-4-yl]methanol were added 8.0 mL of THF, 4.0 mL of methanol, and 4.0 mL of a 1 M aqueous sodium hydroxide solution, followed by stirring at room temperature overnight. The reaction mixture was concentrated under reduced pressure, and the residue was extracted with ethyl acetate. The organic layer was dried over anhydrous sodium sulfate. After filtration, the filtrate was concentrated under reduced pressure, and added, to a mixture of 376 mg of the obtained crude product, 429 mg of methyl 2,6-dichloro-5-fluoronicotinate, and 289 mg of potassium carbonate was added 10 mL of DMSO at room temperature, and the mixed solution was stirred at room temperature for 5 hours. To the mixture was added ethyl acetate, the insolubles were removed by filtration, and the filtrate was then concentrated under reduced pressure. The obtained residue was purified by silica gel column chromatography (hexane-ethyl acetate) to obtain 493 mg of methyl rel-2-chloro-5-fluoro-6-[(3R,4R)-4-(hydroxymethyl)-3-phenylpiperidin-1-yl]nicotinate as a colorless foamy substance. ESI+: 379

(2) To a mixture of 488 mg of methyl rel-2-chloro-5-fluoro-6-[(3R,4R)-4-(hydroxymethyl)-3-phenylpiperidin-1-yl]nicotinate, 428 mg of ammonium formate, and 12 mL of methanol was added 70 mg of 10% palladium/carbon while suspending it in 1 mL of water and 6 mL of methanol. The reaction mixture was vigorously stirred at 60° C. for 2 hours. After cooling to room temperature, the insolubles were filtered on a celite layer, and the filtrate was concentrated under reduced pressure. To the obtained residue was added chloroform, followed by washing with saturated aqueous sodium bicarbonate The organic layer was dried over anhydrous sodium sulfate. After filtration, the filtrate was concentrated under reduced pressure, and the residue was purified by silica gel column chromatography (hexane-ethyl acetate) to obtain 283 mg of methyl rel-5-fluoro-6-[(3R,4R)-4-(hydroxymethyl)-3-phenylpiperidin-1-yl]nicotinate as a colorless foamy substance.

Production Example 20

To a mixed solution of 5.00 g of a low-polarity fraction diastereomer of tert-butyl [(1R)-1-(1-naphthyl)ethyl] {[3-phenyl-1-(trifluoroacetyl)piperidin-4-yl]methyl}carbamate collected by separation in Production Example 18, 40 mL of THF, and 40 mL of methanol was added 18.5 mL of a 1 M aqueous sodium hydroxide solution. After stirring at room temperature for 3 days, the reaction mixture was concentrated under reduced pressure. To the residue was added water, followed by extraction with chloroform, and the organic layer was then dried over anhydrous sodium sulfate. After filtration, the filtrate was concentrated under reduced pressure, and the residue was purified by silica gel column chromatography (chloroform-methanol) to obtain 3.78 g of tert-butyl[(1R)-1-(1-naphthyl)ethyl][(3-phenylpiperidin-4-yl)methyl]carbamate as a colorless foamy substance.

Production Example 21

900 mg of a low-polarity fraction diastereomer of tert-butyl [(1R)-1-(1-naphthyl)ethyl] {[3-phenyl-1-(trifluoroacetyl)piperidin-4-yl]methyl}carbamate collected by separation in Production Example 18, and 900 mg of a high-polarity fraction were mixed, followed by addition with 5 mL of THF, 2.5 mL of methanol, and 2.5 mL of a 1 M aqueous sodium hydroxide solution. After stirring at room temperature for 3 hours, the reaction mixture was concentrated under reduced pressure. To the residue was added water, followed by extraction with chloroform, and the organic layer was then dried over anhydrous sodium sulfate. After filtration, the filtrate was concentrated under reduced pressure, and dried to obtain 1.55 g of tert-butyl[(1R)-1-(1-naphthyl)ethyl][(3-phenylpiperidin-4-yl)methyl]carbamate as a colorless foamy substance.

Production Example 22

To a mixture of 500 mg of methyl 4,6-dichloronicotinate and 5.0 mL of THF was added dropwise 157 mg of sodium ethoxide (28 wt % of methanol solution) under cooling in an ice bath. It was warmed to room temperature, followed by stirring overnight. The reaction mixture was concentrated under reduced pressure, and the residue was then purified by silica gel column chromatography to obtain 162 mg of methyl 6-chloro-4-methoxynicotinate as a white solid.

Production Example 23

To 10 mL of methanol was added dropwise 2.5 mL of thionylchloride under cooling in an ice bath over 30 minutes. To the reaction mixture was added 500 mg of 3,5-difluoropyridine-2-carboxylic acid, and warmed to room temperature, followed by stirring for 3 days. The reaction mixture was concentrated under reduced pressure, and a saturated aqueous sodium hydrogen carbonate solution was added thereto, followed by extraction with ethyl acetate. The organic layer was washed with saturated brine, and then dried over anhydrous sodium sulfate. After filtration, it was concentrated under reduced pressure to obtain 496 mg of methyl 3,5-difluoropyridine-2-carboxylate.

In the same manner as the methods of Production Examples 1 to 23, the compounds of Production Examples 24 to 52 as shown in the following table were produced. The structures, the production processes, and the physicochemical data of the compounds of Production Examples are each shown in Tables 4 to 14.

Example 1

(1) A solution of 1.37 mL of DMSO in 20 mL of dichloromethane was cooled to −78° C., and added dropwise 0.845 mL of oxalyl chloride (internal temperature −60° C. or lower). After stirring at the same temperature for 20 minutes, a solution of 1.46 g of rel-[(3R,4S)-4-phenyl-1-(trifluoroacetyl)piperidin-3-yl]methanol in 20 mL of dichloromethane was added dropwise thereto, followed by stirring for additional 20 minutes. 4.40 mL of triethylamine was added dropwise thereto, and the reaction temperature was then elevated to −30° C., followed by stirring for additional 15 minutes. To the reaction mixture was added a saturated ammonium chloride solution to stop the reaction, followed by warming to room temperature, and then extraction with chloroform. The organic layer was washed with water, and then dried over anhydrous sodium sulfate. After filtration, the filtrate was concentrated under reduced pressure to obtain 1.597 g of rel-(3R,4S)-4-phenyl-1-(trifluoroacetyl)piperidine-3-carbaldehyde as a crude product.

(2) To a mixture of 868 mg of (1R)-1-(1-naphthyl)ethaneamine, 0.073 mL of acetic acid, 1.29 g of sodium triacetoxyborohydride, and 75 mL of 1,2-dichloroethane was added dropwise a solution of 1.446 g of a crude rel-(3R,4S)-4-phenyl-1-(trifluoroacetyl)piperidine-3-carbaldehyde in 25 mL of 1,2-dichloroethane at room temperature, followed by stirring overnight. To the reaction mixture was added a saturated aqueous sodium hydrogen carbonate solution, followed by vigorously stirring for 10 minutes, and then extracting with chloroform, and the organic layer was dried over anhydrous sodium sulfate. After filtration, the filtrate was concentrated under reduced pressure, and the residue was purified by silica gel column chromatography (chloroform-methanol) to obtain 1.84 g of (1R)-1-(1-naphthyl)-N-{[4-phenyl-1-(trifluoroacetyl)piperidin-3-yl]methyl}ethaneamine as a colorless foamy substance.

(3) 200 mg of (1R)-1-(1-naphthyl)-N-{[4-phenyl-1-(trifluoroacetyl)piperidin-3-yl]methyl}ethaneamine was dissolved in 4.0 mL of ethanol, and 300 μL of a 4 M hydrogen chloride/1,4-dioxane solution was added thereto at room temperature. After stirring for 5 min, the reaction mixture was concentrated under reduced pressure, and the residue was crystallized from isopropanol to obtain 173 mg of (1R)-1-(1-naphthyl)-N-{[4-phenyl-1-(trifluoroacetyl)piperidin-3-yl]methyl}ethaneamine hydrochloride as a white powder.

Example 2

220 mg of (1R)-1-(1-naphthyl)-N-{[4-phenyl-1-(trifluoroacetyl)piperidin-3-yl]methyl}ethaneamine as a mixture of diastereomers was subjected to high performance liquid chromatography (manufactured by KANTO CHEMICAL Co. Inc. column, Mightysil, RP-18, GP 250-20, 5 μm, eluting solvent: acetonitrile-water) to collect (1R)-1-(1-naphthyl)-N-{[4-phenyl-1-(trifluoroacetyl)piperidin-3-yl]methyl}ethaneamine (low-polarity fraction, HPLC retention time: 12 min) and (1R)-1-(1-naphthyl)-N-{[4-phenyl-1-(trifluoro acetyl)piperidin-3-yl]methyl}ethaneamine (high-polarity fraction: HPLC retention time: 8.7 min) by separation (preparative high performance liquid chromatography condition, column: TSK-GEL, ODS-80™ (TOSO), inner diameter of 4.6 mm, and length of 150 mm), flow rate: 1 ml/min., 0.01 M aqueous potassium dihydrogen phosphate solution/acetonitrile=30/70). They were each separately treated with a 4 M hydrogen chloride/1,4-dioxane solution, and solidified from isopropanol to obtain 69 mg of (1R)-1-(1-naphthyl)-N-{[4-phenyl-1-(trifluoroacetyl)piperidin-3-yl]methyl}ethaneamine hydrochloride (Example 2-1, low-polarity fraction) and 78 mg of (1R)-1-(1-naphthyl)-N-{[4-phenyl-1-(trifluoroacetyl)piperidin-3-yl]methyl}ethaneamine hydrochloride (Example 2-2, high-polarity fraction) as white powders.

Example 3

159 mg of methyl 3-methoxy-4-({[3-({[(1R)-1-(1-naphthyl)ethyl]amino}methyl)-4-phenylpiperidin-1-yl]carbonyl}amino)benzoate was dissolved in 6.0 mL of THF-3.0 mL of methanol, and 3.0 mL of a 1 M aqueous sodium hydroxide solution was added thereto, followed by stirring overnight. The reaction mixture was neutralized by addition with 30 mL of 1 M hydrochloric acid, and then concentrated under reduced pressure. To the residue was added water, followed by extraction with chloroform, and the organic layer was dried over anhydrous sodium sulfate. After filtration, the filtrate was concentrated, and the residue was purified by silica gel column chromatography (methanol-chloroform) to obtain 144 mg of methyl 3-methoxy-4-({[3-({[(1R)-1-(1-naphthyl)ethyl]amino}methyl)-4-phenylpiperidin-1-yl]carbonyl}amino)benzoate as a colorless amorphous substance. The obtained amorphous substance was dissolved in chloroform, followed by addition of hexane, and solidification. The precipitate was collected by filtration, and dried under reduced pressure to obtain 102 mg of 3-methoxy-4-({[3-({[(1R)-1-(1-naphthyl)ethyl]amino}methyl)-4-phenylpiperidin-1-yl]carbonyl}amino)benzoic acid as a white solid.

Example 4

610 mg of a low-polarity fraction diastereomer of (1R)-1-(1-naphthyl)-N-{[4-phenyl-1-(trifluoroacetyl)piperidin-3-yl]methyl}ethaneamine hydrochloride (Example 2-1) collected by separation in Example 2 was suspended in 4 mL of THF and 2 mL of methanol, and 3 mL of a 1 M aqueous sodium hydroxide solution was added thereto. After stirring at room temperature for 2 hours, the reaction mixture was concentrated under reduced pressure. To the residue was added water, followed by extraction with ethyl acetate, and the organic layer was then dried over anhydrous sodium sulfate. After filtration, the filtrate was concentrated under reduced pressure to obtain 475 mg of (1R)-1-(1-naphthyl)-N-[(4-phenylpiperidin-3-yl)methyl]ethaneamine.

Example 5

(1) To a solution of 0.3 mL of oxalyl chloride in 5 mL of dichloromethane was added dropwise 0.5 mL of DMSO at −78° C., followed by stirring for 10 minutes. To the reaction mixture was added dropwise a solution of 664 mg of 4-(methoxycarbonyl)phenyl rel-(3R,4S)-4-(4-fluorophenyl)-3-(hydroxymethyl)piperidine-1-carboxylate in 5 mL of dichloromethane at −78° C., followed by stirring for 15 min, and a solution of 1.8 mL of diisopropylethylamine in 3 mL of dichloromethane was then added dropwise, followed by elevation to room temperature over 2 hours. The reaction mixture was concentrated under reduced pressure, and to the residue was added diethylether, followed by washing with saturated brine, and drying over anhydrous sodium sulfate. After filtration, the filtrate was concentrated under reduced pressure to obtain 4-(methoxycarbonyl)phenyl rel-(3R,4S)-4-(4-fluorophenyl)-3-formylpiperidine-1-carboxylate as a crude product. ESI+: 386

(2) A solution of the obtained crude product 4-(methoxycarbonyl)phenyl rel-(3R,4S)-4-(4-fluorophenyl)-3-formylpiperidine-1-carboxyate in 4 mL of 1,2-dichloroethane was added to a mixture of 311 mg of (1R)-1-(1-naphthyl)ethaneamine, 0.030 mL of acetic acid, 1.09 g of sodium triacetoxyborohydride, and 6 mL of 1,2-dichloroethane, followed by stirring at room temperature overnight. Until the reaction mixture was neutralized, a saturated aqueous sodium hydrogen carbonate solution was added thereto, followed by extraction with chloroform. The organic layer was dried over anhydrous sodium sulfate, and filtered, and the filtrate was then concentrated under reduced pressure. The obtained residue was purified by silica gel column chromatography (chloroform-methanol) to obtain 888 mg of 4-(methoxycarbonyl)phenyl 4-(4-fluorophenyl)-3-({[(1R)-1-(1-naphthyl)ethyl]amino}methyl)piperidine-1-carboxylate as a pale yellow foamy substance.

Example 6

To a solution of 175 mg of the crude product of (1R)-1-(1-naphthyl)-N-[(4-phenylpiperidin-3-yl)methyl]ethaneamine and 142 μL of triethylamine in 3.5 mL of THF was added 120 mg of methyl 4-[(chlorocarbonyl)oxy]benzoate (Fluka) under ice-cooling. After stirring at room temperature for 30 minutes, the reaction mixture was concentrated under reduced pressure, and the residue was purified by silica gel column chromatography (hexane-ethyl acetate) to obtain 237 mg of 4-(methoxycarbonyl)phenyl 3-({[(1R)-1-(1-naphthyl)ethyl]amino}methyl)-4-phenylpiperidine-1-carboxylate.

Example 7

To a solution of 158 mg of (1R)-1-(1-naphthyl)-N-[(4-phenylpiperidin-3-yl)methyl]ethaneamine and 0.100 mL of triethylamine in 3.0 mL of toluene was added 83 mg of methyl 2-isocyanatobenzoate at room temperature. It was stirred at 90° C. overnight, and then cooled to room temperature. The reaction mixture was concentrated under reduced pressure, and the residue was purified by silica gel column chromatography (chloroform-methanol) to obtain 27.3 mg of methyl 2-({[3-({[(1R)-1-(1-naphthyl)ethyl]amino}methyl)-4-phenylpiperidin-1-yl]carbonyl}amino)benzoate as a colorless foamy substance.

Example 8

To a solution of 217 mg of the crude product of (1R)-1-(1-naphthyl)-N-[(4-phenylpiperidin-3-yl)methyl]ethaneamine and 0.175 mL of triethylamine in 4.0 mL of THF was added 243 mg of methyl 3-chloro-4-{[(4-nitrophenoxy)carbonyl]amino}benzoate. After stirring at room temperature overnight, the reaction mixture was concentrated under reduced pressure. The obtained residue was purified by silica gel column chromatography (hexane-ethyl acetate) to obtain 214 mg of methyl 3-chloro-4-({[3-({[(1R)-1-(1-naphthyl)ethyl]amino}methyl)-4-phenylpiperidin-1-yl]carbonyl}amino) benzoate.

Example 9

(1) To a solution of 150 mg of the crude product of tert-butyl[(1R)-1-(1-naphthyl)ethyl][(4-phenylpiperidin-3-yl)methyl]carbamate and 0.094 mL of triethylamine in 3 mL of THF was added 62.3 mg of 2,2-dimethylglutaric anhydride at room temperature. After stirring at room temperature overnight, the reaction mixture was concentrated under reduced pressure. The residue was dissolved in ethyl acetate, and then washed with 1 M hydrochloric acid, and the organic layer was dried over anhydrous sodium sulfate. After filtration, the filtrate was concentrated under reduced pressure to obtain 5-[3-({(tert-butoxycarbonyl)[(1R)-1-(1-naphthyl)ethyl]amino}methyl)-4-phenylpiperidin-1-yl]-2,2-dimethyl-5-oxopentanoic acid (colorless foamy substance, 225 mg) as a crude product. ESI+: 587

(2) To 225 mg of the crude 5-[3-({(tert-butoxycarbonyl)[(1R)-1-(1-naphthyl)ethyl]amino}methyl)-4-phenylpiperidin-1-yl]-2,2-dimethyl-5-oxopentanoic acid was added 2.0 mL of a 4 M hydrogen chloride/1,4-dioxane solution 2.0 mL, followed by stirring at room temperature for 1 hour. The reaction mixture was concentrated under reduced pressure, and the residue was then dissolved in THF. Diisopropylether was added dropwise thereto, and the precipitate was isolated by filtration. This was dried under reduced pressure at 50° C. to obtain 170 mg of 2,2-dimethyl-5-[3-({[(1R)-1-(1-naphthyl)ethyl]amino}methyl)-4-phenylpiperidin-1-yl]-5-oxopentanoic acid hydrochloride as a white solid.

Example 10

(1) To a solution of 238 mg of the crude tert-butyl[(1R)-1-(1-naphthyl)ethyl][(4-phenylpiperidin-3-yl)methyl]carbamate in 3 mL of THF was added 200 mg of sodium hydrogen carbonate while suspending it in 2 mL of water. The reaction mixture was added 170 mg of methyl 4-[(chlorocarbonyl)oxy]benzoate (Fluka). After stirring at room temperature overnight, the mixed solution was extracted with ethyl acetate. The organic layer was washed with water and saturated brine in this order, and dried over anhydrous sodium sulfate. After filtration, the filtrate was concentrated under reduced pressure, and the residue was purified by silica gel column chromatography (hexane-ethyl acetate) to obtain 4-(methoxycarbonyl)phenyl 3-({(tert-butoxycarbonyl)[(1R)-1-(1-naphthyl)ethyl]amino}methyl)-4-phenylpiperidine-1-carboxylate (353 mg, colorless foamy substance) as a crude product. ESI+: 623

(2) To 333 mg of the obtained crude product of 4-(methoxycarbonyl)phenyl 3-({(tert-butoxycarbonyl)[(1R)-1-(1-naphthyl)ethyl]amino}methyl)-4-phenylpiperidine-1-carboxylate were added 3.0 mL of THF, 3.0 mL of methanol, and 1.5 mL of a 1 M aqueous sodium hydroxide solution, followed by stirring at room temperature overnight. It was neutralized by addition of 1.6 mL of 1 M hydrochloric acid, and extraction with ethyl acetate, and the organic layer was dried over anhydrous sodium sulfate. After filtration, the filtrate was concentrated under reduced pressure, and the residue was purified by silica gel column chromatography (chloroform-methanol) to obtain 260 mg of 4-({[3-({(tert-butoxycarbonyl)[(1R)-1-(1-naphthyl)ethyl]amino}methyl)-4-phenylpiperidin-1-yl]carbonyl}oxy)benzoic acid as a pale yellow foamy substance. ESI+: 609

(3) To 255 mg of 4-({[3-({(tert-butoxycarbonyl)[(1R)-1-(1-naphthyl)ethyl]amino}methyl)-4-phenylpiperidin-1-yl]carbonyl}oxy)benzoic acid was added 3.0 mL of a 4 M hydrogen chloride/1,4-dioxane solution, followed by stirring at room temperature for 1 hour. The reaction mixture was concentrated under reduced pressure, and the residue was then dissolved in THF. Diisopropylether was added dropwise thereto, and the precipitate was isolated by filtration. This was dried under reduced pressure at 50° C. to obtain 159 mg of 4-({[3-({[(1R)-1-(1-naphthyl)ethyl]amino}methyl)-4-phenylpiperidin-1-yl]carbonyl}oxy)benzoic acid hydrochloride as a white solid.

Example 11

(1) To a solution of 300 mg of tert-butyl {[4-(3-fluorophenyl)piperidin-3-yl]methyl}[(1R)-1-(1-naphthyl)ethyl]carbamate in 2 mL of THF were added 0.136 mL of triethylamine and 167 mg of methyl 4-[(chlorocarbonyl)oxy]benzoate (Fluka), followed by stirring at room temperature for 2 hours. It was washed with water, and extracted with ethyl acetate, and the organic layer was then washed with saturated brine, and dried over anhydrous sodium sulfate. After filtration, the filtrate was concentrated under reduced pressure, and to the obtained residue were added 8 mL of THF, 8 mL of isopropanol, and 4 mL of a 1 M aqueous sodium hydroxide solution, followed by stirring at room temperature for 2 days. After neutralizing by addition of 4.1 mL of 1 M hydrochloric acid, the reaction mixture was concentrated under reduced pressure. The obtained residue was extracted with chloroform, and the organic layer was dried over anhydrous sodium sulfate. After filtration, the filtrate was concentrated under reduced pressure, and the residue was purified by silica gel column chromatography (chloroform-methanol) to obtain 387 mg of 4-({[3-({(tert-butoxycarbonyl)[(1R)-1-(1-naphthyl)ethyl]amino}methyl)-4-(3-fluorophenyl)piperidin-1-yl]carbonyl}oxy)benzoic acid as a colorless foamy substance. ESI+: 627

(2) To 385 mg of 4-({[3-({(tert-butoxycarbonyl)[(1R)-1-(1-naphthyl)ethyl]amino}methyl)-4-(3-fluorophenyl)piperidin-1-yl]carbonyl}oxy)benzoic acid was added 2.0 mL of a 4 M hydrogen chloride/1,4-dioxane solution, followed by stirring at room temperature for 2 hours. The reaction mixture was concentrated under reduced pressure, and to the residue was added isopropanol, followed by heating for dissolution. Diisopropylether was added dropwise thereto, and the precipitate was isolated by filtration, and dried under reduced pressure to obtain 178 mg of 4-({[4-(3-fluorophenyl)-

3-({[(1R)-1-(1-naphthyl)ethyl]amino}methyl)piperidin-1-yl]carbonyl}oxy)benzoic acid hydrochloride as a white solid.

Example 12

(1) To a solution of 150 mg of tert-butyl[(1R)-1-(1-naphthyl)ethyl][(4-phenylpiperidin-3-yl)methyl]carbamate in 0.140 mL of triethylamine and 3.0 mL of THF was added 155 mg of methyl 3-methoxy-4-{[(4-nitrophenoxy)carbonyl]amino}benzoate prepared in the same manner as in Production Example 11, followed by stirring at room temperature overnight. The reaction mixture was concentrated under reduced pressure, and the residue was purified by silica gel column chromatography (hexane-ethyl acetate) to obtain methyl 4-({[3-({(tert-butoxycarbonyl)[(1R)-1-(1-naphthyl)ethyl]amino}methyl)-4-phenylpiperidin-1-yl]carbonyl}amino)-3-methoxybenzoate as a crude product (yellow foamy substance, 297 mg). ESI+: 652

(2) To 220 mg of the obtained crude product of methyl 4-({[3-({(tert-butoxycarbonyl)[(1R)-1-(1-naphthyl)ethyl]amino}methyl)-4-phenylpiperidin-1-yl]carbonyl}amino)-3-methoxybenzoate were added 3 mL of THF, 3 mL of methanol and 1.5 mL of a 1 M aqueous sodium hydroxide solution, followed by stirring at room temperature overnight. It was neutralized by addition of 1.6 mL of 1 M hydrochloric acid, and then extracted with ethyl acetate, and the organic layer was dried over anhydrous sodium sulfate. After filtration, the filtrate was concentrated under reduced pressure, and the residue was purified by silica gel column chromatography (chloroform-methanol) to obtain 203 mg of 4-({[3-({(tert-butoxycarbonyl)[(1R)-1-(1-naphthyl)ethyl]amino}methyl)-4-phenylpiperidin-1-yl]carbonyl}amino)-3-methoxybenzoic acid as a pale yellow foamy substance. ESI+: 638

(3) To 197 mg of 4-({[3-({(tert-butoxycarbonyl)[(1R)-1-(1-naphthyl)ethyl]amino}methyl)-4-phenylpiperidin-1-yl]carbonyl}amino)-3-methoxybenzoic acid was added 3.0 mL of a 4 M hydrogen chloride/1,4-dioxane solution, followed by stirring at room temperature for 1 hour. The reaction mixture was concentrated under reduced pressure, and the residue was then dissolved in THF.

Diisopropylether was added dropwise thereto, and the precipitate was isolated by filtration, and dried under reduced pressure at 50° C. to obtain 88 mg of 3-methoxy-4-({[3-({[(1R)-1-(1-naphthyl)ethyl]amino}methyl)-4-phenylpiperidin-1-yl]carbonyl}amino)benzoic acid hydrochloride as a white solid.

Example 13

(1) To a solution of 300 mg of tert-butyl {[4-(3-fluorophenyl)piperidin-3-yl]methyl}[(1R)-1-(1-naphthyl)ethyl]carbamate in 3.0 mL of toluene was added 0.136 mL of triethylamine and 149 mg of ethyl 4-isocyanatobenzoate at room temperature, followed by stirring at 100° C. for 2 days. The reaction mixture was cooled to room temperature, and water was added thereto, followed by extraction with ethyl acetate. The organic layer was washed with saturated brine, and dried over anhydrous sodium sulfate. After filtration, the filtrate was concentrated under reduced pressure, and to the obtained residue were added 8 mL of THF, 4 mL of methanol, and 4 mL of a 1 M aqueous sodium hydroxide solution, followed by stirring at room temperature for 24 hours. The reaction mixture was neutralized by addition of 4.1 mL of 1 M hydrochloric acid, then concentrated under reduced pressure, and extracted with chloroform. The organic layer was dried over anhydrous sodium sulfate, and then filtered, and the filtrate was concentrated under reduced pressure, and the residue was purified by silica gel column chromatography (chloroform-methanol) to obtain 356 mg of 4-({[3-({(tert-butoxycarbonyl)[(1R)-1-(1-naphthyl)ethyl]amino}methyl)-4-(3-fluorophenyl)piperidin-1-yl]carbonyl}amino)benzoic acid as a colorless foamy substance. ESI+: 626

(2) To 354 mg of 4-({[3-({(tert-butoxycarbonyl)[(1R)-1-(1-naphthyl)ethyl]amino}methyl)-4-(3-fluorophenyl)piperidin-1-yl]carbonyl}amino)benzoic acid was added 2.0 mL of a 4 M hydrogen chloride/1,4-dioxane solution, followed by stirring at room temperature for 2 hours. The reaction mixture was concentrated under reduced pressure, and to the residue was added isopropanol, followed by heating for dissolution. Diisopropylether was added dropwise thereto, and the precipitate was isolated by filtration, and dried under reduced pressure to obtain 180 mg of 4-({[4-(3-fluorophenyl)-3-({[(1R)-1-(1-naphthyl)ethyl]amino}methyl)piperidin-1-yl]carbonyl}amino)benzoic acid hydrochloride as a white solid.

Example 14

(1) A mixture of 150 mg of tert-butyl[(1R)-1-(1-naphthyl)ethyl][(4-phenylpiperidin-3-yl)methyl]carbamate, 96.2 mg of methyl 3,4,5-trifluorobenzoate, 93.3 mg of potassium carbonate, and 1.0 mL of DMSO was stirred at 110° C. for 1 hour. After cooling to room temperature, to the reaction mixture was added water, followed by extraction with ethyl acetate. The organic layer was washed with water and saturated brine in this order, and dried over anhydrous sodium sulfate. After filtration, the filtrate was concentrated under reduced pressure, and the residue was purified by silica gel column chromatography (hexane-ethyl acetate) to obtain 127 mg of methyl 4-[3-({(tert-butoxycarbonyl)[(1R)-1-(1-naphthyl)ethyl]amino}methyl)-4-phenylpiperidin-1-yl]-3,5-difluorobenzoate as a colorless foamy substance. ESI+: 615

(2) To 122 mg of methyl 4-[3-({(tert-butoxycarbonyl)[(1R)-1-(1-naphthyl)ethyl]amino}methyl)-4-phenylpiperidin-1-yl]-3,5-difluorobenzoate were added 2.0 mL of THF, 2.0 mL of methanol, and 1.0 mL of a 1 M aqueous sodium hydroxide solution, followed by stirring at room temperature overnight. It was neutralized by addition of 1.1 mL of 1 M hydrochloric acid, and then extracted with ethyl acetate, and the organic layer was dried over anhydrous sodium sulfate. After filtration, the filtrate was concentrated under reduced pressure, and the residue was purified by silica gel column chromatography (chloroform-methanol) to obtain 115 mg of 4-[3-({(tert-butoxycarbonyl)[(1R)-1-(1-naphthyl)ethyl]amino}methyl)-4-phenylpiperidin-1-yl]-3,5-difluorobenzoic acid as a pale yellow oily substance. ESI+: 601

(3) To 127 mg of 4-[3-({(tert-butoxycarbonyl)[(1R)-1-(1-naphthyl)ethyl]amino}methyl)-4-phenylpiperidin-1-yl]-3,5-difluorobenzoic acid was added 3.0 mL of a 4 M hydrogen chloride/1,4-dioxane solution, followed by stirring at room temperature for 1 hour. The reaction mixture was concentrated under reduced pressure, to the residue were added THF, isopropanol, and diisopropylether, and the precipitated solid was isolated by filtration, and dried under reduced pressure to obtain 78 mg of 3,5-difluoro-4-[3-({[(1R)-1-(1-naphthyl)ethyl]amino}methyl)-4-phenylpiperidin-1-yl]benzoic acid hydrochloride as a pale pink solid.

Example 15

(1) A solution of 200 mg of tert-butyl[(1R)-1-(1-naphthyl)ethyl][(4-phenylpiperidin-3-yl)methyl]carbamate, 212 mg of 3,4,5-trifluorobenzonitrile, and 187 mg of potassium carbonate in 4.0 mL of DMSO was heated at 110° C. for 2 hours. The reaction mixture was cooled to room temperature, and water was added thereto, followed by extraction with ethyl acetate. The organic layer was washed with water and saturated brine in this order, and dried over anhydrous sodium sulfate. After filtration, the filtrate was concentrated under reduced pressure, and the residue was purified by silica gel column chromatography (hexane-ethyl acetate) to obtain 191 mg of tert-butyl {[1-(4-cyano-2,6-difluorophenyl)-4-phenylpiperidin-3-yl]methyl}[(1R)-1-(1-naphthyl)ethyl]carbamate as a colorless foamy substance. ESI+: 582

(2) A mixture of 185 mg of tert-butyl {[1-(4-cyano-2,6-difluorophenyl)-4-phenylpiperidin-3-yl]methyl}[(1R)-1-(1-naphthyl)ethyl]carbamate, 414 mg of sodium azide, 876 mg of triethylamine hydrochloride, and 4.0 mL of DMF was stirred at 120° C. overnight. The reaction mixture was cooled to room temperature, and water added thereto, followed by extraction with ethyl acetate. The organic layer was washed with water and a saturated aqueous sodium chloride solution in this order, and dried over anhydrous sodium sulfate. After filtration, the filtrate was concentrated under reduced pressure to obtain tert-butyl ({1-[2,6-difluoro-4-(1H-tetrazol-5-yl)phenyl]-4-phenylpiperidin-3-yl}methyl)[(1R)-1-(1-naphthyl)ethyl]carbamate as a crude product (beige foamy substance, 208 mg). ESI+: 625

(3) To 206 mg of the crude product of tert-butyl ({1-[2,6-difluoro-4-(1H-tetrazol-5-yl)phenyl]-4-phenylpiperidin-3-yl}methyl)[(1R)-1-(1-naphthyl)ethyl]carbamate were added 2.0 mL of 1,4-dioxane and 2.0 mL of a 4 M hydrogen chloride/1,4-dioxane solution, followed by stirring at room temperature for 2 days. The reaction mixture was concentrated under reduced pressure, and to the residue were then added ethyl acetate and a small amount of ethanol, followed by heating for dissolution. Hexane was added thereto, and the precipitate was isolated by filtration, and dried under reduced pressure to obtain 153 mg of (1R)—N-({1-[2,6-difluoro-4-(1H-tetrazol-5-yl)phenyl]-4-phenylpiperidin-3-yl}methyl)-1-(1-naphthyl)ethaneamine hydrochloride as a beige solid.

Example 16

To 232 mg of 4-(methoxycarbonyl)phenyl 3-({[(1R)-1-(1-naphthyl)ethyl]amino}methyl)-4-phenylpiperidine-1-carboxylate were added 6.0 mL of THF, 3.0 mL of methanol, and 3.0 mL of a 1 M aqueous sodium hydroxide solution, followed by stirring at room temperature overnight. After neutralizing by addition of 3.0 mL of 1 M hydrochloric acid, the reaction mixture was concentrated under reduced pressure. To the residue was added water, followed by extraction with chloroform, and the organic layer was dried over anhydrous sodium sulfate. After filtration, the filtrate was concentrated under reduced pressure, and the residue was purified by silica gel column chromatography (chloroform-methanol). This was dissolved in a small amount of chloroform, and hexane was added thereto. Then, the precipitate was isolated by filtration, and dried under reduced pressure at 50° C. to obtain 66 mg of 4-({[3-({[(1R)-1-(1-naphthyl)ethyl]amino}methyl)-4-phenylpiperidin-1-yl]carbonyl}oxy)benzoic acid as a white solid.

Example 17

(1) To a mixture of 192 mg of tert-butyl {[4-(2-fluorophenyl)piperidin-3-yl]methyl}[(1R)-1-(1-naphthyl)ethyl]carbamate and 157 mg of sodium hydrogen carbonate were added 3 mL of THF and 1.5 mL of water, followed by addition of 133 mg of methyl 4-[(chlorocarbonyl)oxy]benzoate (Fluka). It was stirred at room temperature for 1 hour, and then extracted with ethyl acetate. The organic layer was washed with water and saturated brine in this order, and dried over anhydrous sodium sulfate. After filtration, the filtrate was concentrated under reduced pressure, and to 327 mg of the obtained residue were added 4 mL of THF, 2 mL of methanol, and 2.5 mL of a 1 M aqueous sodium hydroxide solution, followed by stirring at room temperature overnight. The reaction mixture was neutralized by addition of 2.6 mL of 1 M hydrochloric acid, concentrated under reduced pressure, and extracted with ethyl acetate. The organic layer was dried over anhydrous sodium sulfate, and then filtered, and the filtrate was concentrated under reduced pressure. The obtained residue was purified by silica gel column chromatography (chloroform-methanol) to obtain 228 mg of 4-({[3-({(tert-butoxycarbonyl)[(1R)-1-(1-naphthyl)ethyl]amino}methyl)-4-(2-fluorophenyl)piperidin-1-yl]carbonyl}oxy)benzoic acid as a colorless foamy substance. ESI+: 627

(2) To 213 mg of 4-({[3-({(tert-butoxycarbonyl)[(1R)-1-(1-naphthyl)ethyl]amino}methyl)-4-(2-fluorophenyl)piperidin-1-yl]carbonyl}oxy)benzoic acid was added 3.0 mL of a 4 M hydrogen chloride/1,4-dioxane solution, followed by stirring at room temperature overnight. The reaction mixture was concentrated under reduced pressure, and to the obtained residue was added chloroform, followed by washing with a saturated aqueous sodium hydrogen carbonate solution (1.0 mL). The organic layer was dried over anhydrous sodium sulfate, and then filtered, and the filtrate was concentrated under reduced pressure. The obtained residue was dissolved in ethyl acetate, and hexane was added thereto. Then, the precipitate was isolated by filtration. It was dried under reduced pressure to obtain 135 mg of 4-({[4-(2-fluorophenyl)-3-({[(1R)-1-(1-naphthyl)ethyl]amino}methyl)piperidin-1-yl]carbonyl}oxy)benzoic acid as a white solid.

Example 18

(1) Under an argon atmosphere, to a solution of 1.62 mL of DMSO in 40 mL of dichloromethane cooled in a dry ice-acetone bath was added dropwise 0.996 mL of oxalyl chloride, while keeping the inner temperature at −70° C. or lower. After stirring for 10 minutes, a solution of 1.64 g of rel-[(3R,4R)-3-phenyl-1-(trifluoroacetyl)piperidin-4-yl]methanol in 25 mL of dichloromethane was added dropwise thereto over 20 minutes. After stirring over 10 min while keeping it at −70° C. or lower, 4.77 mL of triethylamine was added dropwise thereto over 15 min, and the reaction system was warmed to −30° C., followed by stirring for 15 minutes. To the reaction mixture was added a saturated aqueous ammonium chloride solution, followed by warming to room temperature. After extraction with chloroform, the organic layer was washed with water, and dried over anhydrous sodium sulfate. After filtration, the filtrate was concentrated under reduced pressure to obtain rel-(3R,4R)-3-phenyl-1-(trifluoroacetyl)piperidine-4-carbaldehyde as a crude product (as a pale yellow oily substance, 1.78 g).

(2) To a mixture of 1.03 g of (1R)-1-(1-naphthyl)ethaneamine, 0.327 mL of acetic acid, 3.63 g of sodium triacetoxyborohydride, and 70 mL of 1,2-dichloroethane was added dropwise a solution of 1.78 g of the obtained crude rel-(3R,4R)-3-phenyl-1-(trifluoroacetyl)piperidine-4-carbaldehyde in 30 mL of 1,2-dichloroethane at room temperature, followed by stirring overnight. A saturated aqueous sodium hydrogen carbonate solution was added thereto, followed by stirring for 10 minutes, and extracting with chloroform, and the organic layer was dried over anhydrous sodium sulfate. After filtration, the filtrate was concentrated under reduced pressure, and the residue was purified by silica gel column chromatography (hexane-ethyl acetate) to obtain 2.19 g of (1R)-1-(1-naphthyl)-N-{[3-phenyl-1-(trifluoroacetyl)piperidin-4-yl]methyl}ethaneamine as a colorless foamy substance.

Example 19

(1) To a solution of 1.50 g of rel-[(3R,4R)-3-(3-fluorophenyl)-1-(trifluoroacetyl)piperidin-4-yl]methanol in 15 mL of dichloromethane was added 2.29 of Dess-Martin Periodinane at room temperature, followed by stirring for 1.5 hours. To the reaction mixture were added a saturated aqueous sodium thiosulfate solution and a saturated aqueous sodium hydrogen carbonate solution, followed by extraction with chloroform. The organic layer was washed with water and saturated brine in this order, and dried over sodium sulfate. After filtration, the filtrate was concentrated under reduced pressure to obtain 1.83 g of crude rel-(3R,4R)-3-(3-fluorophenyl)-1-(trifluoroacetyl)piperidine-4-carbaldehyde as an orange oily compound.

(2) To a solution of 882 mg of the obtained crude rel-(3R, 4R)-3-(3-fluorophenyl)-1-(trifluoroacetyl)piperidine-4-carbaldehyde and (1R)-1-(1-naphthyl)ethaneamine in 20 mL of dichloromethane was added 3.12 g of sodium triacetoxyborohydride at room temperature, followed by stirring for 1 hour. To the reaction mixture was added a saturated aqueous sodium hydrogen carbonate solution, followed by extraction with chloroform. The organic layer was washed with water and saturated brine in this order, and dried over anhydrous sodium sulfate. After filtration, the filtrate was concentrated under reduced pressure, and the residue was purified by NH silica gel (FUJI SILISIA CHEMICAL. Ltd., Japan) column chromatography (hexane-ethyl acetate) to obtain 1.64 g of (1R)—N-{[3-(3-fluorophenyl)-1-(trifluoroacetyl)piperidin-4-yl]methyl}-1-(1-naphthyl)ethaneamine as a colorless foamy substance.

Example 20

(1) To a solution of 100 mg of tert-butyl[(1R)-1-(1-naphthyl)ethyl][(3-phenylpiperidin-4-yl)methyl]carbamate and 0.038 mL of triethylamine in 3 mL of THF was added 46.9 mg of methyl 4-(chlorocarbonyl)benzoate, followed by stirring at room temperature overnight. To the reaction mixture was added a saturated aqueous sodium hydrogen carbonate solution, followed by extraction with chloroform, and the organic layer was dried over anhydrous sodium sulfate. After filtration, the filtrate was concentrated under reduced pressure, and the residue was purified by silica gel column chromatography (hexane-ethyl acetate) to obtain 56.0 mg of methyl 4-{[4-({(tert-butoxycarbonyl)[(1R)-1-(1-naphthyl)ethyl]amino}methyl)-3-phenylpiperidin-1-yl]carbonyl}benzoate as a colorless foamy substance. FAB+: 607

(2) To 55 mg of methyl 4-{[4-({(tert-butoxycarbonyl)[(1R)-1-(1-naphthyl)ethyl]amino}methyl)-3-phenylpiperidin-1-yl]carbonyl}benzoate were added 2.0 mL of THF, 1.0 mL of methanol, and 1.00 mL of a 1 M aqueous sodium hydroxide solution, followed by stirring at room temperature overnight. It was neutralized by addition of 1.1 mL of 1 M hydrochloric acid, and then extracted with chloroform, and the organic layer was dried over anhydrous sodium sulfate. After filtration, the filtrate was concentrated under reduced pressure, and dried to obtain 4-{[4-({(tert-butoxycarbonyl)[(1R)-1-(1-naphthyl)ethyl]amino}methyl)-3-phenylpiperidin-1-yl]carbonyl}benzoic acid as a crude product(colorless foamy substance, 57.5 mg).

(3) To 57.5 mg of the obtained crude product of 4-{[4-({(tert-butoxycarbonyl)[(1R)-1-(1-naphthyl)ethyl]amino}methyl)-3-phenylpiperidin-1-yl]carbonyl}benzoic acid was added 2.0 mL of a 4 M hydrogen chloride/1,4-dioxane solution. After stirring at room temperature for 2 hours, the reaction mixture was concentrated under reduced pressure. To the obtained residue was added ethanol-ethyl acetate, followed by crystallization to obtain 15.6 mg of 4-{[4-({[(1R)-1-(1-naphthyl)ethyl]amino}methyl)-3-phenylpiperidin-1-yl]carbonyl}benzoic acid hydrochloride as a white solid.

Example 21

(1) A mixture of 100 mg of tert-butyl[(1R)-1-(1-naphthyl)ethyl][(3-phenylpiperidin-4-yl)methyl]carbamate, 44.6 mg of monomethyl isophthalate, and 51.7 mg of HOBt was dissolved in 1.0 mL of dichloromethane, and 36.5 mg of WSC/hydrochloride was added thereto, followed by stirring at room temperature for 2 days. The reaction mixture was concentrated under reduced pressure, and the residue was purified by silica gel column chromatography (hexane-ethyl acetate) to obtain 122 mg of methyl 3-{[4-({(tert-butoxycarbonyl)[(1R)-1-(1-naphthyl)ethyl]amino}methyl)-3-phenylpiperidin-1-yl]carbonyl}benzoate as a colorless foamy substance.

(2) To 122 mg of the obtained methyl 3-{[4-({(tert-butoxycarbonyl)[(1R)-1-(1-naphthyl)ethyl]amino}methyl)-3-phenylpiperidin-1-yl]carbonyl}benzoate were added 2.0 mL of THF, 1.0 mL of methanol, and 1.0 mL of a 1 M aqueous sodium hydroxide solution, followed by stirring at room temperature overnight. It was neutralized by addition of 1.1 mL of 1 M hydrochloric acid, and then extracted with ethyl acetate, and the organic layer was dried over anhydrous sodium sulfate. After filtration, the filtrate was concentrated under reduced pressure, and dried to obtain 3-{[4-({(tert-butoxycarbonyl)[(1R)-1-(1-naphthyl)ethyl]amino}methyl)-3-phenylpiperidin-1-yl]carbonyl}benzoic acid as a crude product (colorless foamy substance, 121 mg).

(3) To 118 mg of the obtained crude 3-{[4-({(tert-butoxycarbonyl)[(1R)-1-(1-naphthyl)ethyl]amino}methyl)-3-phenylpiperidin-1-yl]carbonyl}benzoic acid was added 2.0 mL of a 4 M hydrogen chloride/1,4-dioxane solution. After stirring at room temperature overnight, the reaction mixture was concentrated under reduced pressure.

The obtained residue was heated for dissolution in isopropanol, and diisopropylether was added thereto to give a crude precipitate of a desired product. The precipitate was filtered, and to the obtained white solid was added a saturated aqueous sodium hydrogen carbonate solution, followed by extraction with chloroform. Then, the organic layer was dried over anhydrous sodium sulfate. After filtration, the filtrate was concentrated under reduced pressure, and to the obtained residue was added 0.5 mL of a 4 M hydrogen chloride/1,4-dioxane solution, followed by concentration. The obtained white solid was washed with isopropanol, and dried to obtain 93 mg of 3-{[4-({[(1R)-1-(1-naphthyl)ethyl]amino}methyl)-3-phenylpiperidin-1-yl]carbonyl}benzoic acid hydrochloride as a white solid.

Example 22

(1) A mixture of 100 mg of tert-butyl[(1R)-1-(1-naphthyl)ethyl][(3-phenylpiperidin-4-yl)methyl]carbamate, 57.7 mg of 2,2'-[(tert-butoxycarbonyl)imino]diacetic acid (Fluka), and 51.7 mg of HOBt was dissolved in 1.0 mL of dichloromethane, and 36.5 mg of WSC/hydrochloride was added thereto, followed by stirring at room temperature for 2 days. The reaction mixture was concentrated under reduced pressure, and the residue was purified by silica gel column chromatography (chloroform-methanol) to obtain 139 mg of [(tert-butoxycarbonyl) {2-[4-({(tert-butoxycarbonyl)[(1R)-1-(1-naphthyl)ethyl]amino}methyl)-3-phenylpiperidin-1-yl]-2-oxoethyl}amino]acetic acid as a colorless foamy substance.

(2) To 138 mg of [(tert-butoxycarbonyl){2-[4-({(tert-butoxycarbonyl)[(1R)-1-(1-naphthyl)ethyl]amino}methyl)-3-phenylpiperidin-1-yl]-2-oxoethyl}amino]acetic acid was added 2.0 mL of a 4 M hydrogen chloride/1,4-dioxane solution. After stirring at room temperature for 2 hours, the reaction mixture was concentrated under reduced pressure, and to the obtained residue were added isopropanol and diisopropylether, and the precipitated solid was collected by filtration to obtain 83.9 mg of ({2-[4-({[(1R)-1-(1-naphthyl)ethyl]amino}methyl)-3-phenylpiperidin-1-yl]-2-oxoethyl}amino)acetic acid hydrochloride as a white solid.

Example 23

(1) To a mixture of 139 mg of tert-butyl {[3-(3-fluorophenyl)piperidin-4-yl]methyl}[(1R)-1-(1-naphthyl)ethyl]carbamate, 54 mg of ethyl 4-chloro-4-oxobutanoate, and 4.0 mL of THF was added 0.084 mL of triethylamine at room temperature, followed by stirring for 3 days. To the reaction mixture was added a saturated aqueous ammonium chloride solution, followed by extraction with ethyl acetate. Then, the organic layer was washed with water and saturated brine, and then dried over anhydrous sodium sulfate. After filtration, the filtrate was concentrated under reduced pressure to obtain 177 mg of ethyl 4-[4-({(tert-butoxycarbonyl)[(1R)-1-(1-naphthyl)ethyl]amino}methyl)-3-(3-fluorophenyl)piperidin-1-yl]-4-oxobutanoate as a colorless oily compound. ESI+: 591

(2) To a solution of 177 mg of ethyl 4-[4-({(tert-butoxycarbonyl)[(1R)-1-(1-naphthyl)ethyl]amino}methyl)-3-(3-fluorophenyl)piperidin-1-yl]-4-oxobutanoate in 2.0 mL of ethanol was added 1.00 mL of a 1 M aqueous sodium hydroxide solution at room temperature, followed by stirring for 2 hours. It was neutralized by addition of 1.00 mL of 1 M hydrochloric acid. It was extracted with ethyl acetate, and the organic layer was washed with saturated brine, and then dried over anhydrous sodium sulfate. After filtration, the filtrate was concentrated under reduced pressure to obtain 174 mg of 4-[4-({(tert-butoxycarbonyl)[(1R)-1-(1-naphthyl)ethyl]amino}methyl)-3-(3-fluorophenyl)piperidin-1-yl]-4-oxobutanoic acid as a colorless oily compound. ESI+: 563

(3) To a solution of 174 mg of 4-[4-({(tert-butoxycarbonyl)[(1R)-1-(1-naphthyl)ethyl]amino}methyl)-3-(3-fluorophenyl)piperidin-1-yl]-4-oxobutanoic acid in 1.0 mL of ethyl acetate was added 1.00 mL of a 4 M hydrogen chloride/ethyl acetate solution at room temperature, followed by stirring for 2 hours. Diisopropylether was added thereto, and the resulting precipitate was collected by filtration, and then dried under reduced pressure to obtain 100 mg of 4-[3-(3-fluorophenyl)-4-({[(1R)-1-(1-naphthyl)ethyl]amino}methyl)piperidin-1-yl]-4-oxobutanoic acid hydrochloride as a white solid.

Example 24

(1) A mixed solution of 169 mg of 4-[4-({(tert-butoxycarbonyl)[(1R)-1-(1-naphthyl)ethyl]amino}methyl)-3-(3-fluorophenyl)piperidin-1-yl]-4-oxobutanoic acid, 54 mg of methyl 4-aminobenzoate, 61 mg of WSC/hydrochloride, 45 mg of HOBt, and 2.00 mL of DMF was stirred at room temperature for 2 hours, and a saturated aqueous sodium hydrogen carbonate solution was added thereto. It was extracted with ethyl acetate, and the organic layer was washed with water and saturated brine, and dried over anhydrous sodium sulfate. After filtration, the filtrate was concentrated under reduced pressure to obtain 208 mg of methyl 4-({4-[4-({(tert-butoxycarbonyl)[(1R)-1-(1-naphthyl)ethyl]amino}methyl)-3-(3-fluorophenyl)piperidin-1-yl]-4-oxobutanoyl}amino)benzoate as a pale brown oily compound. ESI+: 696

(2) To a solution of 208 mg of methyl 4-({4-[4-({(tert-butoxycarbonyl)[(1R)-1-(1-naphthyl)ethyl]amino}methyl)-3-(3-fluorophenyl)piperidin-1-yl]-4-oxobutanoyl}amino)benzoate in 2.0 mL of THF and 1.0 mL of methanol was added 1.00 mL of a 1 M aqueous sodium hydroxide solution at room temperature, followed by stirring at 60° C. for 2 hours. The reaction mixture was cooled to room temperature, ethyl acetate and water were added thereto, and a liquid separation operation was conducted. The obtained aqueous layer was neutralized by addition of 1.00 mL of 1 M hydrochloric acid, and then extracted with ethyl acetate. The organic layer was washed with saturated brine, and then dried over anhydrous sodium sulfate. After filtration, the filtrate was concentrated under reduced pressure. The residue was purified by silica gel column chromatography (chloroform-methanol) to obtain 107 mg of 4-({4-[4-({(tert-butoxycarbonyl)[(1R)-1-(1-naphthyl)ethyl]amino}methyl)-3-(3-fluorophenyl)piperidin-1-yl]-4-oxobutanoyl}amino)benzoic acid as a yellow oily compound. ESI−: 680

(3) To a solution of 107 mg of 4-({4-[4-({(tert-butoxycarbonyl)[(1R)-1-(1-naphthyl)ethyl]amino}methyl)-3-(3-fluorophenyl)piperidin-1-yl]-4-oxobutanoyl}amino)benzoic acid in 2.0 mL of ethyl acetate was added 1.00 mL of a 4 M hydrogen chloride/ethyl acetate solution at room temperature, followed by stirring for 2 hours. Diisopropylether was added thereto, and the resulting precipitate was collected by filtration, and dried under reduced pressure to obtain 28 mg of 4-({4-[3-(3-fluorophenyl)-4-({[(1R)-1-(1-naphthyl)ethyl]amino}methyl)piperidin-1-yl]-4-oxobutanoyl}amino)benzoic acid hydrochloride as a pale yellow solid.

Example 25

(1) To a solution of 220 mg of the crude tert-butyl[(1R)-1-(1-naphthyl)ethyl][(3-phenylpiperidin-4-yl)methyl]carbamate and 0.104 mL of triethylamine in 4.0 mL of THF was added 127 mg of methyl 4-[(chlorocarbonyl)oxy]benzoate (Fluka) at room temperature. After stirring at room temperature for 1 hour, the reaction mixture was concentrated under reduced pressure, and the residue was purified by silica gel column chromatography (hexane-ethyl acetate) to obtain 264 mg of 4-(methoxycarbonyl)phenyl 4-({(tert-butoxycarbonyl)[(1R)-1-(1-naphthyl)ethyl]amino}methyl)-3-phenylpiperidine-1-carboxylate in the form of a colorless amorphous substance as a crude product. ESI+: 623

(2) To 260 mg of the obtained crude product of 4-(methoxycarbonyl)phenyl 4-({(tert-butoxycarbonyl)[(1R)-1-(1-naphthyl)ethyl]amino}methyl)-3-phenylpiperidine-1-carboxylate were added 4.0 mL of THF, 2.0 mL of methanol, and 1.0 mL of a 1 M aqueous sodium hydroxide solution, followed by stirring at room temperature overnight. It was neutralized by addition of 1.1 mL of 1 M hydrochloric acid, and then extracted with chloroform, and the organic layer was dried over anhydrous sodium sulfate. After filtration, the filtrate was concentrated under reduced pressure, and the residue was purified by silica gel column chromatography (chloroform-methanol) to obtain 197 mg of 4-({[4-({(tert-butoxycarbonyl)[(1R)-1-(1-naphthyl)ethyl]amino}methyl)-3-phenylpiperidin-1-yl]carbonyl}oxy)benzoic acid as a pale yellow foamy substance. ESI+: 609

(3) To 193 mg of 4-({[4-({(tert-butoxycarbonyl)[(1R)-1-(1-naphthyl)ethyl]amino}methyl)-3-phenylpiperidin-1-yl]carbonyl}oxy)benzoic acid was added 2.0 mL of a 1,4-dioxane, and 2.0 mL of a 4 M hydrogen chloride/1,4-dioxane solution, followed by stirring at room temperature for 5 hours. The reaction mixture was concentrated under reduced pressure, the residue was heated in isopropanol under reflux, and the mixture was left to be cooled at room temperature. The precipitate was collected by filtration, and dried under reduced pressure to obtain 117 mg of 4-({[4-({[(1R)-1-(1-naphthyl)ethyl]amino}methyl)-3-phenylpiperidin-1-yl]carbonyl}oxy)benzoic acid hydrochloride as a white solid.

Example 26

(1) To a suspension of 5.000 g of methyl 3-hydroxybenzoate, 6.955 g of 4-nitrophenyl chloroformate, and 100 mL of toluene was added 4.81 mL of triethylamine at room temperature, followed by stirring overnight. The insolubles were removed by filtration, and as solvent was removed by distillation under reduced pressure to obtain 5.948 g of methyl 3-{[(4-nitrophenoxy)carbonyl]oxy}benzoate as a pale yellow solid. To a mixture of 100 mg of methyl 3-{[(4-nitrophenoxy)carbonyl]oxy}benzoate, 139 mg of tert-butyl {[3-(3-fluorophenyl)piperidin-4-yl]methyl}[(1R)-1-(1-naphthyl)ethyl]carbamate, and 4 ml of THF was added 0.084 mL of triethylamine at room temperature, followed by stirring overnight. A saturated aqueous sodium hydrogen carbonate solution was added thereto, followed by extraction with ethyl acetate. The organic layer was washed with water and saturated brine, and dried over anhydrous sodium sulfate. After filtration, the filtrate was concentrated under reduced pressure to obtain 196 mg of 3-(methoxycarbonyl)phenyl 4-({(tert-butoxycarbonyl)[(1R)-1-(1-naphthyl)ethyl]amino}methyl)-3-(3-fluorophenyl)piperidine-1-carboxylate as a pale yellow oily compound.

(2) To a solution of 196 mg of 3-(methoxycarbonyl)phenyl 4-({(tert-butoxycarbonyl)[(1R)-1-(1-naphthyl)ethyl]amino}methyl)-3-(3-fluorophenyl)piperidine-1-carboxylate in 2.0 mL of THF and 1.0 mL of methanol was added 1.00 mL of a 1 M aqueous sodium hydroxide solution at room temperature, followed by stirring for 1 hour. To the reaction mixture were added ethyl acetate and water, and a liquid separation operation was then conducted. The obtained aqueous layer was neutralized by addition of 1.00 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 88 mg of 3-({[4-({(tert-butoxycarbonyl)[(1R)-1-(1-naphthyl)ethyl]amino}methyl)-3-(3-fluorophenyl)piperidin-1-yl]carbonyl}oxy)benzoic acid. ESI−: 625

(3) To a solution of 88 mg of 3-({[4-({(tert-butoxycarbonyl)[(1R)-1-(1-naphthyl)ethyl]amino}methyl)-3-(3-fluorophenyl)piperidin-1-yl]carbonyl}oxy)benzoic acid in 2.0 mL of ethyl acetate was added 1.00 mL of a 4 M hydrogen chloride/ethyl acetate solution at room temperature, followed by stirring for 2 hours. The resulting precipitate was collected by filtration, and dried under reduced pressure to obtain 22 mg of 3-({[3-(3-fluorophenyl)-4-({[(1R)-1-(1-naphthyl)ethyl]amino}methyl)piperidin-1-yl]carbonyl}oxy)benzoic acid hydrochloride as a white solid.

Example 27

(1) To a solution of 181 mg of the crude tert-butyl[(1R)-1-(1-naphthyl)ethyl][(3-phenylpiperidin-4-yl)methyl]carbamate and 0.114 mL of triethylamine and 2.7 mL of THF was added 117 mg of ethyl 4-isocyanatobenzoate at room temperature. The reaction vessel was tightly sealed, followed by stirring at 100° C. overnight. The reaction mixture was cooled to room temperature, and a saturated aqueous sodium hydrogen carbonate solution was then added thereto, followed by extraction with chloroform. Then, the organic layer was dried over anhydrous sodium sulfate. After filtration, the filtrate was concentrated under reduced pressure to obtain 357 mg of ethyl 4-({[4-({(tert-butoxycarbonyl)[(1R)-1-(1-naphthyl)ethyl]amino}methyl)-3-phenylpiperidin-1-yl]carbonyl}amino)benzoate as a crude product. ESI+: 636

(2) To 355 mg of the obtained crude product of ethyl 4-({[4-({(tert-butoxycarbonyl)[(1R)-1-(1-naphthyl)ethyl]amino}methyl)-3-phenylpiperidin-1-yl]carbonyl}amino)benzoate were added 4.0 mL of THF, 2.0 mL of methanol, and 2.0 mL of a 1 M aqueous sodium hydroxide solution, followed by stirring at room temperature overnight. It was neutralized by addition of 2.2 mL of 1 M hydrochloric acid, and then extracted with chloroform, and the organic layer was dried over anhydrous sodium sulfate. After filtration, the filtrate was concentrated under reduced pressure, and the residue was purified by silica gel column chromatography (chloroform-methanol) to obtain 291 mg of 4-({[4-({(tert-butoxycarbonyl)[(1R)-1-(1-naphthyl)ethyl]amino}methyl)-3-phenylpiperidin-1-yl]carbonyl}amino)benzoic acid as a crude product. ESI+: 608

(3) To 289 mg of the crude product of 4-({[4-({(tert-butoxycarbonyl)[(1R)-1-(1-naphthyl)ethyl]amino}methyl)-3-phenylpiperidin-1-yl]carbonyl}amino)benzoic acid was added 2.0 mL of a 4 M hydrogen chloride/1,4-dioxane solution, followed by stirring at room temperature for 2 hours. The reaction mixture was concentrated under reduced pressure, and the residue was then heated under reflux for dissolution in isopropanol. Diisopropylether was added dropwise thereto, and the precipitate was isolated by filtration, and dried under reduced pressure to obtain 159 mg of 4-({[4-({[(1R)-1-(1-naphthyl)ethyl]amino}methyl)-3-phenylpiperidin-1-yl]carbonyl}amino)benzoic acid hydrochloride as a white solid.

Example 28

(1) To a solution of 181 mg of the crude tert-butyl[(1R)-1-(1-naphthyl)ethyl][(3-phenylpiperidin-4-yl)methyl]carbamate and 0.114 mL of triethylamine in 3.0 mL of THF was added 171 mg of methyl 3-chloro-4-{[(4-nitrophenoxy)carbonyl]amino}benzoate at room temperature, followed by stirring overnight. To the reaction mixture was added a saturated aqueous sodium hydrogen carbonate solution, followed by extraction with chloroform, and the organic layer was dried over anhydrous sodium sulfate. After filtration, the filtrate was concentrated under reduced pressure to obtain 352 mg of methyl 4-({[4-({(tert-butoxycarbonyl)[(1R)-1-(1-naphthyl)ethyl]amino}methyl)-3-phenylpiperidin-1-yl]carbonyl}amino)-3-chlorobenzoate as a crude product. ESI+: 656

(2) To 347 mg of the obtained crude product of methyl 4-({[4-({(tert-butoxycarbonyl)[(1R)-1-(1-naphthyl)ethyl]amino}methyl)-3-phenylpiperidin-1-yl]carbonyl}amino)-3- chlorobenzoate were added 4.0 mL of THF, 2.0 mL of methanol, and 2.0 mL of a 1 M aqueous sodium hydroxide solution, followed by stirring at room temperature overnight. It was neutralized by addition of 2.2 mL of 1 M hydrochloric acid, extracted with chloroform, and the organic layer was dried over anhydrous sodium sulfate. After filtration, the filtrate was concentrated under reduced pressure, and the residue was purified by silica gel column chromatography (chloroform-methanol) to obtain 306 mg of 4-({[4-({(tert-butoxycarbonyl)[(1R)-1-(1-naphthyl)ethyl]amino}methyl)-3-phenylpiperidin-1-yl]carbonyl}amino)-3-chlorobenzoic acid as a crude product. ESI+: 642

(3) To 302 mg of the crude product of 4-({[4-({(tert-butoxycarbonyl)[(1R)-1-(1-naphthyl)ethyl]amino}methyl)-3-phenylpiperidin-1-yl]carbonyl}amino)-3-chlorobenzoic acid was added 2.0 mL of a 4 M hydrogen chloride/1,4-dioxane solution, followed by stirring at room temperature for 2 hours. The reaction mixture was concentrated under reduced pressure, and to the residue was then added isopropanol, followed by heating under reflux. The mixture was cooled to room temperature, and the precipitate was then isolated by filtration, and dried under reduced pressure to obtain 147 mg of 3-chloro-4-({[4-({[(1R)-1-(1-naphthyl)ethyl]amino}methyl)-3-phenylpiperidin-1-yl]carbonyl}amino)benzoic acid hydrochloride as a white solid.

Example 29

(1) To a solution of 231 mg of tert-butyl {[3-(3-fluorophenyl)piperidin-4-yl]methyl}[(1R)-1-(1-naphthyl)ethyl]carbamate and 210 mg of methyl 3-chloro-4-{[(4-nitrophenoxy)carbonyl]amino}benzoate in 4.0 mL of THF was added 0.139 mL of triethylamine at room temperature, followed by stirring overnight. To the reaction mixture was added a saturated aqueous sodium hydrogen carbonate solution, followed by extraction with ethyl acetate. The organic layer was washed with water and saturated brine in this order, and dried over anhydrous sodium sulfate. After filtration, the filtrate was concentrated under reduced pressure to obtain 394 mg of a pale yellow foamy substance of methyl 4-({[4-({(tert-butoxycarbonyl)[(1R)-1-(1-naphthyl)ethyl]amino}methyl)-3-(3-fluorophenyl)piperidin-1-yl]carbonyl}amino)-3-chlorobenzoate as a crude product. ESI+: 674

(2) 241 mg of the crude methyl 4-({[4-({(tert-butoxycarbonyl)[(1R)-1-(1-naphthyl)ethyl]amino}methyl)-3-(3-fluorophenyl)piperidin-1-yl]carbonyl}amino)-3-chlorobenzoate was dissolved in a solution of 4.0 mL of a 4 M hydrogen chloride/1,4-dioxane solution at room temperature, followed by stirring overnight. The reaction mixture was concentrated under reduced pressure, and the residue was then purified by silica gel column chromatography (chloroform-methanol) to obtain a yellow oily compound of methyl 3-chloro-4-({[4-(3-fluorophenyl)-3-({[(1R)-1-(1-naphthyl)ethyl]amino}methyl)piperidin-1-yl]carbonyl}amino)benzoate as a crude product.

(3) To a mixed solution of the obtained crude methyl 3-chloro-4-({[4-(3-fluorophenyl)-3-({[(1R)-1-(1-naphthyl)ethyl]amino}methyl)piperidin-1-yl]carbonyl}amino)benzoate, 2.0 mL of methanol, and 2.0 mL of THF was added 2.00 mL of a 1 M aqueous sodium hydroxide solution at room temperature, followed by stirring at 65° C. for 2.5 hours. The reaction mixture was cooled to room temperature, the aqueous layer was then washed with ethyl acetate, and the aqueous layer was neutralized by addition of 1 M hydrochloric acid, and extracted with ethyl acetate.

The organic layer was washed with saturated brine, and dried over anhydrous sodium sulfate. After filtration, the filtrate was concentrated under reduced pressure to obtain 3-chloro-4-({[3-(3-fluorophenyl)-4-({[(1R)-1-(1-naphthyl)ethyl]amino}methyl)piperidin-1-yl]carbonyl}amino)benzoic acid as a crude product.

(4) To a mixed solution of the obtained crude 3-chloro-4-({[3-(3-fluorophenyl)-4-({[(1R)-1-(1-naphthyl)ethyl]amino}methyl)piperidin-1-yl]carbonyl}amino)benzoic acid in 2.0 mL of methanol and 2.0 mL of THF was added 1.00 mL of a 4 M hydrogen chloride/ethyl acetate solution at room temperature, followed by stirring for 3 hours.

The reaction mixture was concentrated under reduced pressure, and the residue was washed with ethyl acetate and THF, and isolated by collection through filtration. It was dried under reduced pressure to obtain 92 mg of 3-chloro-4-({[3-(3-fluorophenyl)-4-({[(1R)-1-(1-naphthyl)ethyl]amino}methyl)piperidin-1-yl]carbonyl}amino)benzoic acid hydrochloride as a white solid.

Example 30

(1) A mixture of 100 mg of tert-butyl[(1R)-1-(1-naphthyl)ethyl][(3-phenylpiperidin-4-yl)methyl]carbamate, 46 mg of ethyl 6-chloropyridine-2-carboxylate, 37 mg of potassium carbonate, and 2.0 mL of DMSO was stirred at 100° C. overnight.

The reaction mixture was cooled to room temperature, and water was added thereto, followed by extraction with ethyl acetate. The organic layer was washed with saturated brine, and dried over anhydrous sodium sulfate. After filtration, the filtrate was concentrated under reduced pressure. The residue was purified by silica gel column chromatography (hexane-ethyl acetate) to obtain 75 mg of ethyl 6-[4-({(tert-butoxycarbonyl)[(1R)-1-(1-naphthyl)ethyl]amino}methyl)-3-phenylpiperidin-1-yl]pyridine-2-carboxylate as a colorless resinous compound. ESI+: 594

(2) To a solution of 75 mg of ethyl 6-[4-({(tert-butoxycarbonyl)[(1R)-1-(1-naphthyl)ethyl]amino}methyl)-3-phenylpiperidin-1-yl]pyridine-2-carboxylate in 2.0 mL of THF and 1.0 mL of methanol was added 1.00 mL of a 1 M aqueous sodium hydroxide solution at room temperature, followed by stirring overnight. It was neutralized by addition of 1.00 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 75 mg of a colorless resinous compound of 6-[4-({(tert-butoxycarbonyl)[(1R)-1-(1-naphthyl)ethyl]amino}methyl)-3-phenylpiperidin-1-yl]pyridine-2-carboxylic acid as a crude product. ESI+: 566

(3) To a solution of 75 mg of the crude 6-[4-({(tert-butoxycarbonyl)[(1R)-1-(1-naphthyl)ethyl]amino}methyl)-3-phenylpiperidin-1-yl]pyridine-2-carboxylic acid in 2.0 mL of ethyl acetate was added 1.00 mL of a 4 M hydrogen chloride/ethyl acetate solution at room temperature, followed by stirring for 2 hours. To the reaction mixture was added diisopropylether, and the resulting precipitate was then collected by filtration, and dried under reduced pressure to obtain 50 mg of 6-[4-({[(1R)-1-(1-naphthyl)ethyl]amino}methyl)-3-phenylpiperidin-1-yl]pyridine-2-carboxylic acid hydrochloride as a pale yellow solid.

Example 31

(1) To a mixture of 100 mg of tert-butyl[(1R)-1-(1-naphthyl)ethyl][(3-phenylpiperidin-4-yl)methyl]carbamate, 59.4 mg of ethyl 5,6-dichloronicotinate, and 37.3 mg of potassium carbonate was added 2.0 mL of DMSO at room temperature, and the mixed solution was stirred at 100° C. overnight. After cooling to room temperature, water was added thereto. After extraction with ethyl acetate, the organic layer was dried over anhydrous sodium sulfate. After filtration, the filtrate was concentrated under reduced pressure, and the residue was purified by silica gel column chromatography (hexane-ethyl acetate) to obtain 128 mg of ethyl 6-[4-({(tert-butoxycarbonyl)[(1R)-1-(1-naphthyl)ethyl]amino}methyl)-3-phenylpiperidin-1-yl]-5-chloronicotinate as a colorless foamy substance. FAB+: 628

(2) To 126 mg of ethyl 6-[4-({(tert-butoxycarbonyl)[(1R)-1-(1-naphthyl)ethyl]amino}methyl)-3-phenylpiperidin-1-yl]-5-chloronicotinte was added a solution of 2.0 mL of THF, 1.0 mL of methanol, and 1.0 mL of a 1 M aqueous sodium hydroxide solution, followed by stirring at room temperature for 2 days. It was neutralized by addition of 1.1 mL of 1 M hydrochloric acid, and then extracted with ethyl acetate, and the organic layer was dried over anhydrous sodium sulfate. After filtration, the filtrate was concentrated under reduced pressure, and dried to obtain 6-[4-({(tert-butoxycarbonyl)[(1R)-1-(1-naphthyl)ethyl]amino}methyl)-3-phenylpiperidin-1-yl]-5-chloronicotinic acid as a crude product (colorless foamy substance, 142 mg).

(3) To 141 mg of the crude product of 6-[4-({(tert-butoxycarbonyl)[(1R)-1-(1-naphthyl)ethyl]amino}methyl)-3-phenylpiperidin-1-yl]-5-chloronicotinic acid was added 2.0 mL of a 4 M hydrogen chloride/1,4-dioxane solution. After stirring at room temperature for 2 hours, the reaction mixture was concentrated under reduced pressure, and to the obtained residue were added ethanol, followed by crystallization to obtain 49.8 mg of 5-chloro-6-[4-({[(1R)-1-(1-naphthyl)ethyl]amino}methyl)-3-phenylpiperidin-1-yl]nicotinic acid hydrochloride as a white solid.

Example 32

(1) A mixture of 116 mg of tert-butyl {[3-(2-fluorophenyl)piperidin-4-yl]methyl}[(1R)-1-(1-naphthyl)ethyl]carbamate, 66 mg of ethyl 5,6-dichloronicotinate, 42 mg of potassium carbonate, and 2.0 mL of DMSO was stirred at 100° C. overnight.

It was left to be cooled to room temperature, water was added to the reaction mixture, and the resulting precipitate was collected by filtration. It was dried under reduced pressure to obtain 110 mg of a white solid of ethyl 6-[4-({(tert-butoxycarbonyl)[(1R)-1-(1-naphthyl)ethyl]amino}methyl)-3-(2-fluorophenyl)piperidin-1-yl]-5-chloronicotinate as a crude product. ESI+: 646

(2) To a solution of the crude ethyl 6-[4-({(tert-butoxycarbonyl)[(1R)-1-(1-naphthyl)ethyl]amino}methyl)-3-(2-fluorophenyl)piperidin-1-yl]-5-chloronicotinate obtained in the aforementioned reaction in 2.0 mL of THF and 1.0 mL of methanol was added 1.00 mL of a 1 M aqueous sodium hydroxide solution, followed by stirring at room temperature overnight. It was neutralized by addition of 1.00 mL of 1 M hydrochloric acid, and extracted with ethyl acetate. The organic layer was washed with saturated brine, and dried over anhydrous sodium sulfate. After filtration, the filtrate was concentrated under reduced pressure to obtain 115 mg of a pale yellow amorphous compound of 6-[4-({(tert-butoxycarbonyl)[(1R)-1-(1-naphthyl)ethyl]amino}methyl)-3-(2-fluorophenyl)piperidin-1-yl]-5-chloronicotinic acid as a crude product. ESI+: 618

(3) To a solution of the crude 6-[4-({(tert-butoxycarbonyl)[(1R)-1-(1-naphthyl)ethyl]amino}methyl)-3-(2-fluorophenyl)piperidin-1-yl]-5-chloronicotinic acid obtained in the aforementioned reaction in 2.0 mL of ethyl acetate was added 1.00 mL of a 4 M hydrogen chloride/ethyl acetate solution, followed by stirring at room temperature for 2 hours. The reaction mixture was concentrated under reduced pressure, and the residue was purified by reverse phase silica gel column chromatography (acetonitrile-0.01 M hydrochloric acid) to obtain 56 mg of 5-chloro-6-[3-(2-fluorophenyl)-4-({[(1R)-1-(1-naphthyl)ethyl]amino}methyl)piperidin-1-yl]nicotinic acid hydrochloride as a white solid.

Example 33

(1) To a mixture of 119 mg of the crude tert-butyl[(1R)-1-(3-methoxyphenyl)ethyl][(3-phenylpiperidin-4-yl)methyl]carbamate, 62 mg of ethyl 5,6-dichloronicotinate, and 39 mg of potassium carbonate was added 1.0 mL of DMSO at room temperature, and the mixed solution was stirred at 100° C. overnight. After cooling to room temperature, to the reaction mixture was added water, followed by extraction with ethyl acetate, and the organic layer was then dried over anhydrous sodium sulfate. After filtration, the filtrate was concentrated under reduced pressure, and the residue was purified by silica gel column chromatography (hexane-ethyl acetate) to obtain 132 mg of ethyl 6-[4-({(tert-butoxycarbonyl)[(1R)-1-(3-methoxyphenyl)ethyl]amino}methyl)-3-phenylpiperidin-1-yl]-5-chloronicotinate as a colorless foamy substance. FAB+: 608

(2) To 131 mg of ethyl 6-[4-({(tert-butoxycarbonyl)[(1R)-1-(3-methoxyphenyl)ethyl]amino}methyl)-3-phenylpiperidin-1-yl]-5-chloronicotinate were added 2.0 mL of THF, 1.0 mL of methanol, and 1.0 mL of a 1 M aqueous sodium hydroxide solution, followed by stirring at room temperature for 2 days. It was neutralized by addition of 1.1 mL of 1 M hydrochloric acid, and then extracted with ethyl acetate, and the organic layer was dried over anhydrous sodium sulfate. After filtration, the filtrate was concentrated under reduced pressure, and dried to obtain 143 mg of a colorless foamy substance of 6-[4-({(tert-butoxycarbonyl)[(1R)-1-(3-methoxyphenyl)ethyl]amino}methyl)-3-phenylpiperidin-1-yl]-5-chloronicotinic acid as a crude product. ESI+: 580

(3) To 142 mg of the crude product of 6-[4-({(tert-butoxycarbonyl)[(1R)-1-(3-methoxyphenyl)ethyl]amino}methyl)-3-phenylpiperidin-1-yl]-5-chloronicotinic acid was added 2.0 mL of a 4 M hydrogen chloride/1,4-dioxane solution. After stirring at room temperature for 2 hours, the reaction mixture was concentrated under reduced pressure, and to the obtained residue was added ethanol and ethyl acetate, followed by heating under reflux, and then being left to be cooled to room temperature. Then, the precipitate was collected by filtration, and dried under reduced pressure to obtain 78 mg of 5-chloro-6-[4-({[(1R)-1-(3-methoxyphenyl)ethyl]amino}methyl)-3-phenylpiperidin-1-yl]nicotinic acid hydrochloride as a white solid.

Example 34

(1) To a mixture of 2.3 mg of tris(dibenzylideneacetone)dipalladium(0), 1.9 mg of 2-(dicyclohexylphosphino)-2'-(dimethylamino)biphenyl, and 0.5 mL of 1,4-dioxane were added 100 mg of tert-butyl[(1R)-1-(1-naphthyl)ethyl][(3-phenylpiperidin-4-yl)methyl]carbamate, 83.8 mg of ethyl 3-iodobenzoate, 105 mg of cesium carbonate, 1.0 mL of 1,4-dioxane, and 1.5 mL of t-butanol, followed by stirring at 100° C. overnight. After cooling to room temperature, to the reaction mixture was added ethyl acetate, the insolubles were removed, and the solvent was removed by distillation under reduced pressure. The residue was purified by silica gel column chromatography (hexane-ethyl acetate) to obtain 108 mg of ethyl 3-[4-({(tert-butoxycarbonyl)[(1R)-1-(1-naphthyl)ethyl]amino}methyl)-3-phenylpiperidin-1-yl]benzoate as a pale yellow foamy substance. ESI+: 593

(2) To 107 mg of ethyl 3-[4-({(tert-butoxycarbonyl)[(1R)-1-(1-naphthyl)ethyl]amino}methyl)-3-phenylpiperidin-1-yl]benzoate were added 2.0 mL of THF, 1.0 mL of methanol, and 1.0 mL of a 1 M aqueous sodium hydroxide solution, followed by stirring at room temperature for 2 days. It was neutralized by addition of 1.1 mL of 1 M hydrochloric acid, and then extracted with ethyl acetate, and the organic layer was dried over anhydrous sodium sulfate. After filtration, the filtrate was concentrated under reduced pressure, and the residue was purified by silica gel column chromatography (chloroform-methanol) to obtain 100 mg of 3-[4-({(tert-butoxycarbonyl)[(1R)-1-(1-naphthyl)ethyl]amino}methyl)-3-phenylpiperidin-1-yl]benzoic acid as a colorless foamy substance. ESI+: 565

(3) To 99 mg of 3-[4-({(tert-butoxycarbonyl)[(1R)-1-(1-naphthyl)ethyl]amino}methyl)-3-phenylpiperidin-1-yl]benzoic acid was added 2.0 mL of a 4 M hydrogen chloride/1,4-dioxane solution of hydrochloric acid. After stirring at room temperature for 2 hours, the reaction mixture was concentrated under reduced pressure, and to the obtained residue were added THF and isopropanol, followed by solidification to obtain 76 mg of 3-[4-({[(1R)-1-(1-naphthyl)ethyl]amino}methyl)-3-phenylpiperidin-1-yl]benzoic acid hydrochloride as a white solid.

Example 35

(1) A mixture of 100 mg of tert-butyl {[3-(2-fluorophenyl)piperidin-4-yl]methyl}[(1R)-1-(1-naphthyl)ethyl]carbamate, 2 mg of 2-dicyclohexylphosphino-2'-(N,N-dimethylamino)biphenyl, 2 mg of tris(dibenzylideneacetone)palladium(0), 106 mg of cesium carbonate, 84 mg of ethyl 3-iodobenzoate, 1.50 mL of t-butyl alcohol, and 1.50 mL of 1,4-dioxane, followed by stirring at 100° C. overnight. The reaction mixture was cooled to room temperature, and then diluted with ethyl acetate, and the insolubles were removed by filtration. The filtrate was concentrated under reduced pressure to obtain 172 mg of a pale yellow oily compound of ethyl 3-[4-({(tert-butoxycarbonyl)[(1R)-1-(1-naphthyl)ethyl]amino}methyl)-3-(2-fluorophenyl)piperidin-1-yl]benzoate as a crude product. ESI+: 611

(2) To a solution of 172 mg of the crude ethyl 3-[4-({(tert-butoxycarbonyl)[(1R)-1-(1-naphthyl)ethyl]amino}methyl)-3-(2-fluorophenyl)piperidin-1-yl]benzoate in 2.0 mL of THF and 1.0 mL of methanol was added 1.00 mL of a 1 M aqueous sodium hydroxide solution at room temperature, followed by stirring overnight. It was stirred at 85° C. for 1 hour. 0.50 mL of a 1 M aqueous sodium hydroxide solution was added thereto, for followed by stirring at 85° C. for 1 hour. The reaction mixture was cooled to room temperature, then neutralized by addition of 1.50 mL of 1 M hydrochloric acid, and extracted with ethyl acetate. The organic layer was washed with saturated brine, and dried over anhydrous sodium sulfate. After filtration, the filtrate was concentrated under reduced pressure to obtain a pale yellow oily compound of 161 mg of 3-[4-({(tert-butoxycarbonyl)[(1R)-1-(1-naphthyl)ethyl]amino}methyl)-3-(2-fluorophenyl)piperidin-1-yl]benzoic acid as a crude product. ESI+: 583

(3) To a solution of 161 mg of the crude 3-[4-({(tert-butoxycarbonyl)[(1R)-1-(1-naphthyl)ethyl]amino}methyl)-3-(2-fluorophenyl)piperidin-1-yl]benzoic acid in 2.0 mL of ethyl acetate was added 1.00 mL of a 4 M hydrogen chloride/ethyl acetate solution at room temperature, followed by stirring for 1 hour. The solvent was removed by distillation under reduced pressure. The residue was purified by reverse phase silica gel column chromatography (acetonitrile-0.001 M hydrochloric acid) to obtain 58 mg of 3-[3-(2-fluorophenyl)-4-({[(1R)-1-(1-naphthyl)ethyl]amino}methyl)piperidin-1-yl]benzoic acid hydrochloride as a white solid.

Example 36

(1) A mixture of 100 mg of tert-butyl[(1R)-1-(1-naphthyl)ethyl][(3-phenylpiperidin-4-yl)methyl]carbamate, 56 mg of methyl 2,6-dichloroisonicotinate, 95 mg of potassium phosphate, 6 mg of bis(tri-tert-butylphosphine)palladium(0), and 2.0 mL of dimethylacetamide was stirred at 100° C. overnight. The reaction mixture was cooled to room temperature, and water was added thereto, followed by extraction with ethyl acetate. The organic layer was washed with saturated brine, and dried over anhydrous sodium sulfate. After filtration, the filtrate was concentrated under reduced pressure. The residue was purified by silica gel column chromatography (hexane-ethyl acetate) to obtain 66 mg of methyl 2-[4-({(tert-butoxycarbonyl)[(1R)-1-(1-naphthyl)ethyl]amino}methyl)-3-phenylpiperidin-1-yl]-6-chloroisonicotinate as a pale yellow oily compound. ESI+: 614

(2) To a solution of 66 mg of methyl 2-[4-({(tert-butoxycarbonyl)[(1R)-1-(1-naphthyl)ethyl]amino}methyl)-3-phenylpiperidin-1-yl]-6-chloroisonicotinate in 2.0 ml of THF and 1.0 mL of methanol was added 1.00 mL of a 1 M aqueous sodium hydroxide solution at room temperature, followed by stirring overnight. It was neutralized by addition of 1.00 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 68 mg of 2-[4-({(tert-butoxycarbonyl)[(1R)-1-(1-naphthyl)ethyl]amino}methyl)-3-phenylpiperidin-1-yl]-6-chloroisonicotinic acid as a pale yellow resinous compound. ESI+: 600

(3) To a solution of 68 mg of 2-[4-({(tert-butoxycarbonyl)[(1R)-1-(1-naphthyl)ethyl]amino}methyl)-3-phenylpiperidin-1-yl]-6-chloroisonicotinic acid in 1.0 mL of 1,4-dioxane was added 1.00 mL of a 4 M hydrogen chloride/ethyl acetate solution at room temperature, followed by stirring for 2 hours. The solvent was removed by distillation under reduced pressure. The residue was washed with diisopropylether, and dried under reduced pressure to obtain 29 mg of 2-chloro-6-[4-({[(1R)-1-(1-naphthyl)ethyl]amino}methyl)-3-phenylpiperidin-1-yl]isonicotinic acid hydrochloride as a pale yellow solid.

Example 37

(1) A mixture of 216 mg of tert-butyl {[3-(3-fluorophenyl)piperidin-4-yl]methyl}[(1R)-1-(1-naphthyl)ethyl]carbamate, 80 mg of benzoyl isothiocyanate, and 2.00 mL of toluene was stirred at room temperature for 2 hours. The solvent was removed by distillation under reduced pressure. To the residue were added 2.0 mL of methanol, and then 0.24 mL of a 9.8 M solution of methylamine in methanol at room temperature, followed by stirring for 2 days. The solvent was removed by distillation under reduced pressure to obtain 303 mg of a pale orange amorphous compound of tert-butyl {[1-(aminocarbonothioyl)-3-(3-fluorophenyl)piperidin-4-yl]methyl}[(1R)-1-(1-naphthyl)ethyl]carbamate as a crude product. ESI+: 522

(2) To a solution of 303 mg of the crude tert-butyl {[1-(aminocarbonothioyl)-3-(3-fluorophenyl)piperidin-4-yl]methyl}[(1R)-1-(1-naphthyl)ethyl]carbamate and 182 mg of ethyl bromopyrubate in 2.0 ml of ethanol was added 2.8 mL of a 1 M aqueous sodium hydroxide solution at room temperature. It was stirred at 85° C. for 3 hours. The reaction mixture was cooled to room temperature, and then concentrated under reduced pressure. To the residue were added water and diethylether, followed by a liquid separation operation. The obtained aqueous layer was acidified by addition of 1 M hydrochloric acid, and extracted with ethyl acetate. The organic layer was washed with saturated brine, and dried over anhydrous sodium sulfate. After filtration, the filtrate was concentrated under reduced pressure to obtain an orange oily compound of 198 mg of 2-[4-({(tert-butoxycarbonyl)[(1R)-1-(1-naphthyl)ethyl]amino}methyl)-3-(3-fluorophenyl)piperidin-1-yl]-1,3-thiazole-4-carboxylic acid as a crude product. ESI+: 590

(3) To a solution of 198 mg of the crude 2-[4-({(tert-butoxycarbonyl)[(1R)-1-(1-naphthyl)ethyl]amino}methyl)-3-(3-fluorophenyl)piperidin-1-yl]-1,3-thiazole-4-carboxylic acid in 2.0 ml of THF was added 1.00 ml of a 4 M aqueous hydrogen chloride/ethyl acetate solution at room temperature, followed by stirring for 1 hour.

The resulting precipitate was collected by filtration, and dried under reduced pressure to obtain 20 mg of 2-[3-(3-fluorophenyl)-4-({[(1R)-1-(1-naphthyl)ethyl]amino}methyl)piperidin-1-yl]-1,3-thiazole-4-carboxylic acid hydrochloride as a white solid.

Example 38

(1) A mixture of 125 mg of the crude tert-butyl {[1-(aminocarbonothioyl)-3-(3-fluorophenyl)piperidin-4-yl]methyl}[(1R)-1-(1-naphthyl)ethyl]carbamate obtained in Example 37 (1), 50 mg of magnesium sulfate, 2000 mg of ethyl 2-chloro-3-oxopropanate (5% benzene suspension), and 5.0 mL of acetone was stirred at 65° C. for 4 hours. The reaction mixture was cooled to room temperature, the insolubles were then separated by filtration, and the filtrate was concentrated under reduced pressure to obtain 223 mg of a pale yellow oily compound of ethyl 2-[4-({(tert-butoxycarbonyl)[(1R)-1-(1-naphthyl)ethyl]amino}methyl)-3-(3-fluorophenyl)piperidin-1-yl]-1,3-thiazole-5-carboxylate. ESI+: 618

(2) To a solution of 223 mg of the crude ethyl 2-[4-({(tert-butoxycarbonyl)[(1R)-1-(1-naphthyl)ethyl]amino}methyl)-3-(3-fluorophenyl)piperidin-1-yl]-1,3-thiazole-5-carboxylate in 2.0 mL of THF and 1.0 mL of methanol was added 1.50 mL of a 1 M aqueous sodium hydroxide solution at room temperature. It was stirred at 85° C. for 1 hour. The reaction mixture was cooled to room temperature, neutralized by addition of 1.50 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 172 mg of a pale yellow oily compound of 2-[4-({(tert-butoxycarbonyl)[(1R)-1-(1-naphthyl)ethyl]amino}methyl)-3-(3-fluorophenyl)piperidin-1-yl]-1,3-thiazole-5-carboxylic acid as a crude product. ESI+: 590

(3) To a solution of 172 mg of the crude 2-[4-({(tert-butoxycarbonyl)[(1R)-1-(1-naphthyl)ethyl]amino}methyl)-3-(3-fluorophenyl)piperidin-1-yl]-1,3-thiazole-5-carboxylic acid in 2.0 mL of THF was added 1.00 mL of a 4 M hydrogen chloride/ethyl acetate solution at room temperature, followed by stirring for 1 hour. The solvent was removed by distillation under reduced pressure. The residue was purified by reverse phase silica gel column chromatography (acetonitrile-0.001 M hydrochloric acid) to obtain 19 mg of 2-[3-(3-fluorophenyl)-4-({[(1R)-1-(1-naphthyl)ethyl]amino}methyl)piperidin-1-yl]-1,3-thiazole-5-carboxylic acid hydrochloride as a white solid.

Example 39

(1) To a mixture of 136 mg of the crude tert-butyl[(1R)-1-(1-naphthyl)ethyl][(3-phenylpiperidin-4-yl)methyl]carbamate, 64 mg of methyl 2-bromo-1,3-thiazole-4-carboxylate, and 38 mg of potassium carbonate was added 1.5 mL of DMSO at room temperature, and the mixed solution was stirred at room temperature overnight. To the reaction mixture was added water, followed by extraction with ethyl acetate, and the organic layer was then washed with water and saturated brine in this order, and then dried over anhydrous sodium sulfate. After filtration, the filtrate was concentrated under reduced pressure, and the residue was purified by silica gel column chromatography (hexane-ethyl acetate) to obtain 113 mg of methyl 2-[4-({(tert-butoxycarbonyl)[(1R)-1-(1-naphthyl)ethyl]amino}methyl)-3-phenylpiperidin-1-yl]-1,3-thiazole-4-carboxylate as a colorless foamy substance. ESI+: 586

(2) To 112 mg of methyl 2-[4-({(tert-butoxycarbonyl)[(1R)-1-(1-naphthyl)ethyl]amino}methyl)-3-phenylpiperidin-1-yl]-1,3-thiazole-4-carboxylate were added 2.0 mL of THF, 1.0 mL of methanol and 1.0 mL of a 1 M aqueous sodium hydroxide solution, followed by stirring at 60° C. overnight. To the mixture was added 1.1 mL of 1 M hydrochloric acid, followed by concentration under reduced pressure, and to the residue were added chloroform and anhydrous sodium sulfate. After filtration, the filtrate was concentrated under reduced pressure, and dried to obtain 116 mg of a colorless foamy substance of 2-[4-({(tert-butoxycarbonyl)[(1R)-1-(1-naphthyl)ethyl]amino}methyl)-3-phenylpiperidin-1-yl]-1,3-thiazole-4-carboxylic acid as a crude product.

(3) To 116 mg of the crude product of 2-[4-({(tert-butoxycarbonyl)[(1R)-1-(1-naphthyl)ethyl]amino}methyl)-3-phenylpiperidin-1-yl]-1,3-thiazole-4-carboxylic acid was added 2.0 mL of a 4 M hydrogen chloride/1,4-dioxane solution. After stirring at room temperature for 2 hours, the reaction mixture was concentrated under reduced pressure, and to the obtained residue were added isopropanol and ethyl acetate, followed by heating under reflux, and then being left to be cooled to room temperature.

The precipitate was collected by filtration, and dried under reduced pressure to obtain 67 mg of 2-[4-({[(1R)-1-(1-naphthyl)ethyl]amino}methyl)-3-phenylpiperidin-1-yl]-1,3-thiazole-4-carboxylic acid hydrochloride as a white solid.

Example 40

(1) A mixture of 2.000 g of methyl 3-amino-4-hydroxy benzoate, 1.918 g of potassium ethylxanthate, and 20.0 ml of ethanol was stirred for 3 days while heating under reflux, and the solvent was removed by distillation under reduced pressure. The residue was dissolved in water, and acidified by addition of acetic acid, and the precipitate was collected by filtration. It was dried under reduced pressure to obtain 2.049 g of methyl 2-sufanyl-1,3-benzoxazole-5-carboxylate. A mixture of 200 mg of methyl 2-sufanyl-1,3-benzooxazole-6-carboxylate, 239 mg of phosphorus pentachloride, 0.78 ml of phosphorus oxychloride, and 1 mL of dichloromethane was stirred at room temperature for 3 hours. The solvent was removed by distillation under reduced pressure. The residue was adjusted to pH 8 by addition of a saturated aqueous sodium hydrogen carbonate solution, and extracted with chloroform. The organic layer was washed with water and saturated brine, and dried over anhydrous sodium sulfate. The solvent was removed by distillation under reduced pressure to obtain 191 mg of methyl 2-chloro-1,3-benzoxazole-5-carboxylate as a pale orange-brown solid. ESI+: 212

(2) To a solution of 185 mg of tert-butyl {[3-(3-fluorophenyl)piperidin-4-yl]methyl}[(1R)-1-(1-naphthyl)ethyl]carbamate in 2.00 mL of DMSO was added 18 mg of sodium hydride (55% dispersion) at room temperature, followed by stirring for 10 minutes. 89 mg of methyl 2-chloro-1,3-benzoxazole-5-carboxylate was added thereto, followed by stirring at 100° C. overnight. 55 mg of methyl 2-chloro-1,3-benzoxazole-5-carboxylate was further added thereto, followed by stirring at 100° C. overnight. The reaction mixture was cooled to room temperature, and water was then added thereto, followed by extraction with ethyl acetate. The organic layer was washed with saturated brine, and dried over anhydrous sodium sulfate. After filtration, the filtrate was concentrated under reduced pressure. The residue was purified by silica gel column chromatography (hexane-ethyl acetate and chloroform-methanol) to obtain 33 mg of methyl 2-[4-({(tert-butoxycarbonyl)[(1R)-1-(1-naphthyl)ethyl]amino}methyl)-3-(3-fluorophenyl)piperidin-1-yl]-1,3-benzoxazole-5-carboxylate as a colorless resinous compound. ESI+: 638

(3) To a solution of 33 mg of methyl 2-[4-({(tert-butoxycarbonyl)[(1R)-1-(1-naphthyl)ethyl]amino}methyl)-3-(3-fluorophenyl)piperidin-1-yl]-1,3-benzoxazole-5-carboxylate in 2.0 mL of THF and 1.0 mL of methanol was added 1.00 mL of a 1 M aqueous sodium hydroxide solution at room temperature, followed by stirring overnight. It was neutralized by addition of 1.00 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 35 mg of 2-[4-({(tert-butoxycarbonyl)[(1R)-1-(1-naphthyl)ethyl]amino}methyl)-3-(3-fluorophenyl)piperidin-1-yl]-1,3-benzoxazole-5-carboxylic acid as a colorless resinous compound. ESI+: 624

(4) To a solution of 35 mg of 2-[4-({(tert-butoxycarbonyl)[(1R)-1-(1-naphthyl)ethyl]amino}methyl)-3-(3-fluorophenyl)piperidin-1-yl]-1,3-benzoxazole-5-carboxylic acid in 1.0 mL of 1,4-dioxane solution was added 1.00 mL of a 4 M hydrogen chloride/ethyl acetate solution at room temperature, followed by stirring for 1 hour. Diisopropyl ether was added thereto, and the resulting precipitate was collected by filtration, and dried under reduced pressure to obtain 14 mg of 2-[3-(3-fluorophenyl)-4-({[(1R)-1-(1-naphthyl)ethyl]amino}methyl)piperidin-1-yl]-1,3-benzoxazole-5-carboxylic acid hydrochloride.

Example 41

(1) A mixture of 228 mg of 2-oxo-2,3-dihydro-1H-benzimidazole-5-carboxylic acid, 2.00 mL of phosphorus oxychloride, and one drop of concentrated hydrochloric acid was stirred at 100° C. overnight. The solvent was removed by distillation under reduced pressure. To the residue was added 4.0 mL of methanol at room temperature, followed by stirring for 1 hour. It was diluted with water and ethyl acetate, and added with potassium carbonate until it had pH 8. The insolubles were separated by filtration, and then extracted with ethyl acetate. The organic layer was washed with saturated brine, and dried over anhydrous sodium sulfate. After filtration, the filtrate was concentrated under reduced pressure to obtain 313 mg of methyl 2-chloro-1H-benzimidazole-6-carboxylate as a pale brown solid. ESI+: 211

(2) A solution of 313 mg of methyl 2-chloro-1H-benzimidazole-6-carboxylate and 100 mg of tert-butyl {[3-(3-fluorophenyl)piperidin-4-yl]methyl}[(1R)-1-(1-naphthyl)ethyl]carbamate in 2.00 mL of DMSO was stirred at 130° C. for 9 hours. The reaction mixture was cooled to room temperature, and water was then added thereto, followed by extraction with ethyl acetate. The organic layer was washed with saturated brine, and dried over anhydrous sodium sulfate. After filtration, the filtrate was concentrated under reduced pressure. The residue was purified by silica gel column chromatography (hexane-ethyl acetate) to obtain 48 mg of methyl 2-[4-({(tert-butoxycarbonyl)[(1R)-1-(1-naphthyl)ethyl]amino}methyl)-3-(3-fluorophenyl)piperidin-1-yl]-1H-benzimidazole-6-carboxylate as a pale yellow solid. ESI+: 637

(3) To a solution of 48 mg of methyl 2-[4-({(tert-butoxycarbonyl)[(1R)-1-(1-naphthyl)ethyl]amino}methyl)-3-(3-fluorophenyl)piperidin-1-yl]-1H-benzimidazole-6-carboxylate in 2.0 mL of THF and 1.0 mL of methanol was added 1.00 mL of a 1 M aqueous sodium hydroxide solution at room temperature, followed by stirring overnight, and then stirring at 80° C. for 6 hours. The reaction mixture was cooled to room temperature, neutralized by addition of 1.00 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 19 mg of 2-[4-({(tert-butoxycarbonyl)[(1R)-1-(1-naphthyl)ethyl]amino}methyl)-3-(3-fluorophenyl)piperidin-1-yl]-1H-benzimidazole-6-carboxylic acid as a pale yellow amorphous compound. ESI+: 623

(4) A solution of 19 mg of 2-[4-({(tert-butoxycarbonyl)[(1R)-1-(1-naphthyl)ethyl]amino}methyl)-3-(3-fluorophenyl)piperidin-1-yl]-1H-benzimidazole-6-carboxylic acid in 1.00 mL of 4 M hydrogen chloride/1,4-dioxane solution was stirred at room temperature for 2 hours. Diisopropyl ether was added thereto, and the resulting precipitate was collected by filtration, and dried under reduced pressure to obtain 15 mg of 2-[3-(3-fluorophenyl)-4-({[(1R)-1-(1-naphthyl)ethyl]amino}methyl)piperidin-1-yl]-1H-benzimidazole-6-carboxylic acid dihydrochloride.

Example 42

To a solution of 282 mg of methyl rel-5-fluoro-6-[(3R,4R)-4-(hydroxymethyl)-3-phenylpiperidin-1-yl]nicotinate in 3.0 mL of dichloromethane was added 382 mg of Dess-Martin Periodinane at room temperature, followed by stirring for 1.5 hours. This reaction mixture was washed with 1,2-dichloroethane, transferred to a dropping funnel, and added dropwise to a mixture of 147 mg of (1R)-1-(1-naphthyl)ethaneamine, 521 mg of sodium triacetoxyborohydride, 49 mg of acetic acid, and 10 mL of 1,2-dichloroethane at room temperature. To the reaction mixture was added a saturated aqueous sodium hydrogen carbonate solution, followed by vigorously stirring for 10 minutes, and then extraction with chloroform. The organic layer was washed with water and saturated brine in this order, and dried over anhydrous sodium sulfate. After filtration, the filtrate was concentrated under reduced pressure, and the residue was purified by NH silica gel (FUJI SILISIA CHEMICAL. Ltd., Japan) column chromatography (hexane-ethyl acetate) to obtain 314 mg of methyl 5-fluoro-6-[4-({[(1R)-1-(1-naphthyl)ethyl]amino}methyl)-3-phenylpiperidin-1-yl]nicotinate as a colorless foamy substance.

Example 43

(1) To a solution of 312 mg of methyl 5-fluoro-6-[4-({[(1R)-1-(1-naphthyl)ethyl]amino}methyl)-3-phenylpiperidin-1-yl]nicotinate in 5 mL of THF were added 0.35 mL of triethylamine and 274 mg of di-tert-butyl-dicarbonate at room temperature, and the mixture was stirred at 60° C. overnight. The reaction mixture was cooled to room temperature, and then concentrated under reduced pressure, and the obtained residue was purified by silica gel column chromatography (hexane-ethyl acetate) to obtain 174 mg of methyl 6-[4-({(tert-butoxycarbonyl)[(1R)-1-(1-naphthyl)ethyl] amino}methyl)-3-phenylpiperidin-1-yl]-5-fluoronicotinate (low-polarity fraction, Rf value of 0.23 (eluting solvent: hexane/ethyl acetate=7/1), FAB+: 598) and 176 mg of methyl 6-[4-({(tert-butoxycarbonyl)[(1R)-1-(1-naphthyl)ethyl] amino}methyl)-3-phenylpiperidin-1-yl]-5-fluoronicotinate (high-polarity fraction, Rf value of 0.15 (eluting solvent: hexane/ethyl acetate=7/1), FAB+: 598) as a colorless foamy substance, respectively.

(2) To 173 mg of a low-polarity fraction diastereomer of methyl 6-[4-({(tert-butoxycarbonyl)[(1R)-1-(1-naphthyl) ethyl]amino}methyl)-3-phenylpiperidin-1-yl]-5-fluoronicotinate collected by separation were added 2.0 mL of THF, 1.0 mL of methanol, and 1.0 mL of a 1 M aqueous sodium hydroxide solution, followed by stirring at room temperature for 2 days. It was neutralized by addition of 1.1 mL of 1 M hydrochloric acid, and then extracted with ethyl acetate, and the organic layer was dried over anhydrous sodium sulfate. After filtration, the filtrate was concentrated under reduced pressure, and dried to obtain 188 mg of a crude product of 6-[4-({(tert-butoxycarbonyl)[(1R)-1-(1-naphthyl)ethyl] amino}methyl)-3-phenylpiperidin-1-yl]-5-fluoronicotinic acid as an off-white foamy substance.

(3) To 187 mg of the crude product of 6-[4-({(tert-butoxycarbonyl)[(1R)-1-(1-naphthyl)ethyl]amino}methyl)-3-phenylpiperidin-1-yl]-5-fluoronicotinic acid was added 2.0 mL of a 4 M hydrogen chloride/1,4-dioxane solution. After stirring at room temperature for 2 hours, the reaction mixture was concentrated under reduced pressure, and to the obtained residue were added isopropanol and ethyl acetate, followed by heating under reflux, and then being left to be cooled to room temperature. The precipitate was collected by filtration, and dried under reduced pressure to obtain 106 mg of 5-fluoro-6-[4-({[(1R)-1-(1-naphthyl)ethyl]amino}methyl)-3-phenylpiperidin-1-yl]nicotinic acid hydrochloride as a white solid.

Example 44

(1) To a solution of 139 mg of tert-butyl {[3-(3-fluorophenyl)piperidin-4-yl]methyl}[(1R)-1-(1-naphthyl)ethyl]carbamate and 48 mg of methyl 6-oxohexanoate in 4.0 mL of dichloromethane was added 191 mg of sodium triacetoxyborohydride at room temperature, followed by stirring overnight. To the reaction mixture was added a saturated aqueous sodium hydrogen carbonate solution, followed by extraction with chloroform. The organic layer was washed with water and saturated brine, and dried over anhydrous sodium sulfate. After filtration, the filtrate was concentrated under reduced pressure to obtain 180 mg of methyl 6-[4-({(tert-butoxycarbonyl)[(1R)-1-(1-naphthyl)ethyl]amino}methyl)-3-(3-fluorophenyl)piperidin-1-yl]hexanoate as a colorless oily compound. ESI+: 591

(2) To a solution of 180 mg of methyl 6-[4-({(tert-butoxycarbonyl)[(1R)-1-(1-naphthyl)ethyl]amino}methyl)-3-(3-fluorophenyl)piperidin-1-yl]hexanoate in 2.0 mL of methanol was added 1.00 mL of a 1 M aqueous sodium hydroxide solution at room temperature, followed by stirring for 1 hour. It was neutralized by addition of 1.00 mL of 1 M hydrochloric acid, and then extracted with ethyl acetate. The organic layer was washed with saturated brine, and dried over anhydrous sodium sulfate. After filtration, the filtrate was concentrated under reduced pressure to obtain 168 mg of 6-[4-({(tert-butoxycarbonyl)[(1R)-1-(1-naphthyl)ethyl]amino}methyl)-3-(3-fluorophenyl)piperidin-1-yl]hexanoic acid. ESI+: 577

(3) To a solution of 168 mg of 6-[4-({(tert-butoxycarbonyl)[(1R)-1-(1-naphthyl)ethyl]amino}methyl)-3-(3-fluorophenyl)piperidin-1-yl]hexanoic acid in 2.0 mL of ethyl acetate was added 1.00 mL of a 4 M hydrogen chloride/ethyl acetate solution at room temperature, followed by stirring for 2 hours. The solvent was removed by distillation under reduced pressure. The residue was purified by reverse phase silica gel column chromatography (acetonitrile-0.001 M hydrochloric acid) to obtain 70 mg of 6-[3-(3-fluorophenyl)-4-({[(1R)-1-(1-naphthyl)ethyl]amino}methyl)piperidin-1-yl]hexanoic acid dihydrochloride as a pale yellow solid.

Example 45

(1) To a mixture of 191 mg of tert-butyl {[4-(2-fluorophenyl)piperidin-3-yl]methyl}[(1R)-1-(1-naphthyl)ethyl]carbamate, 0.115 mL of triethylamine, and 3.0 mL of THF was added 175 mg of methyl 3-chloro-4-{[(4-nitrophenoxy)carbonyl]amino}benzoate at room temperature. After stirring at room temperature overnight, the reaction mixture was concentrated under reduced pressure. The residue was purified by silica gel column chromatography (hexane-ethyl acetate) to obtain 330 mg of methyl 4-({[3-({(tert-butoxycarbonyl) [(1R)-1-(1-naphthyl)ethyl]amino}methyl)-4-(2-fluorophenyl)piperidin-1-yl]carbonyl}amino)-3-chlorobenzoate as a crude product. ESI+: 674

(2) To a mixture of 330 mg of the crude methyl 4-({[3-({(tert-butoxycarbonyl)[(1R)-1-(1-naphthyl)ethyl] amino}methyl)-4-(2-fluorophenyl)piperidin-1-yl] carbonyl}amino)-3-chlorobenzoate and 10 mL of THF-5.0 mL of methanol was added dropwise 5.0 mL of a 1 M aqueous sodium hydroxide solution at room temperature, followed by stirring overnight. It was neutralized by addition of 5.2 mL of 1 M hydrochloric acid, and then extracted with ethyl acetate, and the organic layer was dried over anhydrous sodium sulfate. After filtration, the filtrate was concentrated under reduced pressure, and the residue was purified by silica gel column chromatography (methanol-chloroform) to obtain 274 mg of 4-({[3-({(tert-butoxycarbonyl)[(1R)-1-(1-naphthyl)ethyl]amino}methyl)-4-(2-fluorophenyl)piperidin-1-yl] carbonyl}amino)-3-chlorobenzoic acid as a pale yellow amorphous substance. ESI+: 660

(3) To 274 mg of 4-({[3-({(tert-butoxycarbonyl)[(1R)-1-(1-naphthyl)ethyl]amino}methyl)-4-(2-fluorophenyl)piperidin-1-yl]carbonyl}amino)-3-chlorobenzoic acid was added 3.0 mL of a 4 M hydrogen chloride/1,4-dioxane solution, followed by stirring at room temperature overnight. The reaction mixture was concentrated under reduced pressure, and chloroform and a saturated aqueous sodium hydrogen carbonate solution were added thereto, followed by stirring, separating, and then drying over anhydrous sodium sulfate. After filtration, the filtrate was concentrated under reduced pressure, and the residue was purified by silica gel column chromatography (methanol-chloroform) to obtain 157 mg of 3-chloro-4-({[4-(2-fluorophenyl)-3-({[(1R)-1-(1-naphthyl) ethyl]amino}methyl)piperidin-1-yl]carbonyl}amino)benzoic acid as a colorless amorphous substance. The obtained amorphous substance was dissolved in chloroform, and hexane was added thereto to precipitate a white solid, which was collected by filtration to obtain 136 mg of 3-chloro-4-({[4-(2-fluorophenyl)-3-({[(1R)-1-(1-naphthyl)ethyl]amino}methyl)piperidin-1-yl]carbonyl}amino)benzoic acid as a white solid.

Example 46

To a mixture of 13.3 mg of tert-butyl[(1R)-1-(1-naphthyl)ethyl][(4-phenylpiperidin-3-yl)methyl]carbamate, 6.3 mg of 4-methoxycarbonyl benzoic acid, 4.7 mg of HOBt, and 1 mL of DMF was added 100 mg of PS-Carbodiimide (Argonaut Technologies, USA) at room temperature, followed by stirring overnight. To the reaction mixture was added 50 mg of MP-Carbonate (Argonaut Technologies, USA), 50 mg of PS-Isocyanate (Argonaut Technologies, USA), and 0.5 mL of DMF at room temperature, followed by stirring for 4 hours, and the reaction mixture was filtered. The filtrate was concentrated under reduced pressure to obtain methyl 4-{[3-({(tert-butoxycarbonyl)[(1R)-1-(1-naphthyl)ethyl]amino}methyl)-4-phenylpiperidin-1-yl]carbonyl}benzoate as a crude product. To a solution of the obtained crude product in 0.5 mL of 1,4-dioxane solution was added 0.5 mL of a 4 M hydrogen chloride/ethyl acetate solution at room temperature, followed by stirring overnight. The reaction mixture was concentrated under reduced pressure to obtain methyl 4-{[3-({[(1R)-1-(1-naphthyl)ethyl]amino}methyl)-4-phenylpiperidin-1-yl]carbonyl}benzoate as a crude product. To a solution of the obtained crude product in 0.5 mL of THF were added 0.5 mL of methanol and 0.5 mL of a 1 M aqueous sodium hydroxide solution at room temperature, followed by stirring overnight. To the reaction mixture was added 0.5 mL of 1 M hydrochloric acid, followed by concentration under reduced pressure. The obtained residue was purified by separation using preparative high performance liquid chromatography (column: registered trademark SunFire, Waters, particle diameter of 5 µm, inner diameter of 19 mm, and length of 100 mm), flow rate: 25 ml/min., column temperature: 20° C., methanol—a 0.1% aqueous formic acid solution) to obtain 8.4 mg of 4-{[3-({[(1R)-1-(1-naphthyl)ethyl]amino}methyl)-4-phenylpiperidin-1-yl]carbonyl}benzoic acid.

Example 47

To a mixture of 13.3 mg of tert-butyl[(1R)-1-(1-naphthyl)ethyl][(3-phenylpiperidin-4-yl)methyl]carbamate, 6.3 mg of 4-methoxycarbonyl benzoic acid, 4.7 mg of HOBt, and 1 mL of DMF was added 100 mg of PS-Carbodiimide (Argonaut Technologies, USA) at room temperature, followed by stirring overnight. To the reaction mixture was added 50 mg of MP-Carbonate (Argonaut Technologies, USA), 50 mg of PS-Isocyanate (Argonaut Technologies, USA), and 0.5 mL of DMF at room temperature, followed by stirring for 4 hours, and the reaction mixture was filtered. The filtrate was concentrated under reduced pressure to obtain methyl 4-{[4-({(tert-butoxycarbonyl)[(1R)-1-(1-naphthyl)ethyl]amino}methyl)-3-phenylpiperidin-1-yl]carbonyl}benzoate as a crude product. To 0.5 mL of a 1,4-dioxane solution of the obtained crude product were added 0.5 mL of a 4 M hydrogen chloride/ethyl acetate solution at room temperature, followed by stirring for 6 hours. The reaction mixture was concentrated under reduced pressure to obtain methyl 4-{[4-({[(1R)-1-(1-naphthyl)ethyl]amino}methyl)-3-phenylpiperidin-1-yl]carbonyl}benzoate as a crude product. To 0.5 mL of a THF solution of the obtained crude product was added 0.5 mL of methanol and 0.5 mL of a 1 M aqueous sodium hydroxide solution at room temperature, followed by stirring overnight. To the reaction mixture was added 0.5 mL of 1 M hydrochloric acid, followed by concentration under reduced pressure. The obtained residue was purified by preparative high performance liquid chromatography (column: registered trademark SunFire, Waters, particle diameter of 5 µm, inner diameter of 19 mm, and length of 100 mm), flow rate: 25 ml/min., column temperature: 20° C., methanol—a 0.1% aqueous formic acid solution) to obtain 7.7 mg of 4-{[4-({[(1R)-1-(1-naphthyl)ethyl]amino}methyl)-3-phenylpiperidin-1-yl]carbonyl}benzoic acid.

Example 48

To a mixture of 13.3 mg of tert-butyl[(1R)-1-(1-naphthyl)ethyl][(4-phenylpiperidin-3-yl)methyl]carbamate, 3.4 mg of 3-furaldehyde, 0.050 mL of acetic acid, and 0.5 mL of DMF was added 75 mg of MP-Triacetoxyborohydride (Argonaut Technologies, USA) at room temperature, followed by stirring overnight. To the reaction mixture was added 50 mg of PS-Isocyanate (Argonaut Technologies, USA) at room temperature, followed by stirring for 2 hours, and the reaction mixture was filtered. The filtrate was concentrated under reduced pressure to obtain tert-butyl {[1-(3-furylmethyl)-4-phenylpiperidin-3-yl]methyl}[(1R)-1-(1-naphthyl)ethyl]carbamate as a crude product. To 0.5 mL of a methanol solution of the obtained crude product was added 0.5 mL of a 4 M hydrogen chloride/ethyl acetate solution at room temperature, followed by stirring for 4 hours. The reaction mixture was concentrated under reduced pressure, and the residue was purified by preparative high performance liquid chromatography (column: registered trademark SunFire, Waters, particle diameter of 5 µm, inner diameter of 19 mm, and length of 100 mm), flow rate: 25 ml/min., column temperature: 20° C., methanol—a 0.1% aqueous formic acid solution) to obtain 4.9 mg of (1R)—N-{[1-(3-furylmethyl)-4-phenylpiperidin-3-yl]methyl}-1-(1-naphthyl)ethaneamine.

Example 49

To a mixture of 13.3 mg of tert-butyl[(1R)-1-(1-naphthyl)ethyl][(3-phenylpiperidin-4-yl)methyl]carbamate, 3.4 mg of 3-furaldehyde, 0.050 mL of acetic acid, and 0.5 mL of DMF was added 75 mg of MP-Triacetoxyborohydride (Argonaut Technologies, USA) at room temperature, followed by stirring overnight. To the reaction mixture was added 50 mg of PS-Isocyanate (Argonaut Technologies, USA) at room temperature, followed by stirring for 2 hours, and the reaction mixture was filtered. The filtrate was concentrated under reduced pressure to obtain tert-butyl {[1-(3-furylmethyl)-3-phenylpiperidin-4-yl]methyl}[(1R)-1-(1-naphthyl)ethyl]carbamate as a crude product. To 0.5 mL of a methanol solution of the obtained crude product was added 0.5 mL of a 4 M hydrogen chloride/ethyl acetate solution at room temperature, followed by stirring for 4 hours. The reaction mixture was concentrated under reduced pressure, and the residue was purified by preparative high performance liquid chromatography (column: registered trademark SunFire, Waters, particle diameter of 5 µm, inner diameter of 19 mm, and length of 100 mm), flow rate: 25 ml/min., column temperature: 20° C., methanol—a 0.1% aqueous formic acid solution) to obtain 8.6 mg of (1R)—N-{[1-(3-furylmethyl)-3-phenylpiperidin-4-yl]methyl}-1-(1-naphthyl)ethaneamine.

Example 50

(1) A mixture of 191 mg of tert-butyl {[4-(2-fluorophenyl)piperidin-3-yl]methyl}[(1R)-1-(1-naphthyl)ethyl]carbamate, 118 mg of methyl 3,4,5-trifluorobenzoate, 114 mg of potassium carbonate, and 2.0 mL of THF-2.0 mL of DMSO was stirred at 100° C. overnight. After cooling, to the reaction mixture was added water, followed by extraction with ethyl acetate, and then drying over anhydrous sodium sulfate. After filtration, the filtrate was concentrated under reduced pressure, and the residue was purified by silica gel column chromatography (hexane-ethyl acetate) to obtain 147 mg of methyl 4-[(3R,4S)-3-({(tert-butoxycarbonyl)[(1R)-1-(1-naphthyl)ethyl]amino}methyl)-4-(2-fluorophenyl)piperidin-1-yl]-3,5-difluorobenzoate as a colorless amorphous substance.

(2) 143 mg of methyl 4-[(3R,4S)-3-({(tert-butoxycarbonyl)[(1R)-1-(1-naphthyl)ethyl]amino}methyl)-4-(2-fluorophenyl)piperidin-1-yl]-3,5-difluorobenzoate was dissolved in 4.0 mL of THF-2.0 mL of methanol and added with 2.0 mL of a 1 M aqueous sodium hydroxide solution at room temperature. After stirring at room temperature for 3 days, it was neutralized by addition of 2.1 mL of 1 M hydrochloric acid. The reaction mixture was concentrated under reduced pressure, and then extracted with ethyl acetate, and the organic layer was dried over anhydrous sodium sulfate. After filtration, the filtrate was concentrated under reduced pressure, and the residue was purified by silica gel column chromatography (methanol-chloroform) to obtain 138 mg of 4-[3-({(tert-butoxycarbonyl)[(1R)-1-(1-naphthyl)ethyl]amino}methyl)-4-(2-fluorophenyl)piperidin-1-yl]-3,5-difluorobenzoic acid. ESI+: 619

(3) To 135 mg of 4-[3-({(tert-butoxycarbonyl)[(1R)-1-(1-naphthyl)ethyl]amino}methyl)-4-(2-fluorophenyl)piperidin-1-yl]-3,5-difluorobenzoic acid was added 3.0 mL of a 4 M hydrogen chloride/1,4-dioxane solution, followed by stirring at room temperature overnight. The reaction mixture was concentrated under reduced pressure, and to the obtained residue were added chloroform and a saturated aqueous sodium hydrogen carbonate solution, followed by stirring, and the organic layer was then separated, and dried over anhydrous sodium sulfate. After filtration, the filtrate was concentrated under reduced pressure, and the residue was purified by silica gel column chromatography (methanol-chloroform) to obtain 111 mg of 3,5-difluoro-4-[4-(2-fluorophenyl)-3-({[(1R)-1-(1-naphthyl)ethyl]amino}methyl)piperidin-1-yl]benzoic acid as a colorless amorphous substance. The obtained amorphous substance was dissolved in chloroform, and hexane was added thereto to precipitate a white solid, which was collected by filtration to obtain 93 mg of 3,5-difluoro-4-[4-(2-fluorophenyl)-3-({[(1R)-1-(1-naphthyl)ethyl]amino}methyl)piperidin-1-yl]benzoic acid as a white solid.

Example 51

(1) To a mixture of 181 mg of tert-butyl[(1R)-1-(1-naphthyl)ethyl][(3-phenylpiperidin-4-yl)methyl]carbamate, 0.114 mL of triethylamine, and 3.0 mL of THF was added 64 mg of 3,3-dimethylglutaric anhydride at room temperature, followed by stirring at room temperature overnight. To the reaction mixture was added a saturated aqueous sodium hydrogen carbonate solution, followed by stirring, extracting with chloroform, and drying over anhydrous sodium sulfate. After filtration, the filtrate was concentrated under reduced pressure to obtain 266 mg of 5-[4-({(tert-butoxycarbonyl)[(1R)-1-(1-naphthyl)ethyl]amino}methyl)-3-phenylpiperidin-1-yl]-3,3-dimethyl-5-oxopentanoic acid as a crude product. ESI+: 587

(2) To 265 mg of the crude 5-[4-({(tert-butoxycarbonyl)[(1R)-1-(1-naphthyl)ethyl]amino}methyl)-3-phenylpiperidin-1-yl]-3,3-dimethyl-5-oxopentanoic acid was added 2.0 mL of a 4 M hydrogen chloride/1,4-dioxane solution, followed by stirring at room temperature for 2 hours. The reaction mixture was concentrated under reduced pressure, and the obtained residue was then suspended in isopropanol under heating, and then left to be cooled. The precipitate was isolated by filtration, and dried under reduced pressure to obtain 189 mg of 3,3-dimethyl-5-[4-({[(1R)-1-(1-naphthyl)ethyl]amino}methyl)-3-phenylpiperidin-1-yl]-5-oxopentanoic acid hydrochloride as a white solid.

Example 52

(1) To a mixture of 116 mg of methyl 3,4,5-trifluorobenzoate, 113 mg of potassium carbonate, and 2.0 mL of DMSO was added 181 mg of a solution of tert-butyl [(1R)-1-(1-naphthyl)ethyl][(3-phenylpiperidin-4-yl)methyl]carbamate in 3.0 mL of THF at room temperature. It was stirred at 100° C. overnight, and then cooled. To the reaction mixture was added water, followed by extraction with ethyl acetate, and the organic layer was then washed with water and saturated brine in this order, and dried over anhydrous sodium sulfate. After filtration, the filtrate was concentrated under reduced pressure to obtain 248 mg of methyl 4-[4-({(tert-butoxycarbonyl)[(1R)-1-(1-naphthyl)ethyl]amino}methyl)-3-phenylpiperidin-1-yl]-3,5-difluorobenzoate as a crude product. FAB+: 615

(2) To a mixture of 247 mg of the crude methyl 4-[4-({(tert-butoxycarbonyl)[(1R)-1-(1-naphthyl)ethyl]amino}methyl)-3-phenylpiperidin-1-yl]-3,5-difluorobenzoate, 4.0 mL of THF, and 2.0 mL of methanol was added dropwise a 1 M aqueous sodium hydroxide solution at room temperature, followed by stirring overnight. The reaction mixture was neutralized by addition of 1 M hydrochloric acid, and then extracted with ethyl acetate, and the organic layer was dried over anhydrous sodium sulfate. After filtration, the filtrate was concentrated under reduced pressure, and the residue was purified by silica gel column chromatography (methanol-chloroform) to obtain 233 mg of 4-[4-({(tert-butoxycarbonyl)[(1R)-1-(1-naphthyl)ethyl]amino}methyl)-3-phenylpiperidin-1-yl]-3,5-difluorobenzoic acid as a white solid. FAB+: 601

(3) To 230 mg of 4-[4-({(tert-butoxycarbonyl)[(1R)-1-(1-naphthyl)ethyl]amino}methyl)-3-phenylpiperidin-1-yl]-3,5-difluorobenzoic acid was added 1.5 mL of a 4 M hydrogen chloride/1,4-dioxane solution at room temperature. After stirring at room temperature for 2 hours, the reaction mixture was concentrated under reduced pressure. The obtained residue was solidified by isopropanol and diisopropyl ether, and then collected by filtration. The obtained solid was purified by silica gel column chromatography (methanol-chloroform), and a 4 M hydrogen chloride/1,4-dioxane solution was then added thereto. The mixture was concentrated under reduced pressure, and the obtained individual product was washed with isopropanol to obtain 140 mg of 3,5-difluoro-4-[4-({[(1R)-1-(1-naphthyl)ethyl]amino}methyl)-3-phenylpiperidin-1-yl]benzoic acid hydrochloride.

Example 53

(1) To a mixture of 96 mg of 3,4,5-trifluorobenzonitrile, 113 mg of potassium carbonate, and 3.0 mL of DMSO was added a solution of 181 mg of a crude product of tert-butyl [(1R)-1-(1-naphthyl)ethyl][(3-phenylpiperidin-4-yl)methyl] carbamate in 3.0 mL of THF, the reaction vessel was tightly sealed, and the mixture was heated at 100° C. overnight. The reaction mixture was cooled to room temperature, and water was then added thereto, followed by extraction with ethyl acetate. The organic layer was washed with water and saturated brine in this order, and dried over anhydrous sodium sulfate. After filtration, the filtrate was concentrated under reduced pressure to obtain 232 mg of tert-butyl {[1-(4-cyano-2,6-difluorophenyl)-3-phenylpiperidin-4-yl]methyl}[(1R)-1-(1-naphthyl)ethyl]carbamate as a crude product. FAB+: 582

(2) A mixture of 232 mg of the crude product of tert-butyl {[1-(4-cyano-2,6-difluorophenyl)-3-phenylpiperidin-4-yl]methyl}[(1R)-1-(1-naphthyl)ethyl] carbamate, 518 mg of sodium azide, 1.10 g of triethylamine hydrochloride, and 4.6 mL of DMF was stirred at 120° C. overnight. The reaction mixture was cooled to room temperature, and water was then added thereto, followed by extraction with ethyl acetate. The organic layer was washed with water and a saturated aqueous sodium chloride solution in this order, and dried over anhydrous sodium sulfate. This was filtered, the filtrate was concentrated under reduced pressure, and the residue was purified by silica gel column chromatography (chloroform/methanol) to obtain 208 mg of tert-butyl ({1-[2,6-difluoro-4-(1H-tetrazol-5-yl)phenyl]-3-phenylpiperidin-4-yl}methyl)[(1R)-1-(1-naphthyl)ethyl]carbamate as a yellow oily substance. FAB+: 625

(3) To 205 mg of tert-butyl ({1-[2,6-difluoro-4-(1H-tetrazole-5-yl)phenyl]-3-phenylpiperidin-4-yl}methyl)[(1R)-1-(1-naphthyl)ethyl]carbamate was added 2.0 mL of a 4 M hydrogen chloride/1,4-dioxane solution, followed by stirring at room temperature for 2 hours. The reaction mixture was concentrated under reduced pressure, and to the residue was then added a saturated aqueous sodium hydrogen carbonate solution, followed by extraction with chloroform. The organic layer was dried over anhydrous sodium sulfate. After filtration, the filtrate was concentrated under reduced pressure, and the residue was purified by silica gel column chromatography (chloroform/methanol) to obtain 158 mg of (1R)—N-({1-[2,6-difluoro-4-(1H-tetrazol-5-yl)phenyl]-3-phenylpiperidin-4-yl}methyl)-1-(1-naphthyl)ethaneamine. 2.0 mL of hydrogen chloride/1,4-dioxane solution was added thereto, followed by concentration under reduced pressure, and to the obtained residue was then added about 3 mL of isopropanol, followed by heating. The mixture was left to be cooled to room temperature, and the precipitate was collected by filtration, and dried under reduced pressure to obtain 153 mg of (1R)—N-({1-[2,6-difluoro-4-(1H-tetrazol-5-yl)phenyl]-3-phenylpiperidin-4-yl}methyl)-1-(1-naphthyl)ethaneamine hydrochloride as a white solid.

Example 54

(1) To a mixture of 183 mg of tert-butyl {[1-(4-cyano-2,6-difluorophenyl)-3-phenylpiperidin-4-yl]methyl}[(1R)-1-(1-naphthyl)ethyl]carbamate obtained in Example 53 (1), 44 mg of hydroxylamine hydrochloride, and 2 mL of ethanol was added 0.088 mL of triethylamine, and the mixture was stirred for 4 hours while heating under reflux. The mixture was left to be cooled to room temperature, and water was then added thereto, followed by extraction with ethyl acetate. The organic layer was washed with saturated brine, and dried over anhydrous sodium sulfate. This was filtered, and the filtrate was then concentrated under reduced pressure to obtain a residue (colorless foamy substance, 233 mg). To this residue were added 2 mL of DMF and 0.033 mL of pyridine, the mixture was cooled in an ice bath, and then 0.061 mL of 2-ethylhexyl chloroformate was added thereto, followed by stirring for 1 hour while keeping cooling on ice. The reaction mixture was diluted with ethyl acetate, washed with water and saturated brine in this order, and the organic layer was then dried over anhydrous sodium sulfate. After filtration, the filtrate was concentrated under reduced pressure, to the obtained residue was added 2 mL of xylene, and the mixture was stirred for 5 hours while heating under reflux. This was left to be cooled to room temperature, and then purified by silica gel column chromatography (chloroform/methanol) to obtain 184 mg of tert-butyl ({1-[2,6-difluoro-4-(5-oxo-4,5-dihydro-1,2,4-oxadiazol-3-yl)phenyl]-3-phenylpiperidin-4-yl}methyl)[(1R)-1-(1-naphthyl)ethyl]carbamate as a yellow foamy substance. ESI+: 641

(2) To 183 mg of tert-butyl ({1-[2,6-difluoro-4-(5-oxo-4,5-dihydro-1,2,4-oxadiazol-3-yl)phenyl]-3-phenylpiperidin-4-yl}methyl)[(1R)-1-(1-naphthyl)ethyl]carbamate was added 1.5 mL of a 4 M hydrogen chloride/1,4-dioxane solution. After stirring at room temperature for 2 hours, the reaction mixture was concentrated under reduced pressure, and the residue was purified by silica gel column chromatography (chloroform/methanol), followed by addition of 0.5 mL of a 4 M hydrogen chloride/1,4-dioxane solution, and further concentration under reduced pressure. To the obtained residue were added ethanol and ethyl acetate, followed by heating under reflux, and then being left to be cooled to room temperature. The precipitate was collected by filtration, and dried under reduced pressure, and isopropanol and ethyl acetate were added thereto, followed by heating under reflux, and then being left to be cooled to room temperature. The precipitate was collected by filtration, and dried under reduced pressure to obtain 57 mg of 3-{3,5-difluoro-4-[4-({[(1R)-1-(1-naphthyl)ethyl]amino}methyl)-3-phenylpiperidin-1-yl]phenyl}-1,2,4-oxadiazol-5(4H)-one hydrochloride as a white solid.

In the same manner as the methods of Examples 1 to 54, the compounds of Examples 55 to 297 as shown in the following table were produced using each of the corresponding starting materials. The structures of the compounds of Examples are each shown in Tables 15 to 74, and the physicochemical data and the production processes are shown in Tables 75 to 89.

Furthermore, the structures of other compounds of the present invention are shown in Tables 90 to 97. These can be easily synthesized using the aforementioned Production Processes, the methods described in Examples and the methods apparent to those skilled in the art, or modified methods thereof

TABLE 4

| PEx | PSyn | Structure | Note | Data |
|---|---|---|---|---|
| 1 | 1 | dimethyl 2-cyano-3-phenylpentanedioate | diastereo mixture | ESI+: 262 |
| 2 | 2 | dimethyl 2-cyano-3-(2-fluorophenyl)pentanedioate | diastereo mixture | ESI+: 280 |
| 24 | 2 | dimethyl 2-cyano-3-(3-fluorophenyl)pentanedioate | diastereo mixture | ESI+: 280 |
| 3 | 3 | methyl 6-oxo-4-phenylpiperidine-3-carboxylate | racemic | ESI+: 234<br>NMR2: 2.60 (1 H, dd, J = 10.2, 18.1 Hz), 2.76 (1 H, dd, J = 5.85, 18.1 Hz), 3.01 (1 H, dt, J = 5.12, 9.51 Hz), 3.44 (1 H, dt, J = 5.61, 9.76 Hz), 3.47-3.56 (2 H, m), 3.50 (3 H, s), 3.64 (1 H, m), 6.84 (1 H, brs), 7.18-7.36 (5 H, m) |
| 25 | 3 | methyl 4-(2-fluorophenyl)-6-oxopiperidine-3-carboxylate | racemic | ESI+: 252 |

TABLE 5
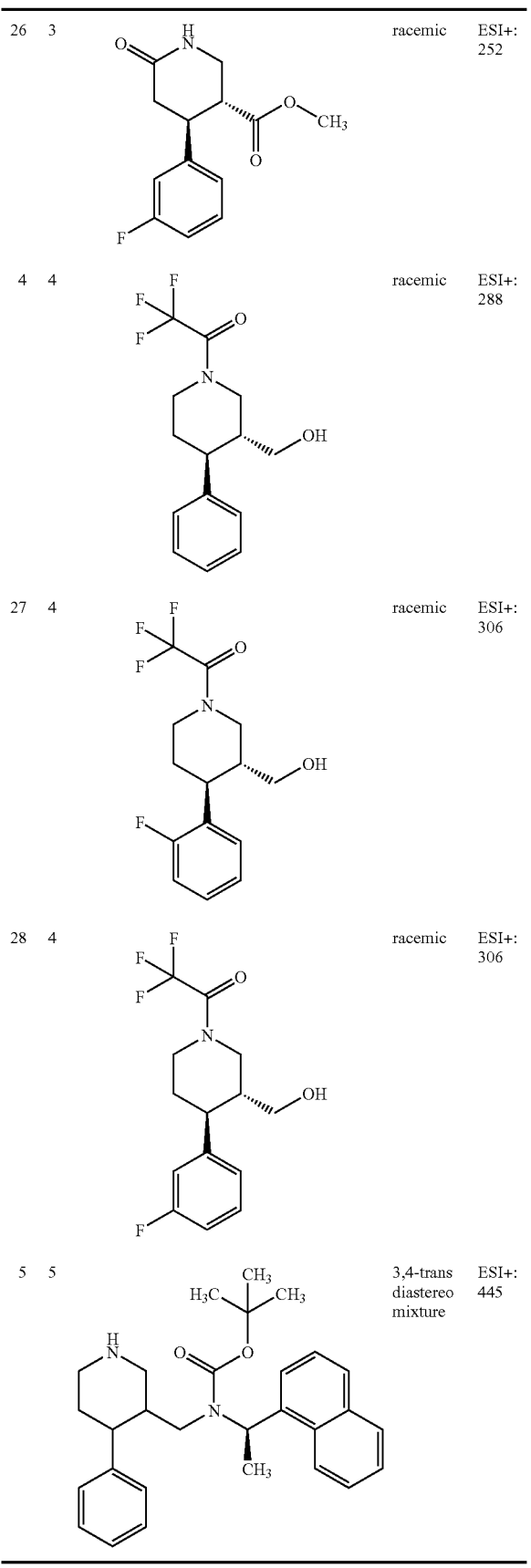
TABLE 6
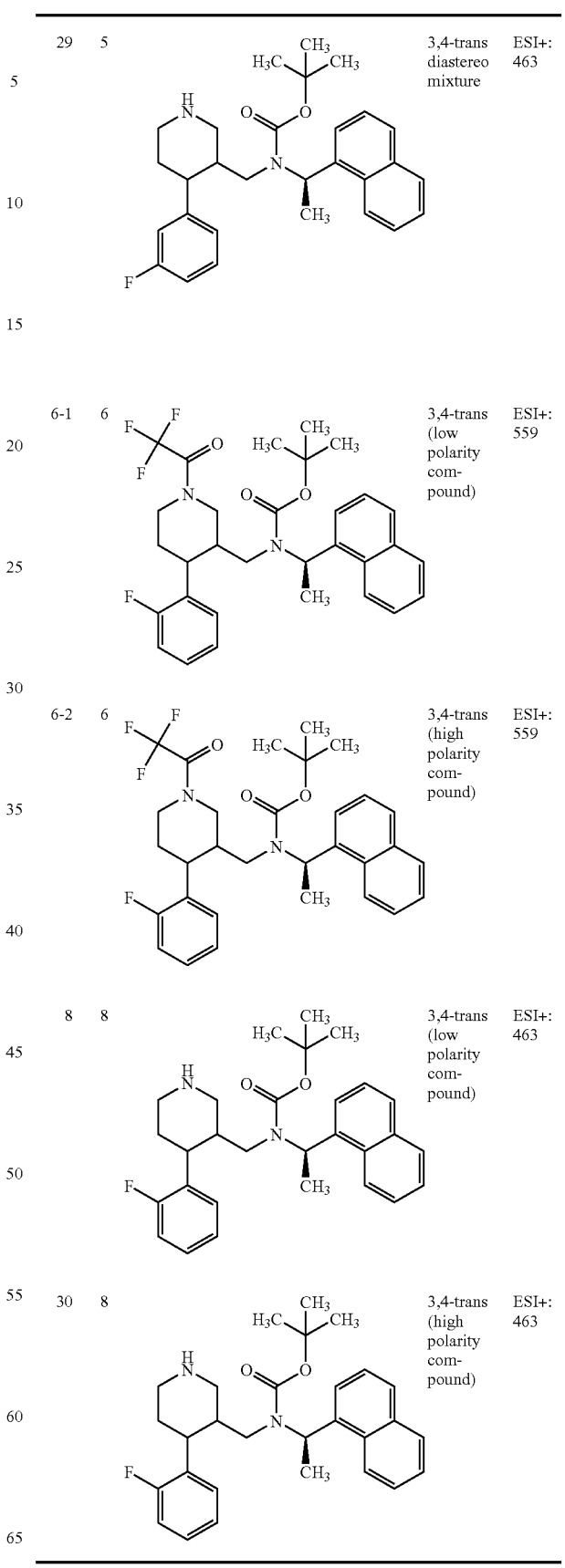

TABLE 7

| 9 | 9 | [structure] | 3,4-trans | FAB+: 388 |
| 10 | 10 | [structure] | 3,4-trans | ESI+: 641 |
| 11 | 11 | [structure] | | FAB+: 351 |
| 12 | 12 | [structure] | | FAB+: 178; NMR1: 1.62 (3 H, d, J = 6.7 Hz), 4.87 (1 H, q, J = 6.7 Hz), 7.40-7.50 (2 H, m), 7.96-8.07 (3 H, m), 8.71 (3 H, brs) |
| 13 | 13 | [structure] | | FAB+: 322 |
| 31 | 31 | [structure] | | ESI+: 340 |

TABLE 8
| | | | | |
|---|---|---|---|---|
| 32 | 13 | 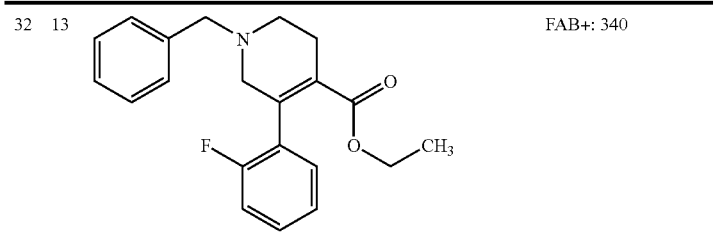 | | FAB+: 340 |
| 14 | 14 | 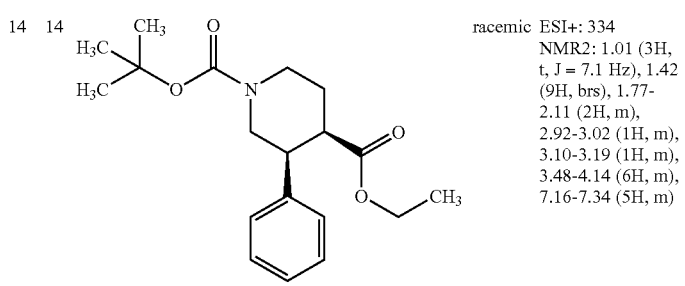 | racemic | ESI+: 334<br>NMR2: 1.01 (3H, t, J = 7.1 Hz), 1.42 (9H, brs), 1.77-2.11 (2H, m), 2.92-3.02 (1H, m), 3.10-3.19 (1H, m), 3.48-4.14 (6H, m), 7.16-7.34 (5H, m) |
| 33 | 14 | 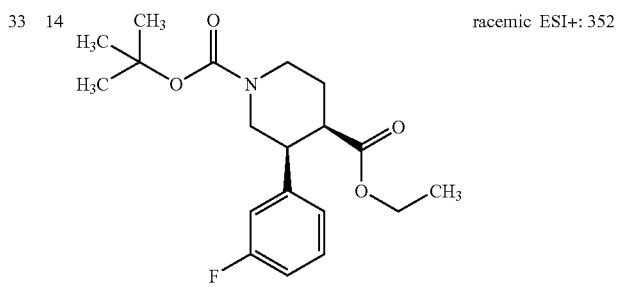 | racemic | ESI+: 352 |
| 34 | 14 | 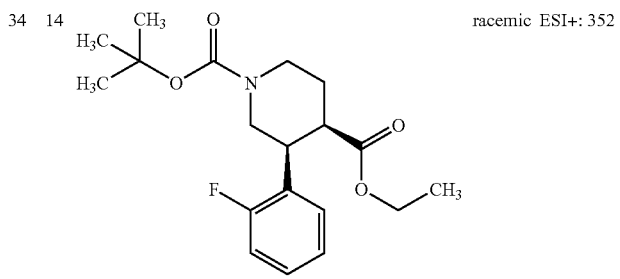 | racemic | ESI+: 352 |
| 15 | 15 | 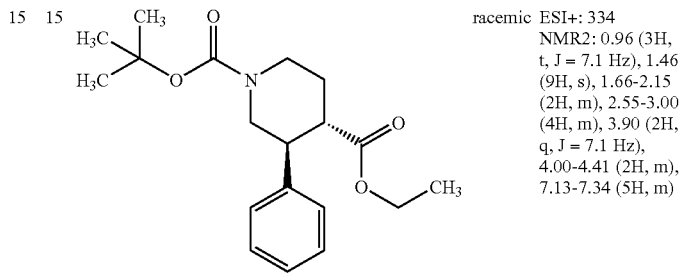 | racemic | ESI+: 334<br>NMR2: 0.96 (3H, t, J = 7.1 Hz), 1.46 (9H, s), 1.66-2.15 (2H, m), 2.55-3.00 (4H, m), 3.90 (2H, q, J = 7.1 Hz), 4.00-4.41 (2H, m), 7.13-7.34 (5H, m) |

TABLE 9
| 35 | 15 | 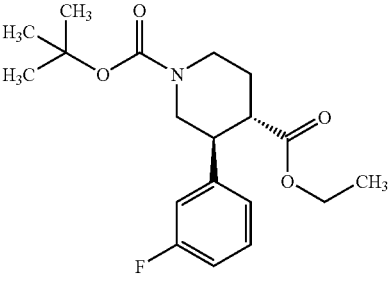 | raceimc ESI+: 352 |
| 36 | 15 | 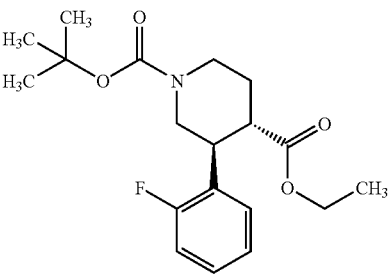 | racemic ESI+: 352 |
| 16 | 16 | 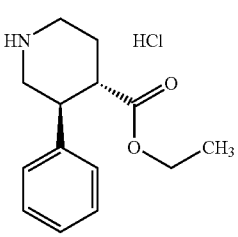 | racemic ESI+: 234 |
| 37 | 16 | 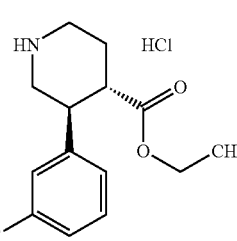 | racemic ESI+: 252 |
| 38 | 16 | 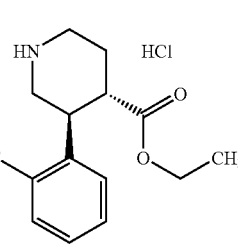 | racemic ESI+: 252 |
| 17 | 17 | 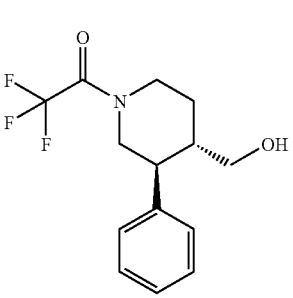 | racemic ESI+: 288 |

TABLE 10

| | | | | |
|---|---|---|---|---|
| 39 | 17 | (structure) | racemic | ESI+: 306 |
| 40 | 17 | (structure) | racemic | ESI+: 306 |
| 18-1 | 18 | (structure) | (low polarity compound) 3,4-trans | ESI+: 541<br>NMR2: −0.12-0.40 (1H, m), 0.90-1.79 (15H, m), 1.92-2.48 (3H, m), 2.83-3.25 (1H, m), 3.50-3.64 (1H, m), 4.09-4.20 (1H, m), 5.90-6.34 (1H, m), 6.54-6.65 (2H, m), 7.12-7.35 (4H, m), 7.49-7.60 (3H, m), 7.87-7.98 (2H, m), 8.12-8.22 (1H, m) |

TABLE 11

| | | | | |
|---|---|---|---|---|
| 18-2 | 18 | (structure) | (high polarity compound) 3,4-trans | ESI+: 541<br>NMR2: −0.18-0.40 (1H, m), 1.10-1.72 (13H, m), 1.95-3.03 (6H, m), 3.46-3.82 (1H, m), 4.16-4.40 (1H, m), 5.86-6.34 (1H, m), 6.95-7.14 (2H, m), 7.17-7.55 (7H, m), 7.70-7.88 (2H, m), 8.02-8.18 (1H, m) |
| 41 | 18 | (structure) | (low polarity compound) 3,4-trans | ESI+: 547 |

TABLE 11-continued
| 42 | 18 | 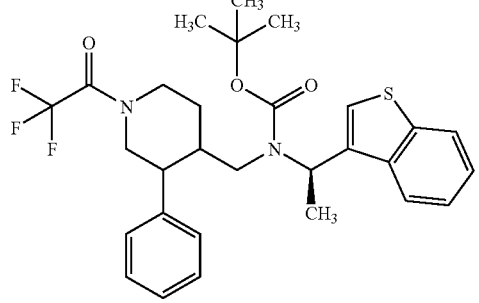 | (high polarity compound) 3,4-trans | ESI+: 547 |
| 43 | 18 | 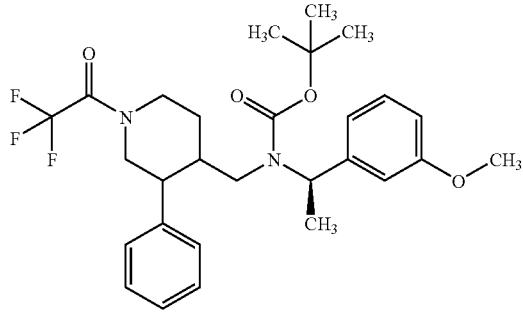 | (low polarity compound) 3,4-trans | FAB+: 521 |
TABLE 12
| 44 | 18 | 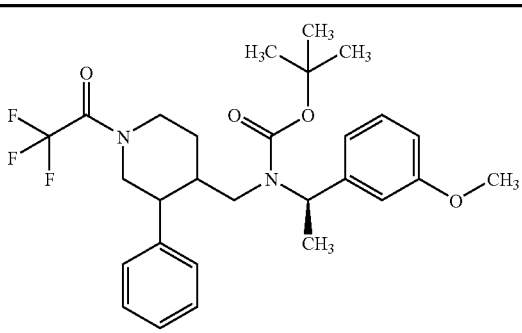 | (high polarity compound) 3,4-trans | FAB+: 521 |
| 45 | 18 | 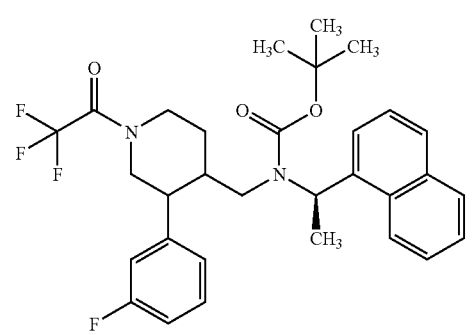 | (low polarity compound) 3,4-trans | FAB+: 559 |

TABLE 12-continued
| | | | | |
|---|---|---|---|---|
| 46 | 18 | 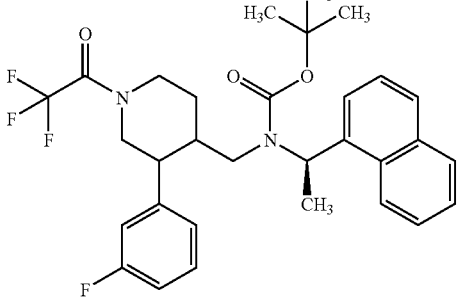 | (high polarity compound) 3,4-trans | FAB+: 559 |
| 47 | 18 | 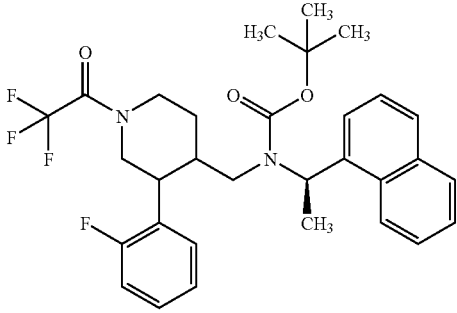 | (low polarity compound) 3,4-trans | ESI+: 559 |
| 48 | 18 | 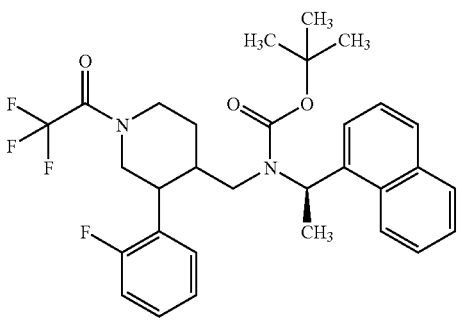 | (high polarity compound) 3,4-trans | ESI+: 559 |
TABLE 13
| | | | | |
|---|---|---|---|---|
| 20 | 20 | 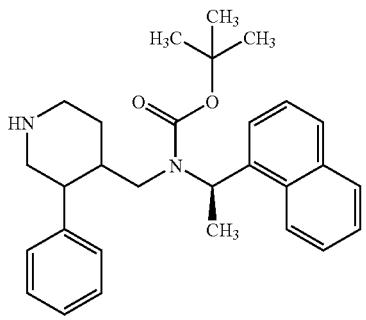 | (low polarity compound) 3,4-trans | ESI+: 445 |

TABLE 13-continued
| 21 | 21 | 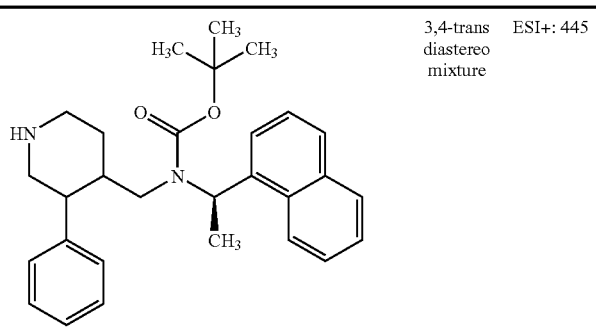 | 3,4-trans diastereo mixture | ESI+: 445 |
| 49 | 20 | 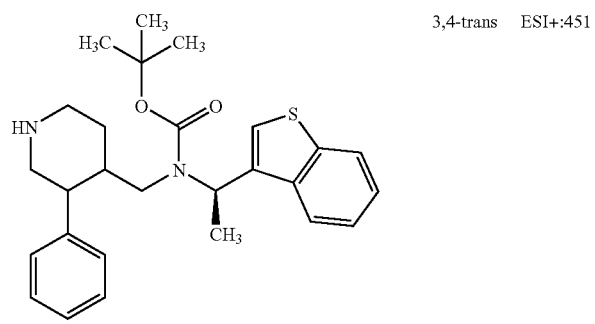 | 3,4-trans | ESI+:451 |
| 50 | 20 | 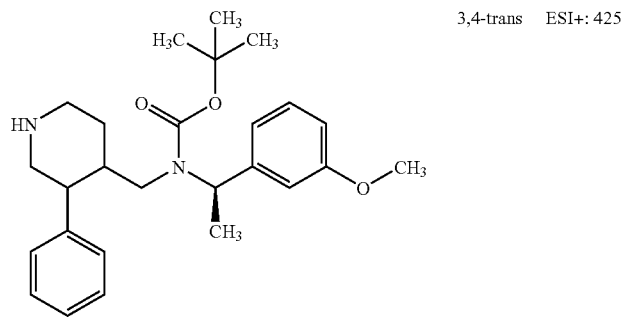 | 3,4-trans | ESI+: 425 |
| 51 | 20 | 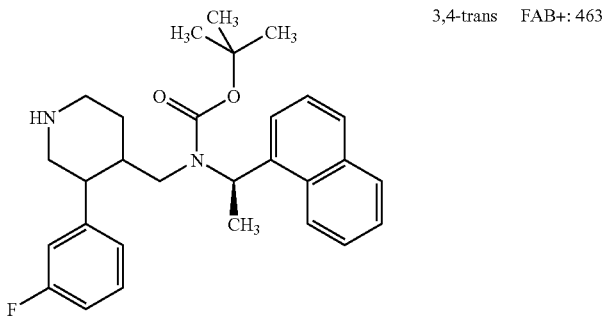 | 3,4-trans | FAB+: 463 |

TABLE 14
| 52 | 20 | 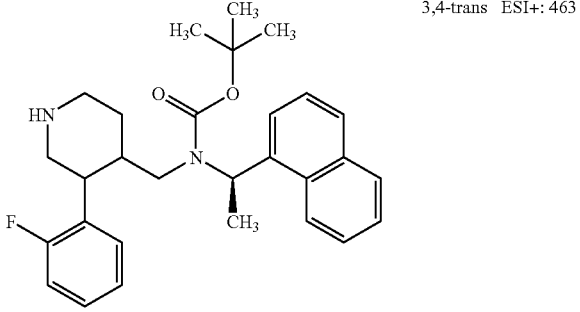 | 3,4-trans | ESI+: 463 |
| 19 | 19 | 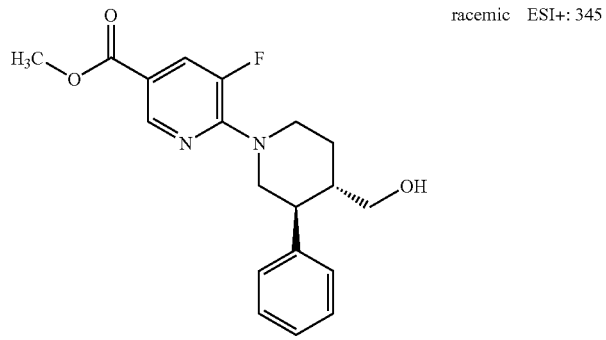 | racemic | ESI+: 345 |
| 7 | 7 | 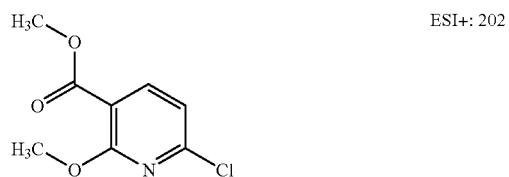 | | ESI+: 202 |
| 22 | 22 | 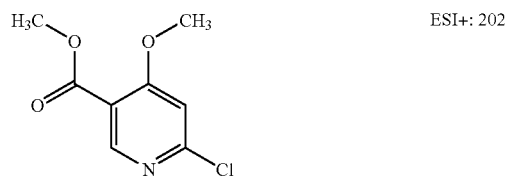 | | ESI+: 202 |
| 23 | 23 | 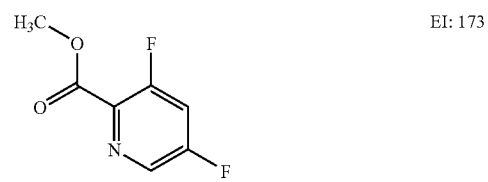 | | EI: 173 |

TABLE 15

| Ex | Structure | Note |
|---|---|---|
| 1 | (trifluoroacetyl-piperidine with 4-phenyl and 3-((1-naphthylethyl)aminomethyl), HCl) | 3,4-trans diastereo mixture |
| 55 | (trifluoroacetyl-piperidine with 4-(2-fluorophenyl) and 3-((1-naphthylethyl)aminomethyl)) | 3,4-trans diastereo mixture |
| 56 | (trifluoroacetyl-piperidine with 4-(3-fluorophenyl) and 3-((1-naphthylethyl)aminomethyl)) | 3,4-trans diastereo mixture |

TABLE 15-continued

| Ex | Structure | Note |
|---|---|---|
| 2-1 | (trifluoroacetyl-piperidine with 4-phenyl and 3-((1-naphthylethyl)aminomethyl), HCl) | 3,4-trans (low polarity compound) |
| 2-2 | (trifluoroacetyl-piperidine with 4-phenyl and 3-((1-naphthylethyl)aminomethyl), HCl) | 3,4-trans (high polarity compound) |

TABLE 16

| | | |
|---|---|---|
| 4 | (piperidine with 4-phenyl and 3-((1-naphthylethyl)aminomethyl)) | 3,4-trans |

TABLE 16-continued
| 5 | 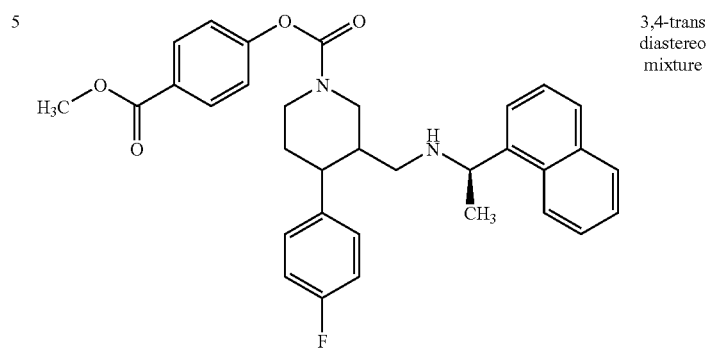 | 3,4-trans diastereo mixture |
| 6 | 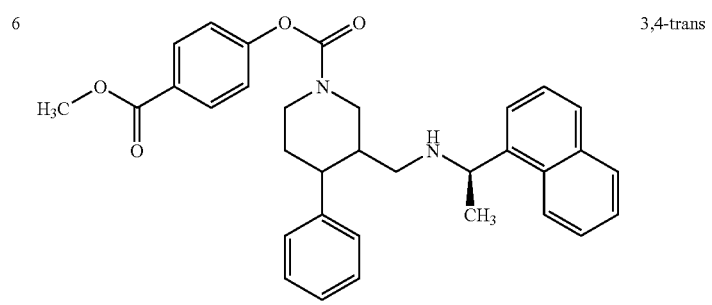 | 3,4-trans |
| 7 | 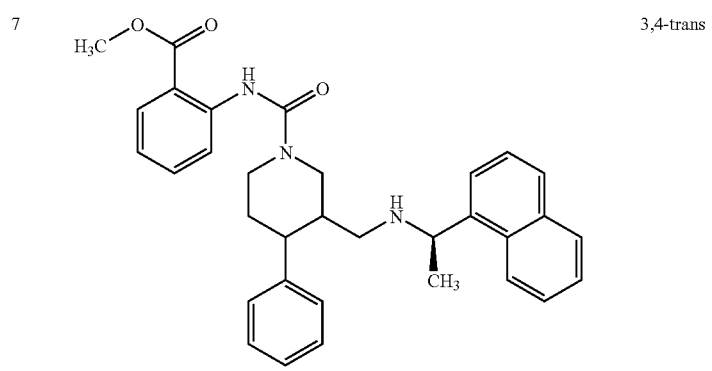 | 3,4-trans |
| 57 | 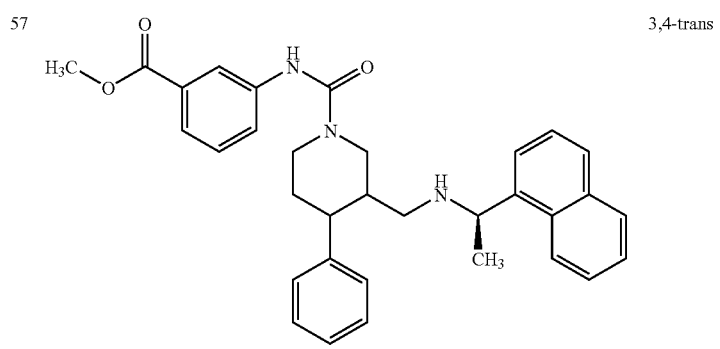 | 3,4-trans |

TABLE 17
| 58 | 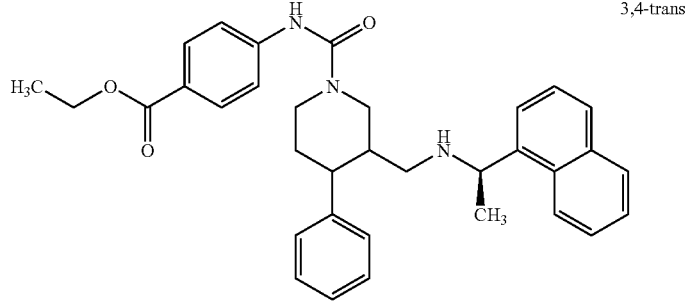 | 3,4-trans |
| --- | --- | --- |
| 8 | 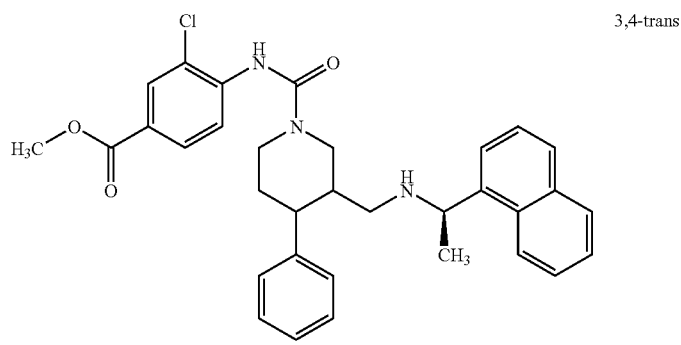 | 3,4-trans |
| 59 | 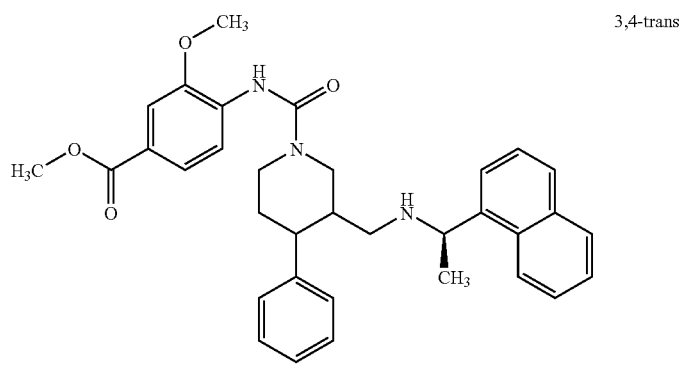 | 3,4-trans |
| 9 | 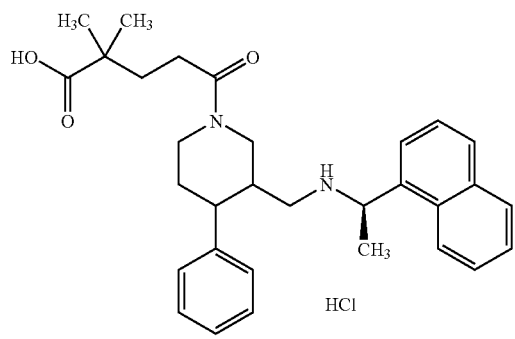 | 3,4-trans diastereo mixture |

TABLE 17-continued
| 60 | 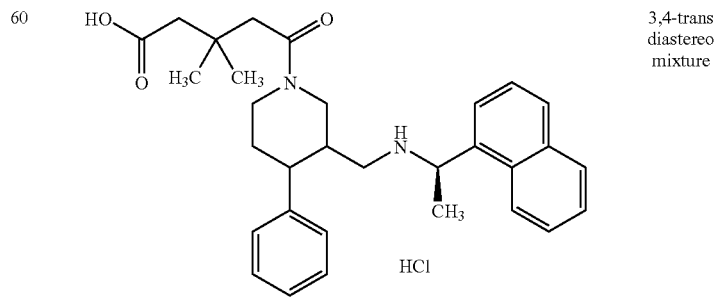 | 3,4-trans diastereo mixture |
TABLE 18
| 10 | 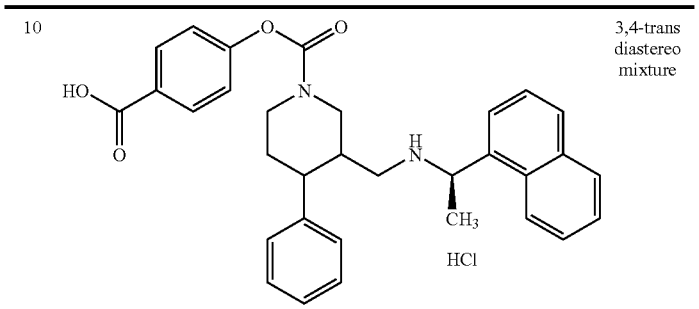 | 3,4-trans diastereo mixture |
| 11 | 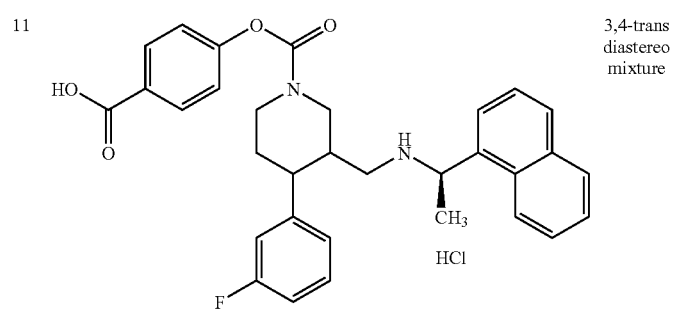 | 3,4-trans diastereo mixture |
| 61 | 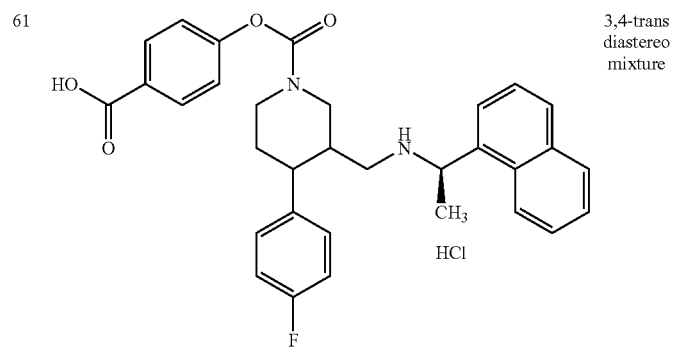 | 3,4-trans diastereo mixture |

TABLE 18-continued
| 12 | 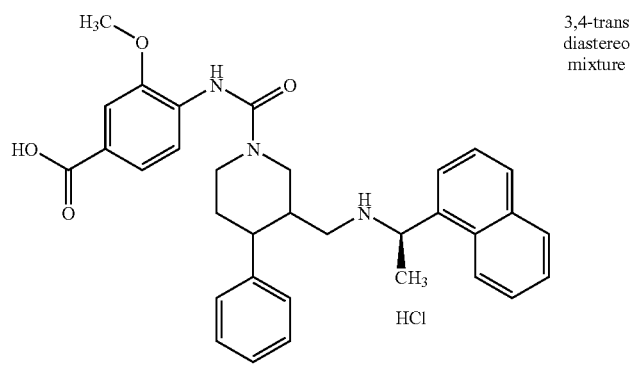 | 3,4-trans diastereo mixture |
| 13 | 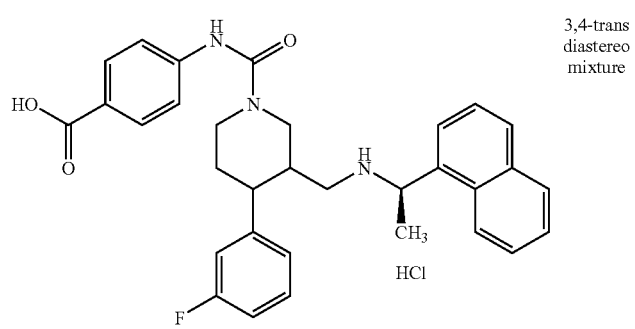 | 3,4-trans diastereo mixture |
TABLE 19
| 14 | 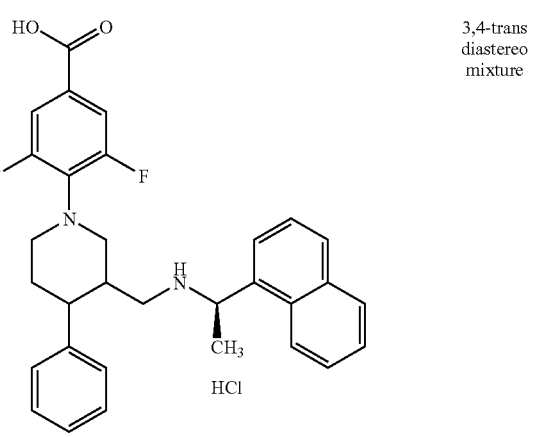 | 3,4-trans diastereo mixture |

TABLE 19-continued
| | | |
|---|---|---|
| 15 | 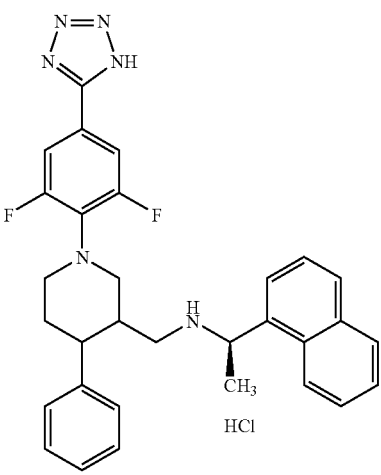 | 3,4-trans diastereo mixture |
| 62 | 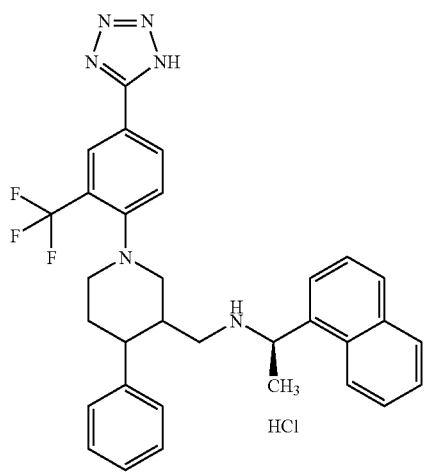 | 3,4-trans diastereo mixture |
| 16 | 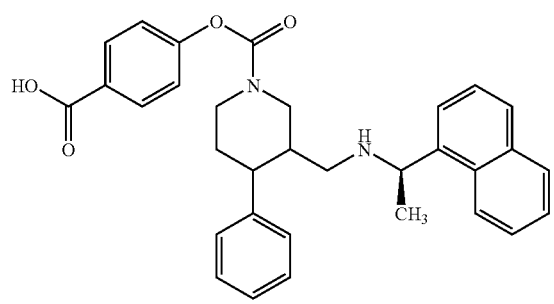 | 3,4-trans |

TABLE 20
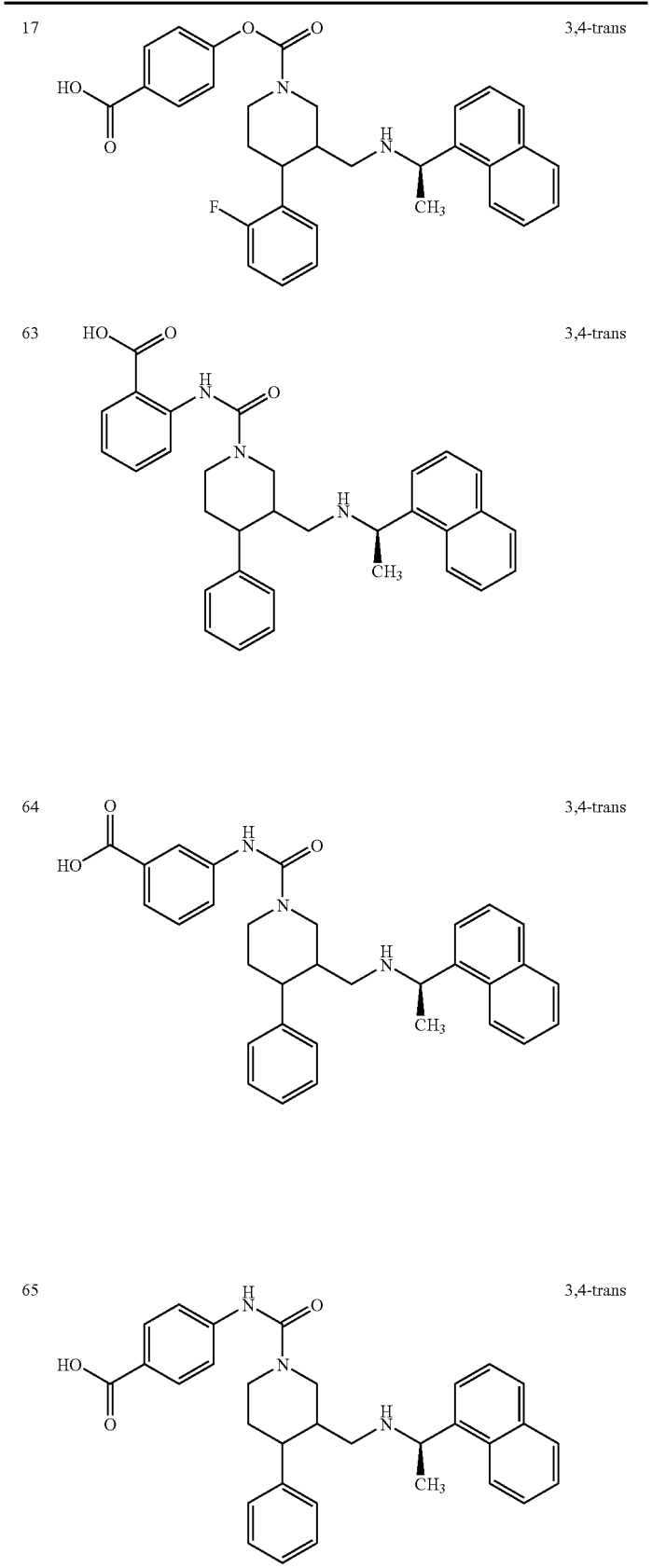

TABLE 20-continued
| 66 | 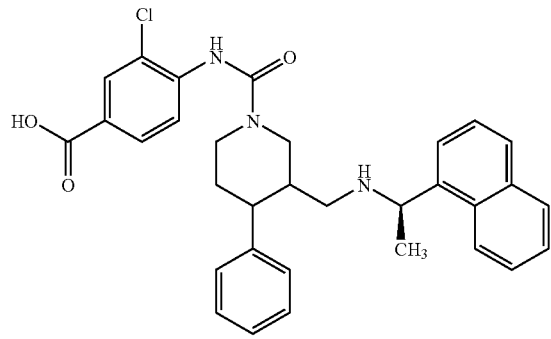 | 3,4-trans |
|---|---|---|
TABLE 21
| 3 | 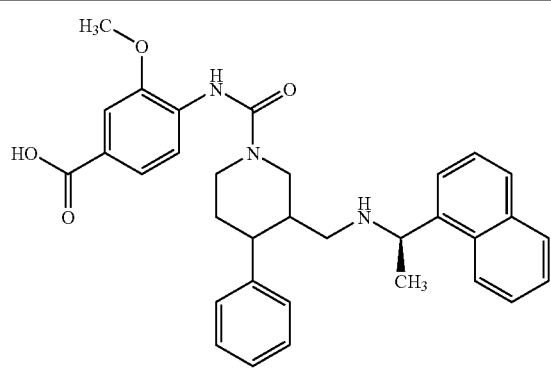 | 3,4-trans |
|---|---|---|
| 45 | 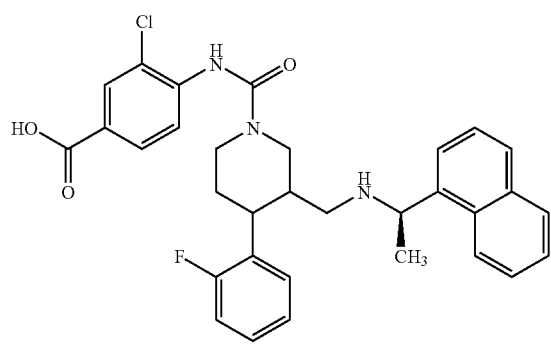 | 3,4-trans |
| 50 | 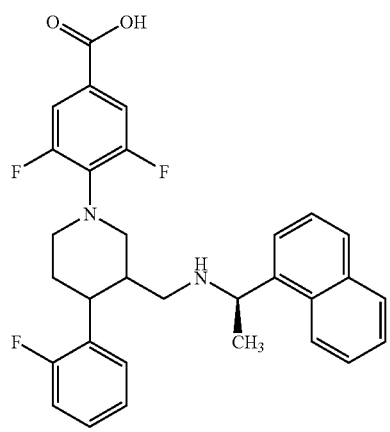 | 3,4-trans |

TABLE 21-continued
| 67 | 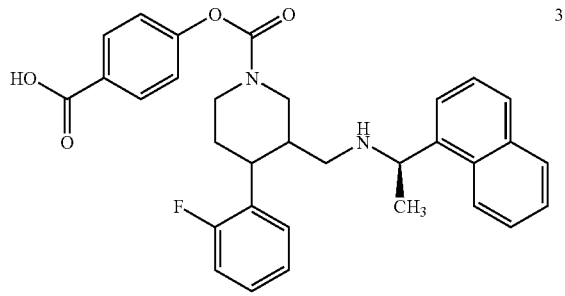 | 3,4-trans |
| --- | --- | --- |
| 18 | 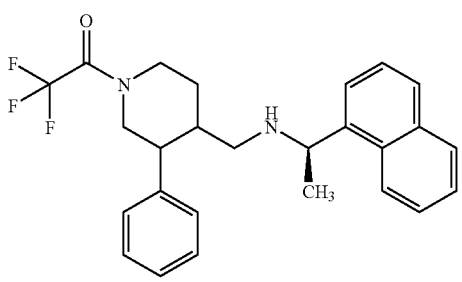 | 3,4-trans diastereo mixture |
TABLE 22
| 68 | 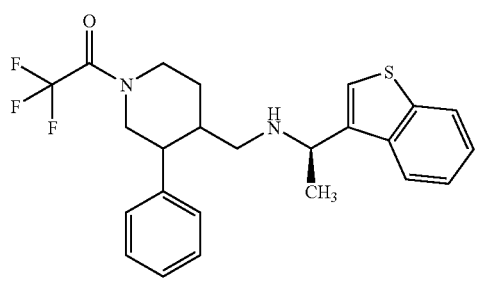 | 3,4-trans diastereo mixture |
| --- | --- | --- |
| 69 | 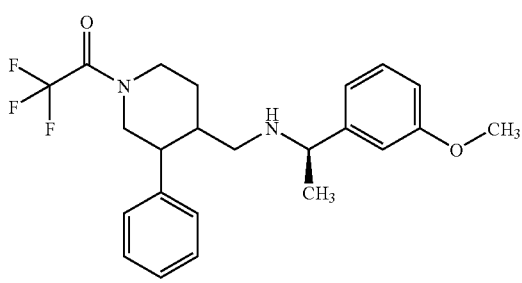 | 3,4-trans diastereo mixture |
| 19 | 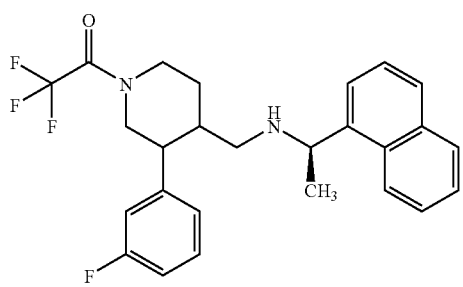 | 3,4-trans diastereo mixture |

TABLE 22-continued
| 70 | 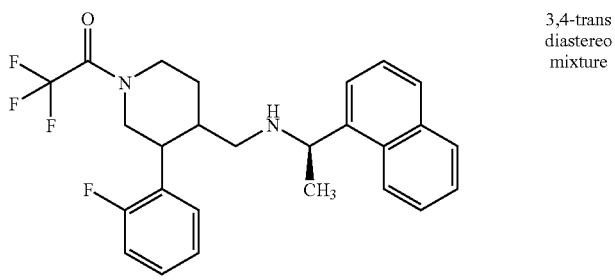 | 3,4-trans diastereo mixture |
| 71 | 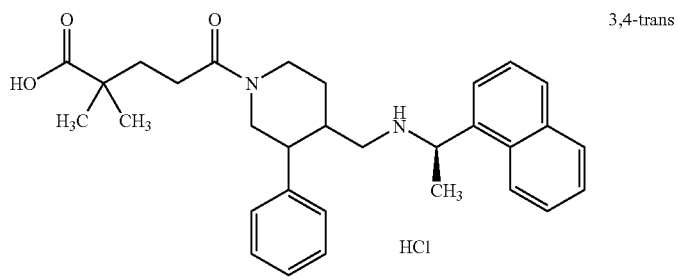 | 3,4-trans |
| 51 | 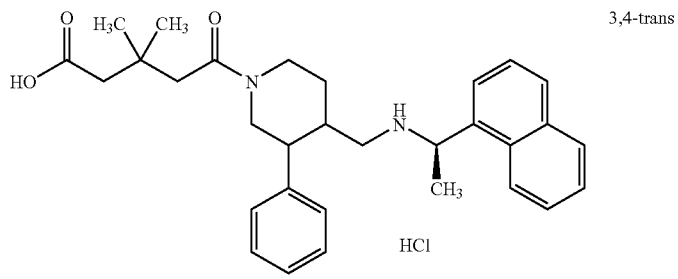 | 3,4-trans |
TABLE 23
| 20 | 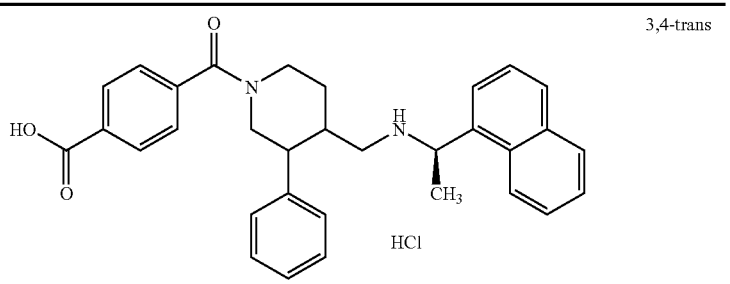 | 3,4-trans |
| 21 | 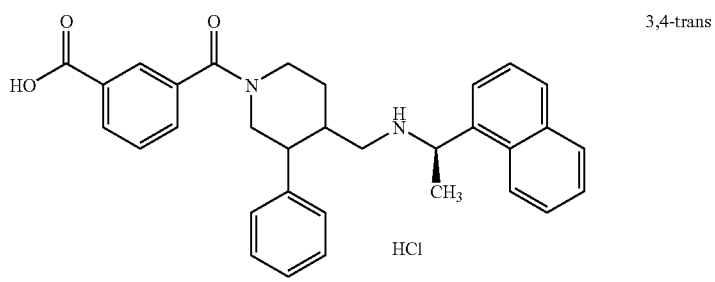 | 3,4-trans |

TABLE 23-continued
| 22 | 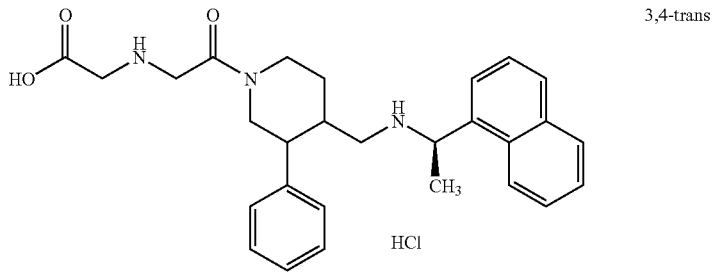 | 3,4-trans |
| 72 | 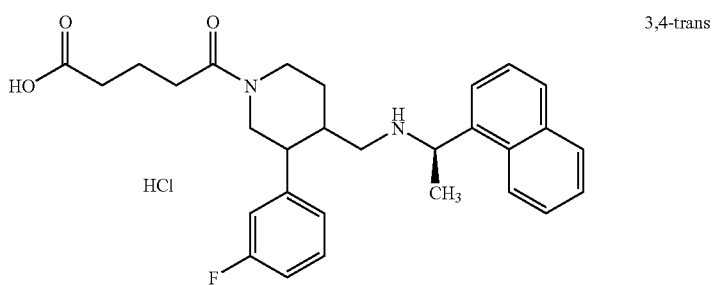 | 3,4-trans |
| 73 | 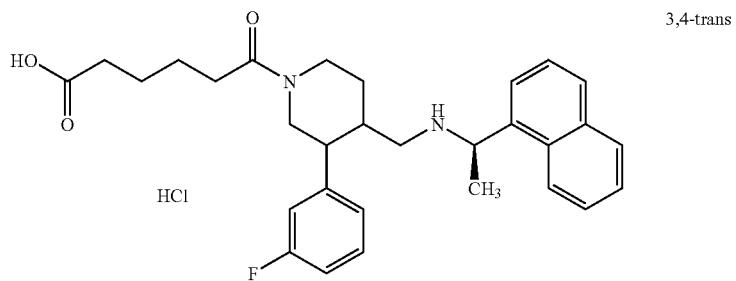 | 3,4-trans |
| 74 | 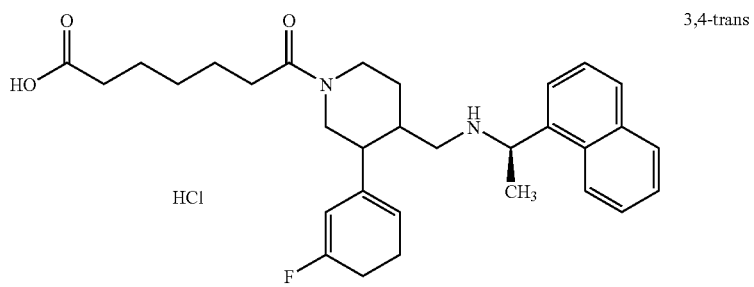 | 3,4-trans |
TABLE 24
| 24 | 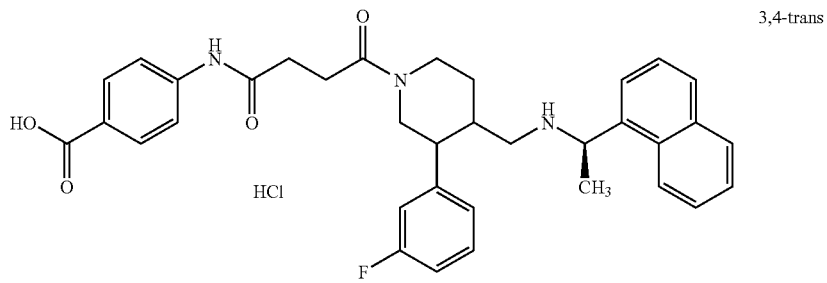 | 3,4-trans |

TABLE 24-continued

| 23 | [structure: 3-(3-fluorophenyl)-4-{[(1-(naphthalen-1-yl)ethyl)amino]methyl}piperidine N-acylated with succinic acid (HOOC-CH2-CH2-C(O)-); HCl salt] | 3,4-trans |
| 75 | [structure: same piperidine core N-acylated with 5-carboxythiophene-2-carbonyl; HCl salt] | 3,4-trans |
| 76 | [structure: same piperidine core N-acylated with HOOC-(CH2)5-C(O)-; HCl salt] | 3,4-trans |
| 25 | [structure: 3-phenyl-4-{[(1-(naphthalen-1-yl)ethyl)amino]methyl}piperidine N-carboxylated as 4-carboxyphenyl carbamate; HCl salt] | 3,4-trans |

TABLE 25

| 77 | [structure: 3-phenyl-4-{[(1-(benzo[b]thiophen-3-yl)ethyl)amino]methyl}piperidine N-carboxylated as 4-carboxyphenyl carbamate; HCl salt] | 3,4-trans |

TABLE 25-continued
| 78 | 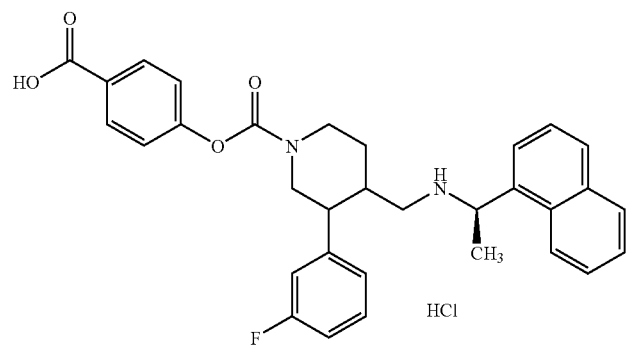 | 3,4-trans |
| 79 | 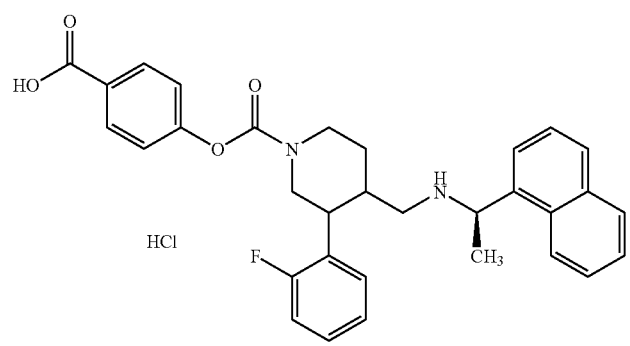 | 3,4-trans |
| 80 | 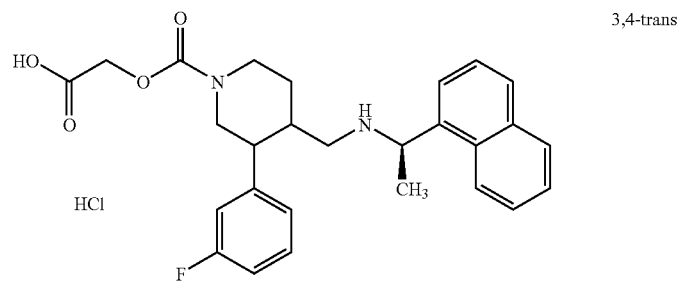 | 3,4-trans |
| 26 | 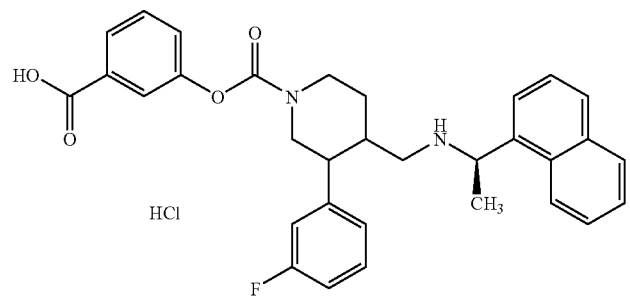 | 3,4-trans |

TABLE 26
27 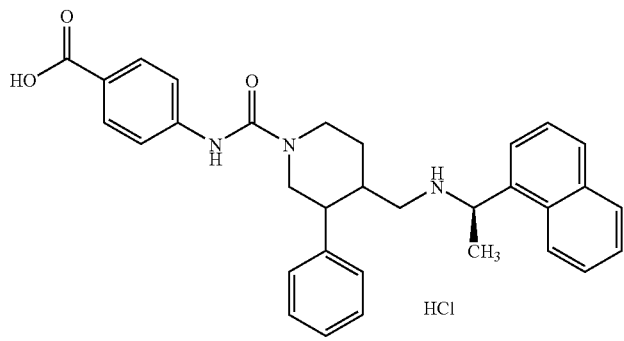 3,4-trans
81 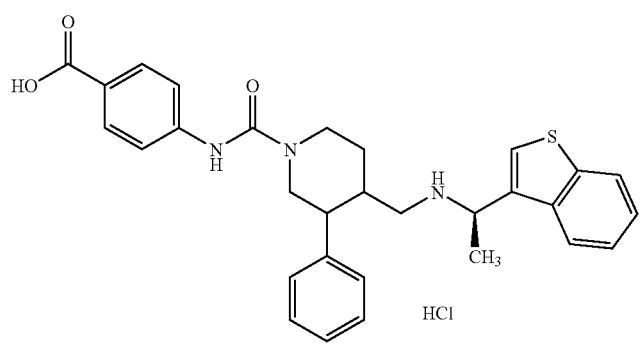 3,4-trans
82 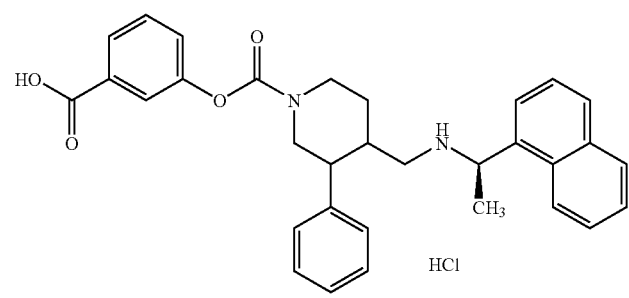 3,4-trans
28 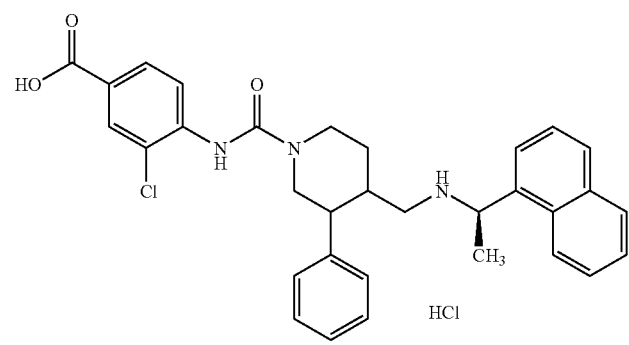 3,4-trans TABLE 26-continued
| 83 | 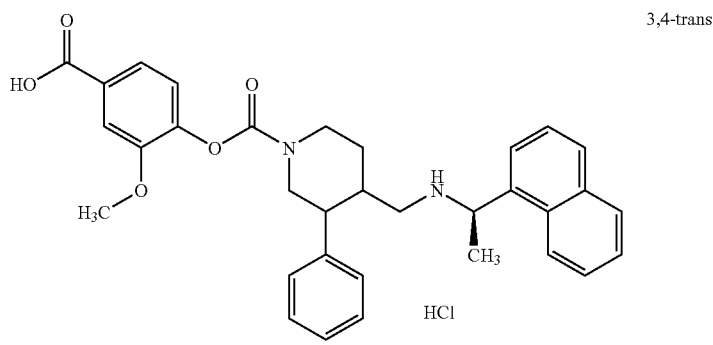 | 3,4-trans |
TABLE 27
| 29 | 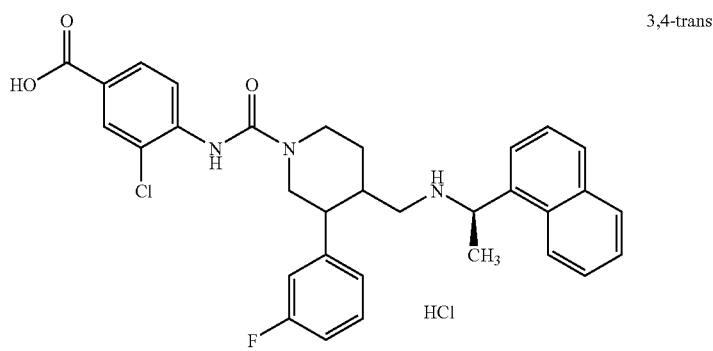 | 3,4-trans |
| 84 | 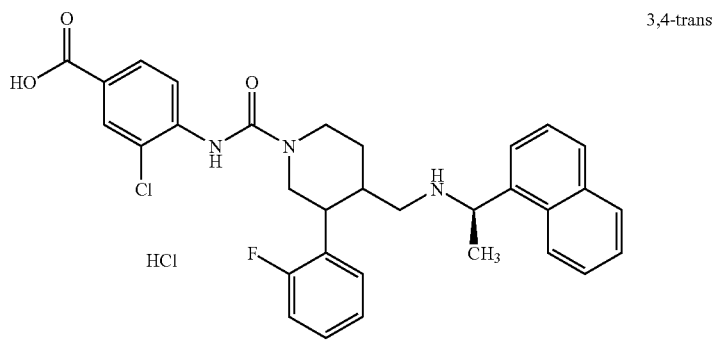 | 3,4-trans |
| 85 | 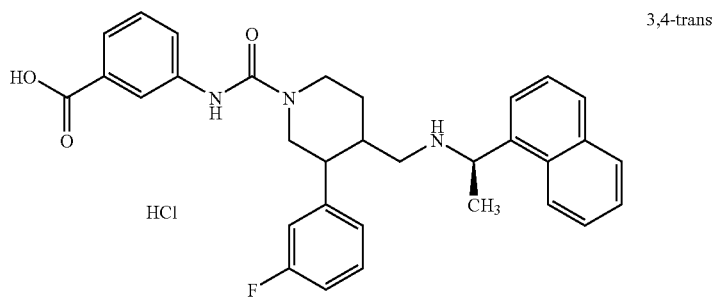 | 3,4-trans |

TABLE 27-continued
| 86 | 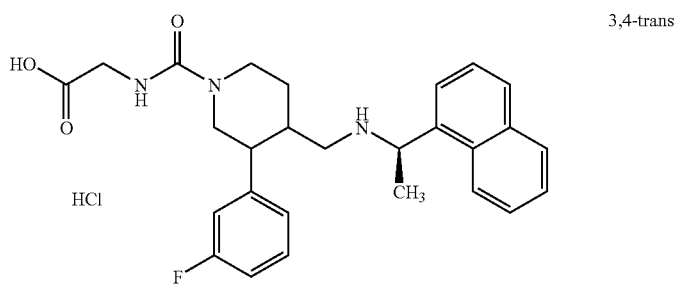 HCl | 3,4-trans |
|---|---|---|
| 42 | 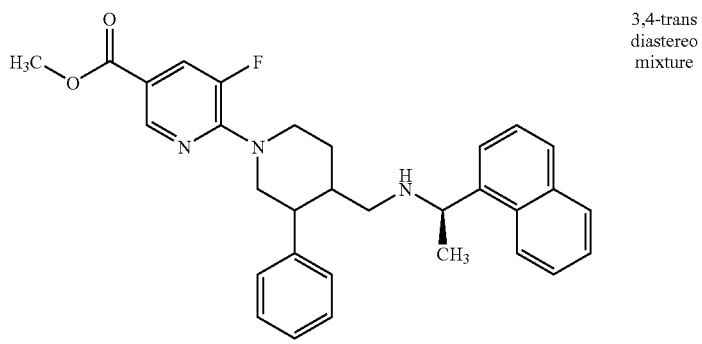 | 3,4-trans diastereo mixture |
TABLE 28
| 52 | 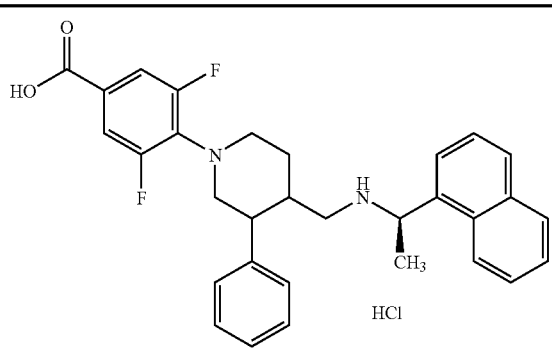 HCl | 3,4-trans |
|---|---|---|
| 87 | 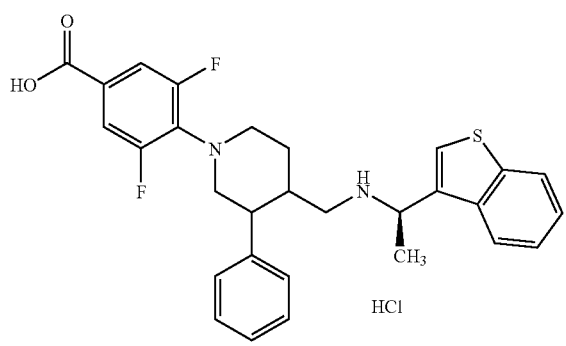 HCl | 3,4-trans |

TABLE 28-continued
| 88 | 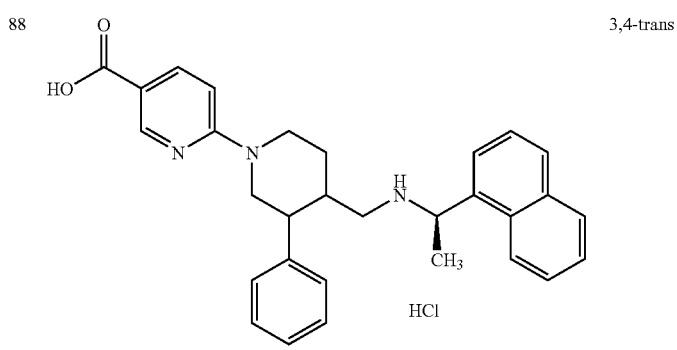 | 3,4-trans |
| 31 | 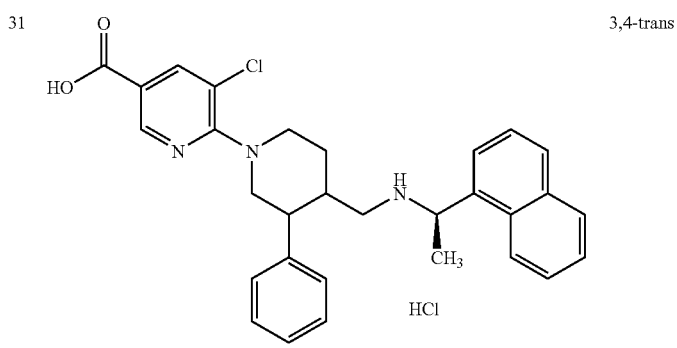 | 3,4-trans |
| 89 | 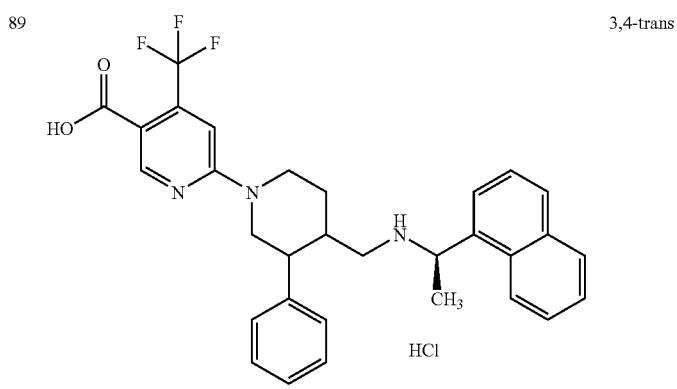 | 3,4-trans |
TABLE 29
| 90 | 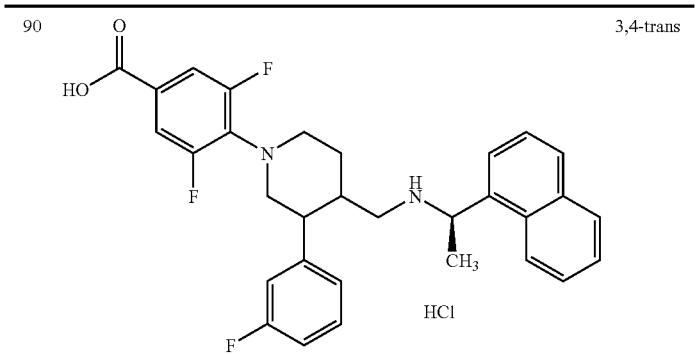 | 3,4-trans |

TABLE 29-continued
| 34 | 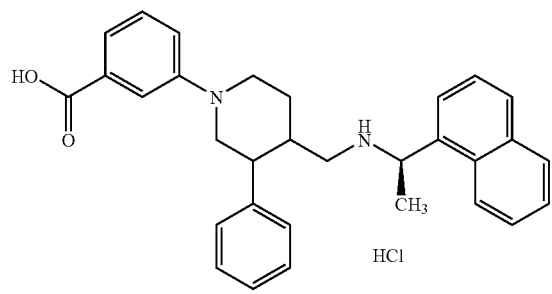 | 3,4-trans |
| --- | --- | --- |
| 91 | 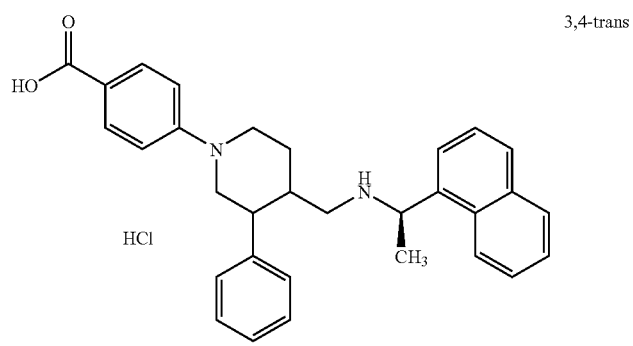 | 3,4-trans |
| 92 | 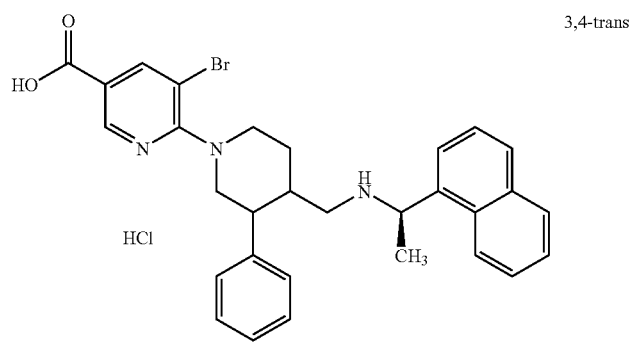 | 3,4-trans |
| 93 | 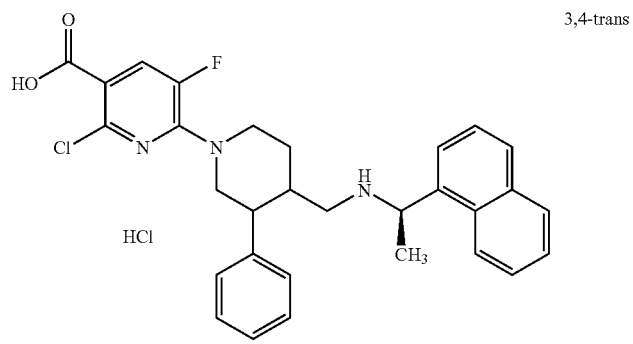 | 3,4-trans |

TABLE 30
| 94 | 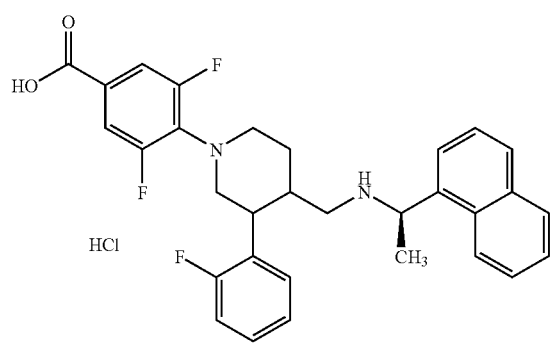 | 3,4-trans |
| 95 | 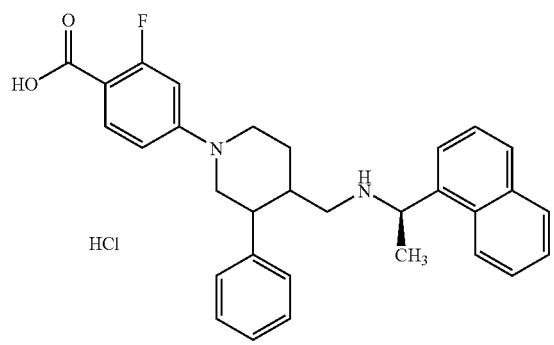 | 3,4-trans |
| 96 | 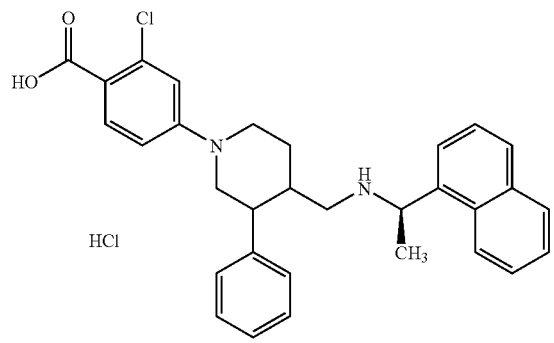 | 3,4-trans |
| 97 | 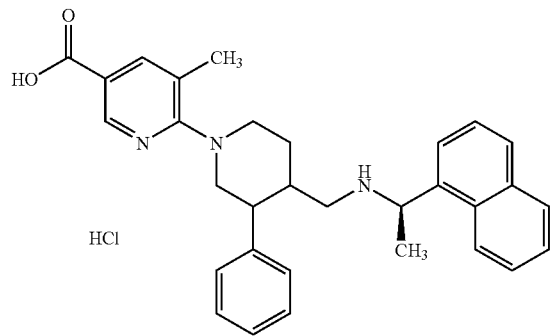 | 3,4-trans |

TABLE 30-continued
| | | |
|---|---|---|
| 98 | 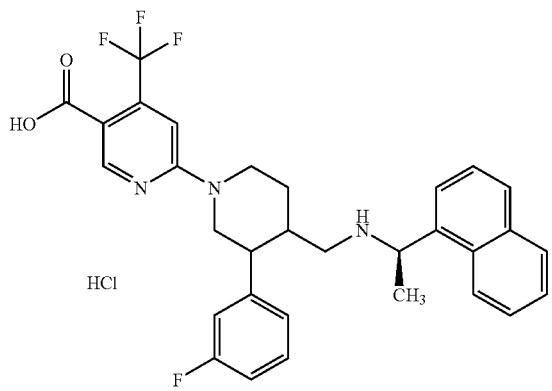 | 3,4-trans |
TABLE 31
| | | |
|---|---|---|
| 99 | 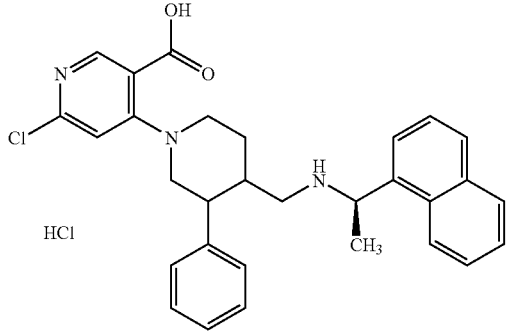 | 3,4-trans |
| 100 | 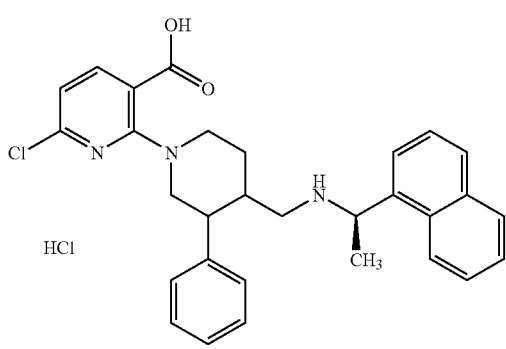 | 3,4-trans |
| 37 | 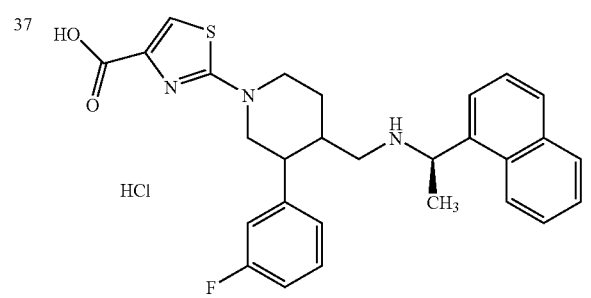 | 3,4-trans |

TABLE 31-continued
| 101 | 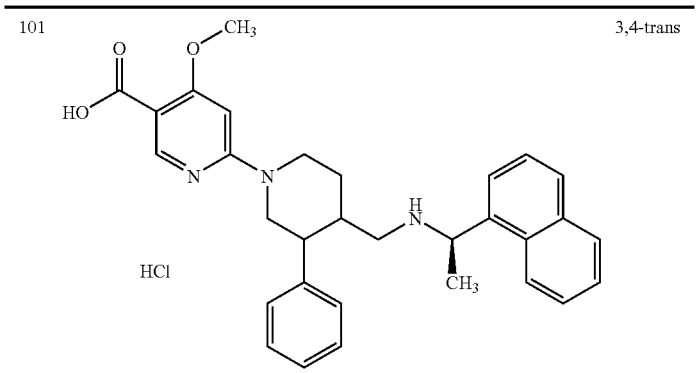 | 3,4-trans |
| 102 | 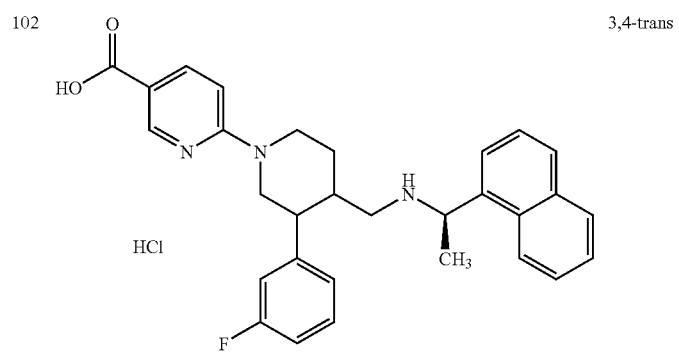 | 3,4-trans |
TABLE 32
| 103 | 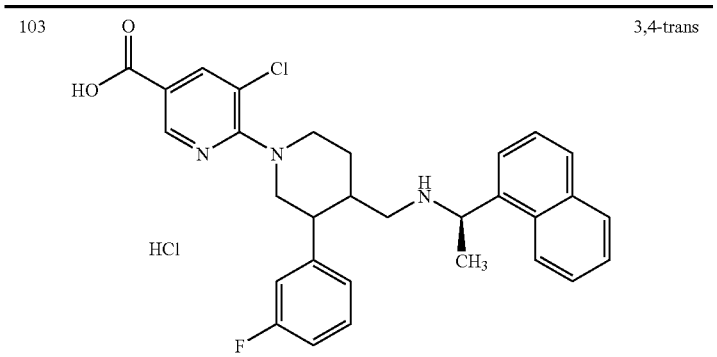 | 3,4-trans |
| 104 | 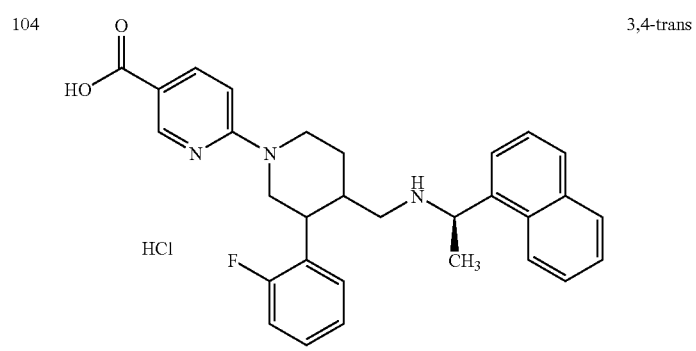 | 3,4-trans |

TABLE 32-continued
| 32 | 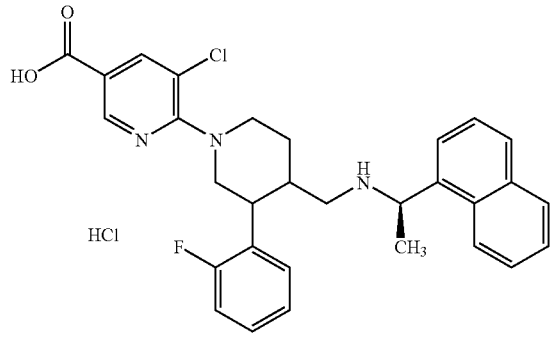 | 3,4-trans |
| 105 | 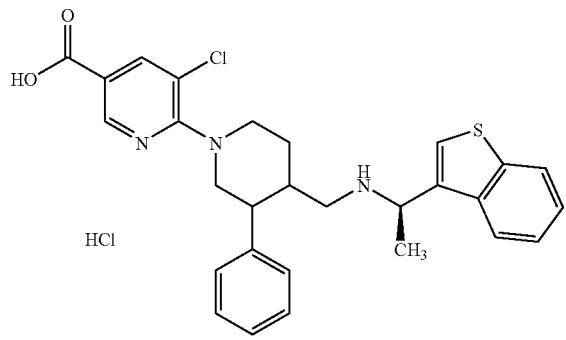 | 3,4-trans |
| 106 | 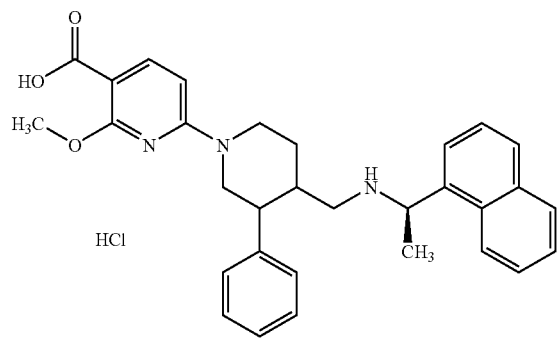 | 3,4-trans |
TABLE 33
| 107 | 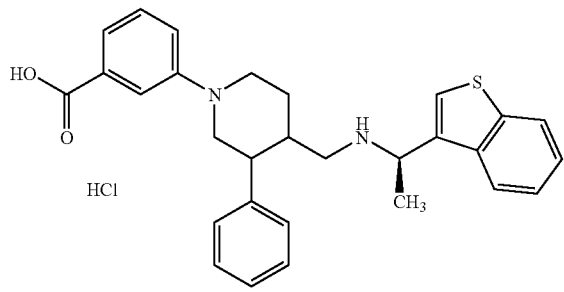 | 3,4-trans |

TABLE 33-continued
| 38 | 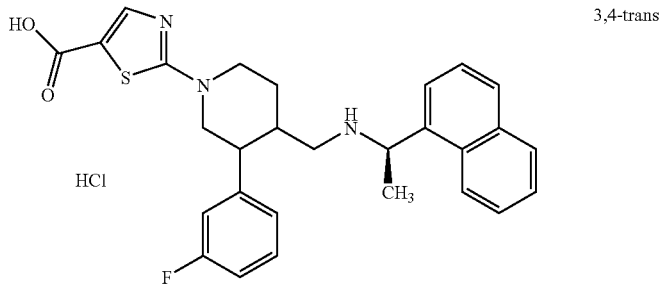 | 3,4-trans |
| 108 | 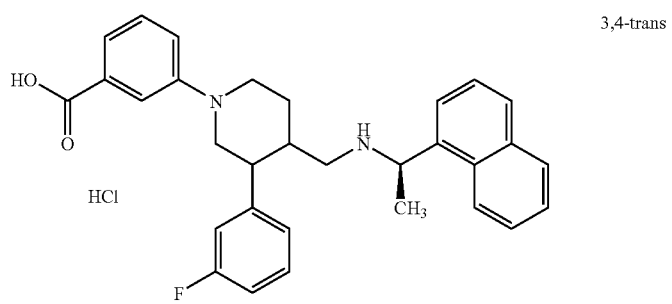 | 3,4-trans |
| 35 | 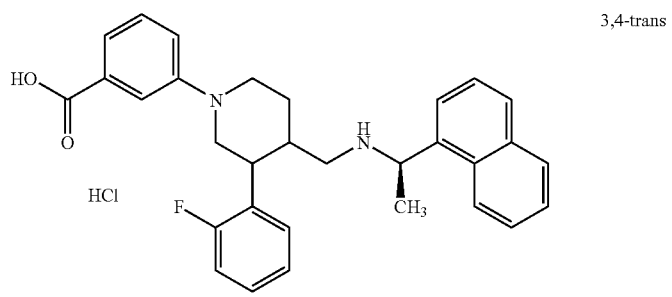 | 3,4-trans |
| 33 | 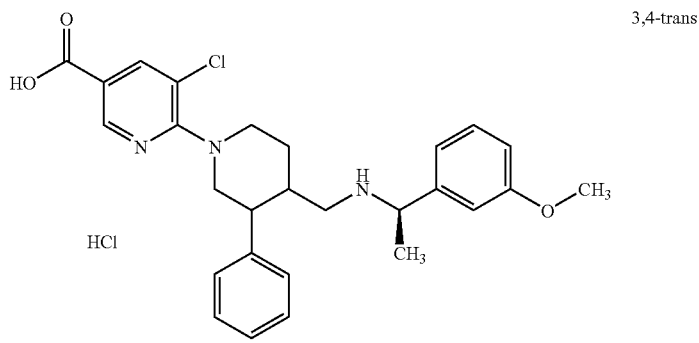 | 3,4-trans |

TABLE 34
30 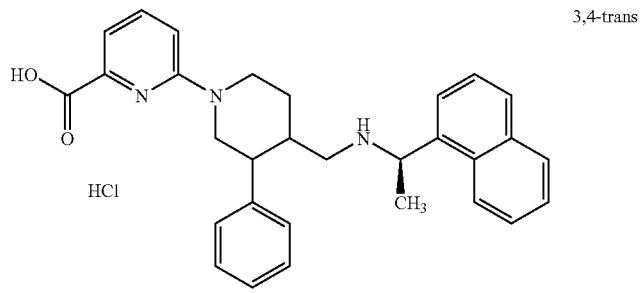 3,4-trans
109 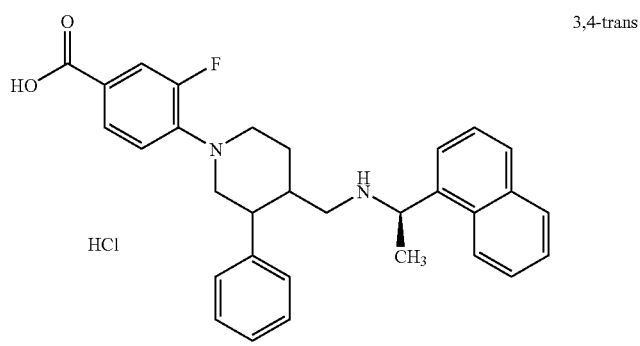 3,4-trans
110 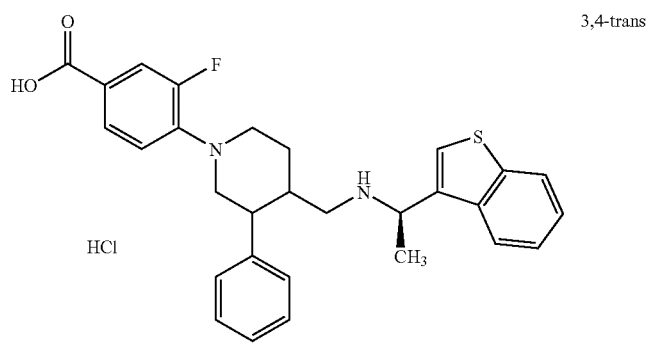 3,4-trans
111 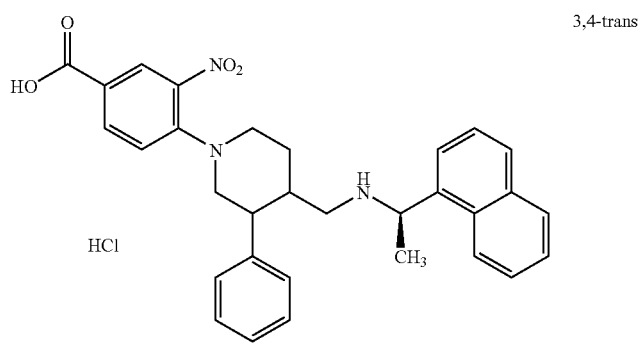 3,4-trans

TABLE 34-continued
| 112 | 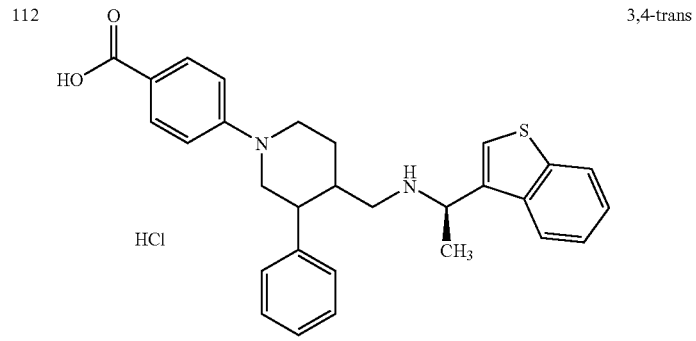 | 3,4-trans |
TABLE 35
| 113 | 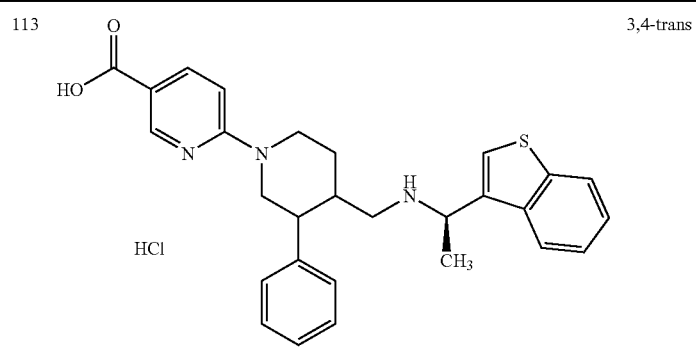 | 3,4-trans |
| 114 | 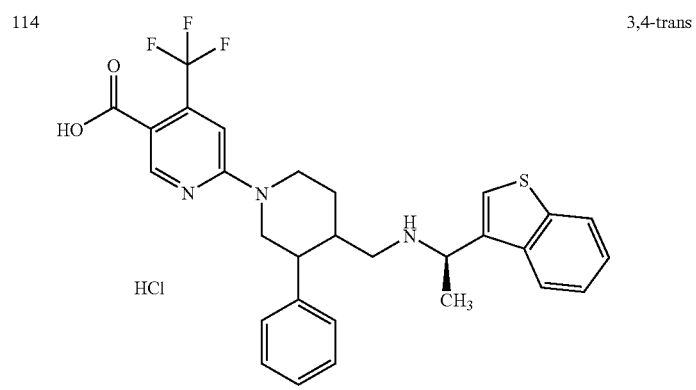 | 3,4-trans |
| 115 | 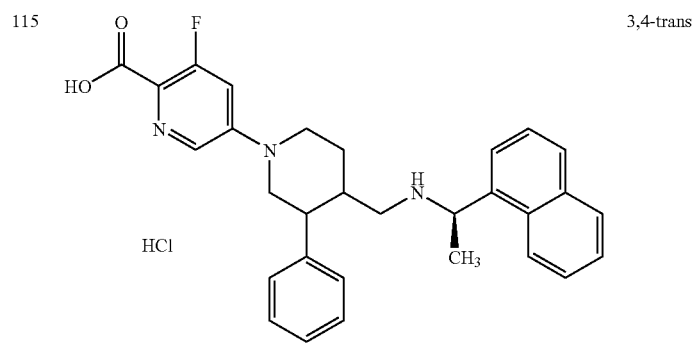 | 3,4-trans |

TABLE 35-continued
| 116 | 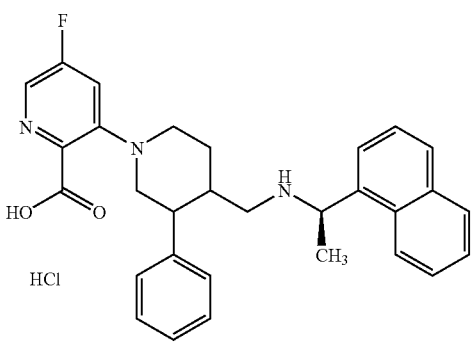 | 3,4-trans |
TABLE 36
| 36 | 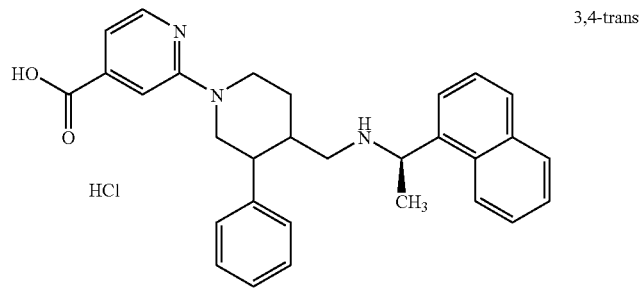 | 3,4-trans |
| 117 | 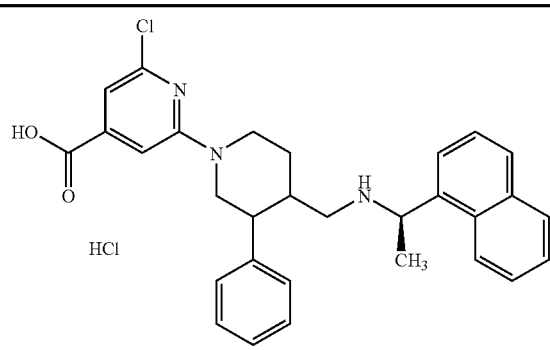 | 3,4-trans |
| 39 | 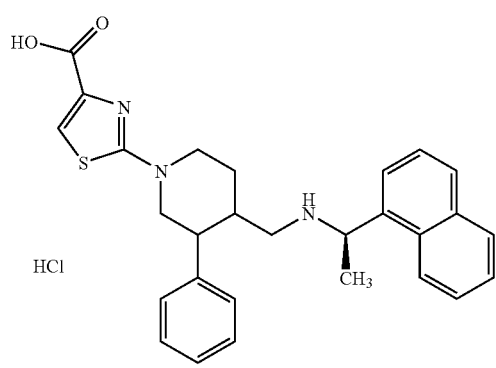 | 3,4-trans |

TABLE 36-continued
| 118 | 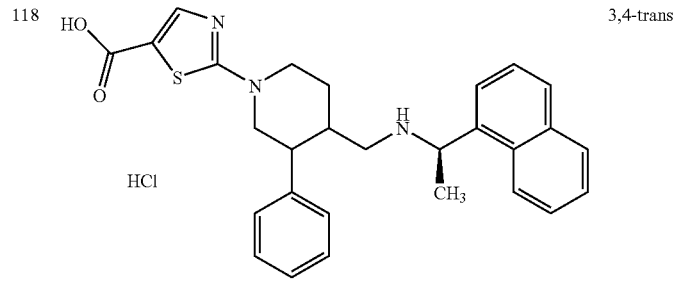 | 3,4-trans |
| 119 | 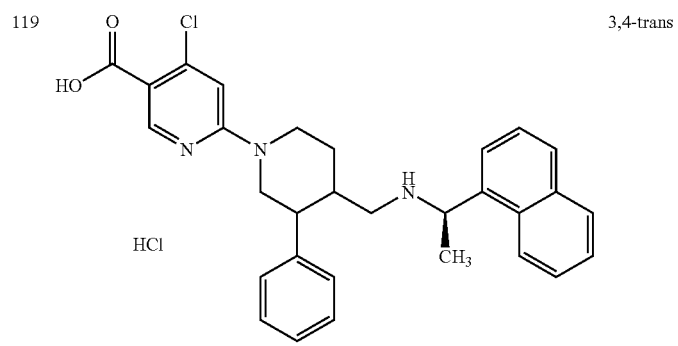 | 3,4-trans |
| 120 | 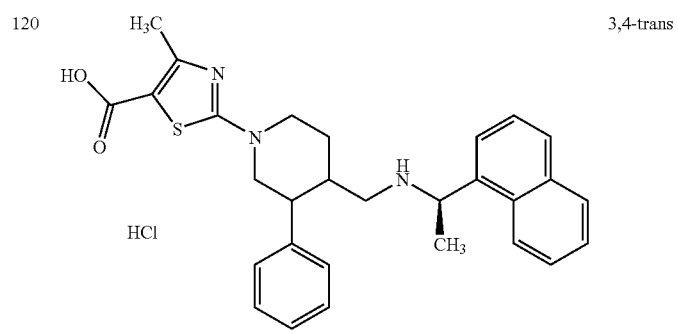 | 3,4-trans |
TABLE 37
| 40 | 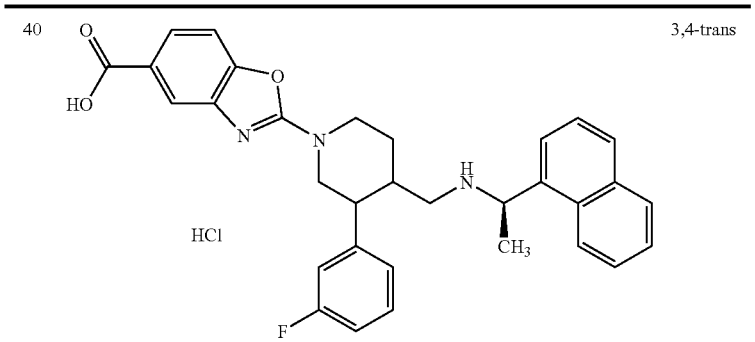 | 3,4-trans |

TABLE 37-continued
| 121 | 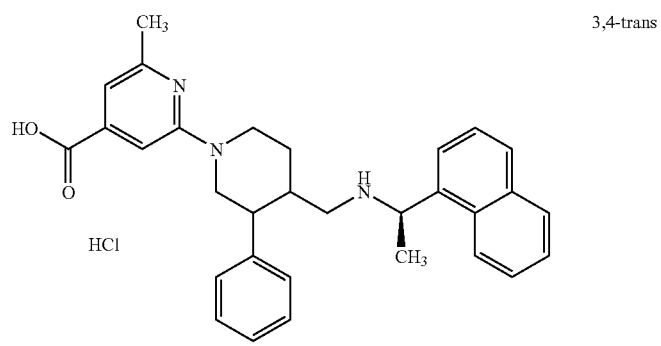 | 3,4-trans |
| 122 | 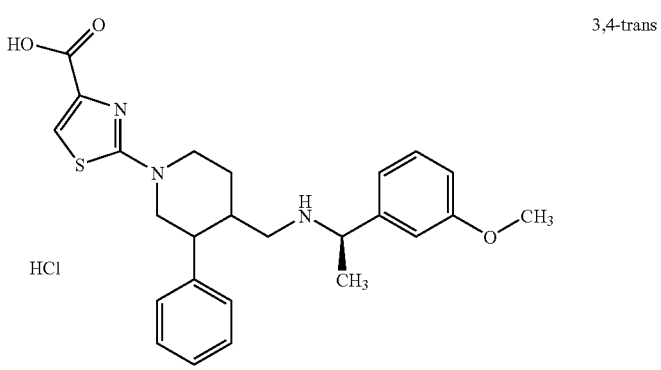 | 3,4-trans |
| 123 | 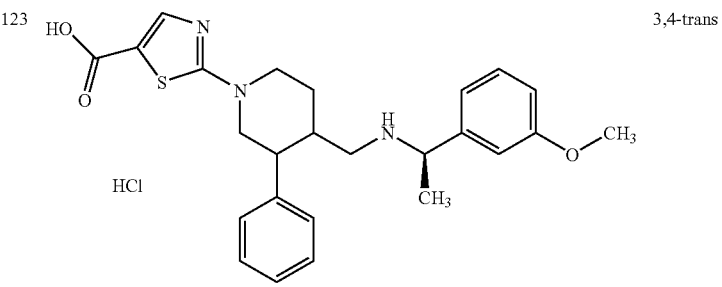 | 3,4-trans |
| 124 | 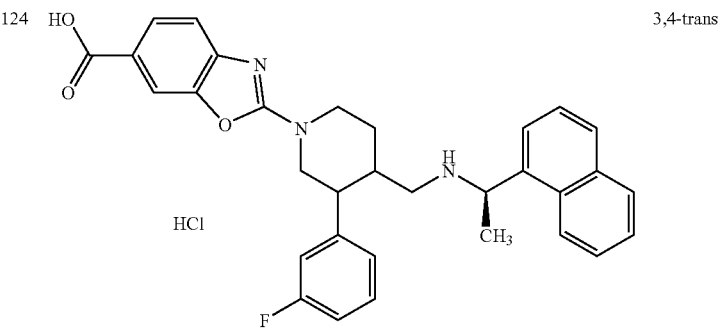 | 3,4-trans |

TABLE 38
| 125 | 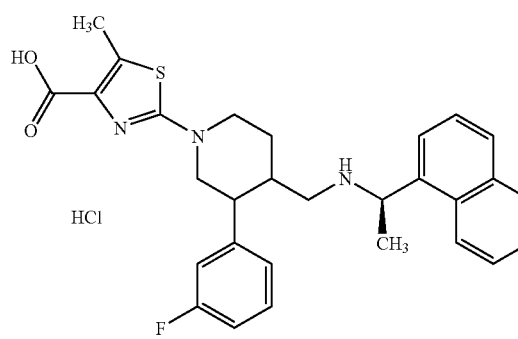 | 3,4-trans |
| --- | --- | --- |
| 41 | 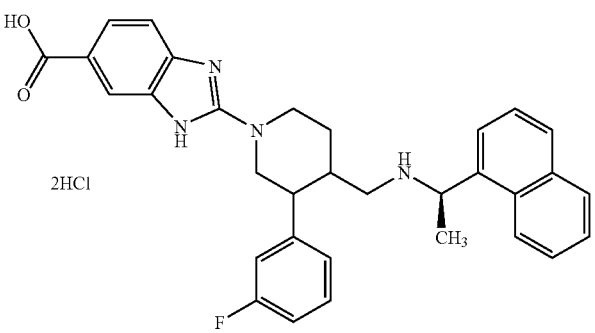 | 3,4-trans |
| 126 | 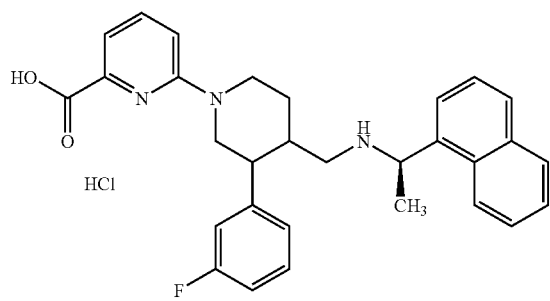 | 3,4-trans |
| 127 | 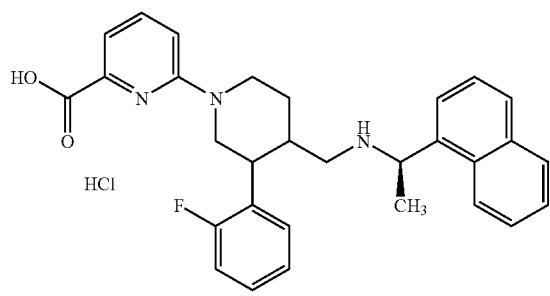 | 3,4-trans |
| 128 | 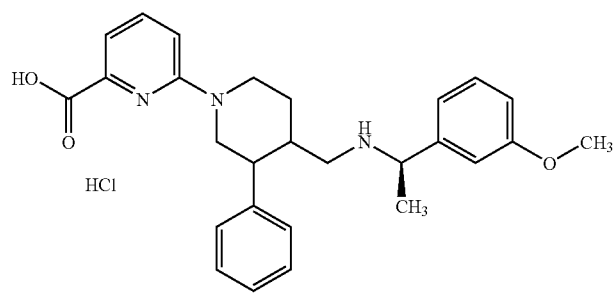 | 3,4-trans |

TABLE 39
| 43 | 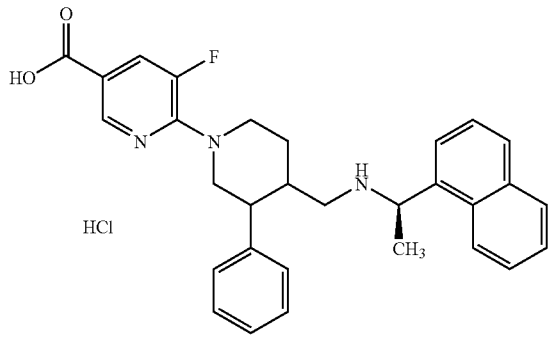 | 3,4-trans |
| --- | --- | --- |
| 44 | 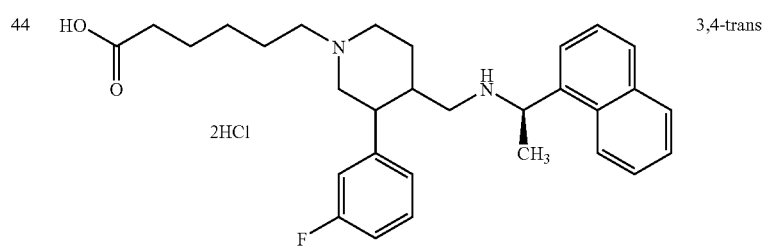 | 3,4-trans |
| 53 | 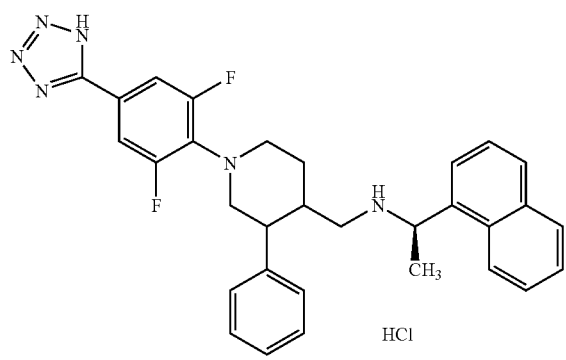 | 3,4-trans |
| 129 | 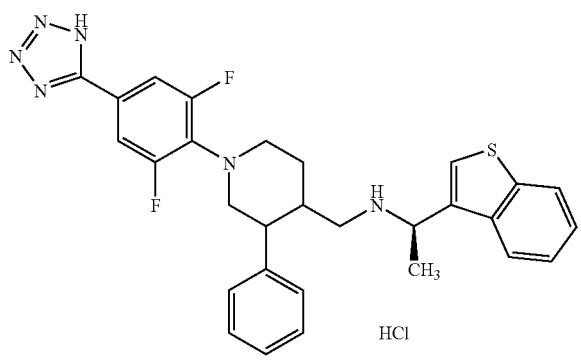 | 3,4-trans |

TABLE 39-continued
| 130 | 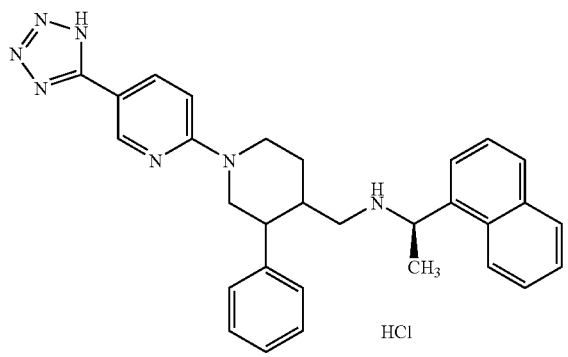 | 3,4-trans |
TABLE 40
| 54 | 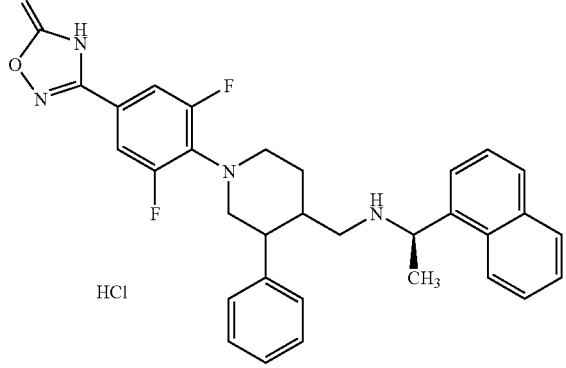 | 3,4-trans |
| 131 | 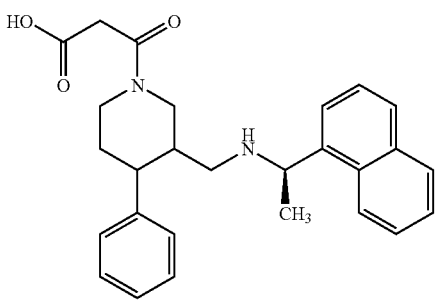 | 3,4-trans diastereo mixture |
| 132 | 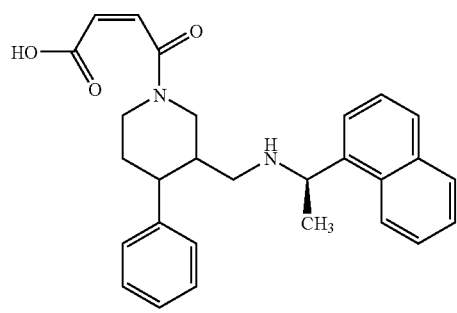 | 3,4-trans diastereo mixture |

TABLE 40-continued
| 133 | 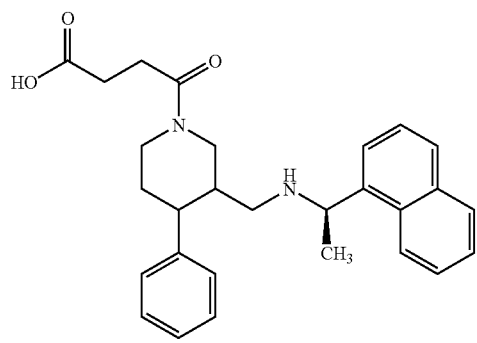 | 3,4-trans diastereo mixture |
|---|---|---|
| 134 | 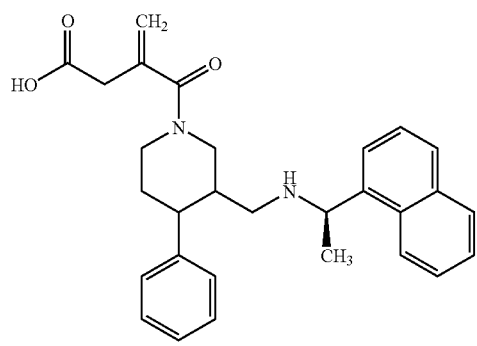 | 3,4-trans diastereo mixture |
TABLE 41
| 135 | 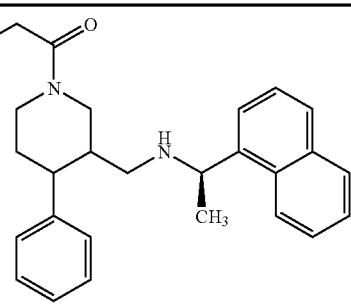 | 3,4-trans diastereo mixture |
|---|---|---|
| 136 | 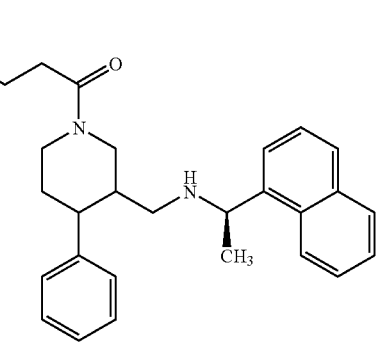 | 3,4-trans diastereo mixture |

TABLE 41-continued

| 137 | [structure: 3-methyl-4-carboxybutanoyl group on N of 3-{[(1-(naphthalen-1-yl)ethyl)amino]methyl}-4-phenylpiperidine] | 3,4-trans diastereo mixture |
|---|---|---|
| 138 | [structure: 2-methyl-5-carboxypentanoyl group on N of 3-{[(1-(naphthalen-1-yl)ethyl)amino]methyl}-4-phenylpiperidine] | 3,4-trans diastereo mixture |
| 139 | [structure: 2-carboxycyclopentanecarbonyl group on N of 3-{[(1-(naphthalen-1-yl)ethyl)amino]methyl}-4-phenylpiperidine] | 3,4-trans 1',2'-cis diastereo mixture |

TABLE 42

| 140 | [structure: 2-carboxycyclopentanecarbonyl group on N of 3-{[(1-(naphthalen-1-yl)ethyl)amino]methyl}-4-phenylpiperidine] | 3,4-trans 1',2'-trans diastereo mixture |

TABLE 42-continued
| 141 | 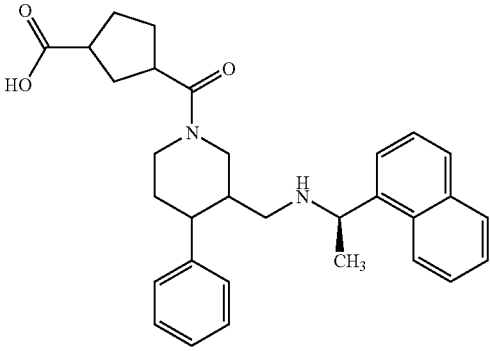 | 3,4-trans 1',3'-cis diastereo mixture |
| --- | --- | --- |
| 142 | 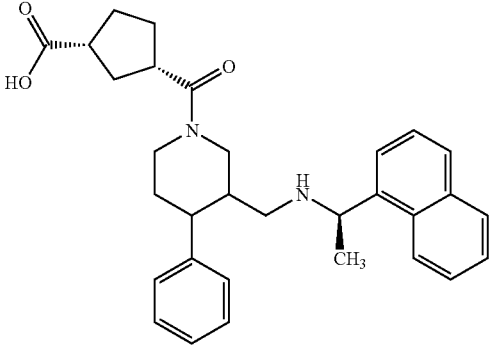 | 3,4-trans diastereo mixture |
| 143 | 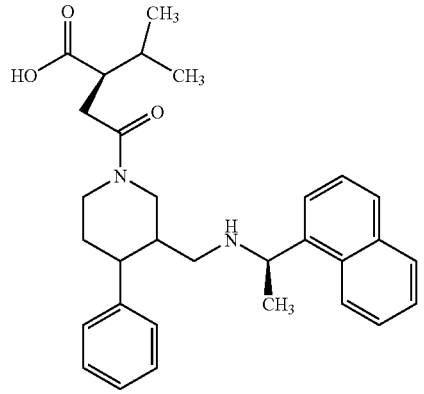 | 3,4-trans diastereo mixture |
TABLE 43
| 46 | 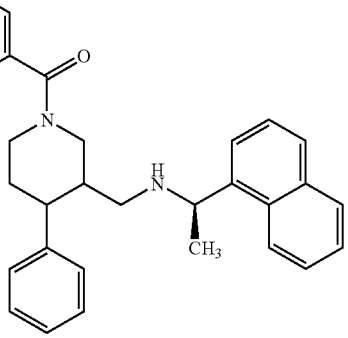 | 3,4-trans diastereo mixture |
| --- | --- | --- |

TABLE 43-continued
| 144 | 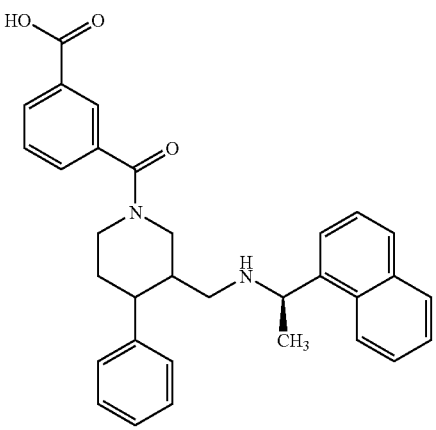 | 3,4-trans diastereo mixture |
|---|---|---|
| 145 | 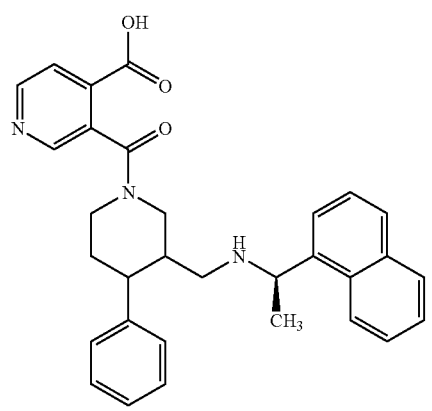 | 3,4-trans diastereo mixture |
| 146 | 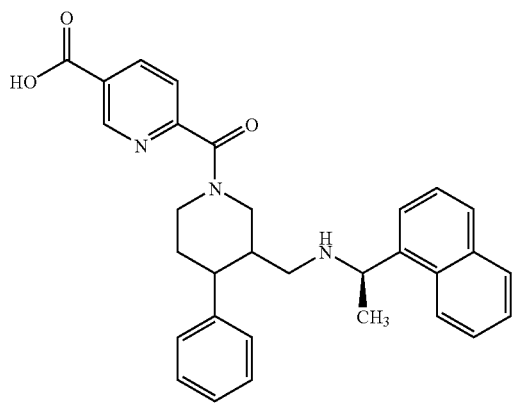 | 3,4-trans diastereo mixture |

TABLE 44
| | | |
|---|---|---|
| 147 | 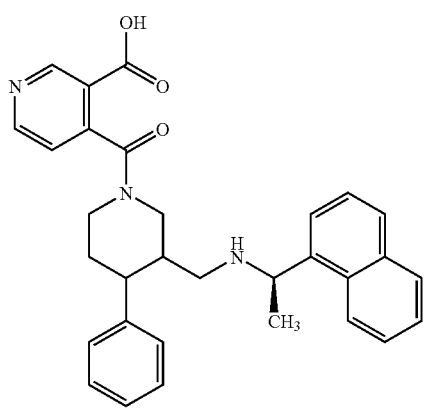 | 3,4-trans diastereo mixture |
| 148 | 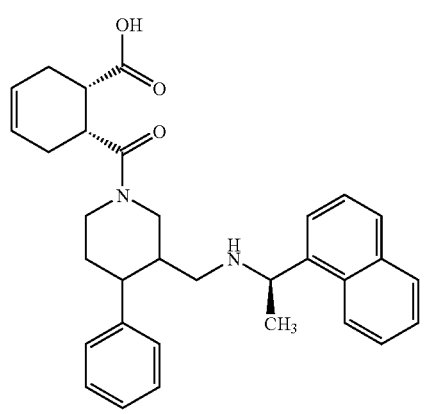 | 3,4-trans diastereo mixture |
| 149 | 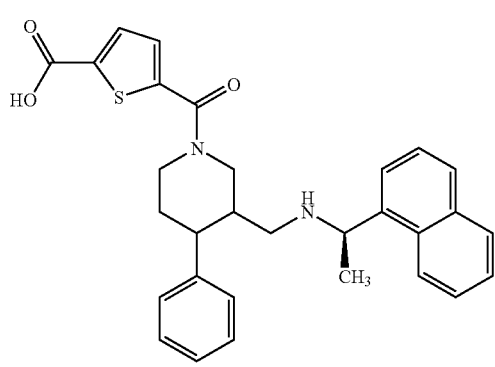 | 3,4-trans diastereo mixture |
| 150 | 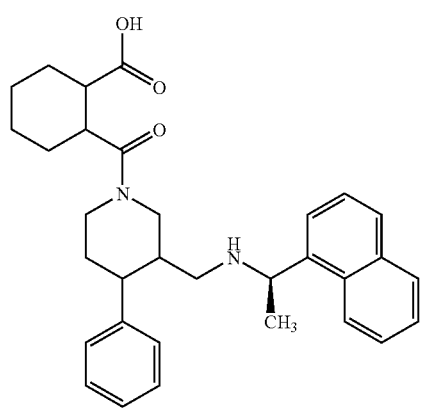 | 3,4-trans 1',2'-trans diastereo mixture |

TABLE 45
| | | |
|---|---|---|
| 151 | 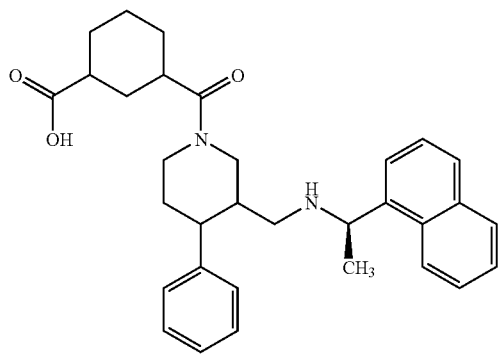 | 3,4-trans 1',3'-cis diastereo mixture |
| 152 | 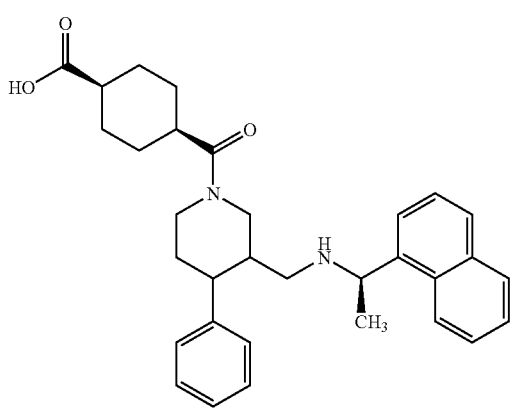 | 3,4-trans diastereo mixture |
| 153 | 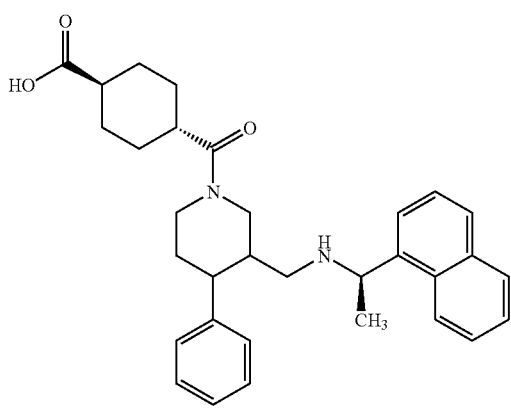 | 3,4-trans diastereo mixture |
| 154 | 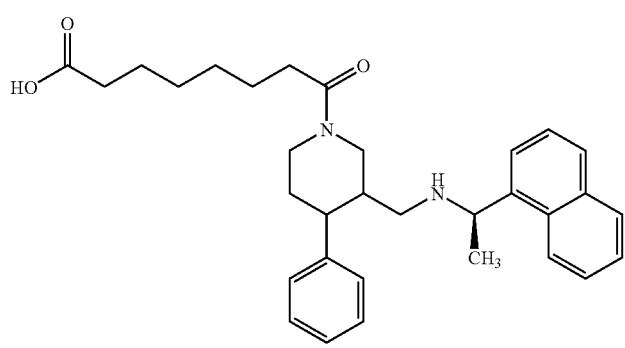 | 3,4-trans diastereo mixture |

TABLE 46
| | | |
|---|---|---|
| 155 | 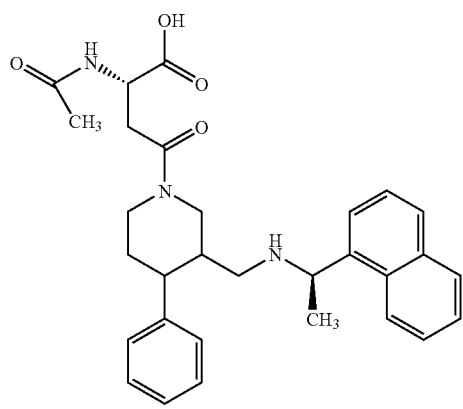 | 3,4-trans diastereo mixture |
| 156 | 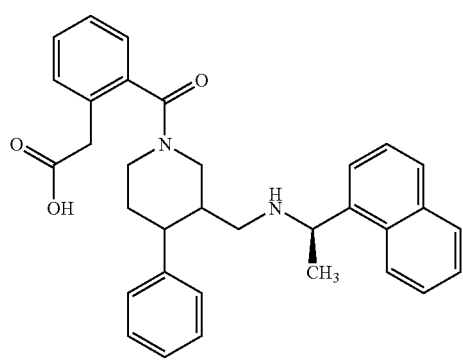 | 3,4-trans diastereo mixture |
| 157 | 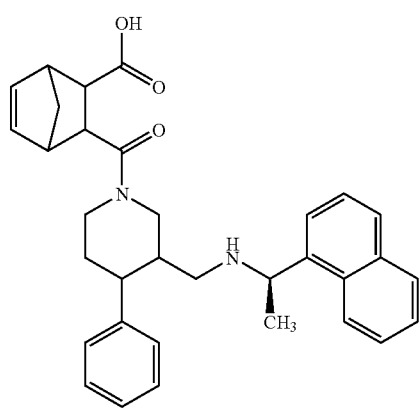 | 3,4-trans diastereo mixture |
| 158 | 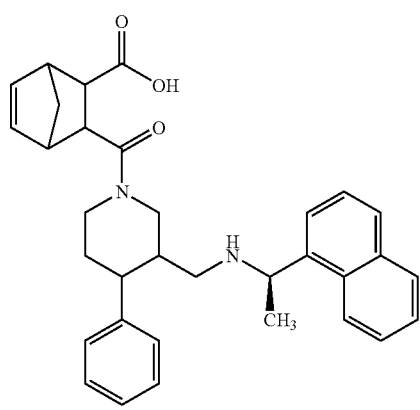 | 3,4-trans 2′,3′-cis-endo diastereo mixture |

TABLE 47
| 159 | 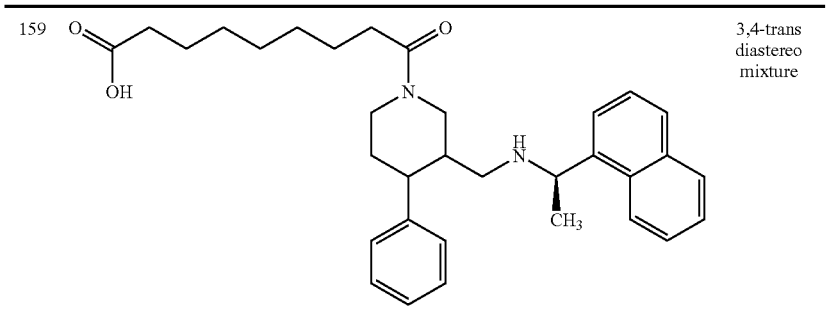 | 3,4-trans diastereo mixture |
| --- | --- | --- |
| 160 | 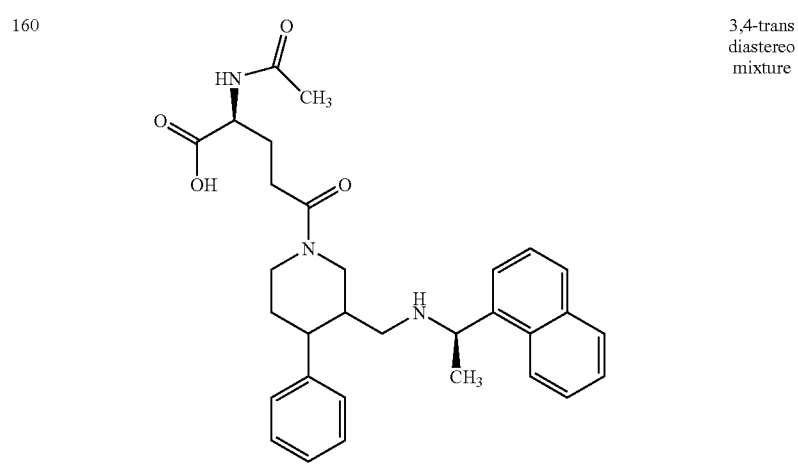 | 3,4-trans diastereo mixture |
| 161 | 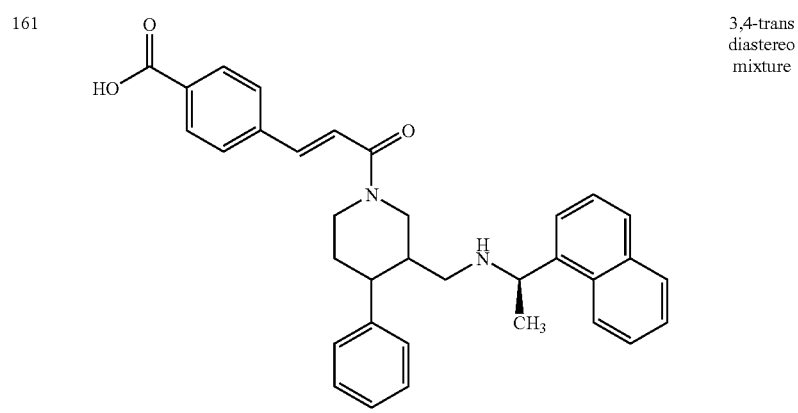 | 3,4-trans diastereo mixture |
| 162 | 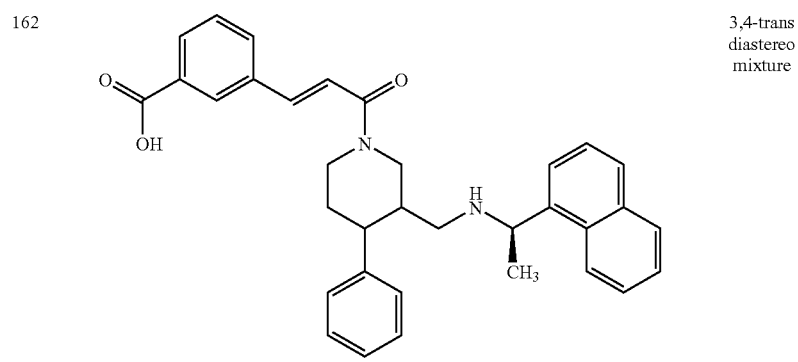 | 3,4-trans diastereo mixture |

TABLE 48
| | | |
|---|---|---|
| 163 | 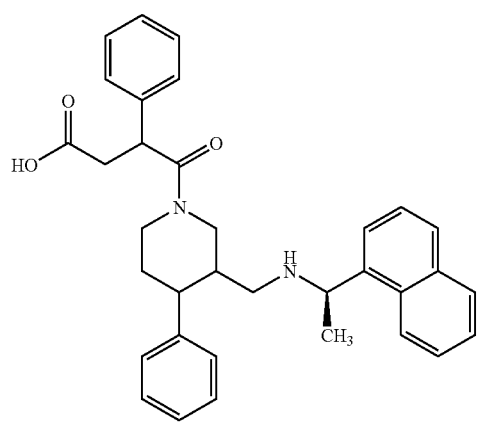 | 3,4-trans diastereo mixture |
| 164 | 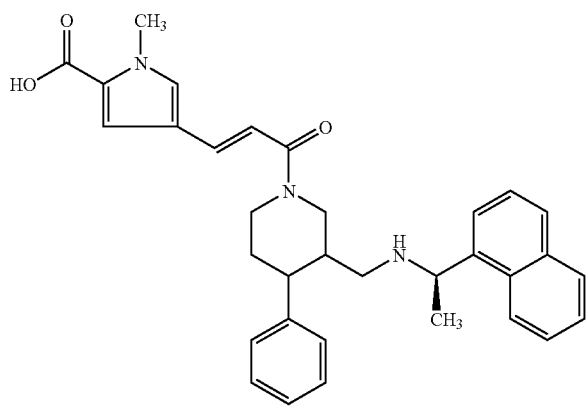 | 3,4-trans diastereo mixture |
| 165 | 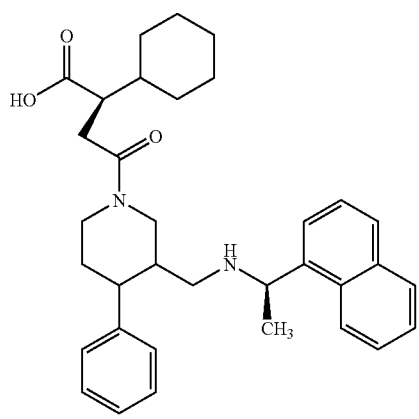 | 3,4-trans diastereo mixture |
| 166 | 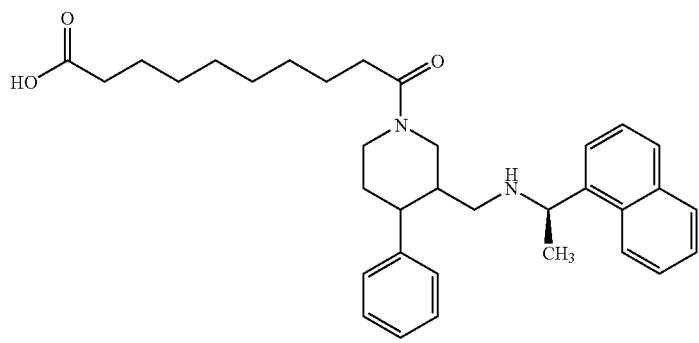 | 3,4-trans diastereo mixture |

TABLE 49
| 167 | 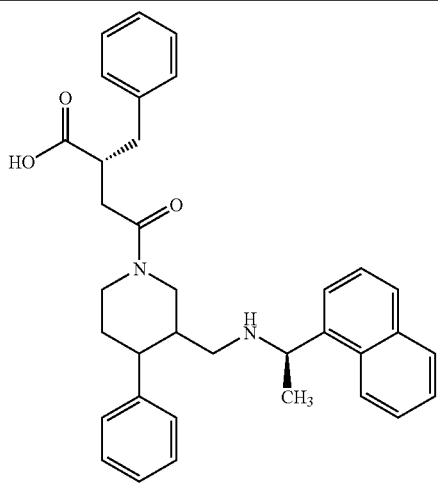 | 3,4-trans diastereo mixture |
| --- | --- | --- |
| 168 | 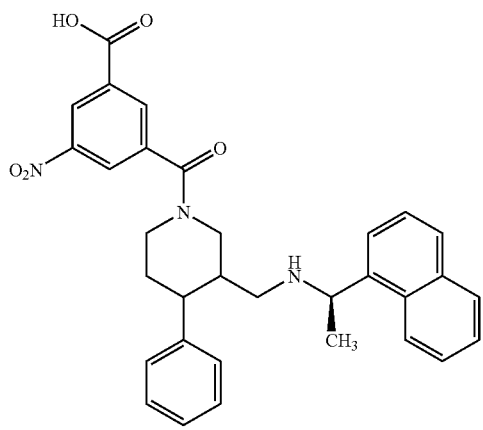 | 3,4-trans diastereo mixture |
| 169 | 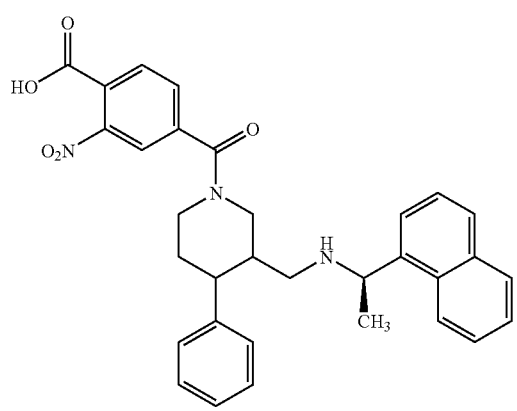 | 3,4-trans diastereo mixture |

TABLE 49-continued
| 170 | 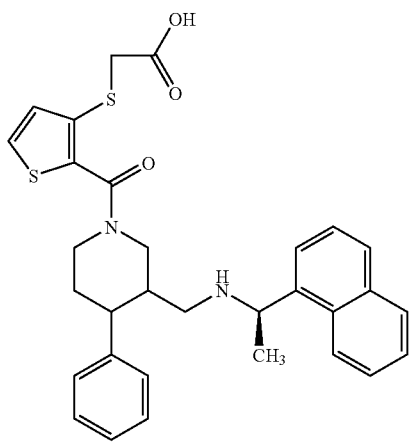 | 3,4-trans diastereo mixture |
TABLE 50
| 171 | 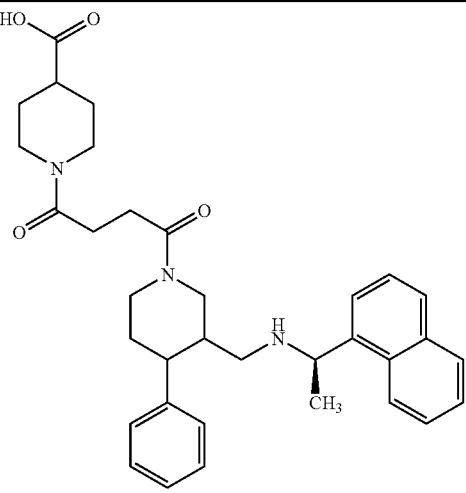 | 3,4-trans diastereo mixture |
| 172 | 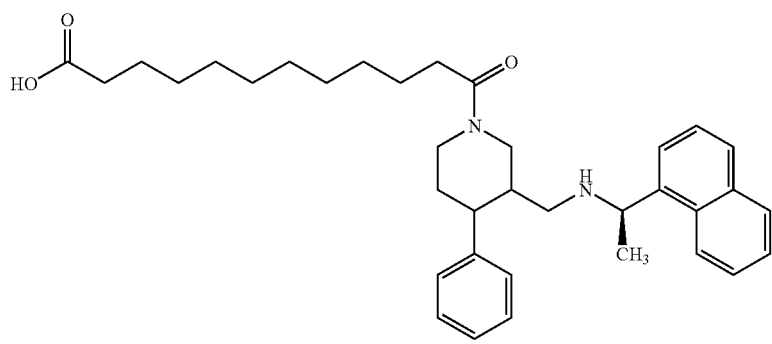 | 3,4-trans diastereo mixture |

TABLE 50-continued
| 173 | 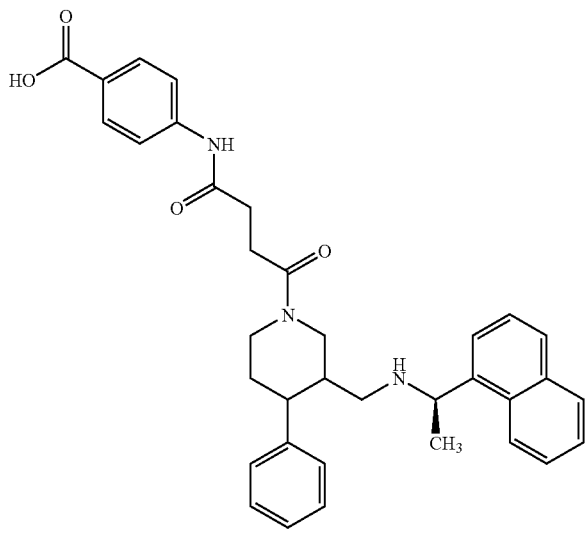 | 3,4-trans diastereo mixture |
|---|---|---|
| 174 | 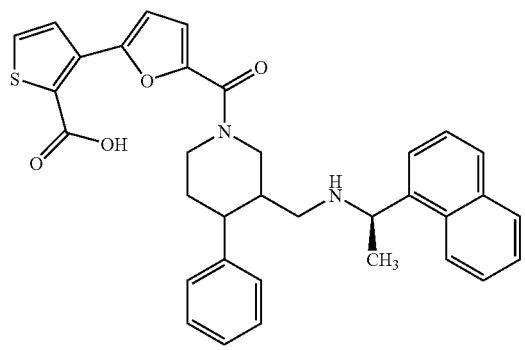 | 3,4-trans diastereo mixture |
TABLE 51
| 175 | 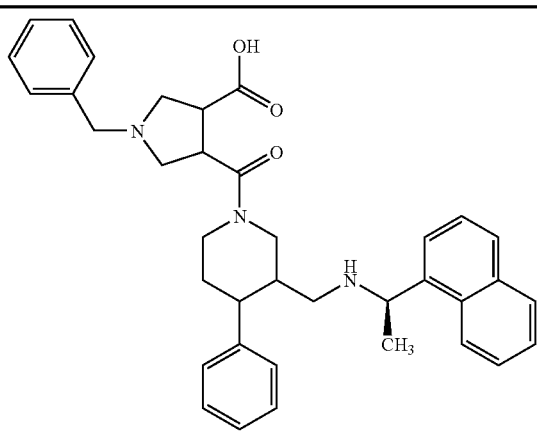 | 3,4-trans diastereo mixture |

TABLE 51-continued
| 176 | 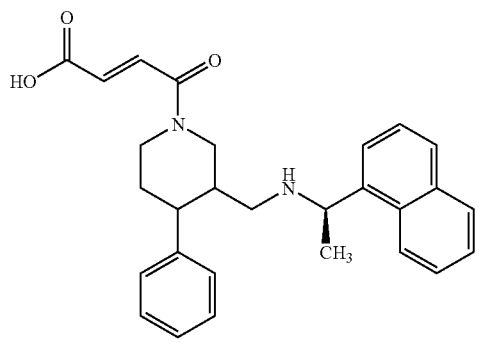 | 3,4-trans diastereo mixture |
| 177 | 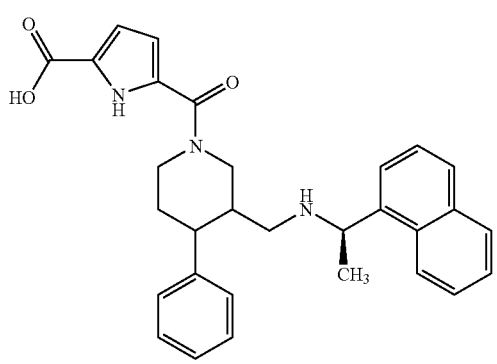 | 3,4-trans diastereo mixture |
| 178 | 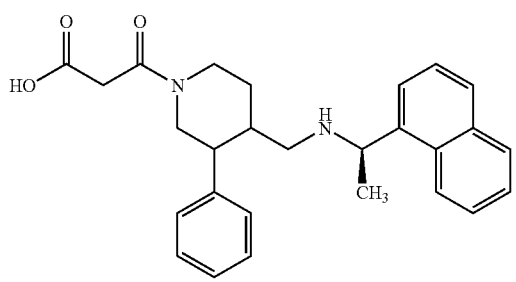 | 3,4-trans diastereo mixture |
| 179 | 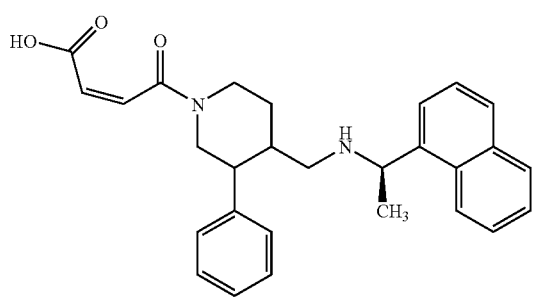 | 3,4-trans diastereo mixture |

TABLE 52
| 180 | 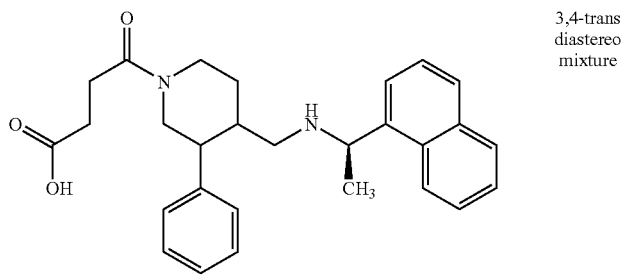 | 3,4-trans diastereo mixture |
| 181 | 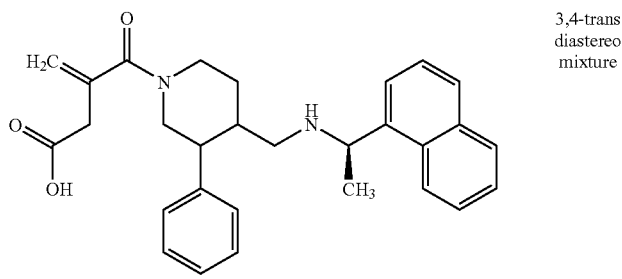 | 3,4-trans diastereo mixture |
| 182 | 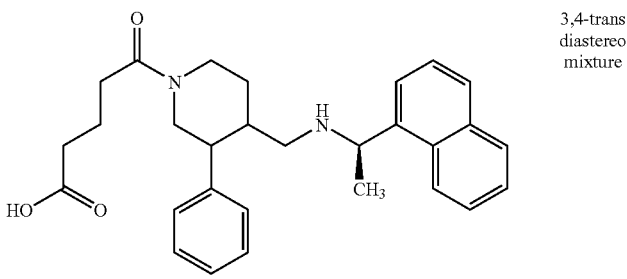 | 3,4-trans diastereo mixture |
| 183 | 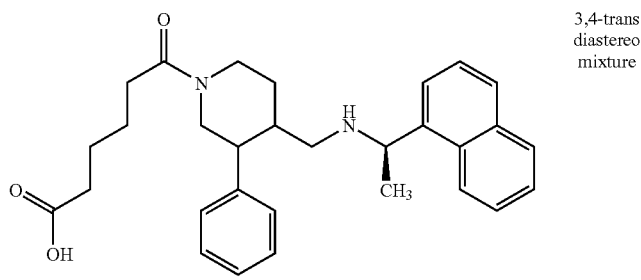 | 3,4-trans diastereo mixture |
| 184 | 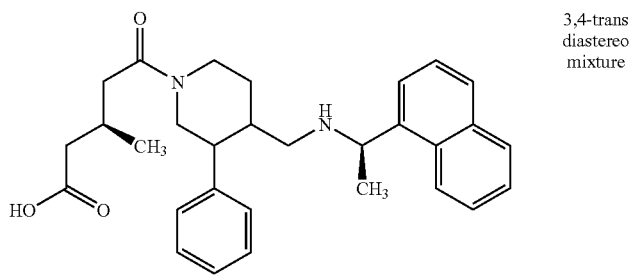 | 3,4-trans diastereo mixture |

TABLE 52-continued
| 185 | 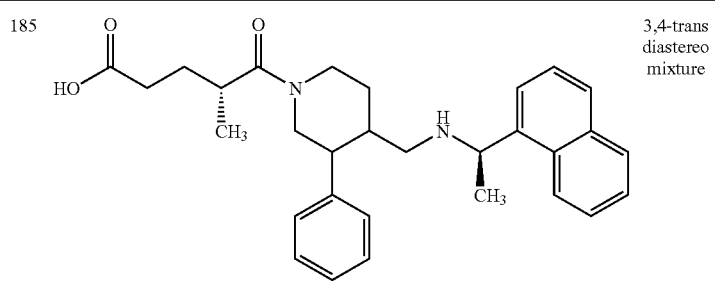 | 3,4-trans diastereo mixture |
TABLE 53
| 186 | 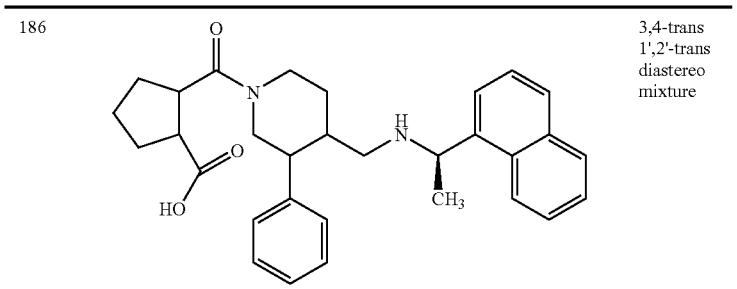 | 3,4-trans 1',2'-trans diastereo mixture |
| 187 | 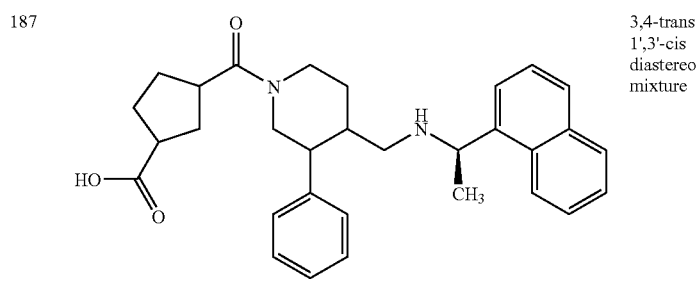 | 3,4-trans 1',3'-cis diastereo mixture |
| 188 | 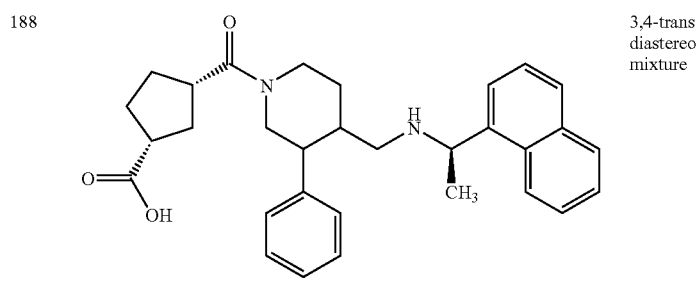 | 3,4-trans diastereo mixture |
| 47 | 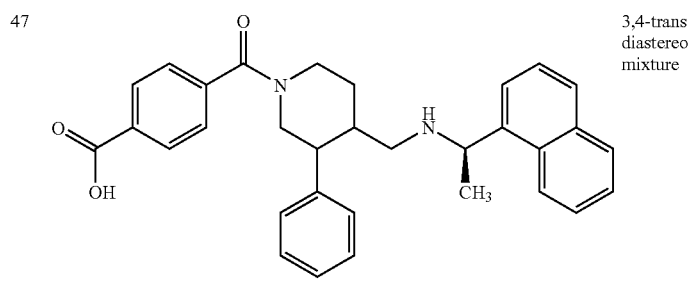 | 3,4-trans diastereo mixture |

TABLE 53-continued
| 189 | 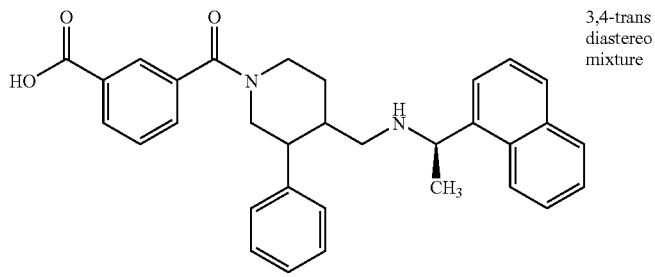 | 3,4-trans diastereo mixture |
| 190 | 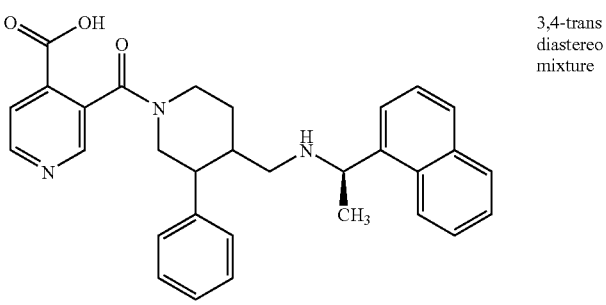 | 3,4-trans diastereo mixture |
TABLE 54
| 191 | 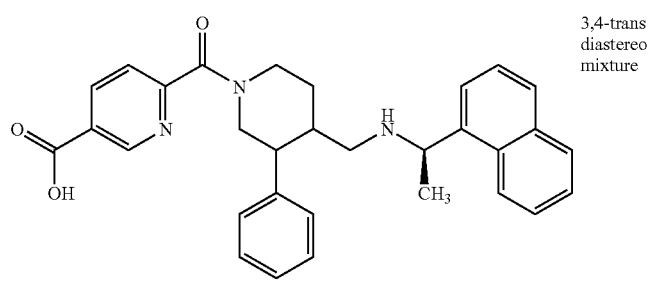 | 3,4-trans diastereo mixture |
| 192 | 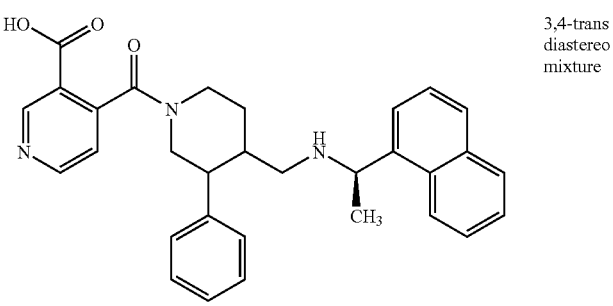 | 3,4-trans diastereo mixture |
| 193 | 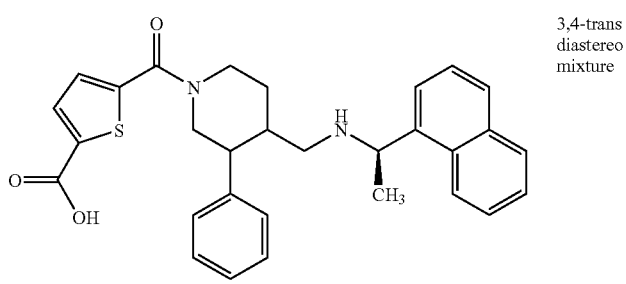 | 3,4-trans diastereo mixture |

TABLE 54-continued
| 194 | 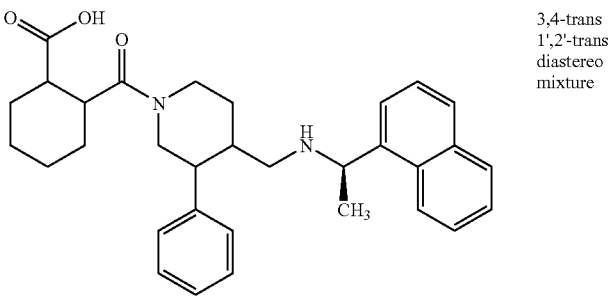 | 3,4-trans 1′,2′-trans diastereo mixture |
| 195 | 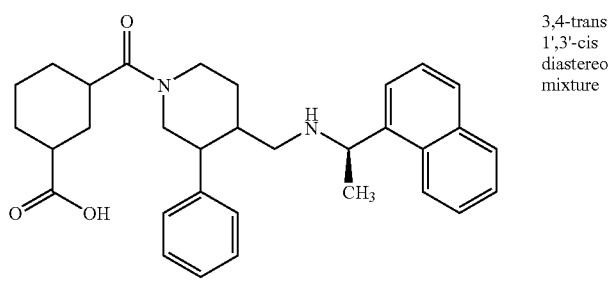 | 3,4-trans 1′,3′-cis diastereo mixture |
| 196 | 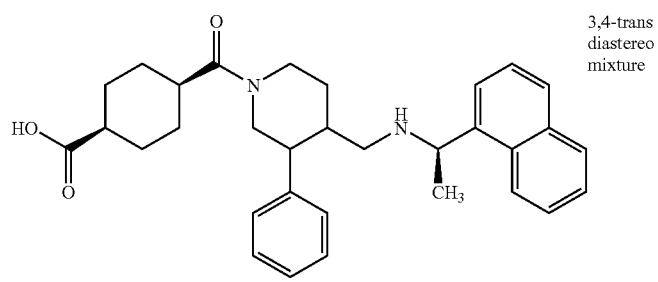 | 3,4-trans diastereo mixture |
TABLE 55
| 197 | 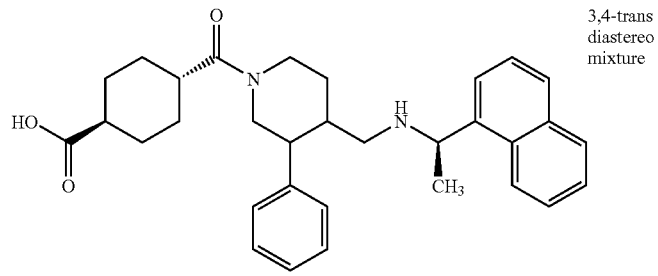 | 3,4-trans diastereo mixture |
| 198 | 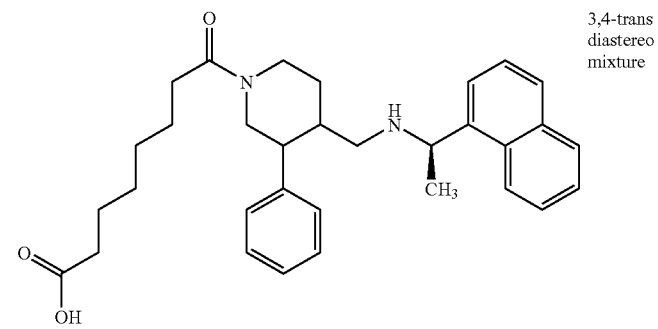 | 3,4-trans diastereo mixture |

TABLE 55-continued
| 199 | 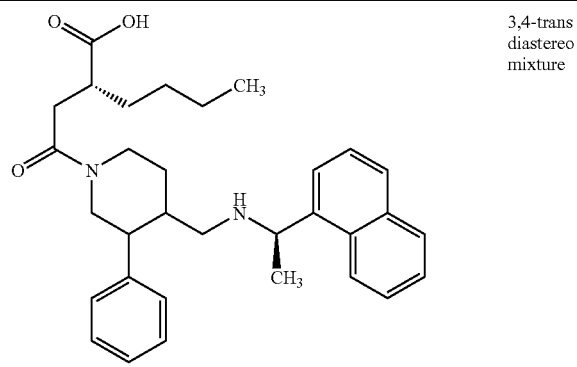 | 3,4-trans diastereo mixture |
|---|---|---|
| 200 | 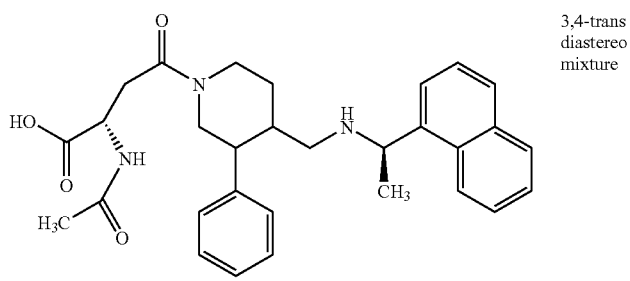 | 3,4-trans diastereo mixture |
| 201 | 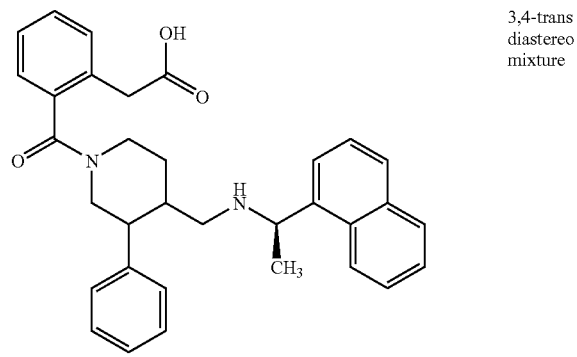 | 3,4-trans diastereo mixture |
TABLE 56
| 202 | 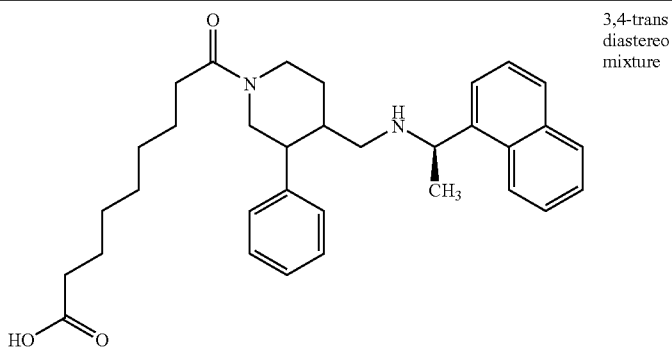 | 3,4-trans diastereo mixture |
|---|---|---|

TABLE 56-continued
| 203 | 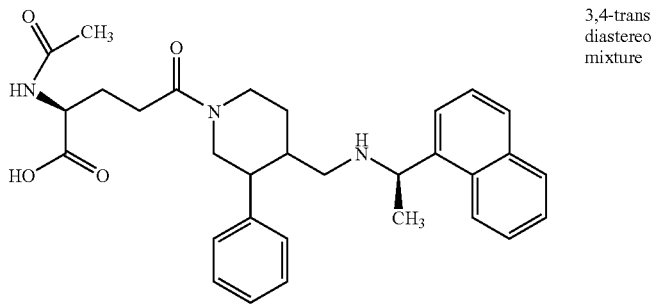 | 3,4-trans diastereo mixture |
|---|---|---|
| 204 | 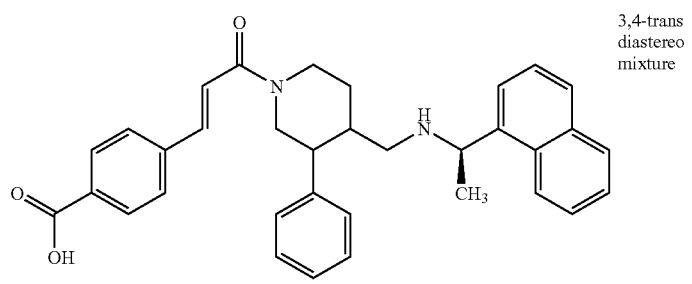 | 3,4-trans diastereo mixture |
| 205 | 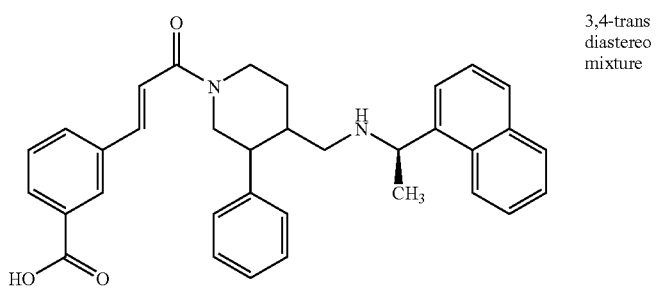 | 3,4-trans diastereo mixture |
| 206 | 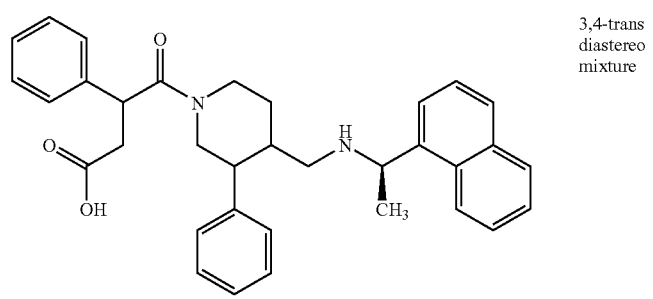 | 3,4-trans diastereo mixture |
TABLE 57
| 207 | 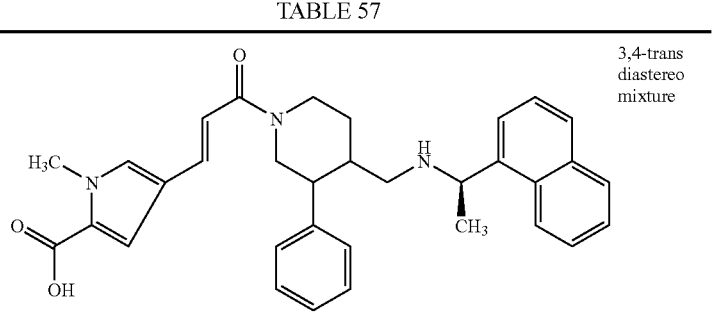 | 3,4-trans diastereo mixture |
|---|---|---|

TABLE 57-continued
| 208 | 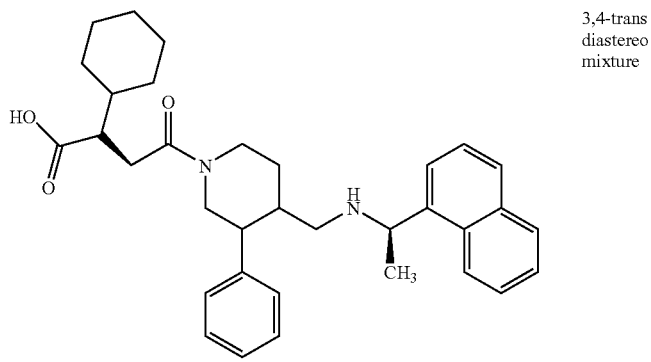 | 3,4-trans diastereo mixture |
| 209 | 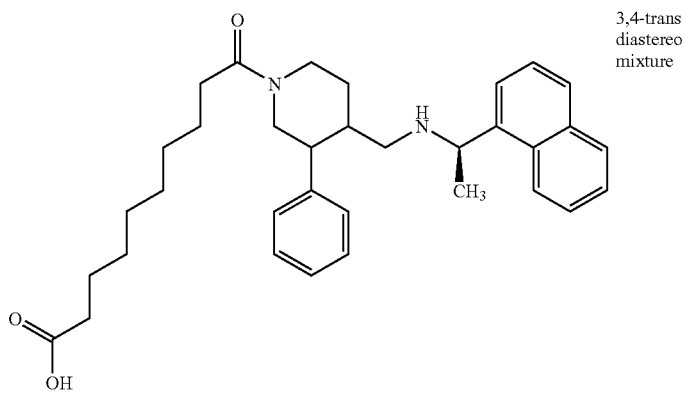 | 3,4-trans diastereo mixture |
| 210 | 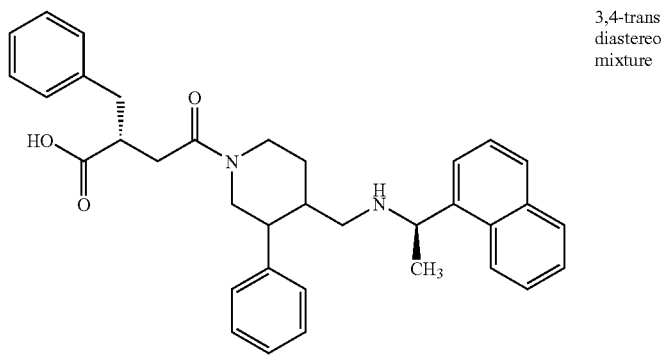 | 3,4-trans diastereo mixture |
| 211 | 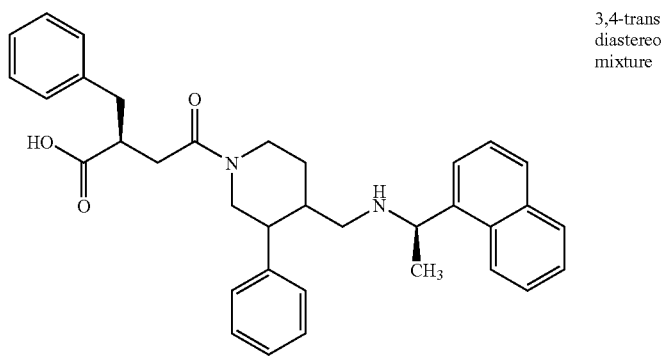 | 3,4-trans diastereo mixture |

TABLE 58
| 212 | 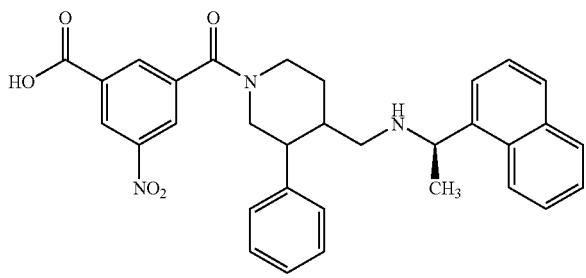 | 3,4-trans diastereo mixture |
| --- | --- | --- |
| 213 | 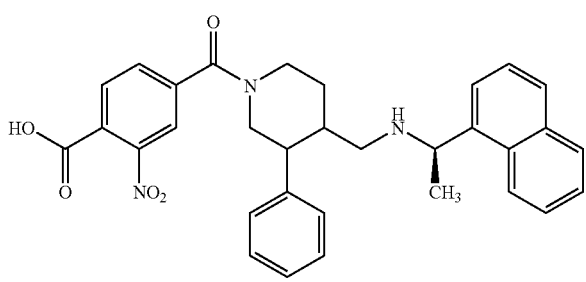 | 3,4-trans diastereo mixture |
| 214 | 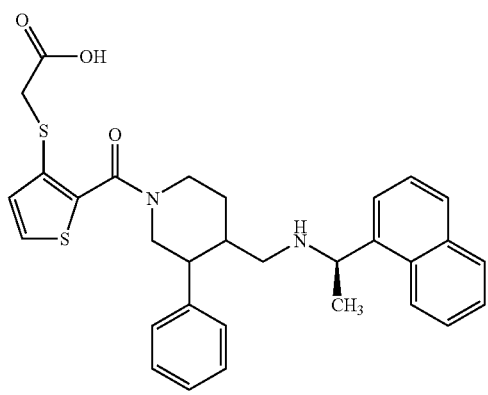 | 3,4-trans diastereo mixture |
| 215 | 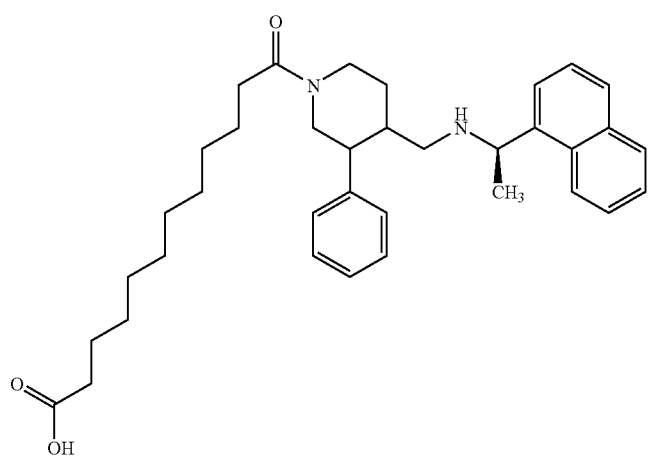 | 3,4-trans diastereo mixture |

TABLE 58-continued
| 216 | 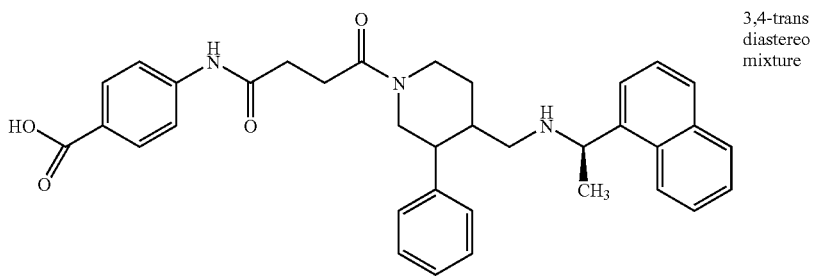 | 3,4-trans diastereo mixture |
TABLE 59
| 217 | 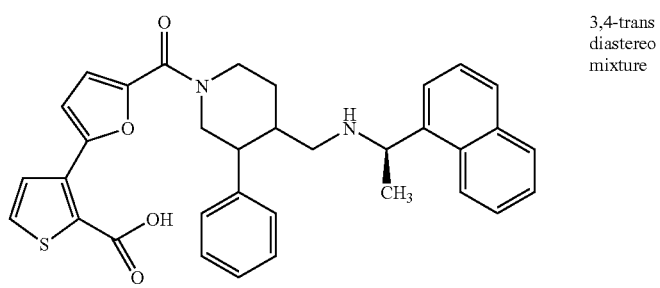 | 3,4-trans diastereo mixture |
| 218 | 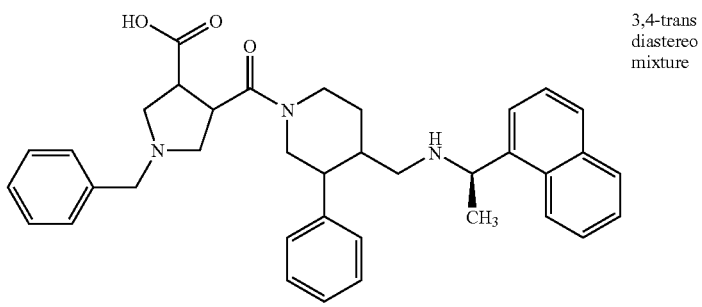 | 3,4-trans diastereo mixture |
| 219 | 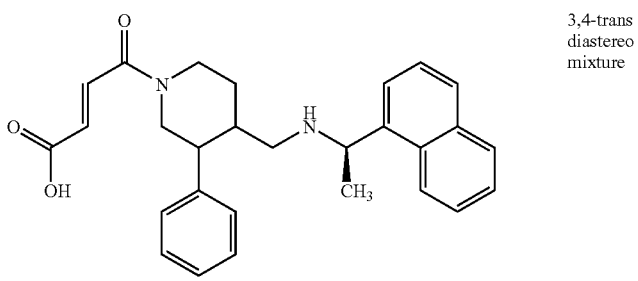 | 3,4-trans diastereo mixture |
| 220 | 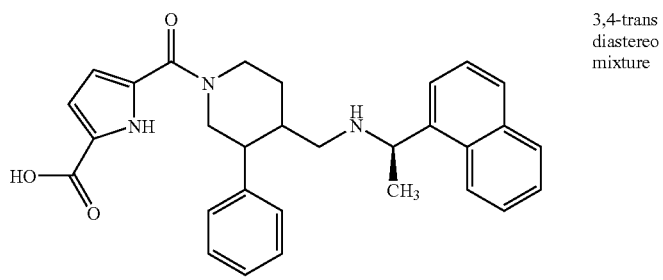 | 3,4-trans diastereo mixture |

TABLE 59-continued
| | | |
|---|---|---|
| 221 | 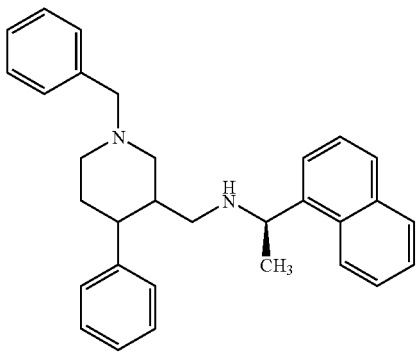 | 3,4-trans diastereo mixture |
TABLE 60
| | | |
|---|---|---|
| 222 | 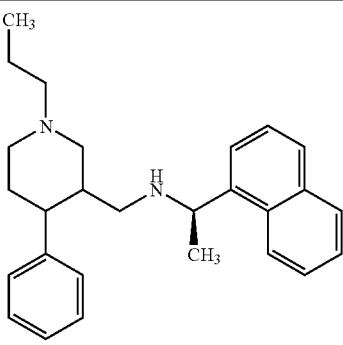 | 3,4-trans diastereo mixture |
| 223 | 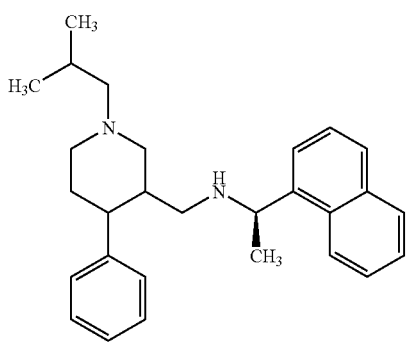 | 3,4-trans diastereo mixture |
| 224 | 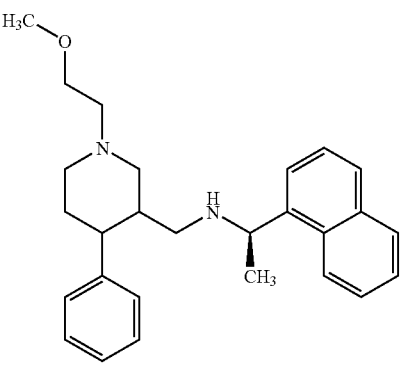 | 3,4-trans diastereo mixture |
TABLE 60-continued
| | | |
|---|---|---|
| 225 | 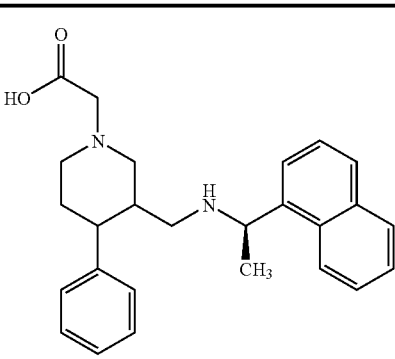 | 3,4-trans diastereo mixture |
| 48 | 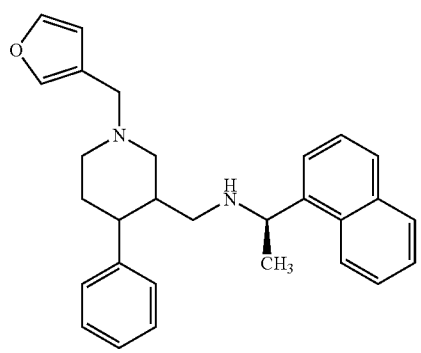 | 3,4-trans diastereo mixture |
TABLE 61
| | | |
|---|---|---|
| 226 | 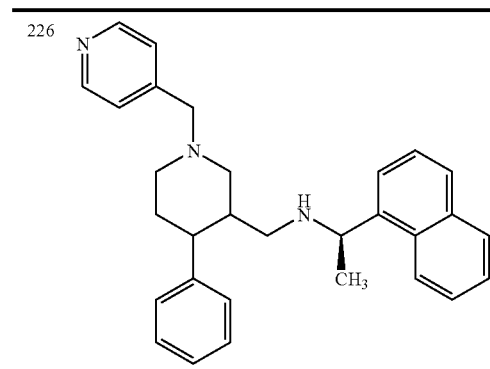 | 3,4-trans diastereo mixture |

TABLE 61-continued
227 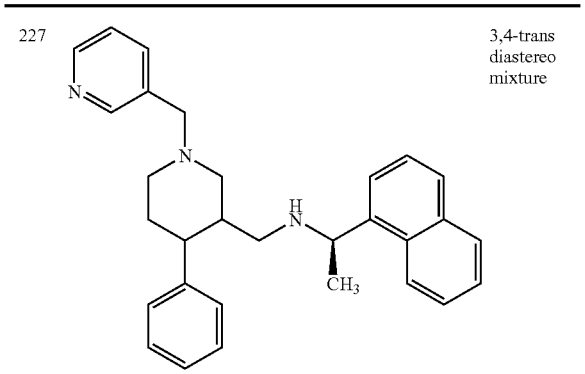 3,4-trans diastereo mixture
228 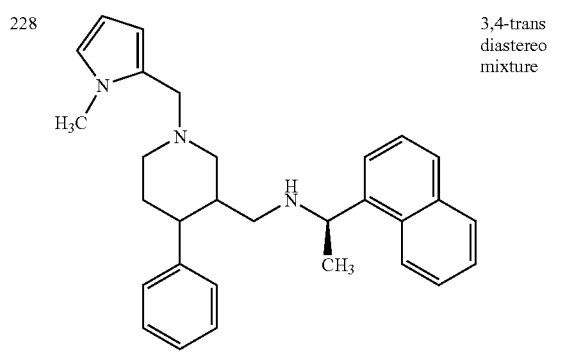 3,4-trans diastereo mixture
229 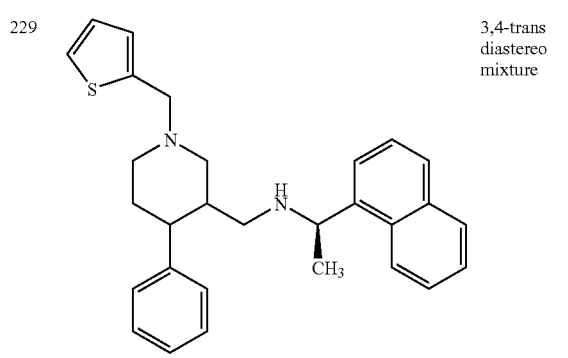 3,4-trans diastereo mixture
230 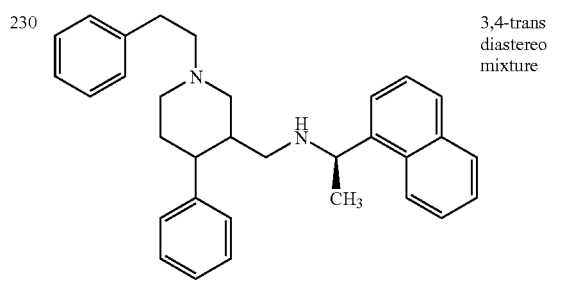 3,4-trans diastereo mixture
TABLE 62
231 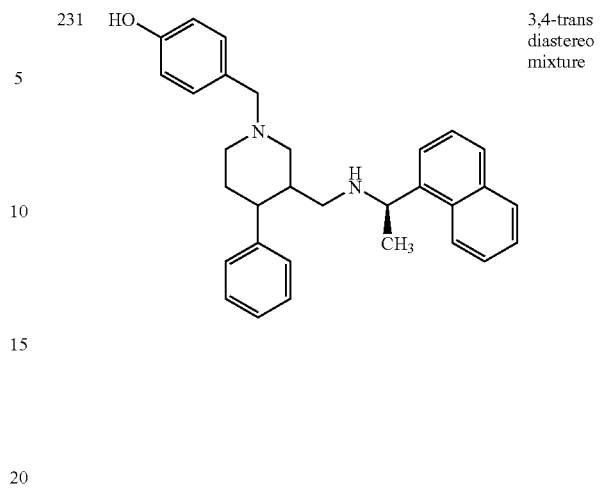 3,4-trans diastereo mixture
232 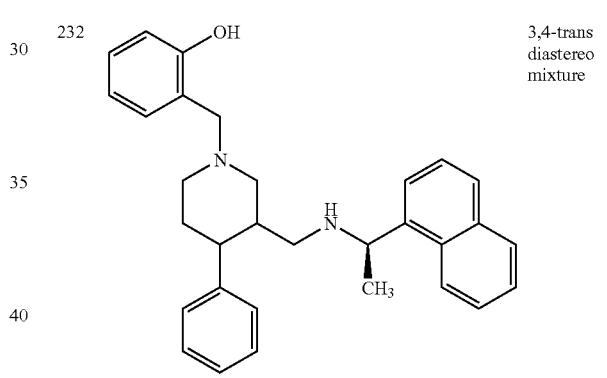 3,4-trans diastereo mixture
233 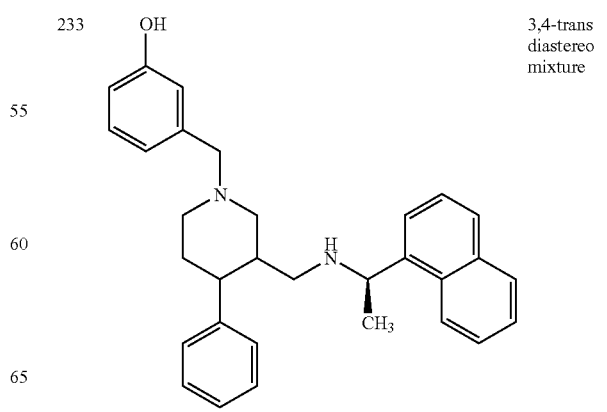 3,4-trans diastereo mixture TABLE 62-continued
| | | | |
|---|---|---|---|
| 234 | 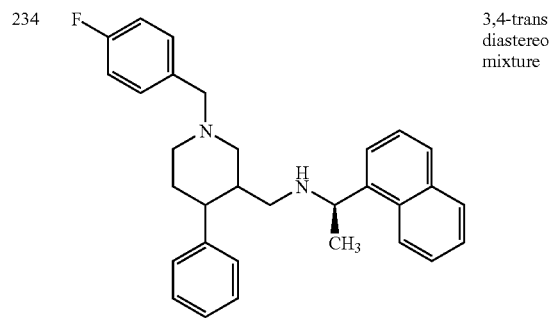 | | 3,4-trans diastereo mixture |
| 235 | 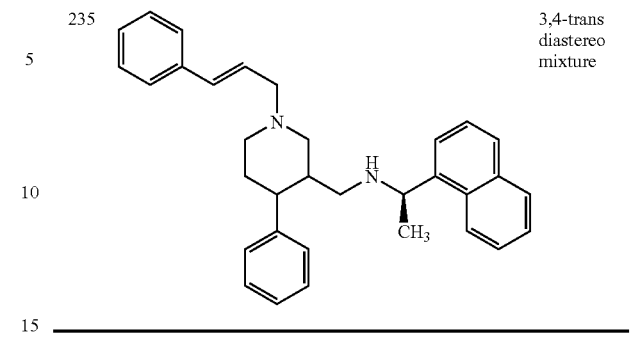 | | 3,4-trans diastereo mixture |
TABLE 63
| | | |
|---|---|---|
| 236 |  | 3,4-trans diastereo mixture |
| 237 |  | 3,4-trans diastereo mixture |
| 238 |  | 3,4-trans diastereo mixture |

TABLE 63-continued
| 239 | 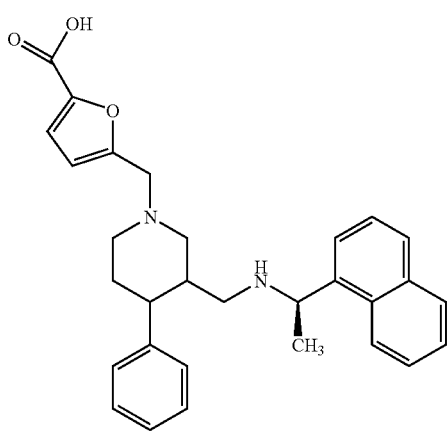 | 3,4-trans diastereo mixture |
TABLE 64
| 240 | 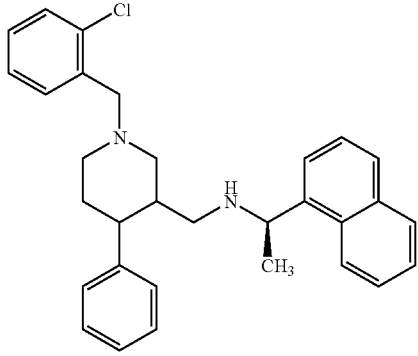 | 3,4-trans diastereo mixture |
| 241 | 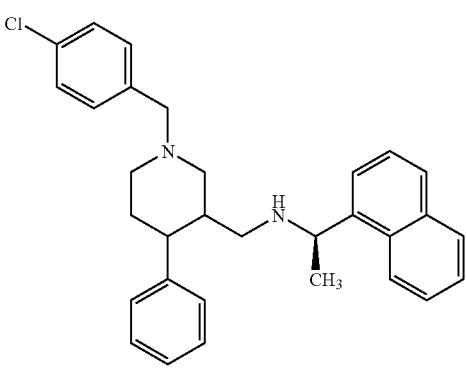 | 3,4-trans diastereo mixture |
| 242 | 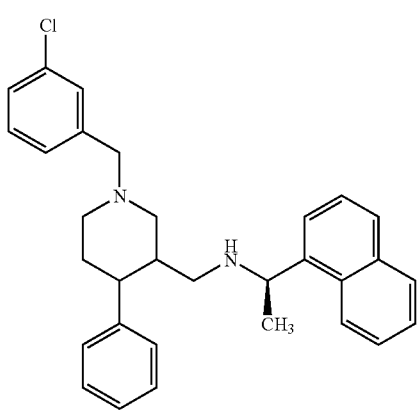 | 3,4-trans diastereo mixture |

TABLE 64-continued
| 243 | 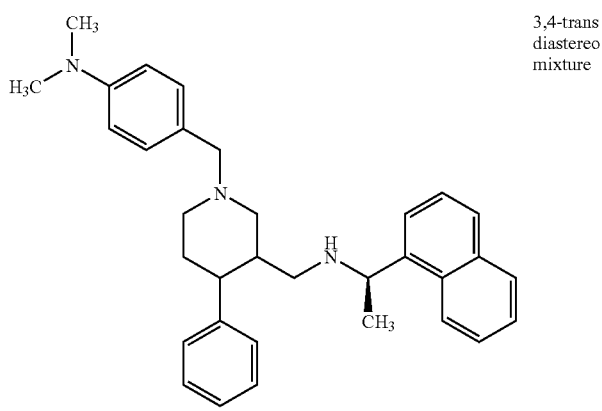 | 3,4-trans diastereo mixture |
TABLE 65
| 244 | 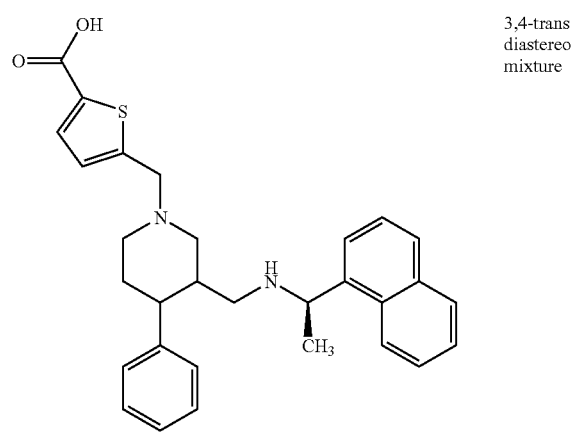 | 3,4-trans diastereo mixture |
| 245 | 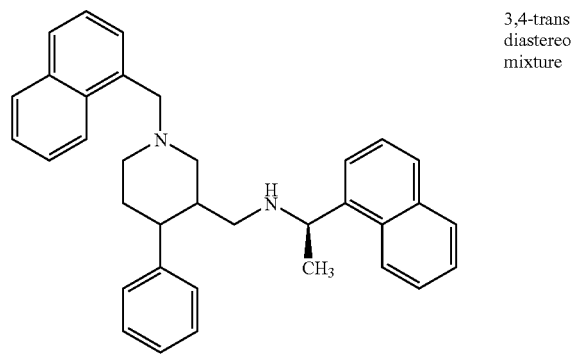 | 3,4-trans diastereo mixture |

TABLE 65-continued
| 246 | 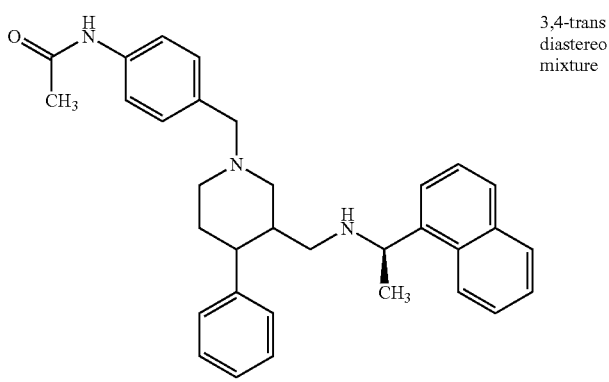 | 3,4-trans diastereo mixture |
| 247 | 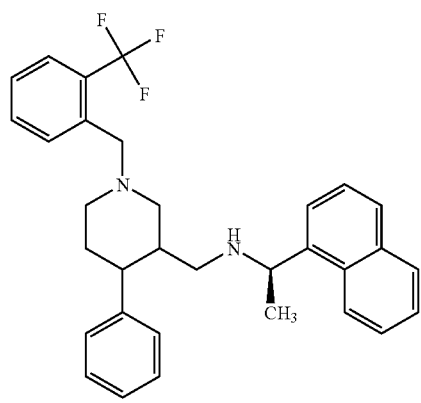 | 3,4-trans diastereo mixture |
TABLE 66
| 248 | 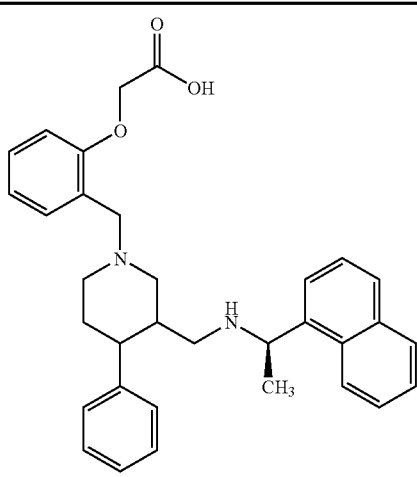 | 3,4-trans diastereo mixture |

TABLE 66-continued

| 249 | [structure: 2-(4-((3-(((1-(naphthalen-1-yl)ethyl)amino)methyl)-4-phenylpiperidin-1-yl)methyl)phenoxy)acetic acid] | 3,4-trans diastereo mixture |
|---|---|---|
| 250 | [structure: 1-([1,1'-biphenyl]-4-ylmethyl)-N-((1-(naphthalen-1-yl)ethyl))-4-phenylpiperidin-3-yl)methanamine] | 3,4-trans diastereo mixture |
| 251 | [structure: N-((1-((1H-pyrrol-2-yl)methyl)-4-phenylpiperidin-3-yl)methyl)-1-(naphthalen-1-yl)ethan-1-amine] | 3,4-trans diastereo mixture |

TABLE 67

| 252 | [structure: N-((1-(furan-2-ylmethyl)-4-phenylpiperidin-3-yl)methyl)-1-(naphthalen-1-yl)ethan-1-amine] | 3,4-trans diastereo mixture |
| 253 | [structure: 1-(naphthalen-1-yl)-N-((4-phenyl-1-(thiophen-3-ylmethyl)piperidin-3-yl)methyl)ethan-1-amine] | 3,4-trans diastereo mixture |

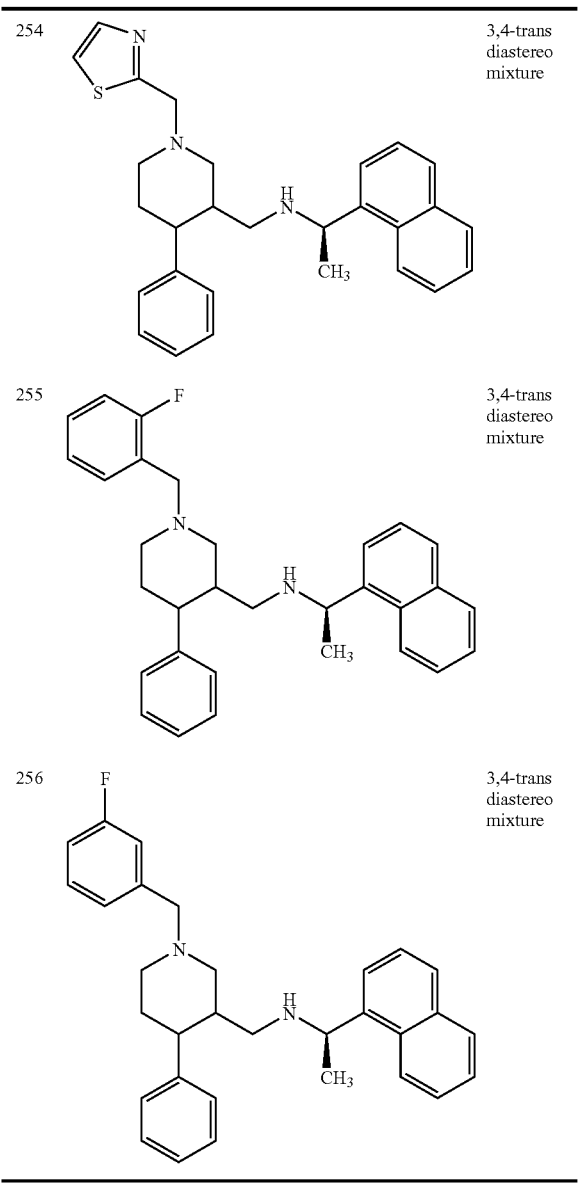
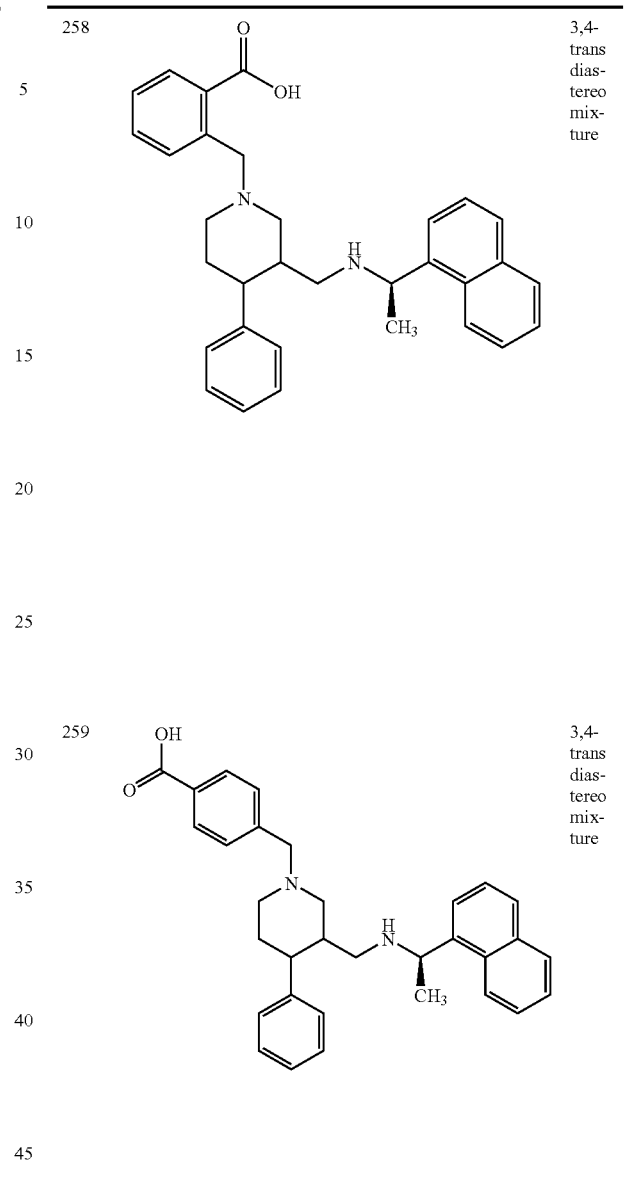
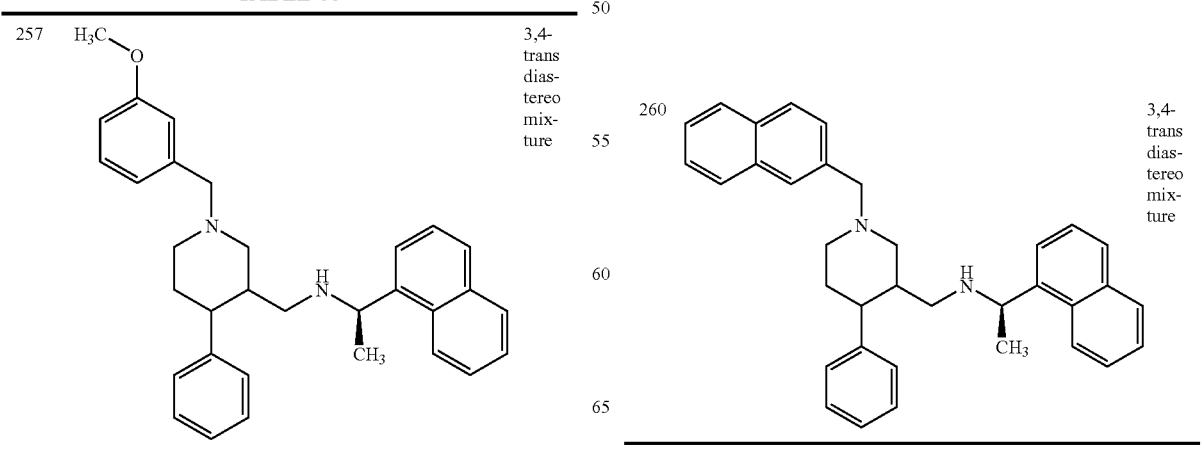

TABLE 69
| 261 | 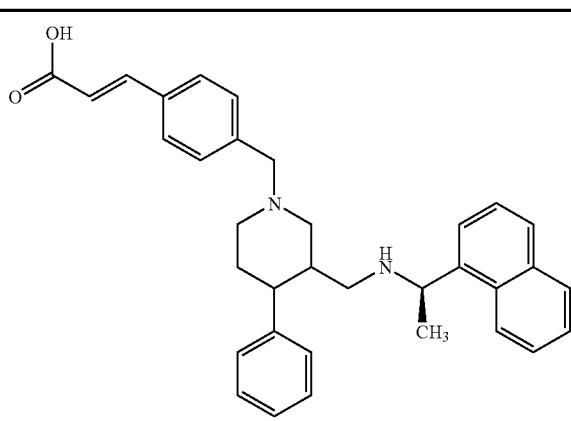 | 3,4-trans diastereo mixture |
| 262 | 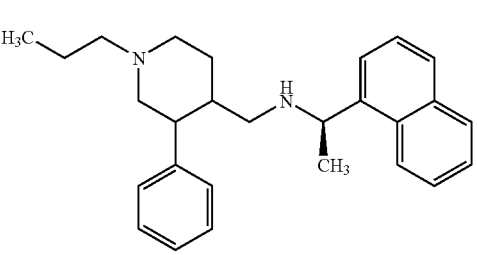 | 3,4-trans diastereo mixture |
| 263 | 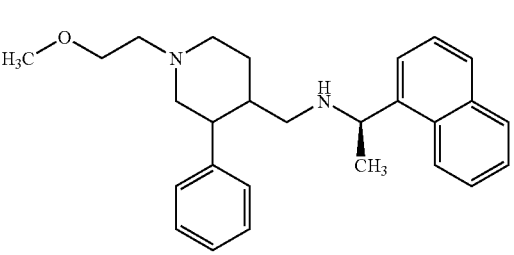 | 3,4-trans diastereo mixture |
| 264 | 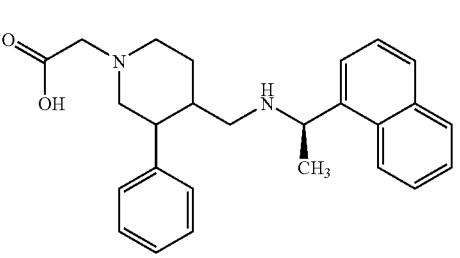 | 3,4-trans diastereo mixture |
| 265 | 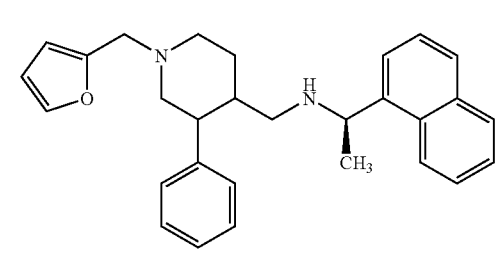 | 3,4-trans diastereo mixture |
| 49 | 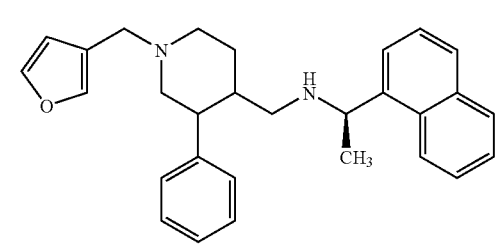 | 3,4-trans diastereo mixture |

TABLE 70

| | | |
|---|---|---|
| 266 | (structure) | 3,4-trans diastereo mixture |
| 267 | (structure) | 3,4-trans diastereo mixture |
| 268 | (structure) | 3,4-trans diastereo mixture |
| 269 | (structure) | 3,4-trans diastereo mixture |
| 270 | (structure) | 3,4-trans diastereo mixture |
| 271 | (structure) | 3,4-trans diastereo mixture |
| 272 | (structure) | 3,4-trans diastereo mixture |

TABLE 71
| 273 | 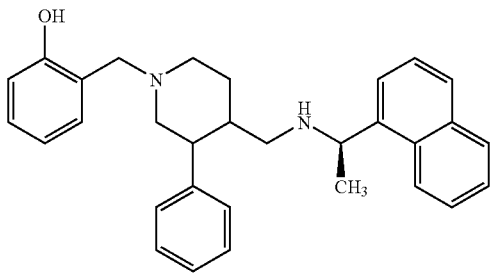 | 3,4-trans diastereo mixture |
| 274 | 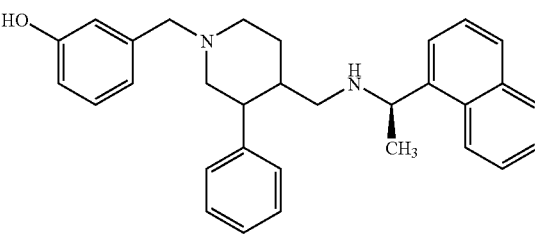 | 3,4-trans diastereo mixture |
| 275 | 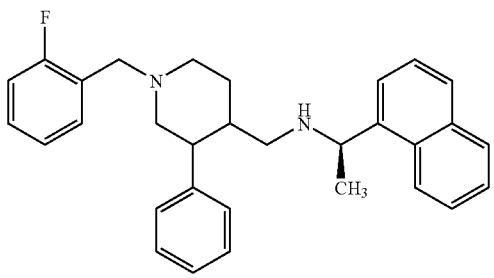 | 3,4-trans diastereo mixture |
| 276 | 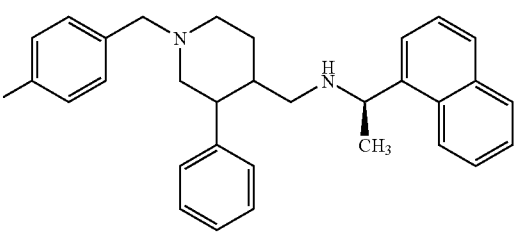 | 3,4-trans diastereo mixture |
| 277 | 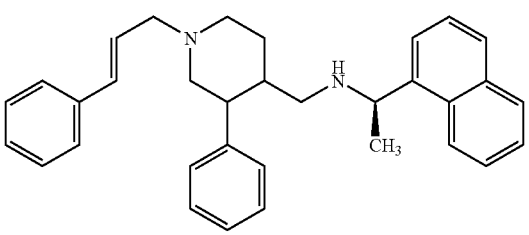 | 3,4-trans diastereo mixture |
| 278 | 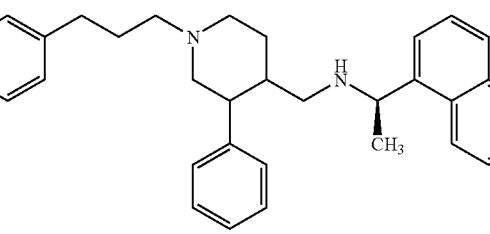 | 3,4-trans diastereo mixture |

TABLE 71-continued
| 279 | 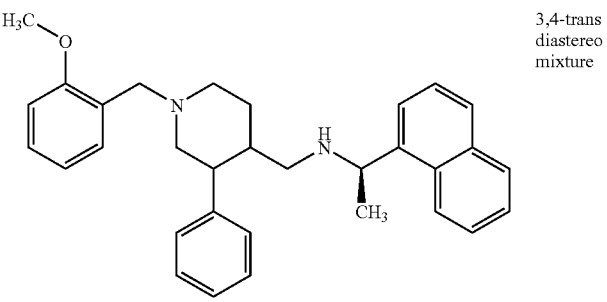 | 3,4-trans diastereo mixture |
TABLE 72
| 280 | 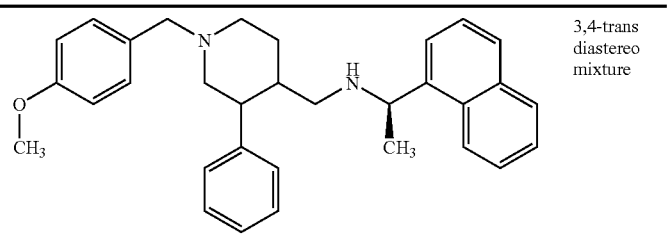 | 3,4-trans diastereo mixture |
| 281 | 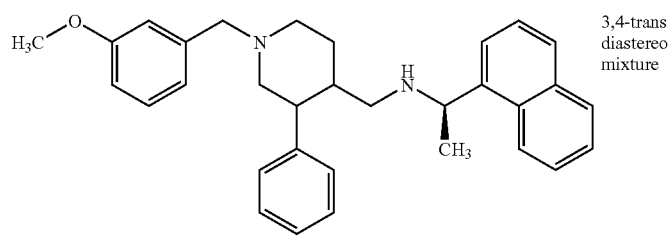 | 3,4-trans diastereo mixture |
| 282 | 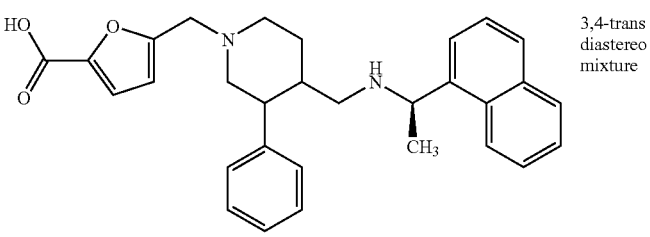 | 3,4-trans diastereo mixture |
| 283 | 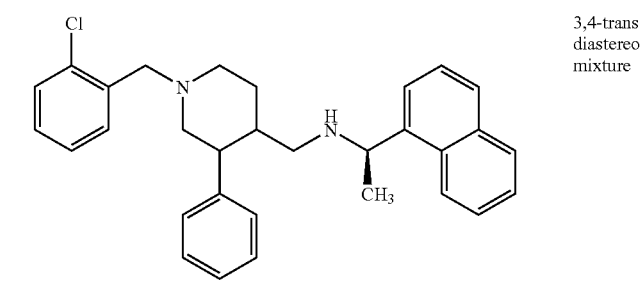 | 3,4-trans diastereo mixture |
| 284 | 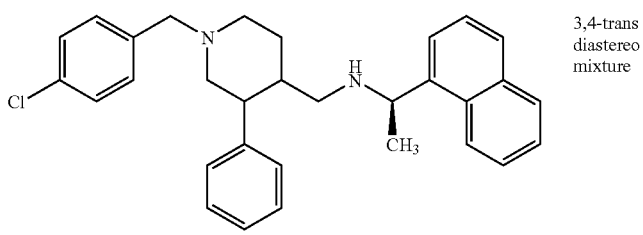 | 3,4-trans diastereo mixture |

TABLE 72-continued
| 285 | 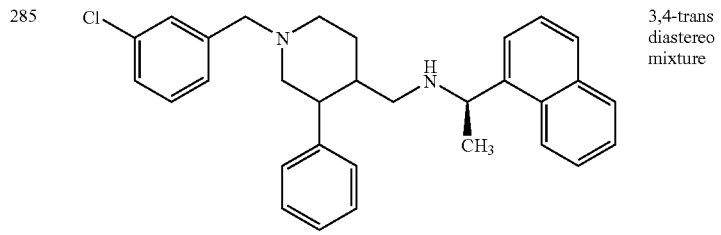 | 3,4-trans diastereo mixture |
| --- | --- | --- |
| 286 | 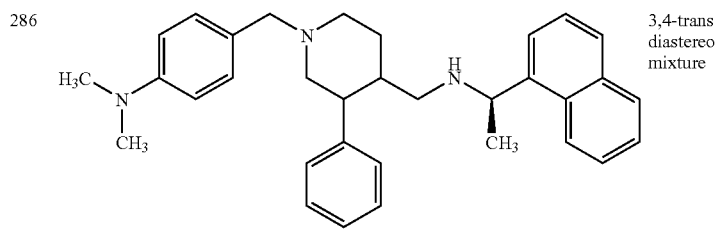 | 3,4-trans diastereo mixture |
TABLE 73
| 287 | 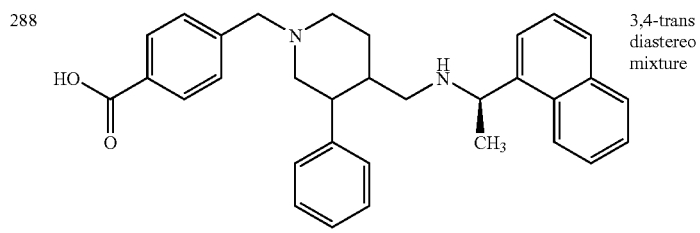 | 3,4-trans diastereo mixture |
| --- | --- | --- |
| 288 | 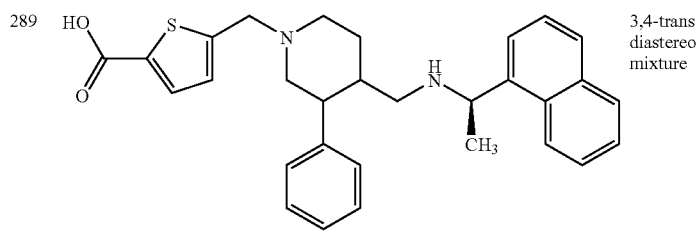 | 3,4-trans diastereo mixture |
| 289 | 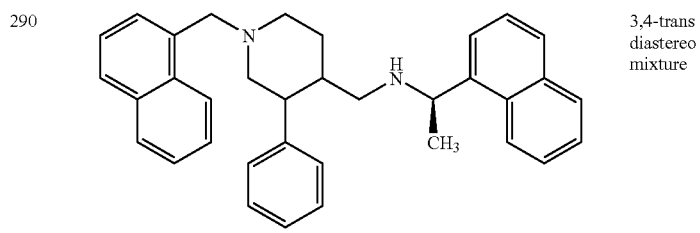 | 3,4-trans diastereo mixture |
| 290 |  | 3,4-trans diastereo mixture |

TABLE 73-continued
| 291 | 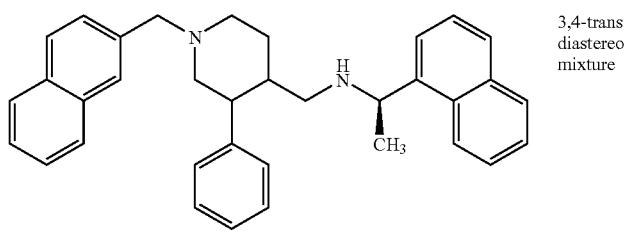 | 3,4-trans diastereo mixture |
| 292 | 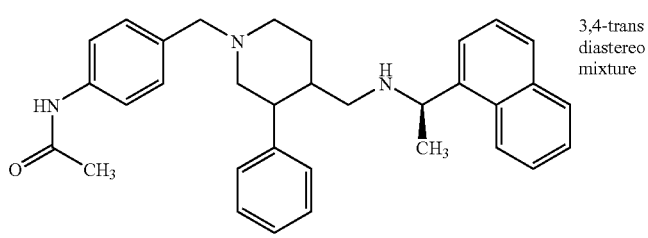 | 3,4-trans diastereo mixture |
TABLE 74
| 293 | 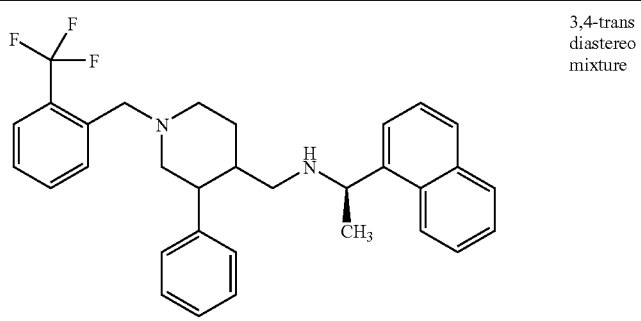 | 3,4-trans diastereo mixture |
| 294 | 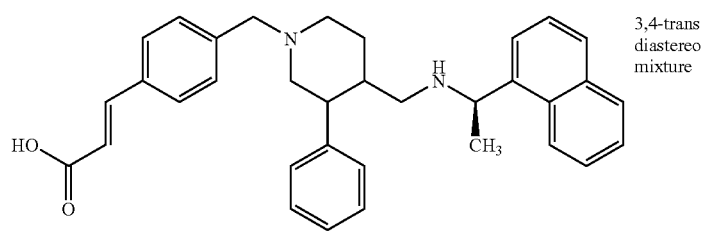 | 3,4-trans diastereo mixture |
| 295 | 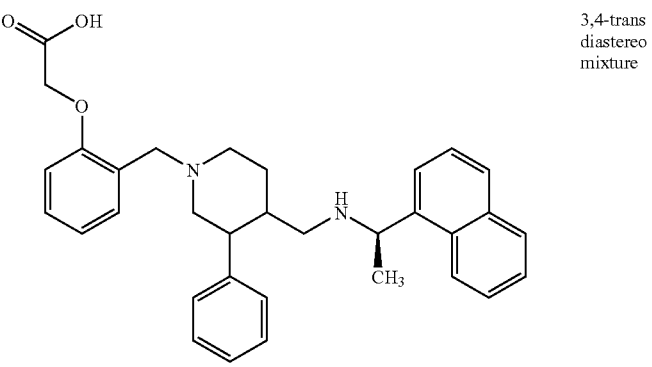 | 3,4-trans diastereo mixture |

TABLE 74-continued

| 296 | 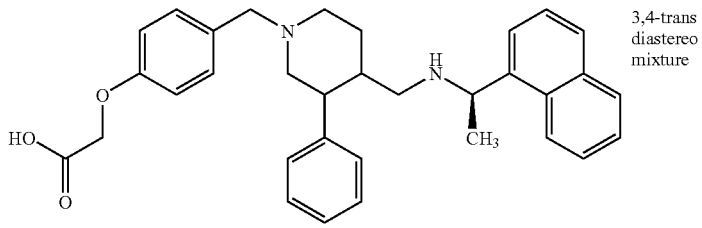 | 3,4-trans diastereo mixture |
| 297 | 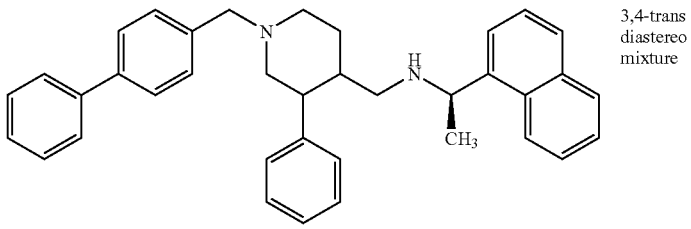 | 3,4-trans diastereo mixture |

TABLE 75

| Ex | Syn | Data |
|---|---|---|
| 1 | 1 | FAB+: 441 |
| 55 | 1(1) 1(2) | ESI+: 459 |
| 56 | 1(1) 1(2) | ESI+: 459 |
| 2-1 | 2 | FAB+: 441<br>NMR1: 1.37-1.68 (4H, m), 1.70-1.84 (1H, m), 2.09-2.37 (1H, m),<br>2.52-2.96 (3H, m), 3.16-3.38 (2H, m), 3.82-5.23 (3H, m), 6.73-6.96 (2H, m),<br>7.02-7.19 (3H, m), 7.46-7.65 (3H, m), 7.78-8.09 (4H, m), 9.40-9.96 (2H, m) |
| 2-2 | 2 | FAB+: 441<br>NMR1: 1.44-1.72 (4H, m), 1.77-1.90 (1H, m), 2.25-3.40 (6H, m),<br>3.84-5.20 (3H, m), 7.02-7.23 (5H, m), 7.36-7.48 (1H, m), 7.52-7.62 (2H, m),<br>7.66-7.74 (1H, m), 7.83-7.99 (2H, m), 8.02-8.12 (1H, m), 9.13 (1H, brs),<br>9.75-10.06 (1H, m) |
| 4 | 4 | ESI+: 345 |
| 5 | 5 | API+: 541 |
| 6 | 6 | ESI+: 523 |
| 7 | 7 | ESI+: 522 |
| 57 | 7 | ESI+: 522 |
| 58 | 7 | ESI+: 536 |
| 8 | 8 | ESI+: 556 |
| 59 | 8 | ESI+: 552 |
| 9 | 9 | FAB+: 487 |
| 60 | 9 | FAB+: 487 |
| 10 | 10 | FAB+: 509 |
| 11 | 11 | FAB+: 527 |
| 61 | 10(2) 10(3) | FAB+: 527 |
| 12 | 12 | FAB+: 538 |
| 13 | 13 | ESI+: 526<br>NMR1: 1.41-1.79 (5H, m), 2.11-2.64 (4H, m), 2.65-2.88 (2H, m),<br>4.16-4.33 (1H, m), 4.90-5.36 (2H, m), 6.66-6.98 (3H, m), 7.06-7.18 (1H, m),<br>7.39-7.62 (3H, m), 7.76-8.19 (8H, m), 9.26-10.14 (3H, m), 12.55 (1H, brs) |

TABLE 76

| 14 | 14 | FAB+: 501;<br>NMR1: 1.45-1.60 (3H, m), 1.62-1.85 (2H, m), 2.25-3.20 (7H, m),<br>3.90-4.05 (1H, m), 5.04-5.22 (1H, m), 6.90-7.18 (5H, m), 7.39-8.12 (9H, m),<br>8.92-9.32 (1H, m), 9.48-9.76 (1H, m), 13.30 (1H, brs) |
| 15 | 15 | FAB+: 525 |
| 62 | 15 | FAB+: 557 |
| 16 | 16 | FAB+: 509 |
| 17 | 17 | ESI+: 527<br>NMR2: 1.63 (3H, d, J = 5.4 Hz), 1.71-1.89 (2H, m), 2.05-3.16 (6H, m),<br>4.25-5.14 (3H, m), 6.79-8.24 (15H, m) |

TABLE 76-continued

| | | |
|---|---|---|
| 63 | 3 | FAB+: 508 |
| 64 | 3 | FAB+: 508 |
| 65 | 3 | ESI+: 508 |
| | | NMR1: 1.29 (3H, d, J = 6.5 Hz), 1.48-1.72 (2H, m), 1.84-2.08 (2H, m), 2.16-2.26 (1H, m), 2.34-2.46 (1H, m), 2.55-2.66 (1H, m), 2.81-2.94 (1H, m), 3.16-3.48 (3H, m), 4.14-4.26 (1H, m), 4.29-4.42 (1H, m), 4.64-4.77 (1H, m), 7.02-7.22 (5H, m), 7.36-7.50 (3H, m), 7.52-7.58 (1H, m), 7.60-7.76 (3H, m), 7.81-7.92 (3H, m), 8.12-8.20 (1H, m), 8.92 (1H, s) |
| 66 | 3 | ESI+: 542 |
| | | NMR2: 1.61 (3H, d, J = 5.7 Hz), 1.73-1.97 (2H, m), 2.18-2.38 (2H, m), 2.54-2.94 (4H, m), 4.48-4.98 (3H, m), 7.04-8.10 (16H, m) |
| 3 | 3 | ESI+: 538 |
| | | NMR2: 1.53 (3H, d, J = 6.6 Hz), 1.77-1.84 (2H, m), 2.08-2.36 (3H, m), 2.47-2.59 (1H, m), 2.65-2.91 (2H, m), 3.85 (3H, s), 4.24-4.35 (1H, m), 4.60-4.74 (2H, m), 6.95-7.05 (2H, m), 7.09-7.23 (3H, m), 7.43-7.52 (5H, m), 7.60-7.79 (3H, m), 7.82-7.90 (1H, m), 8.00-8.13 (2H, m) |
| 45 | 45 | FAB+: 560 |
| | | NMR2: 1.57 (3H, d, J = 6.2 Hz), 1.77-1.98 (2H, m), 2.22-2.38 (1H, m), 2.56-2.93 (5H, m), 4.50-4.94 (3H, m), 6.90-8.15 (15H, m) |
| 50 | 50 | FAB+: 519 |
| 67 | 17 | ESI+: 527 |
| 18 | 18 | ESI+: 441 |
| 68 | 18 | ESI+: 447 |
| 69 | 18 | FAB+: 421 |
| 19 | 19 | ESI+: 459 |
| 70 | 19 | ESI+: 459 |

TABLE 77

| | | |
|---|---|---|
| 71 | 51 | FAB+: 487 |
| 51 | 51 | FAB+: 487 |
| | | NMR1: 0.94-1.25 (7H, m), 1.60 (3H, d, J = 6.5 Hz), 2.15-2.70 (10H, m), 2.87-3.17 (1H, m), 3.70-4.66 (2H, m), 5.24 (1H, brs), 6.79-6.89 (2H, m), 7.03-7.16 (3H, m), 7.45-7.64 (3H, m), 7.80-8.06 (3H, m), 8.12-8.22 (1H, m), 9.26 (1H, brs), 9.71 (1H, brs), 12.01 (1H, brs) |
| 20 | 20 | ESI+: 493 |
| 21 | 21 | ESI+: 493 |
| 22 | 22 | ESI+: 460 |
| 72 | 23 | FAB+: 477 |
| 73 | 23 | FAB+: 491 |
| 74 | 23 | FAB+: 505 |
| 24 | 24 | FAB+: 582 |
| | | NMR1: 1.10-1.31 (1H, m), 1.59 (3H, d, J = 6.6 Hz), 2.14-2.74 (10H, m), 2.98-3.20 (1H, m), 3.64-4.15 (1H, m), 4.15-4.57 (1H, m), 5.16-5.34 (1H, m), 6.52-6.60 (1H, m), 6.70-6.81 (1H, m), 6.81-6.88 (1H, m), 6.88-6.94 (1H, m), 6.94-7.05 (1H, m), 7.07-7.21 (1H, m), 7.53 (1H, t, J = 7.5 Hz), 7.56-7.65 (2H, m), 7.68 (1H, t, J = 8.2 Hz), 7.80 (1H, d, J = 7.5 Hz), 7.83-7.89 (1H, m), 7.94 (1H, d, J = 8.2 Hz), 7.96-8.05 (1H, m), 8.09-8.20 (1H, m), 8.87-9.12 (1H, m), 9.41-9.66 (1H, m), 10.21-10.33 (1H, m) |
| 23 | 23 | FAB+: 463 |
| | | NMR1: 0.95-1.26 (1H, m), 1.60 (3H, d, J = 6.1 Hz), 2.11-2.76 (10H, m), 3.08 (1H, m), 3.61-4.11 (1H, m), 4.52 (1H, m), 5.25 (1H, m), 6.69-6.81 (1H, m), 6.81-6.94 (1H, m), 6.94-7.02 (1H, m), 7.07-7.22 (1H, m), 7.43-7.55 (1H, m), 7.55-7.65 (1H, m), 7.73-7.87 (1H, m), 7.87-7.96 (1H, m), 7.96-8.06 (1H, m), 8.09-8.21 (1H, m), 8.95-9.27 (1H, m), 9.49-9.81 (1H, m), 11.62-12.23 (1H, m) |
| 75 | 21 | FAB+: 517 |
| 76 | 23 | FAB+: 519 |
| 25 | 25 | FAB+: 509 |
| | | NMR1: 1.18-1.48 (1H, m), 1.61 (3H, d, J = 6.4 Hz), 2.18-3.44 (7H, m), 3.76-4.39 (2H, m), 5.25 (1H, brs), 6.80-6.98 (2H, m), 7.04-7.32 (5H, m), 7.45-7.68 (3H, m), 7.77-8.08 (5H, m), 8.13-8.24 (1H, m), 9.25 (1H, brs), 9.70 (1H, brs) |
| 77 | 25 | FAB+: 515 |
| | | NMR1: 1.22-1.48 (1H, m), 1.62 (3H, d, J = 6.7 Hz), 2.20-2.70 (5H, m), 2.82-3.28 (2H, m), 3.79-4.40 (2H, m), 4.88 (1H, brs), 6.89-7.00 (2H, m), 7.06-7.30 (5H, m), 7.40-7.49 (2H, m), 7.85-8.09 (5H, m), 9.42 (1H, brs), 9.55 (1H, brs), 12.94 (1H, brs) |

TABLE 78

| | | |
|---|---|---|
| 78 | 25 | FAB+: 527 |
| | | NMR1: 1.20-1.45 (1H, m), 1.59 (3H, d, J = 6.5 Hz), 2.16-2.37 (2H, m), 2.37-2.75 (3H, m), 2.83-3.43 (2H, m), 3.75-4.08 (1H, m), 4.08-4.40 (1H, m), 5.29 (1H, brs), 6.81 (1H, d, J = 7.5 Hz), 6.92 (1H, d, J = 9.5 Hz), 7.01 (1H, dt, J = 2.4, 8.5 Hz), 7.09-7.31 (3H, m), 7.55 (1H, t, J = 7.5 Hz), 7.60 (2H, dd, J = 3.1, 6.3 Hz), 7.77 (1H, d, J = 7.5 Hz), 7.88-7.99 (3H, m), 7.99-8.06 (1H, m), 8.11-8.22 (1H, m), 8.81-9.07 (1H, m), 9.41 (1H, brs), 12.97 (1H, brs) |
| 79 | 25 | FAB+: 527 |
| 80 | 26 | FAB+: 465 |
| 26 | 26 | FAB+: 527 |
| | | NMR1: 1.11-1.44 (1H, m), 1.44-1.69 (3H, m), 2.08-2.76 (6H, m), 2.80-3.49 (1H, m), 3.78-4.07 (1H, m), 4.07-4.42 (1H, m), 4.98-5.48 (1H, m), 6.76-6.89 (1H, m), 6.89-7.05 (2H, m), 7.09-7.24 (1H, m), 7.30-7.43 (1H, m), 7.43-7.69 (5H, m), 7.69-7.84 (2H, m), 7.87-8.04 (2H, m), 8.09-8.21 (1H, m), 8.78-9.17 (1H, m), 9.25-9.66 (1H, m) |
| 27 | 27 | ESI+: 508 |
| | | NMR1: 1.16-1.32 (1H, m), 1.61 (3H, d, J = 6.4 Hz), 2.12-2.56 (5H, m), 2.69-2.81 (1H, m), 2.86-2.99 (1H, m), 3.96-4.07 (1H, m), 4.26-4.40 (1H, m), 5.26 (1H, brs), 6.82-6.91 (2H, m), 7.02-7.18 (3H, m), 7.45-7.66 (5H, m), 7.73-8.23 (6H, m), 8.89 (1H, s), 9.20 (1H, brs), 9.65 (1H, brs), 12.51 (1H, brs) |
| 81 | 27 | FAB+: 514 |
| 82 | 27 | ESI+: 508 |
| 28 | 28 | FAB+: 542 |
| | | NMR1: 1.19-1.35 (1H, m), 1.61 (3H, d, J = 6.7 Hz), 2.16-2.39 (2H, m), 2.40-2.60 (3H, m), 2.74-2.85 (1H, m), 2.92-3.05 (1H, m), 3.90-4.00 (1H, m), 4.22-4.32 (1H, m), 5.26 (1H, brs), 6.82-6.90 (2H, m), 7.04-7.18 (3H, m), 7.46-7.54 (1H, m), 7.57-7.65 (2H, m), 7.71 (1H, d, J = 8.4 Hz), 7.79-8.06 (5H, m), 8.14-8.23 (1H, m), 8.40 (1H, s), 9.21 (1H, brs), 9.67 (1H, brs), 13.06 (1H, brs) |
| 83 | 28 | ESI+: 538 |
| 29 | 29 | FAB+: 560 |
| | | NMR1: 1.14-1.36 (1H, m), 1.61 (3H, d, J = 6.6 Hz), 2.16-2.29 (1H, m), 2.29-2.40 (1H, m), 2.40-2.60 (3H, m), 2.88 (1H, t, J = 7.4 Hz), 2.99 (1H, t, J = 7.4 Hz), 3.89-4.08 (1H, m), 4.15-4.35 (1H, m), 5.26 (1H, brs), 6.76 (1H, d, J = 7.6 Hz), 6.87 (1H, d, J = 12.6 Hz), 6.98 (1H, dt, J = 2.2, 8.6 Hz), 7.15 (1H, q, J = 7.6 Hz), 7.52 (1H, t, J = 7.6 Hz), 7.56-7.65 (2H, m), 7.70 (1H, d, J = 8.4 Hz), 7.78-7.88 (2H, m), 7.91 (1H, d, J = 1.9 Hz), 7.93 (1H, d, J = 8.4 Hz), 7.97-8.06 (1H, m), 8.12-8.22 (1H, m), 8.41 (1H, s), 9.15 (1H, brs), 9.68 (1H, brs), 13.07 (1H, brs) |

TABLE 79

| | | |
|---|---|---|
| 84 | 28 | FAB+: 560 |
| 85 | 27 | ESI+: 526 |
| 86 | 27 | FAB+: 464 |
| 42 | 42 | ESI+: 498 |
| 52 | 52 | FAB+: 501 |
| | | NMR1: 1.37-1.51 (1H, m), 1.60 (3H, d, J = 6.6 Hz), 2.11-2.25 (1H, m), 2.30-2.39 (1H, m), 2.45-2.69 (3H, m), 2.96-3.07 (1H, m), 3.12-3.42 (2H, m), 3.46-3.56 (1H, m), 5.21-5.34 (1H, m), 6.81-6.87 (2H, m), 7.02-7.15 (3H, m), 7.41-7.55 (3H, m), 7.57-7.66 (2H, m), 7.80 (1H, d, J = 7.1 Hz), 7.95 (1H, d, J = 8.1 Hz), 7.99-8.06 (1H, m), 8.17-8.24 (1H, m), 9.16 (1H, brs), 9.56 (1H, brs), 13.2 (1H, brs) |
| 87 | 52 | FAB+: 507 |
| | | NMR1: 1.36-1.52 (1H, m), 1.61 (3H, d, J = 6.7 Hz), 2.13-2.35 (2H, m), 2.42-2.70 (3H, m), 3.02-3.13 (1H, m), 3.14-3.42 (2H, m), 3.46-3.56 (1H, m), 4.84-4.96 (1H, m), 6.86-6.95 (2H, m), 7.05-7.18 (3H, m), 7.40-7.52 (4H, m), 7.95-8.09 (3H, m), 9.31 (1H, brs), 9.42 (1H, brs), 13.19 (1H, brs) |
| 88 | 31 | ESI+: 466 |
| 31 | 31 | ESI+: 500 |
| | | NMR1: 1.37-1.51 (1H, m), 1.61 (3H, d, J = 6.5 Hz), 2.18-2.70 (5H, m), 2.80-2.94 (1H, m), 2.99-3.10 (1H, m), 3.81-3.93 (1H, m), 4.18-4.30 (1H, m), 5.20-5.34 (1H, m), 6.84-6.95 (2H, m), 7.03-7.17 (3H, m), 7.47-7.66 (3H, m), 7.81 (1H, d, J = 7.4 Hz), 7.94 (1H, d, J = 7.8 Hz), 7.99-8.09 (2H, m), 8.15-8.25 (1H, m), 8.62 (1H, d, J = 2.0 Hz), 9.17 (1H, brs), 9.62 (1H, brs), 13.14 (1H, brs) |
| 89 | 31 | ESI+: 534 |
| | | NMR1: 1.20-1.35 (1H, m), 1.61 (3H, d, J = 6.6 Hz), 2.27-2.59 (5H, m), 2.86-2.99 (1H, m), 3.06-3.19 (1H, m), 4.34-4.48 (1H, m), 4.58-4.74 (1H, m), 5.18-5.33 (1H, m), 6.86-6.96 (2H, m), 7.04-7.20 (4H, m), 7.45-7.64 (3H, m), 7.82-8.03 (3H, m), 8.13-8.24 (1H, m), 8.67 (1H, s), 9.14-9.38 (1H, m), 9.58-9.90 (1H, m) |
| 90 | 52 | FAB+: 519 |
| | | NMR1: 1.32-1.52 (1H, m), 1.61 (3H, d, J = 6.6 Hz), 2.10-2.25 (1H, m), 2.27-2.40 (1H, m), 2.40-2.63 (2H, m), 2.63-2.76 (1H, m), 3.09 (1H, t, J = 11.7 Hz), |

TABLE 79-continued 3.14-3.41 (2H, m), 3.50 (1H, d, J = 11.7 Hz), 5.28 (1H, brs),
6.74 (1H, d, J = 7.7 Hz), 6.85 (1H, d, J = 10.0 Hz), 6.96 (1H, dt, J = 1.9, 8.3 Hz),
7.13 (1H, q, J = 7.2 Hz), 7.40-7.50 (2H, m), 7.53 (1H, t, J = 7.7 Hz),
7.56-7.65 (2H, m), 7.80 (1H, d, J = 7.2 Hz), 7.94 (1H, d, J = 8.3 Hz),
7.98-8.05 (1H, m), 8.13-8.23 (1H, m), 9.06 (1H, brs), 9.55 (1H, brs), 13.18 (1H, brs)

TABLE 80

| | | |
|---|---|---|
| 34 | 34 | ESI+: 465<br>NMR1: 1.38-1.54 (1H, m), 1.62 (3H, d), 2.19-2.36 (1H, m), 2.38-3.10 (6H, m), 3.46-3.56 (1H, m), 3.86-3.96 (1H, m), 5.18-5.32 (1H, m), 6.86-6.97 (2H, m), 7.04-7.18 (3H, m), 7.24-7.66 (7H, m), 7.84-8.06 (3H, m), 8.15-8.22 (1H, m), 9.24-9.45 (1H, m), 9.74-9.95 (1H, m) |
| 91 | 34 | ESI+: 465 |
| 92 | 31 | ESI+: 544 |
| 93 | 31 | ESI+: 518 |
| 94 | 52 | FAB+: 519 |
| 95 | 52 | ESI+: 483 |
| 96 | 52 | ESI+: 499 |
| 97 | 31 | ESI+: 480 |
| 98 | 31 | ESI+: 552<br>NMR1: 1.15-1.33 (1H, m), 1.62 (3H, d, J = 6.6 Hz), 2.27-2.60 (5H, m), 2.96-3.18 (2H, m), 4.36-4.48 (1H, m), 4.59-4.72 (1H, m), 5.25 (1H, brs), 6.79 (1H, 4, J = 7.6 Hz), 6.87-7.02 (2H, m), 7.07-7.21 (2H, m), 7.46-7.62 (3H, m), 7.82-8.03 (3H, m), 8.10-8.19 (1H, m), 8.67 (1H, s), 9.09-9.24 (1H, m), 9.76 (1H, brs) |
| 99 | 31 | ESI+: 500 |
| 100 | 31 | ESI+: 500 |
| 37 | 37 | ESI+: 490<br>NMR1: 1.26-1.45 (1H, m), 1.60 (3H, d, J = 6.6 Hz), 2.19-2.40 (2H, m), 2.40-2.61 (2H, m), 2.61-2.76 (1H, m), 3.10 (1H, t, J = 12.0 Hz), 3.20 (1H, t, J = 12.0 Hz), 3.70-3.80 (1H, m), 3.97-4.10 (1H, m), 5.18-5.35 (1H, m), 6.80 (1H, d, J = 7.6 Hz), 6.91 (1H, d, J = 9.8 Hz), 6.96-7.05 (1H, m), 7.18 (1H, q, J = 7.6 Hz), 7.53 (1H, t, J = 7.6 Hz), 7.56-7.62 (2H, m), 7.63 (1H, s), 7.81 (1H, d, J = 7.1 Hz), 7.93 (1H, d, J = 8.2 Hz), 7.97-8.04 (1H, m), 8.09-8.20 (1H, m), 8.97-9.23 (1H, m), 9.48-9.73 (1H, m) |
| 101 | 31 | ESI+: 496 |
| 102 | 31 | ESI+: 484 |
| 103 | 31 | FAB+: 518 |
| 104 | 31 | ESI+: 484<br>NMR1: 1.19-1.40 (1H, m), 1.59 (3H, d, J = 6.6 Hz), 2.27-2.60 (4H, m), 2.64-2.78 (1H, m), 2.96 (1H, t, J = 12.2 Hz), 3.06 (1H, t, J = 12.2 Hz), 4.27-4.46 (1H, d), 4.54-4.72 (1H, d), 5.18-5.38 (1H, m), 6.87-7.00 (3H, m), 7.05 (1H, t, J = 9.3 Hz), 7.17-7.27 (1H, m), 7.51 (1H, t, J = 7.8 Hz), 7.54-7.64 (1H, m), 7.79 (1H, d, J = 7.2 Hz), 7.86-7.97 (2H, m), 7.97-8.05 (1H, m), 8.09-8.22 (1H, m), 8.59 (1H, d, J = 2.3 Hz), 8.99-9.23 (1H, m), 9.49-9.73 (1H, m), 12.23-12.75 (1H, m) |

TABLE 81

| | | |
|---|---|---|
| 32 | 32 | FAB+: 518<br>NMR1: 1.37-1.53 (1H, m), 1.61 (3H, d, J = 6.5 Hz), 2.25-2.63 (4H, m), 2.80-3.14 (3H, m), 3.81-3.97 (1H, m), 4.15-4.30 (1H, m), 5.18-5.30 (1H, m), 6.83-6.99 (2H, m), 6.99-7.09 (1H, m), 7.15-7.25 (1H, m), 7.51 (1H, t, J = 7.7 Hz), 7.55-7.65 (2H, m), 7.86 (1H, d, J = 7.2 Hz), 7.93 (1H, d, J = 8.2 Hz), 7.97-8.05 (1H, m), 8.05 (1H, d, J = 2.0 Hz), 8.13-8.23 (1H, m), 8.62 (1H, d, J = 2.0 Hz) |
| 105 | 31 | ESI+: 506 |
| 106 | 31 | ESI+: 496 |
| 107 | 34 | ESI+: 471 |
| 38 | 38 | FAB+: 490<br>NMR1: 1.27-1.44 (1H, m), 1.61 (3H, d, J = 6.5 Hz), 2.24-2.60 (m), 2.62-2.76 (1H, m), 3.20 (1H, t, J = 12.1 Hz), 3.30 (1H, t, J = 12.1 Hz), 3.46-4.17 (m), 5.18-5.33 (1H, m), 6.79 (1H, d, J = 7.4 Hz), 6.91 (1H, d, J = 10.1 Hz), 6.95-7.04 (1H, m), 7.17 (1H, q, J = 7.4 Hz), 7.52 (1H, t, J = 15.4 Hz), 7.55-7.63 (2H, m), 7.75 (1H, s), 7.85 (1H, d, J = 7.4 Hz), 7.93 (1H, d, J = 8.2 Hz), 7.96-8.04 (1H, m), 8.11-8.19 (1H, m), 9.06-9.32 (1H, m), 9.65-9.90 (1H, m) |

TABLE 81-continued

| | | |
|---|---|---|
| 108 | 34 | FAB+: 483<br>NMR1: 1.27-1.48 (1H, m), 1.61 (3H, d, J = 6.6 Hz), 2.12-2.30 (1H, m), 2.30-2.42 (1H, m), 2.42-2.62 (2H, m), 2.62-2.73 (1H, m), 2.81 (1H, t, J = 12.1 Hz), 2.93 (1H, t, J = 12.1 Hz), 3.45-4.21 (2H, m), 5.19-5.34 (1H, m), 6.79 (1H, d, J = 7.6 Hz), 6.85-6.95 (1H, m), 6.95-7.03 (1H, m), 7.16 (1H, q, J = 7.6 Hz), 7.20-7.27 (1H, m), 7.31 (1H, t, J = 7.6 Hz), 7.34-7.40 (1H, m), 7.43-7.48 (1H, m), 7.52 (1H, t, J = 7.6 Hz), 7.55-7.66 (2H, m), 7.84 (1H, d, J = 7.0 Hz), 7.91-7.97 (1H, m), 7.91-8.03 (1H, m), 8.11-8.22 (1H, m), 9.01-9.25 (1H, m), 9.57-9.80 (1H, m) |
| 35 | 35 | FAB+: 483<br>NMR1: 1.35-1.50 (1H, m), 1.62 (3H, d, J = 6.6 Hz), 2.27-2.63 (4H, m), 2.77-3.03 (3H, m), 3.50-3.65 (1H, m), 3.90-4.00 (1H, m), 5.22-5.34 (1H, m), 6.86-6.99 (2H, m), 7.01-7.10 (1H, m), 7.16-7.28 (2H, m), 7.31 (1H, t, J = 7.5 Hz), 7.36 (1H, brd, J = 7.5 Hz), 7.47 (1H, brs), 7.52 (1H, t, J = 7.7 Hz), 7.55-7.64 (2H, m), 7.86 (1H, d, J = 7.1 Hz), 7.94 (1H, d, J = 8.2 Hz), 7.97-8.05 (1H, m), 8.13-8.22 (1H, m), 9.14-9.34 (1H, m), 9.66-9.88 (1H, m) |
| 33 | 33 | ESI+: 480<br>NMR1: 1.32-1.47 (1H, m), 1.54 (3H, d, J = 6.7 Hz), 2.30-2.44 (4H, m), 2.59-2.70 (1H, m), 2.91-3.14 (2H, m), 3.74 (3H, s), 3.87-3.98 (1H, m), 4.17-4.33 (2H, m), 6.90 (1H, dd, J = 2.3, 8.2 Hz), 7.02 (1H, d, J = 7.6 Hz), 7.10-7.30 (7H, m), 8.05 (1H, d, J = 2.0 Hz), 8.63 (1H, d, J = 2.0 Hz), 9.13-9.38 (1H, m), 9.55-9.78 (1H, m) |

TABLE 82

| | | |
|---|---|---|
| 30 | 30 | FAB+: 466<br>NMR1: 1.20-1.34 (1H, m), 1.62 (3H, d, J = 6.5 Hz), 2.17-2.57 (5H, m), 2.68-2.79 (1H, m), 2.90-3.02 (1H, m), 4.24-4.34 (1H, m), 4.57 (1H, brd, J = 13.2 Hz), 5.15-5.35 (1H, m), 6.80-6.95 (2H, m), 7.02-7.18 (4H, m), 7.27 (1H, d, J = 7.1 Hz), 7.50 (1H, t, J = 7.8 Hz), 7.52-7.69 (3H, m), 7.85 (1H, d, J = 6.8 Hz), 7.93 (1H, d, J = 8.2 Hz), 7.97-8.05 (1H, m), 8.15-8.23 (1H, m), 9.16-9.34 (1H, m), 9.60-9.80 (1H, m), 12.45-12.80 (1H, m) |
| 109 | 52 | ESI+: 483 |
| 110 | 52 | ESI+: 489 |
| 111 | 52 | ESI+: 510 |
| 112 | 34 | ESI+: 471 |
| 113 | 31 | ESI+: 472 |
| 114 | 31 | ESI+: 540 |
| 115 | 31 | ESI+: 484 |
| 116 | 31 | ESI+: 484 |
| 117 | 31 | FAB+: 466 |
| 36 | 36 | FAB+: 500<br>NMR1: 1.21-1.36 (1H, m), 1.59 (3H, d, J = 6.5 Hz), 2.22-2.45 (2H, m), 2.45-2.61 (3H, m), 2.88 (1H, t, J = 12.1 Hz), 3.06 (1H, t, J = 12.1 Hz), 4.09-4.22 (1H, m), 4.37-4.53 (1H, m), 5.15-5.35 (1H, m), 6.85-7.01 (3H, m), 7.04-7.23 (4H, m), 7.51 (1H, t, J = 7.8 Hz), 7.55-7.66 (2H, m), 7.76 (1H, d, J = 7.2 Hz), 7.93 (1H, d, J = 8.2 Hz), 7.97-8.04 (1H, m), 8.11-8.23 (1H, m), 8.81-9.21 (1H, m), 9.28-9.67 (1H, m) |
| 39 | 39 | ESI+: 472<br>NMR1: 1.30-1.46 (1H, m), 1.60 (3H, d, J = 6.5 Hz), 2.18-2.65 (5H, m), 2.93-3.06 (1H, m), 3.13-3.26 (1H, m), 3.66-3.78 (1H, m), 3.97-4.10 (1H, m), 5.27 (1H, brs), 6.84-6.96 (2H, m), 7.04-7.19 (3H, m), 7.45-7.65 (4H, m), 7.81 (1H, d, J = 7.3 Hz), 7.94 (1H, d, J = 8.2 Hz), 7.98-8.05 (1H, m), 8.13-8.22 (1H, m), 9.19 (1H, brs), 9.62 (1H, brs), 12.61 (1H, brs) |
| 118 | 39 | ESI+: 472 |
| 119 | 31 | ESI+: 500<br>NMR1: 1.18-1.32 (1H, m), 1.60 (3H, d, J = 6.5 Hz), 2.21-2.57 (5H, m), 2.80-2.94 (1H, m), 3.00-3.14 (1H, m), 4.26-4.43 (1H, m), 4.51-4.65 (1H, m), 5.26 (1H, brs), 6.90 (2H, d, J = 6.8 Hz), 7.01 (1H, s), 7.04-7.18 (3H, m), 7.46-7.64 (3H, m), 7.80 (1H, d, J = 7.6 Hz), 7.87-8.06 (2H, m), 8.12-8.24 (1H, m), 8.59 (1H, s), 9.13 (1H, brs), 9.60 (1H, brs), 12.77 (1H, brs) |
| 120 | 39 | ESI+: 486 |

TABLE 83

| | | |
|---|---|---|
| 40 | 40 | FAB+: 524<br>NMR1: 1.32-1.46 (1H, m), 1.61 (3H, d, J = 6.6 Hz), 2.23-2.65 (4H, m), 2.65-2.78 (1H, m), 3.22 (1H, t, J = 12.2 Hz), 3.30 (1H, t, J = 12.2 Hz), 3.93-4.05 (1H, m), 4.23-4.40 (1H, m), 5.15-5.36 (1H, m), 6.81 (1H, d, J = 7.5 Hz), 6.92 (1H, d, J = 9.8 Hz), 6.97-7.06 (1H, m), 7.19 (1H, q, J = 7.5 Hz), 7.47 (1H, d, J = 8.4 Hz), 7.52 (1H, t, J = 7.5 Hz), 7.55-7.62 (2H, m), 7.64-7.70 (1H, m), 7.75-7.79 (1H, m), 7.82 (1H, d, J = 7.1 Hz), 7.93 (1H, d, J = 8.2 Hz), 7.96-8.04 (1H, m), 8.10-8.21 (1H, m), 8.94-9.27 (1H, m), 9.53-9.78 (1H, m) |

TABLE 83-continued

| | | |
|---|---|---|
| 121 | 36 | FAB+: 480 |
| 122 | 39 | ESI+: 452 |
| 123 | 39 | ESI+: 452 |
| 124 | 40 | FAB+: 524 |
| 125 | 37 | FAB+: 504 |
| 41 | 41 | FAB+: 523 |
| | | NMR1: 1.37-1.55 (1H, m), 1.64 (3H, d, J = 6.6 Hz), 2.24-3.77 (7H, m), 3.96-4.09 (1H, m), 4.36-4.53 (1H, m), 5.13-5.38 (1H, m), 6.75-6.85 (1H, m), 6.88-6.99 (1H, m), 6.99-7.06 (1H, m), 7.17 (1H, q, J = 7.3 Hz), 7.45 (1H, d, J = 8.3 Hz), 7.48-7.55 (1H, m), 7.55-7.63 (1H, m), 7.80-8.05 (5H, m), 8.10-8.24 (1H, m), 9.34-9.60 (1H, m), 9.90-10.14 (1H, m) |
| 126 | 30 | ESI+: 484 |
| | | NMR1: 1.13-1.33 (1H, m), 1.54-1.67 (3H, m), 2.18-2.59 (5H, m), 2.74-3.02 (2H, m), 4.25-4.36 (1H, m), 4.50-4.62 (1H, m), 5.20-5.32 (1H, m), 6.73-6.81 (1H, m), 6.84-6.93 (1H, m), 6.94-7.03 (1H, m), 7.06-7.20 (2H, m), 7.27 (1H, d, J = 7.0 Hz), 7.45-7.69 (4H, m), 7.75-8.03 (3H, m), 8.12-8.20 (1H, m) |
| 127 | 30 | ESI+: 484 |
| | | NMR1: 1.21-1.37 (1H, m), 1.60 (3H, d, J = 6.3 Hz), 2.28-2.58 (4H, m), 2.65-3.01 (3H, m), 4.29-4.39 (1H, m), 4.54-4.63 (1H, m), 5.22-5.33 (1H, m), 6.85-7.31 (6H, m), 7.47-7.70 (4H, m), 7.76-7.86 (1H, m), 7.89-8.05 (2H, m), 8.13-8.22 (1H, m), 9.15 (1H, brs), 9.66 (1H, brs) |
| 128 | 30 | ESI+: 446 |
| 43 | 43 | ESI+: 484 |
| | | NMR1: 1.29-1.43 (1H, m), 1.62 (3H, d, J = 6.6 Hz), 2.26-2.62 (5H, m), 2.89-3.00 (1H, m), 3.07-3.21 (1H, m), 4.05-4.17 (1H, m), 4.41-4.54 (1H, m), 5.26 (1H, brs), 6.83-6.92 (2H, m), 7.04-7.17 (3H, m), 7.46-7.54 (1H, m), 7.55-7.65 (2H, m), 7.71-8.06 (4H, m), 7.15-8.23 (1H, m), 8.44-8.50 (1H, m), 9.24 (1H, brs), 9.75 (1H, brs), 12.93 (1H, brs) |

TABLE 84

| | | |
|---|---|---|
| 44 | 44 | ESI+: 477 |
| | | NMR1: 1.20-1.34 (2H, m), 1.41-1.55 (2H, m), 1.55-1.79 (5H, m), 2.12-2.73 (m), 2.79-3.19 (4H, m), 3.20-3.67 (m), 5.15-5.30 (1H, m), 6.82 (1H, d, J = 7.7 Hz), 6.92 (1H, d, J = 9.9 Hz), 7.04 (1H, dt, J = 2.3, 5.4 Hz), 7.09-7.27 (1H, m), 7.52 (1H, t, J = 7.7 Hz), 7.54-7.64 (1H, m), 7.94 (1H, t, J = 8.1 Hz), 7.98-8.06 (1H, m), 8.08-8.20 (1H, m), 9.39-9.55 (1H, m), 10.01-10.19 (1H, m), 10.50-10.70 (1H, m), 11.65-12.31 (1H, m) |
| 53 | 53 | FAB+: 525 |
| | | NMR1: 1.38-1.53 (1H, m), 1.63 (3H, d, J = 6.6 Hz), 2.14-2.28 (1H, m), 2.34-2.69 (4H, m), 2.94-3.55 (4H, m), 5.22-5.34 (1H, m), 6.79-6.86 (2H, m), 7.01-7.14 (3H, m), 7.46-7.76 (5H, m), 7.88 (1H, d, J = 7.1 Hz), 7.95 (1H, d, J = 8.2 Hz), 7.99-8.06 (1H, m), 8.18-8.26 (1H, m), 9.35 (1H, brs), 9.79 (1H, brs) |
| 129 | 53 | FAB+: 531 |
| 130 | 53 | ESI+: 490 |
| 54 | 54 | ESI+: 541 |
| | | NMR1: 1.37-1.53 (1H, m), 1.61 (3H, d, J = 6.7 Hz), 2.12-2.25 (1H, m), 2.30-2.41 (1H, m), 2.45-2.69 (3H, m), 2.96-3.08 (1H, m), 3.12-3.42 (2H, m), 3.46-3.56 (1H, m), 5.23-5.34 (1H, m), 6.85 (2H, d, J = 6.7 Hz), 7.04-7.16 (3H, m), 7.40-7.55 (3H, m), 7.58-7.66 (2H, m), 7.80 (1H, d, J = 7.3 Hz), 7.95 (1H, d, J = 8.2 Hz), 8.00-8.06 (1H, m), 8.17-8.25 (1H, m), 9.14 (1H, brs), 9.54 (1H, brs), 12.97 (1H, brs) |
| 131 | 46 | ESI+: 431 |
| 132 | 46 | ESI+: 443 |
| 133 | 46 | ESI+: 445 |
| 134 | 46 | ESI+: 457 |
| 135 | 46 | ESI+: 459 |
| 136 | 46 | ESI+: 473 |
| 137 | 46 | ESI+: 473 |
| 138 | 46 | ESI+: 473 |
| 139 | 46 | ESI+: 485 |
| 140 | 46 | ESI+: 485 |
| 141 | 46 | ESI+: 485 |
| 142 | 46 | ESI+: 485 |
| 143 | 46 | ESI+: 487 |
| 46 | 46 | ESI+: 493 |
| 144 | 46 | ESI+: 493 |
| 145 | 46 | ESI+: 494 |

TABLE 85

| | | |
|---|---|---|
| 146 | 46 | ESI+: 494 |
| 147 | 46 | ESI+: 494 |
| 148 | 46 | ESI+: 497 |
| 149 | 46 | ESI+: 499 |
| 150 | 46 | ESI+: 499 |
| 151 | 46 | ESI+: 499 |
| 152 | 46 | ESI+: 499 |
| 153 | 46 | ESI+: 499 |
| 154 | 46 | ESI+: 501 |
| 155 | 46 | ESI+: 502 |
| 156 | 46 | ESI+: 507 |
| 157 | 46 | ESI+: 509 |
| 158 | 46 | ESI+: 509 |
| 159 | 46 | ESI+: 515 |
| 160 | 46 | ESI+: 516 |
| 161 | 46 | ESI+: 519 |
| 162 | 46 | ESI+: 519 |
| 163 | 46 | ESI+: 521 |
| 164 | 46 | ESI+: 522 |
| 165 | 46 | ESI+: 527 |
| 166 | 46 | ESI+: 529 |
| 167 | 46 | ESI+: 535 |
| 168 | 46 | ESI+: 538 |
| 169 | 46 | ESI+: 538 |
| 170 | 46 | ESI+: 545 |
| 171 | 46 | ESI+: 556 |
| 172 | 46 | ESI+: 557 |
| 173 | 46 | ESI+: 564 |
| 174 | 46 | ESI+: 565 |
| 175 | 46 | ESI+: 576 |
| 176 | 46 | ESI+: 443 |
| 177 | 46 | ESI+: 482 |
| 178 | 47 | ESI+: 431 |
| 179 | 47 | ESI+: 443 |
| 180 | 47 | ESI+: 445 |
| 181 | 47 | ESI+: 457 |

TABLE 86

| | | |
|---|---|---|
| 182 | 47 | ESI+: 459 |
| 183 | 47 | ESI+: 473 |
| 184 | 47 | ESI+: 473 |
| 185 | 47 | ESI+: 473 |
| 186 | 47 | ESI+: 485 |
| 187 | 47 | ESI+: 485 |
| 188 | 47 | ESI+: 485 |
| 47 | 47 | ESI+: 493 |
| 189 | 47 | ESI+: 493 |
| 190 | 47 | ESI+: 494 |
| 191 | 47 | ESI+: 494 |
| 192 | 47 | ESI+: 494 |
| 193 | 47 | ESI+: 499 |
| 194 | 47 | ESI+: 499 |
| 195 | 47 | ESI+: 499 |
| 196 | 47 | ESI+: 499 |
| 197 | 47 | ESI+: 499 |
| 198 | 47 | ESI+: 501 |
| 199 | 47 | ESI+: 501 |
| 200 | 47 | ESI+: 502 |
| 201 | 47 | ESI+: 507 |
| 202 | 47 | ESI+: 515 |
| 203 | 47 | ESI+: 516 |
| 204 | 47 | ESI+: 519 |
| 205 | 47 | ESI+: 519 |
| 206 | 47 | ESI+: 521 |
| 207 | 47 | ESI+: 522 |
| 208 | 47 | ESI+: 527 |
| 209 | 47 | ESI+: 529 |
| 210 | 47 | ESI+: 535 |
| 211 | 47 | ESI+: 535 |
| 212 | 47 | ESI+: 538 |
| 213 | 47 | ESI+: 538 |
| 214 | 47 | ESI+: 545 |
| 215 | 47 | ESI+: 557 |
| 216 | 47 | ESI+: 564 |

TABLE 87

| | | |
|---|---|---|
| 217 | 47 | ESI+: 565 |
| 218 | 47 | ESI+: 576 |
| 219 | 47 | ESI+: 443 |
| 220 | 47 | ESI+: 482 |
| 221 | 48 | ESI+: 435 |
| 222 | 48 | ESI+: 387 |
| 223 | 48 | ESI+: 401 |
| 224 | 48 | ESI+: 403 |
| 225 | 48 | ESI+: 403 |
| 48 | 48 | ESI+: 425 |
| 226 | 48 | ESI+: 436 |
| 227 | 48 | ESI+: 436 |
| 228 | 48 | ESI+: 438 |
| 229 | 48 | ESI+: 441 |
| 230 | 48 | ESI+: 449 |
| 231 | 48 | ESI+: 451 |
| 232 | 48 | ESI+: 451 |
| 233 | 48 | ESI+: 451 |
| 234 | 48 | ESI+: 453 |
| 235 | 48 | ESI+: 461 |
| 236 | 48 | ESI+: 463 |
| 237 | 48 | ESI+: 465 |
| 238 | 48 | ESI+: 465 |
| 239 | 48 | ESI+: 469 |
| 240 | 48 | ESI+: 469 |
| 241 | 48 | ESI+: 469 |
| 242 | 48 | ESI+: 469 |
| 243 | 48 | ESI+: 478 |
| 244 | 48 | ESI+: 485 |
| 245 | 48 | ESI+: 485 |
| 246 | 48 | ESI+: 492 |
| 247 | 48 | ESI+: 503 |
| 248 | 48 | ESI+: 509 |
| 249 | 48 | ESI+: 509 |
| 250 | 48 | ESI+: 511 |
| 251 | 48 | ESI+: 424 |

TABLE 88

| | | |
|---|---|---|
| 252 | 48 | ESI+: 425 |
| 253 | 48 | ESI+: 441 |
| 254 | 48 | ESI+: 442 |
| 255 | 48 | ESI+: 453 |
| 256 | 48 | ESI+: 453 |
| 257 | 48 | ESI+: 465 |
| 258 | 48 | ESI+: 479 |
| 259 | 48 | ESI+: 479 |
| 260 | 48 | ESI+: 485 |
| 261 | 48 | ESI+: 505 |
| 262 | 49 | ESI+: 387 |
| 263 | 49 | ESI+: 403 |
| 264 | 49 | ESI+: 403 |
| 265 | 49 | ESI+: 425 |
| 49 | 49 | ESI+: 425 |
| 266 | 49 | ESI+: 436 |
| 267 | 49 | ESI+: 438 |
| 268 | 49 | ESI+: 441 |
| 269 | 49 | ESI+: 441 |
| 270 | 49 | ESI+: 442 |
| 271 | 49 | ESI+: 449 |
| 272 | 49 | ESI+: 451 |
| 273 | 49 | ESI+: 451 |
| 274 | 49 | ESI+: 451 |
| 275 | 49 | ESI+: 453 |
| 276 | 49 | ESI+: 453 |
| 277 | 49 | ESI+: 461 |
| 278 | 49 | ESI+: 463 |
| 279 | 49 | ESI+: 465 |
| 280 | 49 | ESI+: 465 |
| 281 | 49 | ESI+: 465 |
| 282 | 49 | ESI+: 469 |
| 283 | 49 | ESI+: 469 |
| 284 | 49 | ESI+: 469 |
| 285 | 49 | ESI+: 469 |
| 286 | 49 | ESI+: 478 |

TABLE 89
| | | |
|---|---|---|
| 287 | 49 | ESI+: 479 |
| 288 | 49 | ESI+: 479 |
| 289 | 49 | ESI+: 485 |
| 290 | 49 | ESI+: 485 |
| 291 | 49 | ESI+: 485 |
| 292 | 49 | ESI+: 492 |
| 293 | 49 | ESI+: 503 |
| 294 | 49 | ESI+: 505 |
| 295 | 49 | ESI+: 509 |
| 296 | 49 | ESI+: 509 |
| 297 | 49 | ESI+: 511 |
TABLE 90
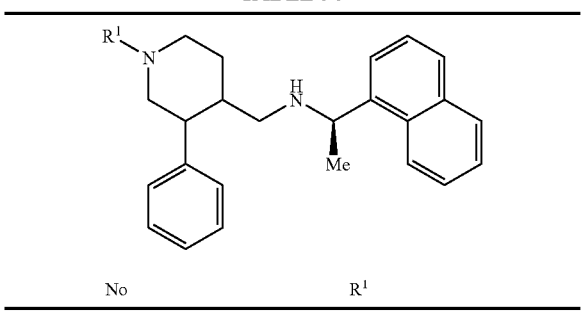
TABLE 90-continued
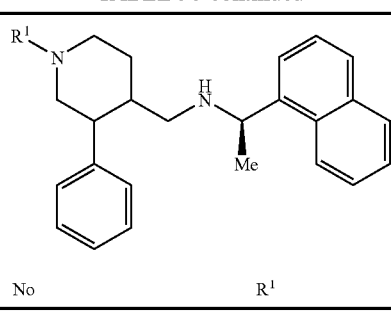

TABLE 90-continued

[Structure: R¹-N-piperidine with 3-phenyl, 4-CH₂-NH-CH(Me)-naphthyl]

| No | R¹ |
|---|---|
| 16 | 2-methyl-1H-imidazole-4-carboxylic acid |

TABLE 91

[Structure: R¹-N-piperidine with 3-phenyl, 4-CH₂-NH-CH(Me)-naphthyl]

| No | R¹ |
|---|---|
| 17 | 2-methyl-oxazole-4-carboxylic acid (HO₂C-oxazole-Me) |
| 18 | 2-chloro-6-methyl-pyridine-3-carboxylic acid (HO₂C, Cl, Me) |
| 19 | 4-chloro-6-methyl-pyridine-3-carboxylic acid (HO₂C, Cl, Me) |
| 20 | 2-trifluoromethyl-6-methyl-pyridine-3-carboxylic acid (HO₂C, CF₃, Me) |
| 21 | 5-methyl-pyrazine-2-carboxylic acid (HO₂C, Me) |
| 22 | 3-chloro-5-methyl-pyrazine-2-carboxylic acid (HO₂C, Cl, Me) |

TABLE 91-continued

[Structure: R¹-N-piperidine with 3-phenyl, 4-CH₂-NH-CH(Me)-naphthyl]

| No | R¹ |
|---|---|
| 23 | 3-fluoro-5-methyl-pyrazine-2-carboxylic acid (HO₂C, F, Me) |
| 24 | 3-chloro-5-methyl-pyrazine-2-carboxylic acid (HO₂C, Cl, Me) |
| 25 | 5-fluoro-6-methyl-pyrazine-2-carboxylic acid (HO₂C, F, Me) |
| 26 | 5-methyl-pyridine-2-carboxylic acid (HO₂C, Me) |
| 27 | 6-chloro-5-methyl-pyridine-2-carboxylic acid (HO₂C, Me, Cl) |
| 28 | 4-chloro-5-methyl-pyridine-2-carboxylic acid (HO₂C, Cl, Me) |
| 29 | 3-chloro-5-methyl-pyridine-2-carboxylic acid (HO₂C, Cl, Me) |
| 30 | 5-methyl-6-trifluoromethyl-pyridine-2-carboxylic acid (HO₂C, Me, CF₃) |
| 31 | 4-trifluoromethyl-5-methyl-pyridine-2-carboxylic acid (HO₂C, CF₃, Me) |

TABLE 91-continued
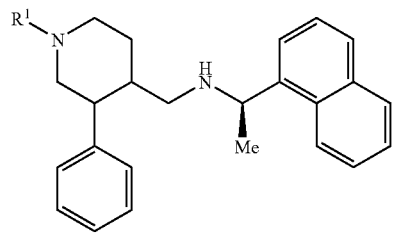
| No | R¹ |
|---|---|
| 32 | 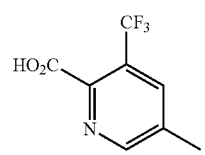 |
TABLE 92
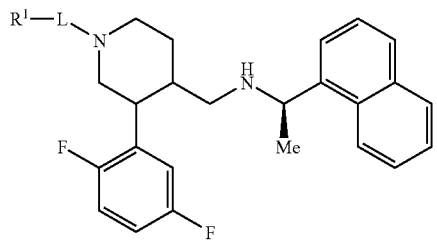
| No | R¹—L— |
|---|---|
| 33 | 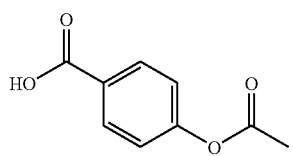 |
| 34 |  |
| 35 | 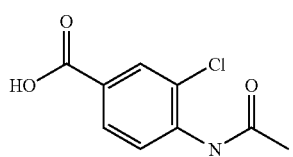 |
| 36 | 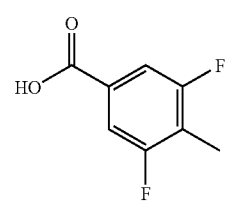 |
TABLE 92-continued
| No | R¹—L— |
|---|---|
| 37 | 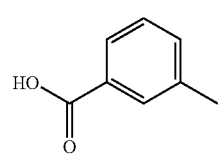 |
| 38 | 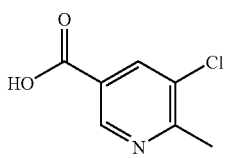 |
| 39 | 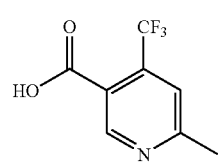 |
| 40 | 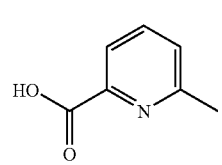 |
TABLE 93
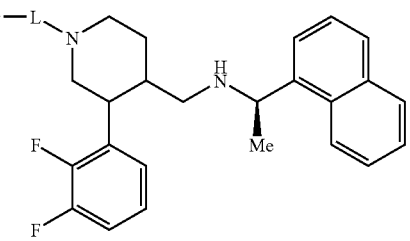
| No | R¹—L— |
|---|---|
| 41 | 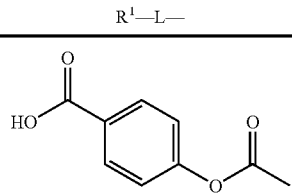 |

TABLE 93-continued
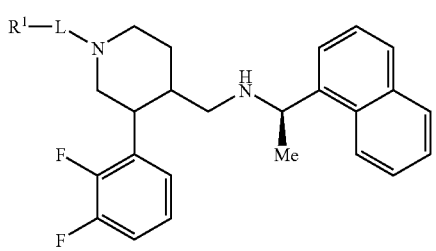
| No | R¹—L— |
|---|---|
| 42 | 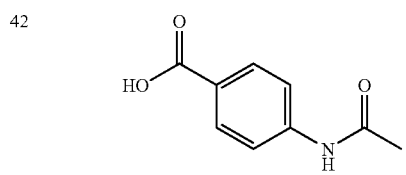 |
| 43 | 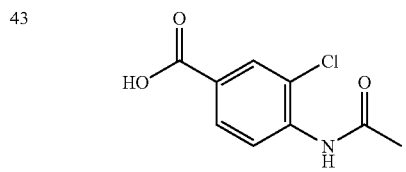 |
| 44 | 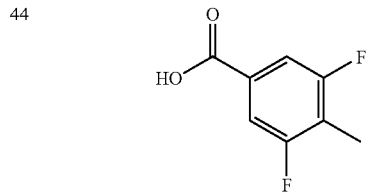 |
| 45 | 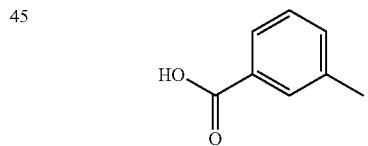 |
| 46 | 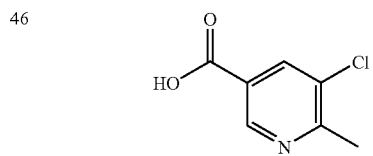 |
TABLE 93-continued
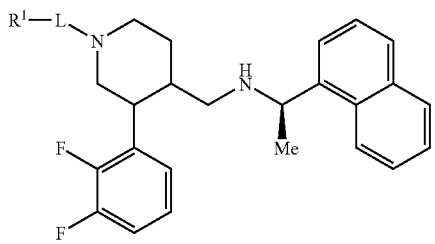
| No | R¹—L— |
|---|---|
| 47 | 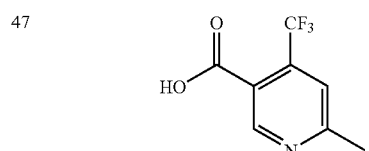 |
| 48 | 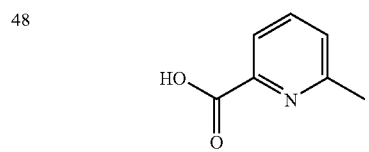 |
TABLE 94
| No | Structure |
|---|---|
| 49 | 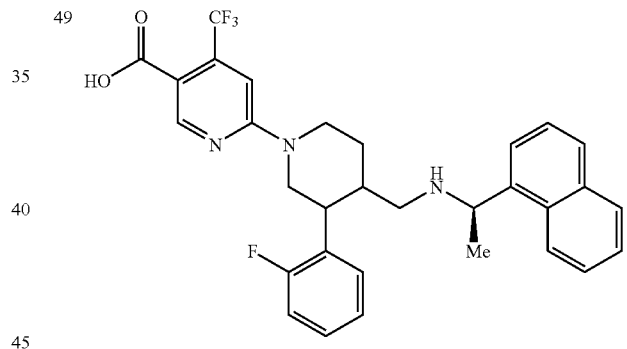 |
TABLE 95
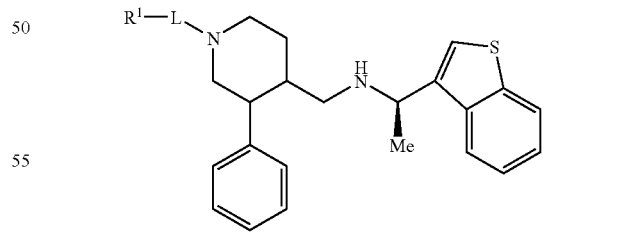
| No | R¹—L— |
|---|---|
| 50 | 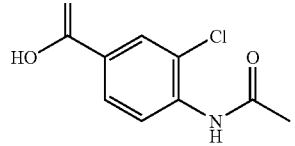 |

TABLE 95-continued
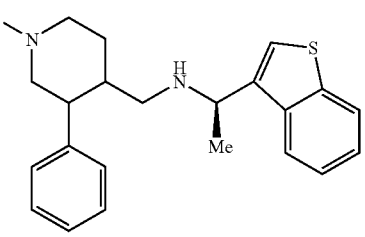
| No | R¹—L— |
|----|-------|
| 51 | 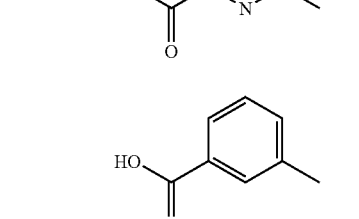 |
| 52 | 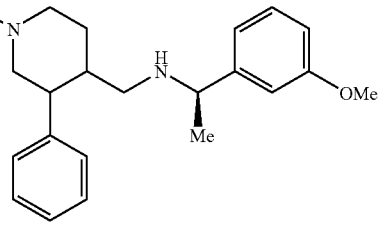 |
TABLE 96
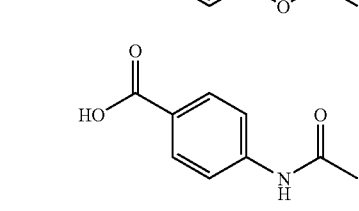
| No | R¹—L— |
|----|-------|
| 53 | 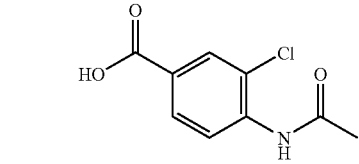 |
| 54 | 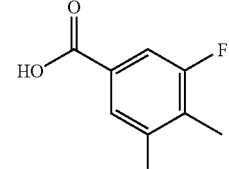 |
| 55 | 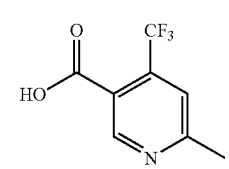 |
TABLE 96-continued
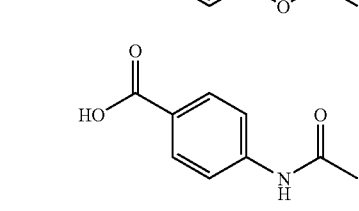
| No | R¹—L— |
|----|-------|
| 56 | 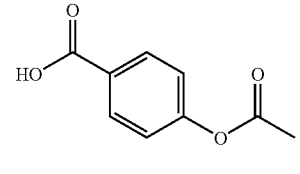 |
| 57 | 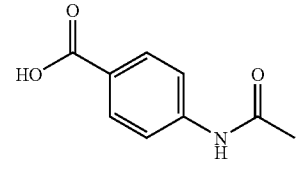 |
TABLE 97
| No | R¹—L— |
|----|-------|
| 58 | 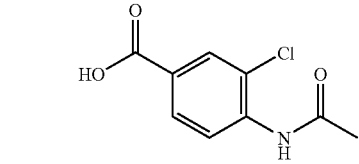 |
| 59 | 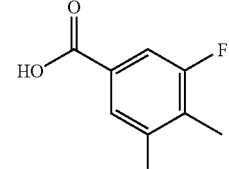 |
| 60 | 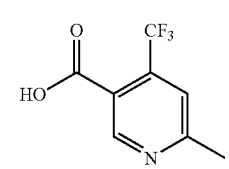 |

TABLE 97-continued

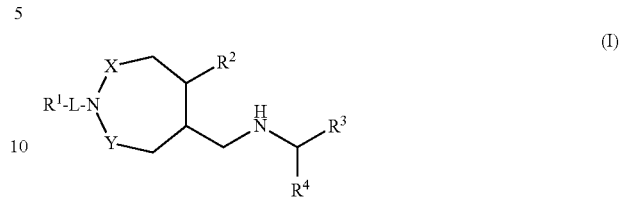

| No | R¹—L— |
|---|---|
| 61 | 3,5-difluoro-4-methylbenzoic acid structure |
| 62 | 3-methylbenzoic acid structure |
| 63 | 5-chloro-6-methylnicotinic acid structure |
| 64 | 6-methyl-4-(trifluoromethyl)nicotinic acid structure |
| 65 | 6-methylpicolinic acid structure |

INDUSTRIAL APPLICABILITY

The compound of the present invention has an excellent CaSR agonistic regulatory effect, and also has excellent selectivity against a CYP2D6 inhibitory action having a possibility of causing drug interaction. In this regard, it is useful as a therapeutic agent for diseases in which CaSR is concerned (hyperparathyroidism, renal osteodystrophy, hypercalcemia, and the like).

The invention claimed is:

1. A piperidine derivative represented by general formula (I) or a pharmaceutically acceptable salt thereof:

$$R^1\text{-L-N}\begin{array}{c}X\\Y\end{array}\begin{array}{c}R^2\\ \\ \end{array}\text{NH}\begin{array}{c}R^3\\R^4\end{array} \quad (I)$$

wherein:
X: a single bond;
Y: —CH₂—;
L: a single bond, *—C(O)—, *—OC(O)—, or *—N(R⁰)C(O)—, wherein * represents the bonding to R¹;
R⁰: —H or lower alkyl;
R¹: —H, or C₁₋₁₂ alkyl, lower alkenyl, cycloalkyl, cycloalkenyl, aryl or a hetero ring group, each of which may be substituted;
R²: phenyl which may be substituted;
R³: aryl or heteroaryl which may be respectively substituted;
R⁴: methyl.

2. The compound represented by general formula (I) or pharmaceutically acceptable salt thereof according to claim 1, wherein R³ is aryl which may be substituted with —O-lower alkyl, or benzothienyl.

3. The compound represented by general formula (I) or pharmaceutically acceptable salt thereof according to claim 2, wherein R² is phenyl which may be substituted with a group selected from the group consisting of halogen, lower alkyl, and halogeno-lower alkyl.

4. The compound represented by general formula (I) or pharmaceutically acceptable salt thereof according to claim 3, wherein L is a single bond.

5. The compound represented by general formula (I) or pharmaceutically acceptable salt thereof according to claim 4, wherein R¹ is aryl or heteroaryl, which is respectively substituted with a group selected from the group consisting of —CO₂H and tetrazole (wherein the aryl and the heteroaryl may be respectively further substituted with a group selected from lower alkyl, halogen, halogeno-lower alkyl, and —O-lower alkyl).

6. The compound represented by general formula (I) according to claim 1, which is selected from the group consisting of:
3-[3-(2-fluorophenyl)-4-({[(1R)-1-(1 naphthyl)ethyl]amino}methyl)piperidin-1-yl]benzoic acid,
5-chloro-6-[4-({[(1R)-1-(3-methoxyphenyl)ethyl]amino}methyl)-3-phenylpiperidin-1-yl]nicotinic acid,
6-[4-({[(1R)-1-(1-naphthyl)ethyl]amino}methyl)-3-phenylpiperidin-1-yl]pyridine-2-carboxylic acid,
6-[4-({[(1R)-1-(1-naphthyl)ethyl]amino}methyl)-3-phenylpiperidin-1-yl]-4-(trifluoromethyl)nicotinic acid,
6-[3-(3-fluorophenyl)-4-({[(1R)-1-(1-naphthyl)ethyl]amino}methyl)piperidin-1-yl]-4-(trifluoromethyl)nicotinic acid,
6-[3-(2-fluorophenyl)-4-({[(1R)-1-(1-naphthyl)ethyl]amino}methyl)piperidin-1-yl]nicotinic acid,
3-[3-(3-fluorophenyl)-4-({[(1R)-1-(1-naphthyl)ethyl]amino}methyl)piperidin-1-yl]benzoic acid,
2-[4-({[(1R)-1-(1-naphthyl)ethyl]amino}methyl)-3-phenylpiperidin-1-yl]-1,3-thiazole-4-carboxylic acid, 4-chloro-6-[4-({[(1R)-1-(1-naphthyl)ethyl]amino}methyl)-3-phenylpiperidin-1-yl]nicotinic acid, 6-[3-(3-fluorophenyl)-4-({[(1R)-1-(1-naphthyl)ethyl]amino}methyl)piperidin-1-yl]pyridine-2-carboxylic acid, 6-[3-(2-fluorophenyl)-4-({[(1R)-1-(1-naphthyl)ethyl]amino}methyl)piperidin-1-yl]pyridine-2-carboxylic acid, and 5-chloro-6-[3-(2-fluorophenyl)-4-({[(1R)-1-(1-naphthyl)ethyl]amino}methyl)piperidin-1-yl]nicotinic acid, or a pharmaceutically acceptable salt thereof.

7. A pharmaceutical composition comprising the compound represented by general formula (I) or pharmaceutically acceptable salt thereof according to claim 1, and a pharmaceutically acceptable carrier.

8. A method for agonizing a calcium sensing receptor comprising administering the compound represented by general formula (I) or pharmaceutically acceptable salt thereof according to claim 1.

9. A method for treating hyperparathyroidism comprising administering a therapeutically effective amount of the compound represented by general formula (I) or pharmaceutically acceptable salt thereof according to claim 1, to a patient in need thereof.

10. A method for treating renal osteodystrophy comprising administering a therapeutically effective amount of the compound represented by general formula (I) or pharmaceutically acceptable salt thereof according to claim 1, to a patient in need thereof.

11. A method for treating hypercalcemia comprising administering a therapeutically effective amount of the compound represented by general formula (I) or pharmaceutically acceptable salt thereof according to claim 1, to a patient in need thereof.

* * * * *